(12) United States Patent
Kim et al.

(10) Patent No.: US 10,100,019 B2
(45) Date of Patent: Oct. 16, 2018

(54) N2-(2-METHOXYPHENYL)PYRIMIDINE DERIVATIVE, METHOD FOR PREPARING SAME, AND PHARMACEUTICAL COMPOSITION FOR CANCER PREVENTION OR TREATMENT CONTAINING SAME AS ACTIVE INGREDIENT

(71) Applicant: KOREA RESEARCH INSTITUTE OF CHEMICAL TECHNOLOGY, Daejeon (KR)

(72) Inventors: Pilho Kim, Daejeon (KR); Hyoung Rae Kim, Daejeon (KR); Sung Yun Cho, Daejeon (KR); Jae Du Ha, Daejeong (KR); Hee Jung Jung, Daejeon (KR); Chang Soo Yun, Daejeon (KR); Jong Yeon Hwang, Jeollabuk-do (KR); Chi Hoon Park, Daejeon (KR); Chong Ock Lee, Seoul (KR); Sunjoo Ahn, Daejoen (KR); Chong Hak Chae, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 15/565,897

(22) PCT Filed: Apr. 6, 2016

(86) PCT No.: PCT/KR2016/003597
§ 371 (c)(1),
(2) Date: Oct. 11, 2017

(87) PCT Pub. No.: WO2016/167511
PCT Pub. Date: Oct. 20, 2016

(65) Prior Publication Data
US 2018/0111905 A1 Apr. 26, 2018

(30) Foreign Application Priority Data
Apr. 14, 2015 (KR) .................. 10-2015-0052572
Apr. 5, 2016 (KR) .................. 10-2016-0041920

(51) Int. Cl.
C07D 239/48 (2006.01)
A61K 31/505 (2006.01)
A61P 35/00 (2006.01)
A23L 33/10 (2016.01)
A23L 33/00 (2016.01)
C07D 401/12 (2006.01)
C07D 403/12 (2006.01)

(52) U.S. Cl.
CPC .......... *C07D 239/48* (2013.01); *A23L 33/10* (2016.08); *A23L 33/30* (2016.08); *A23L 33/40* (2016.08); *A61K 31/505* (2013.01); *A61P 35/00* (2018.01); *C07D 401/12* (2013.01); *C07D 403/12* (2013.01); *A23V 2002/00* (2013.01)

(58) Field of Classification Search
CPC .. C07D 239/48; C07D 401/12; C07D 403/12; C07D 413/12; A61K 31/505; A61K 31/506
USPC ..... 544/323, 295, 296, 114; 514/275, 231.5, 514/252.13
See application file for complete search history.

(56) References Cited

U.S. PATENT DOCUMENTS

2006/0247241 A1* 11/2006 Garcia-Echeverria ............... C07D 239/48 514/235.5
2011/0257154 A1* 10/2011 Michellys ............ C07D 417/12 514/210.18

FOREIGN PATENT DOCUMENTS

| EP | 1 524 262 A1 | 4/2005 |
|---|---|---|
| KR | 10-2006-7003056 | 5/2006 |
| KR | 10-2009-0087127 | 8/2009 |
| WO | WO 2004/080980 A1 | 9/2004 |
| WO | WO 2008/051547 A1 | 5/2008 |
| WO | WO 2009/143389 A1 | 11/2009 |
| WO | WO 2014/173291 A1 | 10/2014 |
| WO | WO 2014/203152 A1 | 12/2014 |
| WO | WO 2015/031666 A1 | 3/2015 |

OTHER PUBLICATIONS

Zhao et al., Cancer Biology & Therapy 16:12, 1691--1701, 2015.*
Cecil Textbook of Medicine, edited by Bennet, J.C., and Plum F., 20th edition, vol. 1, 1004-1010, 1996.*
Cohen et al., Current Opinion in Chemical Biology, 3,459-465, 1999.*
Dermeret al., Bio/Technology, 1994, 12:320.*

(Continued)

*Primary Examiner* — Venkataraman Balasubramanian
(74) *Attorney, Agent, or Firm* — Klarquist Sparkman, LLP

(57) ABSTRACT

The present invention relates to a N2-(2-methoxyphenyl) pyrimidine derivative, a preparation method thereof, and a pharmaceutical composition for the prevention or treatment of cancer comprising the same as an active ingredient. The N2-(2-methoxyphenyl)pyrimidine derivative, the optical isomer thereof, or the pharmaceutically acceptable salt thereof of the present invention is very effective in suppressing anaplastic lymphoma kinase (ALK) activity and as a result it can improve the effectiveness of treatment on cancer cells having anaplastic lymphoma kinase (ALK) fusion proteins such as EML4-ALK and NPM-ALK, so that it can be effectively used as a pharmaceutical composition for preventing or treating cancer.

4 Claims, 1 Drawing Sheet

(56) References Cited

OTHER PUBLICATIONS

Freshney et al., Culture of Animal Cells, a Manual of Basic Technique, Alan R. Liss, Inc., 1983, New York, p. 4.*
Golub et al., Science, 286, 531-537, 1999.*

* cited by examiner

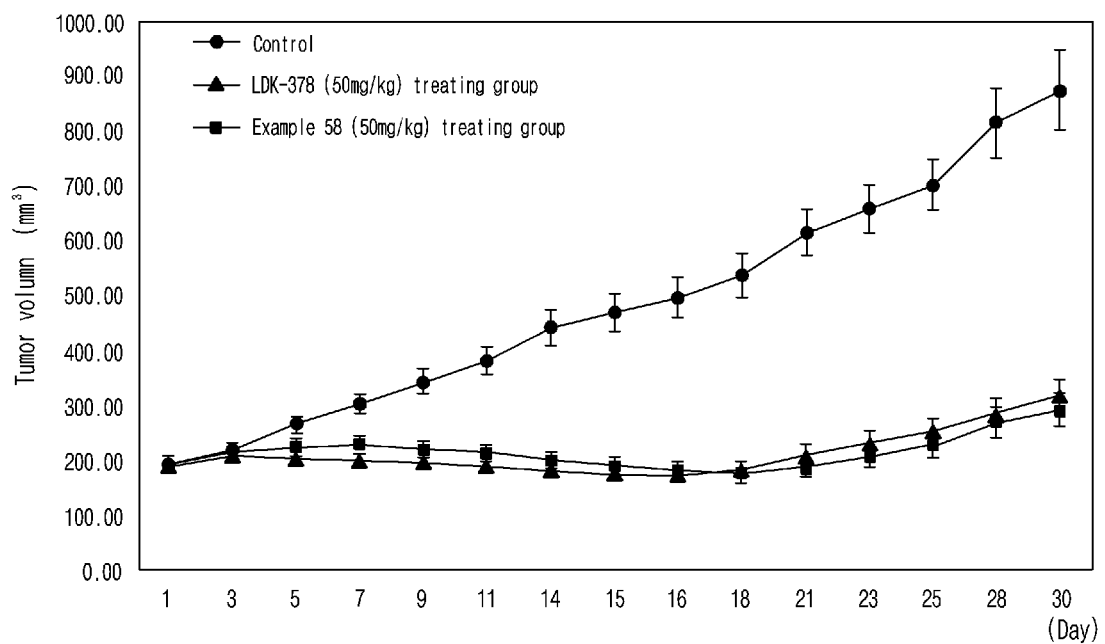

N2-(2-METHOXYPHENYL)PYRIMIDINE DERIVATIVE, METHOD FOR PREPARING SAME, AND PHARMACEUTICAL COMPOSITION FOR CANCER PREVENTION OR TREATMENT CONTAINING SAME AS ACTIVE INGREDIENT

BACKGROUND OF THE INVENTION

1. Field of the Invention

The present invention relates to a N2-(2-methoxyphenyl) pyrimidine derivative, a preparation method thereof, and a pharmaceutical composition for the prevention or treatment of cancer comprising the same as an active ingredient.

2. Description of the Related Art

Cells are the smallest units that make up a human body. Cells are divided and grow by the regulatory function of the cells themselves. When they reach their lifespan or become damaged, they kill themselves and maintain an overall balance of numbers. However, when the regulatory function of these cells is not functioning normally due to various reasons, the cells to be killed are abnormally proliferated and invade tissues around and other organs to form a mass, leading to the formation of a tumor.

Unlike a normal cell that is proliferated or suppressed according to a certain rule and a necessary manner, the cancer cell is unlimitedly proliferated in a tissue in disregard of such necessary rules and manners, and cancer is a cell mass made of such unlimitedly proliferating undifferentiated cells. The unlimitedly proliferating cancer cells invade into the tissues around and even to the other organs with causing a serious pain and problems and even death, so that cancer is regarded as an incurable disease.

According to the report by American Cancer Society, new patients diagnosed with cancer in 2007 world-widely were at least 12 million people, among which 7.6 million people were dead, indicating that approximately 20,000 patients were dead by cancer every day. In Korea, death of cancer was the number 1 cause of death in 2006, according to the report by Statistics Korea. Therefore, it is urgently requested to develop an anticancer agent which is excellent in cancer treating effect in order to reduce emotional and physical pain caused by cancer outbreak and experienced in the course of treating cancer and at the same time to increase quality of life of a patient.

The mechanism of normal cells being cancer cells has not been clearly understood. Cancer is developed by the combined actions of external factors such as environmental factors, chemicals, radiation, and virus and internal factors such as genetic factors and immunological factors. Genes involved in the cancer development are oncogenes and tumor suppressor genes. When the balance between the two cancer-associated genes is broken by any internal or external factors mentioned above, cancer is developed.

Cancer is largely divided into blood cancer that show abnormalities in the number of blood cells and solid cancer in the form of cell masses with constant hardness and morphology in the body. Cancer can be developed in almost every body parts, resulting in lung cancer, stomach cancer, breast cancer, oral cavity cancer, liver cancer, uterine cancer, esophageal cancer, and skin cancer, etc. Surgical operation, radiotherapy, and chemotherapy to suppress cell proliferation are the major anticancer treatment methods.

However, the chemotherapy is not the targeted therapy and the biggest problem of the conventional chemotherapy is side effect caused by cytotoxicity and drug resistance, which is the reason of failure in the treatment using an anticancer agent even after the successful early treatment with it. To overcome the limit of the chemotherapy, it is constantly required to develop a targeted agent based on the clear understanding on the anticancer mechanism of it.

Thus, studies have been undergoing with specific molecular biological factors involved in tumor formation, in order to develop a targeted agent. In particular, the molecular biological factors are used in the prediction of cancer prognosis or in making decision of chemotherapy or radiotherapy.

Recently, drugs such as Gleevec or Herceptin have been used as a targeted agent for bone marrow cancer or breast cancer. Gleevec is the drug that can suppress tyrosine kinase receptor, one of the molecular biological factors involved in cancer. Gleevec displays an anticancer effect by suppressing Bcr-Abl fusion gene formed by translocation in Philadelphia chromosome observed in chronic myelocytic leukemia, which is one of tyrosine kinase inhibitors and has been effective in treating chronic myelocytic leukemia. Gleevec is a tyrosine kinase inhibitor that is used as a targeted agent for chronic myelocytic leukemia. When Gleevec is administered to patients with chronic myelocytic leukemia, it has achieved satisfactory therapeutic results.

Other anticancer agents as a tyrosine kinase inhibitor are Gefitinib and Erlotinib which are EGFR (epidermal growth factor receptor) tyrosine kinase suppressors used in the treatment of non-small cell lung cancer, and Sorafenib and Sunitinib which are used in the treatment of renal cell carcinoma. However, these drugs display such side effects as hemorrhage, heart attack, heart failure, and liver failure, etc.

Recently, anaplastic lymphoma kinase (ALK) was identified in various tumors, so that it has been a target of study.

In the ALK-mediated cancer development, the ALK-NPM (Nucleophosmin) fusion gene found in anaplastic large cell lymphoma is known to be a key factor. Once ALK is activated by gene fusion, tyrosine kinase included in ALK starts abnormal action to cause cancer. That is, the abnormally activated anaplastic lymphoma kinase (ALK) induces cell proliferation, interrupts apoptosis in order to prevent cell death, to rearrange cytoskeleton, and accordingly to transform cell shape.

Oncogenic conversion of anaplastic lymphoma kinase (ALK) is accomplished by the interaction between ALK and its downstream molecule. The downstream molecule is a material to mediate the intracellular signal transduction. ALK interacts with normal genes or other oncogenic converted tyrosine kinase genes to activate various other pathways.

In particular, ALK gene in the lung cancer cell is fused with EML4 (Echinoderm Microtubule-Associated Protein-Like 4) gene to produce EML4-ALK, the active tyrosine kinase. At this time, the cancer inducing activity of EML4-ALK is dependent on the enzyme activity. It has been also reported by Mosse, et al that about 26% ALK gene amplification has been confirmed in 491 neuroblastoma samples. In addition, the ALK gene is found in many nonhematopoietic cell tumors including large B-cell lymphoma, systemic histiocytosis, inflammatory myofibroblastoma, esophageal squamous cell carcinoma, non-small cell lung cancer, rhabdomysarcoma, myofibroblastic tumor, breast cancer, and melanoma cell lines. In inflammatory myeloid blastoma, which is a rare disease, different kinds of anaplastic lymphoma kinase (ALK) fusion proteins are frequently observed, suggesting that such fusion proteins are involved deeply in the tumor development.

An anticancer agent targeting ALK-NPM is under development by using the method to block the ALK activation pathway. It has been recently confirmed by Pfizer that Crizotinib (PF-02341066) which is one of the small molecule tyrosine kinase inhibitors developed as a tumorigenic mutation specific inhibitor is effective in treating non-small cell lung cancer by inhibiting ATP competitive c-Met/HGFR (hepatocyte growth factor receptor) and ALK and accordingly it has been approved as a new drug by FDA in 2011. It was also confirmed that LDK-378 (Ceritinib) developed by Novartis. And clinical trials of multiple anaplastic lymphoma kinase (ALK) inhibitors are in progress.

Patent references 1-3 describe that the therapeutic agent candidates having various frames are under development in order to suppress ALK activity and a pyrimidine derivative can selectively inhibit ALK so that it can be developed as an anticancer agent.

Thus, the present inventors tried to develop a compound which is effective in suppressing anaplastic lymphoma kinase (ALK) activity. As a result, the inventors found out that a N2-(2-methoxyphenyl)pyrimidine derivative in a specific structure was excellent in inhibiting ALK activity so that it could be used as a cancer preventive or cancer treating agent, leading to the completion of this invention.

PRIOR ART REFERENCE

Patent Reference

WO 2009143389 A1
WO 2008051547 A1
WO 2004080980 A1

SUMMARY OF THE INVENTION

It is an object of the present invention to provide a N2-(2-methoxyphenyl)pyrimidine derivative, an optical isomer thereof, or a pharmaceutically acceptable salt of the same.

It is another object of the present invention to provide a method for preparing the said N2-(2-methoxyphenyl)pyrimidine derivative.

It is also an object of the present invention to provide a pharmaceutical composition comprising the said N2-(2-methoxyphenyl)pyrimidine derivative, the optical isomer thereof, or the pharmaceutically acceptable salt of the same as an active ingredient for the prevention or treatment of cancer.

It is further an object of the present invention to provide a health functional food composition comprising the said N2-(2-methoxyphenyl)pyrimidine derivative, the optical isomer thereof, or the pharmaceutically acceptable salt of the same as an active ingredient for the prevention or improvement of cancer.

To achieve the above objects, the present invention provides a compound represented by formula 1, an optical isomer thereof, or a pharmaceutically acceptable salt of the same.

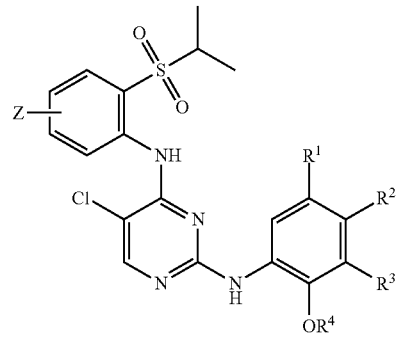

Formula 1

In the formula 1, $R^1$ is hydrogen, $C_{1-5}$ straight or branched alkyl, $-(CR^5R^6)_\alpha-(CR^7R^8)_\beta-(CR^9R^{10})_\gamma-NR^{11}R^{12}$, or $-(CH_2)_p-C(=O)-R^{13}$, $R^5$, $R^6$, $R^7$, $R^8$, $R^9$, and $R^{10}$ are independently hydrogen or $C_{1-10}$ straight or branched alkyl, $R^5$ and $R^6$ can form unsubstituted $C_{3-8}$ cycloalkyl along with the carbon atoms conjugated to the same, $R^7$ and $R^8$ can form unsubstituted $C_{3-10}$ cycloalkyl or oxo group (=O) along with the carbon atoms conjugated to the same, $R^{11}$ and $R^{12}$ are independently hydrogen, $C_{1-10}$ straight or branched alkyl wherein unsubstituted or one or more hydroxyl groups are substituted, $C_{1-10}$ straight or branched alkyl sulfonyl, unsubstituted $C_{6-10}$ aryl $C_{1-5}$ straight or branched alkyl, $-(CH_2)_n-C(=X)R^{14}$, unsubstituted $C_{6-10}$ heteroaryl containing one or more hetero atoms selected from the group consisting of N, O, and S, or unsubstituted $C_{6-10}$ aryl, wherein, X is O or S, $R^{14}$ is hydrogen, $-OH$, $C_{1-10}$ straight or branched alkoxy, $C_{1-10}$ straight or branched alkyl wherein unsubstituted or one or more halogens are substituted, unsubstituted $C_{6-10}$ aryl $C_{1-5}$ straight or branched alkyl, or $-NR^{15}R^{16}$, $R^{15}$ and $R^{16}$ are independently hydrogen, $C_{1-5}$ straight or branched alkyl, unsubstituted $C_{5-10}$ cycloalkyl, unsubstituted $C_{6-10}$ aryl, or unsubstituted $C_{6-10}$ aryl $C_{1-5}$ alkyl, and n is an integer of 0-5, $R^{11}$ and $R^{12}$ can form unsubstituted $C_{5-10}$ heterocycloalkyl containing one or more hetero atoms selected from the group consisting of N, O, and S along with the nitrogen atoms conjugated to the same, $\alpha$, $\beta$, and $\gamma$ are independently integers of 0-2, $R^{13}$ is $-OH$ or $-(OCH_2CH_2)_q-H$, wherein q is an integer of 1-2, p is an integer of 1-2;

$R^2$ is hydrogen, halogen, unsubstituted or substituted $C_{5-10}$ heteroaryl containing one or more hetero atoms selected from the group consisting of N, O, and S, $C_{1-10}$ straight or branched alkyl wherein unsubstituted or one or more nitrile groups ($-CN$) are substituted, $C_{1-10}$ straight or branched alkyl wherein unsubstituted or one or more amine groups ($-NH_2$) are substituted, unsubstituted $C_{6-10}$, $-(CR^7R^8)_k-(CR^{19}R^{20})_j-NR^{21}R^{22}$, $-C(=CH_2)-R^{23}$, or $-CH_2-N^+(CH_3)_3$ $I^-$, the substituted $C_{5-10}$ heteroaryl can be substituted with $C_{1-5}$ straight or branched alkyl, $R^{17}$, $R^{18}$, $R^{19}$, and $R^{20}$ are independently hydrogen or $C_{1-5}$ straight or branched alkyl, and k and j are independently integers of 0-2, $R^{21}$ and $R^{22}$ are independently hydrogen, formyl group ($-C(=O)H$), or $C_{1-5}$ straight or branched alkyl, $R^{23}$ is $C_{1-5}$ straight or branched alkyl;
$R^3$ is hydrogen;
$R^4$ is hydrogen or $C_{1-5}$ straight or branched alkoxy; and
Z is hydrogen, F, Cl, or Br.

The present invention also provides a method for preparing the compound represented by formula 1 containing the step of preparing the compound represented by formula 1 by reacting the compound represented by formula 2 with the compound represented by formula 3 (step 1) as shown in reaction formula 1 below.

Reaction Formula 1

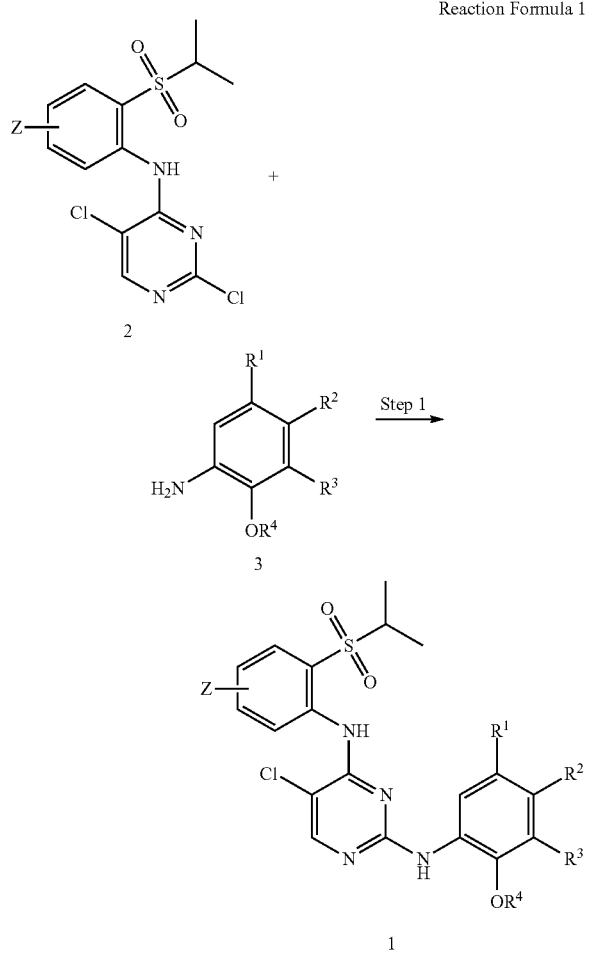

In the reaction formula 1,
$R^1$, $R^2$, $R^3$, $R^4$, and Z are as defined in formula 1.

The present invention also provides a pharmaceutical composition comprising the compound represented by formula 1, the optical isomer thereof, or the pharmaceutically acceptable salt of the same as an active ingredient for the prevention or treatment of cancer.

In addition, the present invention provides a health functional food composition comprising the compound represented by formula 1, the optical isomer thereof, or the pharmaceutically acceptable salt of the same as an active ingredient for the prevention or improvement of cancer.

Advantageous Effect

The N2-(2-methoxyphenyl)pyrimidine derivative, the optical isomer thereof, or the pharmaceutically acceptable salt thereof of the present invention is very effective in suppressing anaplastic lymphoma kinase (ALK) activity and as a result it can improve the effectiveness of treatment on cancer cells having anaplastic lymphoma kinase (ALK) fusion proteins such as EML4-ALK and NPM-ALK, so that it can be effectively used as a pharmaceutical composition for preventing or treating cancer.

BRIEF DESCRIPTION OF THE DRAWING

FIG. 1 is a graph of tumor volume versus time for a control group, a group treated with LDK378, and a group treated with the compound of Example 58 (5-chloro-N2-(4-(2-(dimethylamino)ethyl)-2-methoxy-5-methylphenyl)-N4-(2-(isopropylsulfonyl)phenyl)pyrimidine-2,4-diamine).

DESCRIPTION OF THE PREFERRED EMBODIMENTS

Hereinafter, the present invention is described in detail.

The present invention provides a compound represented by formula 1, an optical isomer thereof, or a pharmaceutically acceptable salt of the same.

Formula 1

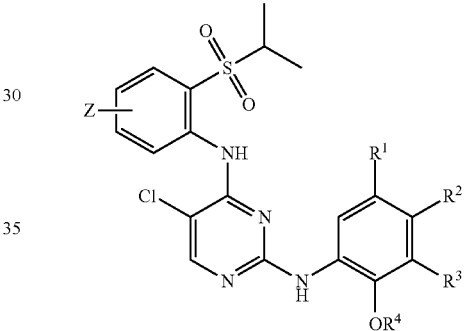

In the formula 1,
$R^1$ is hydrogen, $C_{1-5}$ straight or branched alkyl, —$(CR^5R^6)_\alpha$—$(CR^7R^8)_\beta$—$(CR^9R^{10})_\gamma$—$NR^{11}R^{12}$, or —$(CH_2)_p$—$C(=O)$—$R^{13}$,
$R^5$, $R^6$, $R^7$, $R^8$, $R^9$, and $R^{10}$ are independently hydrogen or $C_{1-10}$ straight or branched alkyl,
$R^5$ and $R^6$ can form unsubstituted $C_{3-8}$ cycloalkyl along with the carbon atoms conjugated to the same,
$R^7$ and $R^8$ can form unsubstituted $C_{3-10}$ cycloalkyl or oxo group (=O) along with the carbon atoms conjugated to the same,
$R^{11}$ and $R^{12}$ are independently hydrogen, $C_{1-10}$ straight or branched alkyl wherein unsubstituted or one or more hydroxyl groups are substituted, $C_{1-10}$ straight or branched alkyl sulfonyl, unsubstituted $C_{6-10}$ aryl $C_{1-5}$ straight or branched alkyl, —$(CH_2)_n$—$C(=X)R^{14}$, unsubstituted $C_{6-10}$ heteroaryl containing one or more hetero atoms selected from the group consisting of N, O, and S, or unsubstituted $C_{6-10}$ aryl,
wherein, X is O or S, $R^{14}$ is hydrogen, —OH, $C_{1-10}$ straight or branched alkoxy, $C_{1-10}$ straight or branched alkyl wherein unsubstituted or one or more halogens are substituted, unsubstituted $C_{6-10}$ aryl $C_{1-5}$ straight or branched alkyl, or —$NR^{15}R^{16}$, $R^{15}$ and $R^{16}$ are independently hydrogen, $C_{1-5}$ straight or branched alkyl, unsubstituted $C_{5-10}$ cycloalkyl, unsubstituted $C_{6-10}$ aryl, or unsubstituted $C_{6-10}$ aryl $C_{1-5}$ alkyl, and n is an integer of 0-5, $R^{11}$ and $R^{12}$ can form unsubstituted $C_{5-10}$ heterocycloalkyl containing one or more hetero atoms selected from the group consisting of N, O, and S along with the nitrogen atoms conjugated to the same, α, β, and γ are independently integers of 0-2, $R^{13}$ is —OH or —$(OCH_2CH_2)_q$—H, wherein q is an integer of 1-2, p is an integer of 1-2;

$R^2$ is hydrogen, halogen, unsubstituted or substituted $C_{5-10}$ heteroaryl containing one or more hetero atoms selected from the group consisting of N, O, and S, $C_{1-10}$ straight or branched alkyl wherein unsubstituted or one or more nitrile groups (—CN) are substituted, $C_{1-10}$ straight or branched alkyl wherein unsubstituted or one or more amine groups (—$NH_2$) are substituted, unsubstituted $C_{6-10}$, —$(CR^{17}R^{18})_k$—$(CR^{19}R^{20})_j$—$NR^{21}R^{22}$, —$C(=CH_2)$—$R^{23}$, or —$CH_2$—$N^+(CH_3)_3$ $I^-$, the substituted $C_{5-10}$ heteroaryl can be substituted with $C_{1-5}$ straight or branched alkyl, $R^{17}$, $R^{18}$, $R^{19}$, and $R^{20}$ are independently hydrogen or $C_{1-5}$ straight or branched alkyl, and k and j are independently integers of 0-2, $R^{21}$ and $R^{22}$ are independently hydrogen, formyl group (—$C(=O)H$), or $C_{1-5}$ straight or branched alkyl, $R^{23}$ is $C_{1-5}$ straight or branched alkyl;

$R^3$ is hydrogen;

$R^4$ is hydrogen or $C_{1-5}$ straight or branched alkoxy; and

Z is hydrogen, F, Cl, or Br.

Preferably, $R^1$ is hydrogen, $C_{1-5}$ straight or branched alkyl, —$(CR^5R^6)_α$—$(CR^7R^8)_β$—$(CR^9R^{10})_γ$—$NR^{11}R^{12}$, or —$(CH_2)_p$—$C(=O)$—$R^{13}$, $R^5$, $R^6$, $R^7$, $R^8$, $R^9$, and $R^{10}$ are independently hydrogen or $C_{1-10}$ straight or branched alkyl, $R^5$ and $R^6$ can form unsubstituted $C_{3-8}$ cycloalkyl along with the carbon atoms conjugated to the same, $R^7$ and $R^8$ can form unsubstituted $C_{3-8}$ cycloalkyl or oxo group (=O) along with the carbon atoms conjugated to the same, $R^{11}$ and $R^{12}$ are independently hydrogen, $C_{1-5}$ straight or branched alkyl wherein unsubstituted or one or more hydroxyl groups are substituted, $C_{1-5}$ straight or branched alkyl sulfonyl, unsubstituted $C_{6-8}$ aryl $C_{1-3}$ straight or branched alkyl, —$(CH_2)_n$—$C(=X)R^{14}$, unsubstituted $C_{6-10}$ heteroaryl containing one or more hetero atoms selected from the group consisting of N, O, and S, or unsubstituted $C_{6-10}$ aryl, wherein, X is O or S, $R^{14}$ is hydrogen, —OH, $C_{1-5}$ straight or branched alkoxy, $C_{1-5}$ straight or branched alkyl wherein unsubstituted or one or more halogens are substituted, unsubstituted $C_{6-8}$ aryl $C_{1-3}$ straight or branched alkyl, or —$NR^{15}R^{16}$, $R^{15}$ and $R^{16}$ are independently hydrogen, $C_{1-3}$ straight or branched alkyl, unsubstituted $C_{5-8}$ cycloalkyl, unsubstituted $C_{6-8}$ aryl, or unsubstituted $C_{6-8}$ aryl $C_{1-3}$ alkyl, and n is an integer of 0-3, $R^{11}$ and $R^{12}$ can form unsubstituted $C_{5-8}$ heterocycloalkyl containing one or more hetero atoms selected from the group consisting of N, O, and S along with the nitrogen atoms conjugated to the same, α, β, and γ are independently integers of 0-1, $R^{13}$ is —OH or —$(OCH_2CH_2)_q$—H, wherein q is an integer of 1-2, p is an integer of 1-2;

$R^2$ is hydrogen, halogen, unsubstituted or substituted $C_{5-8}$ heteroaryl containing one or more hetero atoms selected from the group consisting of N, O, and S, $C_{1-5}$ straight or branched alkyl wherein unsubstituted or one or more nitrile groups (—CN) are substituted, $C_{1-5}$ straight or branched alkyl wherein unsubstituted or one or more amine groups (—$NH_2$) are substituted, unsubstituted $C_{6-8}$, —$(CR^{17}R^{18})_k$—$(CR^{19}R^{20})_j$—$NR^{21}R^{22}$, —$C(=CH_2)$—$R^{23}$, or —$CH_2$—$N^+(CH_3)_3$ $I^-$, the substituted $C_{5-8}$ heteroaryl can be substituted with $C_{1-5}$ straight or branched alkyl, $R^{17}$, $R^{18}$, $R^{19}$, and $R^{20}$ are independently hydrogen or $C_{1-3}$ straight or branched alkyl, and k and j are independently integers of 0-2, $R^{21}$ and $R^{22}$ are independently hydrogen, formyl group (—$C(=O)H$), or $C_{1-3}$ straight or branched alkyl, $R^{23}$ is $C_{1-3}$ straight or branched alkyl;

$R^3$ is hydrogen;

$R^4$ is hydrogen or $C_{1-5}$ straight or branched alkoxy; and

Z is hydrogen, F, Cl, or Br.

More preferably, $R^1$ is methyl,

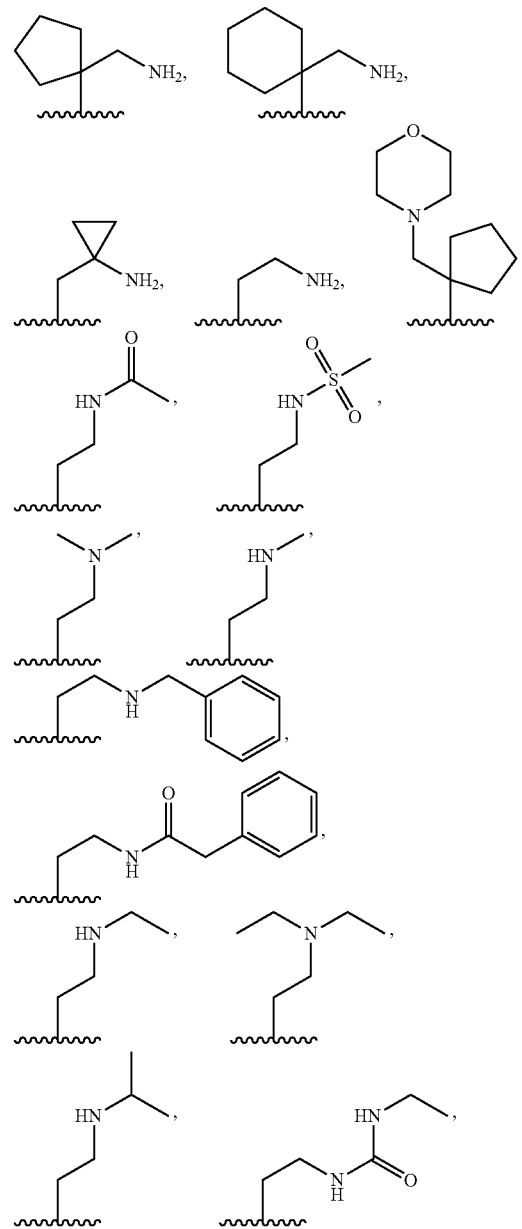

-continued
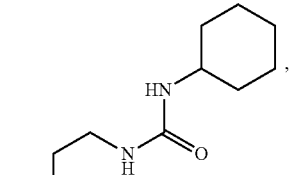,
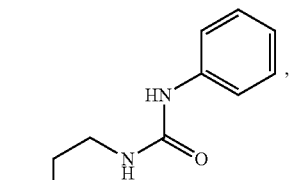,
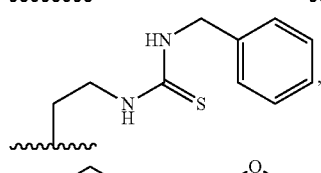,
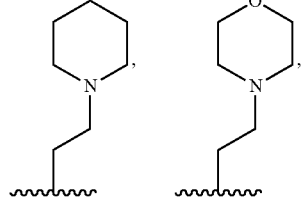,
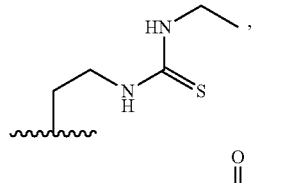,
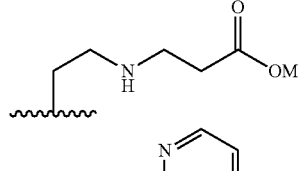,
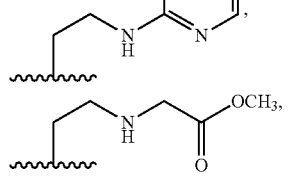,
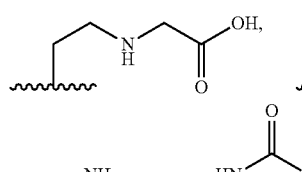,
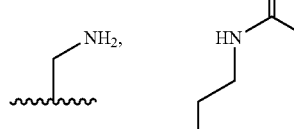,
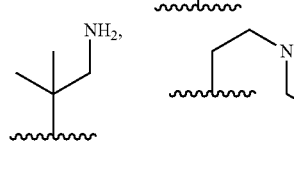,
-continued
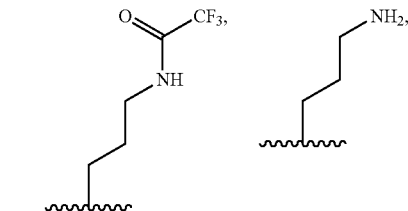
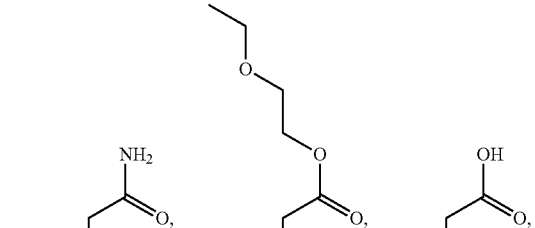
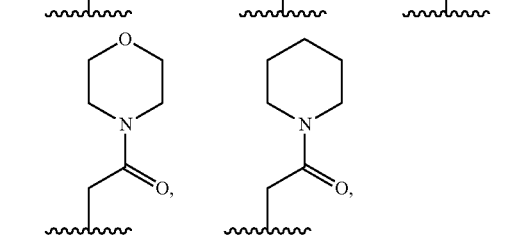
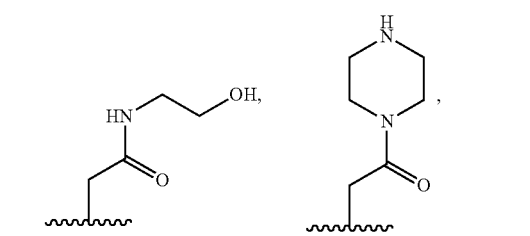
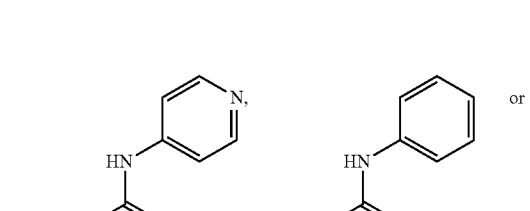
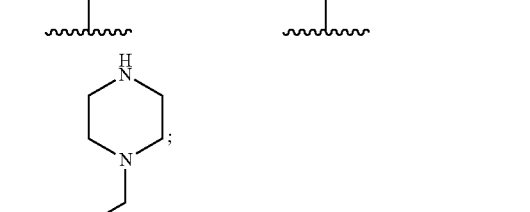
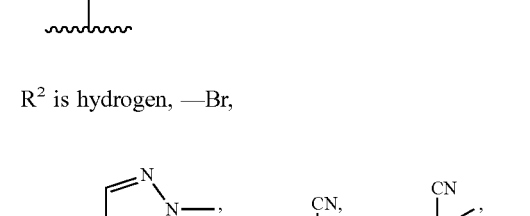;
$R^2$ is hydrogen, —Br,
 or -continued

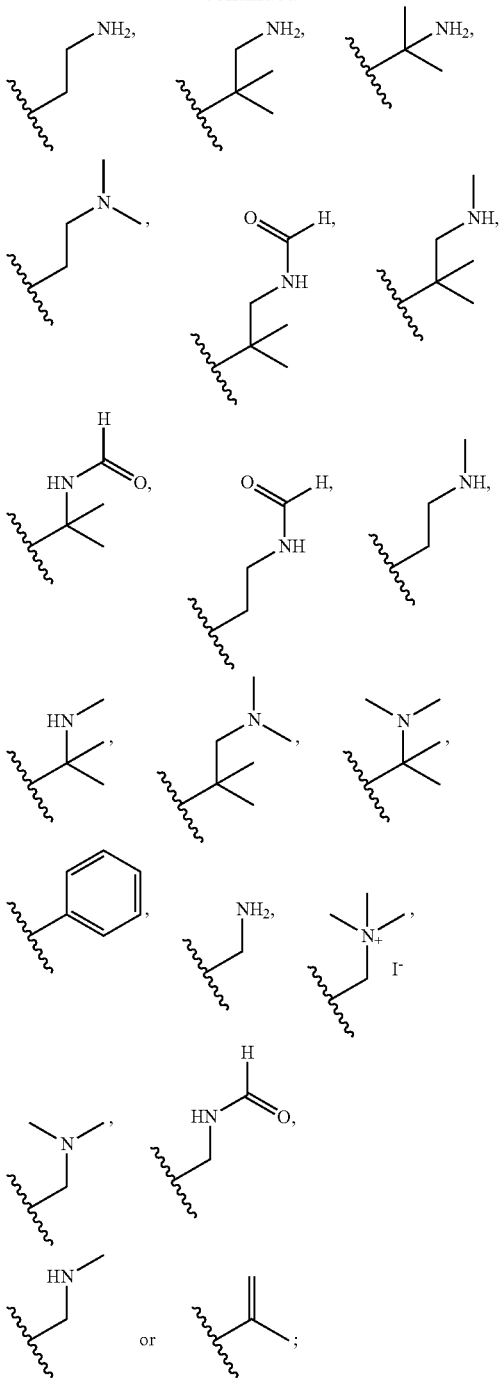

R³ is hydrogen;
R⁴ is methoxy, ethoxy, or iso-propoxy;
Z is hydrogen or F.

The compound represented by formula 1 of the present invention can be exemplified by the following compounds:

(1) N2-(5-(1-(aminomethyl)cyclopentyl)-2-methoxyphenyl)-5-chloro-N4-(2-(isopropylsulfonyl)phenyl)pyrimidine-2,4-diamine;
(2) N2-(5-(1-(aminomethyl)cyclohexyl)-2-methoxyphenyl)-5-chloro-N4-(2-(isopropylsulfonyl)phenyl)pyrimidine-2,4-diamine;
(3) N2-(5-((1-aminocyclopropyl)methyl)-2-methoxyphenyl)-5-chloro-N4-(2-(isopropylsulfonyl)phenyl)pyrimidine-2,4-diamine;
(4) N2-(5-(2-aminoethyl)-2-methoxyphenyl)-5-chloro-N4-(2-(isopropylsulfonyl)phenyl) pyrimidine-2,4-diamine;
(5) 5-chloro-N4-(2-(isopropylsulfonyl)phenyl-N2-(2-methoxy-5-(1-(piperidine-1-ylmethyl)cyclopentyl) phenyl)pyrimidine-2,4-diamine;
(6) 5-chloro-N4-(2-(isopropylsulfonyl)phenyl)-N2-(2-methoxy-5-(1-(morpholinomethyl)cyclopentyl)phenyl) pyrimidine-2,4-diamine;
(7) N-(3-(5-chloro-4-(2-(isopropylsulfonyl)phenylamino) pyrimidine-2-ylamino)-4-methoxyphenethyl)acetamide;
(8) N-(3-(5-chloro-4-(2-(isopropylsulfonyl)phenylamino) pyrimidine-2-ylamino)-4-methoxyphenethyl)methanesulfonamide;
(9) 5-chloro-N2-(5-(2-(dimethylamino)ethyl)-2-methoxyphenyl)-N4-(2-(isopropylsulfonyl)phenyl)pyrimidine-2,4-diamine;
(10) 5-chloro-N4-(2-(isopropylsulfonyl)phenyl)-N2-(2-methoxy-5-(2-(methylamino)ethyl)phenyl)pyrimidine-2,4-diamine;
(11) N2-(5-(2-(benzylamino)ethyl)-2-methoxyphenyl)-5-chloro-N4-(2-(isopropylsulfonyl)phenyl)pyrimidine-2,4-diamine;
(12) N-(3-(5-chloro-4-(2-(isopropylsulfonyl)phenylamino) pyrimidine-2-ylamino)-4-methoxyphenethyl)-2-phenylacetamide;
(13) 5-chloro-N2-(5-(2-(ethylamino)ethyl)-2-methoxyphenyl)-N4-(2-(isopropylsulfonyl)phenyl)pyrimidine-2,4-diamine;
(14) 5-chloro-N2-(5-(2-(diethylamino)ethyl)-2-methoxyphenyl)-N4-(2-(isopropylsulfonyl)phenyl)pyrimidine-2,4-diamine;
(15) 5-chloro-N2-(5-(2-(isopropylamino)ethyl)-2-methoxyphenyl)-N4-(2-(isopropylsulfonyl)phenyl)pyrimidine-2,4-diamine;
(16) 1-(3-(5-chloro-4-(2-(isopropylsulfonyl)phenylamino) pyrimidine-2-ylamino)-4-methoxyphenethyl)-3-ethylurea;
(17) 1-(3-(5-chloro-4-(2-(isopropylsulfonyl)phenylamino) pyrimidine-2-ylamino)-4-methoxyphenethyl)-3-cyclohexylurea;
(18) 1-(3-(5-chloro-4-(2-(isopropylsulfonyl)phenylamino) pyrimidine-2-ylamino)-4-methoxyphenethyl)-3-phenylurea;
(19) 1-(3-(5-chloro-4-(2-(isopropylsulfonyl)phenylamino) pyrimidine-2-ylamino)-4-methoxyphenethyl)-3-methylthiourea;
(20) 1-benzyl-3-(3-(5-chloro-4-(2-(isopropylsulfonyl)phenylamino)pyrimidine-2-ylamino)-4-methoxyphenethyl) thiourea;
(21) 5-chloro-N4-(2-(isopropylsulfonyl)phenyl)-N2-(2-methoxy-5-(2-(piperidine-1-yl)ethyl)phenyl)pyrimidine-2,4-diamine;
(22) 5-chloro-N4-(2-(isopropylsulfonyl)phenyl)-N2-(2-methoxy-5-(2-morpholinoethyl)phenyl)pyrimidine-2,4-diamine;
(23) 1-(3-(5-chloro-4-(2-(isopropylsulfonyl)phenylamino) pyrimidine-2-ylamino)-4-methoxyphenethyl)-3-ethylthiourea;
(24) methyl 3-(3-(5-chloro-4-(2-(isopropylsulfonyl)phenylamino)pyrimidine-2-ylamino)-4-methoxyphenethylamino)propanoate;
(25) 5-chloro-N4-(2-(isopropylsulfonyl)phenyl)-N2-(2-methoxy-5-(2-(pyrimidine-2-ylamino)ethyl)phenyl)pyrimidine-2,4-diamine;

(26) methyl 2-(3-(5-chloro-4-(2-(isopropylsulfonyl)phenylamino)pyrimidine-2-ylamino)-4-methoxyphenethylamino)acetate;
(27) 2-(3-(5-chloro-4-(2-(isopropylsulfonyl)phenylamino)pyrimidine-2-ylamino)-4-methoxyphenethylamino)acetic acid;
(28) N-(3-((5-chloro-4-((2-(isopropylsulfonyl)phenyl)amino)pyrimidine-2-yl)amino-4-methoxybenzyl)-2,2,2-trifluoroacetamide;
(29) N2-(5-(aminomethyl)-2-methoxyphenyl)-5-chloro-N4-(2-(isopropylsulfonyl)phenyl)pyrimidine-2,4-diamine;
(30) N-(3-(5-chloro-4-(2-(isopropylsulfonyl)phenylamino)pyrimidine-2-ylamino)-4-methoxyphenethyl)-2,2,2-trifluoroacetamide;
(31) N2-(5-(2-aminoethyl)-2-isopropoxyphenyl)-5-chloro-N4-(2-(isopropylsulfonyl)phenyl)pyrimidine-2,4-diamine;
(32) N2-(5-(2-aminoethyl)-2-methoxyphenyl)-5-chloro-N4-(4-fluoro-2-(isopropylsulfonyl)phenyl)pyrimidine-2,4-diamine;
(33) N2-(5-(2-aminoethyl)-2-methoxyphenyl)-5-chloro-N4-(5-fluoro-2-(isopropylsulfonyl)phenyl)pyrimidine-2,4-diaminehydrochloride;
(34) N2-(5-(2-aminoethyl)-2-methoxyphenyl)-5-chloro-N4-(2-fluoro-6-(isopropylsulfonyl)phenyl)pyrimidine-2,4-diaminehydrochloride;
(35) N2-(5-(1-amino-2-methylpropane-2-yl)-2-methoxyphenyl)-5-chloro-N4-(2-(isopropylsulfonyl)phenyl)pyrimidine-2,4-diamine;
(36) N2-(5-(1-amino-2-methylpropane-2-yl)-2-methoxyphenyl)-5-chloro-N4-(4-fluoro-2-(isopropylsulfonyl)phenyl)pyrimidine-2,4-diamine;
(37) N2-(5-(1-amino-2-methylpropane-2-yl)-2-methoxyphenyl)-5-chloro-N4-(5-fluoro-2-(isopropylsulfonyl)phenyl)pyrimidine-2,4-diamine;
(38) N2-(5-(1-amino-2-methylpropane-2-yl)-2-methoxyphenyl)-5-chloro-N4-(2-fluoro-6-(isopropylsulfonyl)phenyl)pyrimidine-2,4-diamine;
(39) 2,2'-(3-(5-chloro-4-(2-(isopropylsulfonyl)phenylamino)pyrimidine-2-ylamino)-4-methoxyphenethylazeindiyl) diethanol;
(40) N-(3-(3-((5-chloro-4-((2-(isopropylsulfonyl)phenyl)amino)pyrimidine-2-yl)amino)-4-methoxyphenyl)propyl)-2,2,2-trifluoroacetamide;
(41) N2-(5-(3-aminopropyl)-2-methoxyphenyl)-5-chloro-N4-(2-(isopropylsulfonyl)phenyl)pyrimidine-2,4-diamine;
(42) 2-(3-((5-chloro-4-((2-(isopropylsulfonyl)phenyl)amino)pyrimidine-2-yl)amino)-4-methoxyphenyl)acetamide;
(43) 2-ethoxyethyl 2-(3-((5-chloro-4-((2-(isopropylsulfonyl)phenyl)amino)pyrimidine-2-yl)amino)-4-methoxyphenyl)acetate;
(44) 2-(3-((5-chloro-4-((2-(isopropylsulfonyl)phenyl)amino)pyrimidine-2-yl)amino)-4-methoxyphenyl)acetic acid;
(45) 2-(3-((5-chloro-4-((2-(isopropylsulfonyl)phenyl)amino)pyrimidine-2-yl)amino)-4-methoxyphenyl)-1-morpholinoethane-1-one;
(46) 2-(3-((5-chloro-4-((2-(isopropylsulfonyl)phenyl)amino)pyrimidine-2-yl)amino)-4-methoxyphenyl)-1-(piperidine-1-yl)ethane-1-one;
(47) 2-(3-((5-chloro-4-((2-(isopropylsulfonyl)phenyl)amino)pyrimidine-2-yl)amino)-4-methoxyphenyl)-N-(hydroxymethyl)acetamide;
(48) 2-(3-((5-chloro-4-((2-(isopropylsulfonyl)phenyl)amino)pyrimidine-2-yl)amino)-4-methoxyphenyl)-1-(piperazine-1-yl)ethane-1-one;
(49) 2-(3-((5-chloro-4-((2-(isopropylsulfonyl)phenyl)amino)pyrimidine-2-yl)amino)-4-methoxyphenyl)-N-(pyridine-4-yl)acetamide;
(50) 2-(3-((5-chloro-4-((2-(isopropylsulfonyl)phenyl)amino)pyrimidine-2-yl)amino)-4-methoxyphenyl)-N-phenylacetamide;
(51) N2-(5-(2-aminoethyl)-4-bromo-2-methoxyphenyl)-5-chloro-N4-(2-(isopropylsulfonyl)phenyl)pyrimidine-2,4-diamine;
(52) N2-(5-(2-aminoethyl)-2-methoxy-4-(1-methyl-H-pyrazole-4-yl)phenyl)-5-chloro-N4-(2-(isopropylsulfonyl)phenyl)pyrimidine-2,4-diamine;
(53) 2-(4-((5-chloro-4-((2-(isopropylsulfonyl)phenyl)amino)pyrimidine-2-yl)amino)-5-methoxy-2-methylphenyl) acetonitrile;
(54) 2-(4-((5-chloro-4-((2-(isopropylsulfonyl)phenyl)amino)pyrimidine-2-yl)amino)-5-methoxy-2-methylphenyl)-2-methylpropanenitrile;
(55) N2-(4-(2-aminoethyl)-2-methoxy-5-methylphenyl)-5-chloro-N4-(2-(isopropylsulfonyl)phenyl)pyrimidine-2,4-diamine;
(56) N2-(4-(1-amino-2-methylpropane-2-yl)-2-methoxy-5-methylphenyl)-5-chloro-N4-(2-(isopropylsulfonyl)phenyl)pyrimidine-2,4-diamine;
(57) N2-(4-(2-aminopropane-2-yl)-2-methoxy-5-methylphenyl)-5-chloro-N4-(2-(isopropylsulfonyl)phenyl)pyrimidine-2,4-diamine;
(58) 5-chloro-N2-(4-(2-(dimethylamino)ethyl)-2-methoxy-5-methylphenyl)-N4-(2-(isopropylsulfonyl)phenyl)pyrimidine-2,4-diamine;
(59) N-(2-(4-((5-chloro-4-((2-(isopropylsulfonyl)phenyl)amino)pyrimidine-2-yl)amino)-5-methoxy-2-methylphenyl)-2-methylpropyl) formamide;
(60) 5-chloro-N4-(2-(isopropylsulfonyl)phenyl)-N2-(2-methoxy-5-methyl-4-(2-methyl-1-(methylamino)propane-2-yl)phenyl)pyrimidine-2,4-diamine;
(61) N-(2-(4-((5-chloro-4-((2-(isopropylsulfonyl)phenyl)amino)pyrimidine-2-yl)amino)-5-methoxy-2-methylphenyl) propane-2-yl) formamide;
(62) N-(4-((5-chloro-4-((2-(isopropylsulfonyl)phenyl)amino)pyrimidine-2-yl)amino)-5-methoxy-2-methylphenethyl) formamide;
(63) 5-chloro-N4-(2-(isopropylsulfonyl)phenyl)-N2-(2-methoxy-5-methyl-4-(2-(methylamino)ethyl)phenyl)pyrimidine-2,4-diamine;
(64) 5-chloro-N4-(2-(isopropylsulfonyl)phenyl)-N2-(2-methoxy-5-methyl-4-(2-(methylamino) propane-2-yl) phenyl)pyrimidine-2,4-diamine;
(65) 5-chloro-N2-(4-(1-(dimethylamino)-2-methylpropane-2-yl)-2-methoxy-5-methylphenyl)-N4-(2-(isopropylsulfonyl)phenyl)pyrimidine-2,4-diamine;
(66) 5-chloro-N2-(4-(2-(dimethylamino)propane-2-yl)-2-methoxy-5-methylphenyl)-N4-(2-(isopropylsulfonyl)phenyl)pyrimidine-2,4-diamine;
(67) N2-(2-(2-aminoethyl)-5-methoxybiphenyl-4-yl)-5-chloro-N4-(2-isopropylsulfonyl)phenyl)pyrimidine-2,4-diamine;
(68) N2-(4-(aminomethyl)-2-methoxy-5-methylphenyl)-5-chloro-N4-(2-(isopropylsulfonyl)phenyl)pyrimidine-2,4-diamine;
(69) 1-(4-((5-chloro-4-((2-(isopropylsulfonyl)phenyl)amino)pyrimidine-2-yl)amino)-5-methoxy-2-methylphenyl)-N, N, N-trimethylmethanealuminum iodide;

(70) 5-chloro-N2-(4-((dimethylamino)methyl)-2-methoxy-5-methylphenyl)-N4-(2-(isopropylsulfonyl)phenyl)pyrimidine-2,4-diamine;
(71) N-(4-((5-chloro-4-((2-(isopropylsulfonyl)phenyl)amino)pyrimidine-2-yl)amino)-5-methoxy-2-methylbenzyl) formamide;
(72) 5-chloro-N4-(2-(isopropylsulfonyl)phenyl)-N2-(2-methoxy-5-methyl-4-(methylamino)methyl)phenyl)pyrimidine-2,4-diamine;
(73) 5-chloro-N4-(2-(isopropylsulfonyl)phenyl)-N2-(2-methoxy-5-(2-(piperazine-1-yl)ethyl)phenyl)pyrimidine-2,4-diamine;
(74) N2-(5-(2-aminoethyl)-2-ethoxy-4-(prop-1-ene-2-yl)phenyl)-5-chloro-N4-(2-(isopropylsulfonyl)phenyl)pyrimidine-2,4-diamine; and
(75) N2-(5-(2-aminoethyl)-2-methoxy-4-(prop-1-ene-2-yl)phenyl)-5-chloro-N4-(2-(isopropylsulfonyl)phenyl)pyrimidine-2,4-diamine.

The compound represented by formula 1 of the present invention can be used as a form of a pharmaceutically acceptable salt, in which the salt is preferably acid addition salt formed by pharmaceutically acceptable free acids.

The acid addition salt herein can be obtained from inorganic acids such as hydrochloric acid, nitric acid, phosphoric acid, sulfuric acid, hydrobromic acid, hydriodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

The present invention includes not only the compound represented by formula 1 but also a pharmaceutically acceptable salt thereof, and a solvate, an optical isomer, or a hydrate possibly produced from the same.

The present invention also provides a method for preparing the compound represented by formula 1 containing the step of preparing the compound represented by formula 1 by reacting the compound represented by formula 2 with the compound represented by formula 3 (step 1) as shown in reaction formula 1 below.

Reaction Formula 1

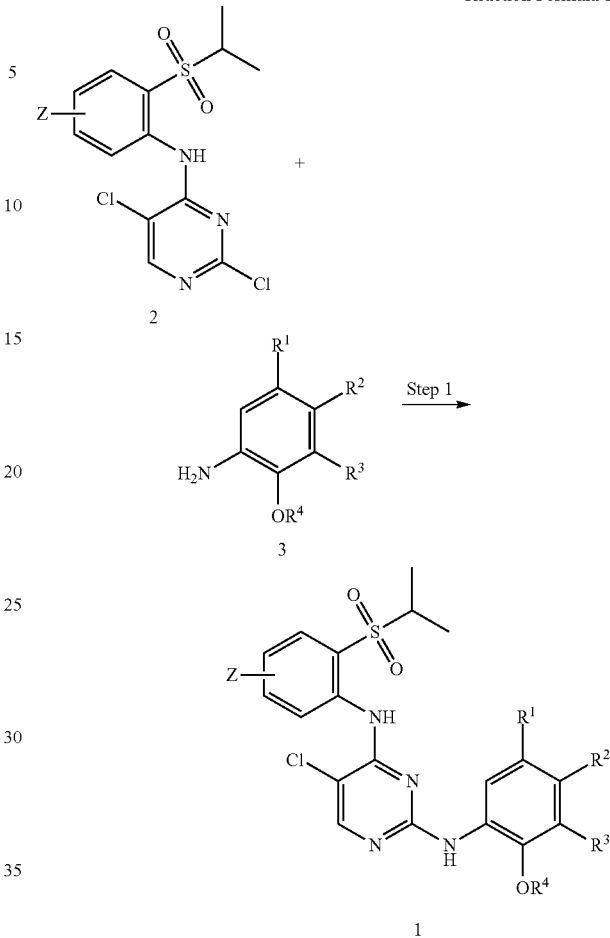

In the reaction formula 1, $R^1$, $R^2$, $R^3$, $R^4$, and Z are as defined in formula 1.

Hereinafter, the method for preparing the compound represented by formula 1 of the present invention is described in more detail.

In the method for preparing the compound represented by formula 1 of the present invention, the compound represented by formula 1 was prepared by reacting the compound represented by formula 2 with the compound represented by formula 3. Particularly, the compound represented by formula 1 was prepared by reacting the compound represented by formula 2 with the compound represented by formula 3 in the presence of an organic solvent and an acid.

At this time, the organic solvent used herein was selected from the group consisting of tetrahydrofuran (THF); dioxane; ether solvents including ethylether and 1,2-dimethoxyethane; lower alcohols including methanol, ethanol, propanol, and butanol; dimethylformamide (DMF), dimethylsulfoxide (DMSO), dichloromethane (DCM), dichloroethane, water, acetonagensulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate, and dimethylformamide (DMF) was preferably selected.

The acid used herein was selected from the group consisting of acetic acid, trifluoroacetic acid, hydrochloric acid, sulfuric acid, and toluene sulfonic acid, and hydrochloric acid was preferably selected.

At this time, the reaction was preferably performed at a temperature between 0° C. and the boiling point of the solvent, and the reaction time was not particularly limited, but it was preferably 0.5-40 hours.

The present invention also provide a pharmaceutical composition comprising the compound represented by formula 1, the optical isomer thereof, or the pharmaceutically acceptable salt of the same as an active ingredient for the prevention or treatment of cancer. The pharmaceutical composition is characterized by the inhibition of the expression and the growth of cancer cells by suppressing the activation of anaplastic lymphoma kinase (ALK). The cancer herein is exemplified by non-small cell lung cancer, neuroblastoma, inflammatory myelofibroblastoma, rhabdomyosarcoma, myofibroblastoma, breast cancer, stomach cancer, lung cancer, and melanoma.

ALK is the gene inducing the proliferation of cancer cells, which is activated by gene fusion. At this time, a tyrosine kinase included in ALK starts acting abnormally to induce cell proliferation, interrupt apoptosis, re-arrange cytoskeleton, transform cell shape, and activates other pathways or interacts with other tyrosine kinases which are either normal or oncogenic.

Particularly, the compound of the present invention was confirmed to reduce efficiently the activity of ALK WT containing ALK enzyme (see Table 2 of Experimental Example 1); to inhibit ALK L1196M also containing ALK enzyme (see Table 3 of Experimental Example 2); and to inhibit the activity of IR protein containing ALK (see Table 4 of Experimental Example 3).

The compound of the present invention also displayed cytotoxic effect on H3122 and H2228 (non-small cell lung cancer cells) (see Tables 5 and 6 of Experimental Examples 4 and 5) and EML4 (Echiinoderm Microtubule-Associated Protein-like 4)-ALK and L1196M mutant cells (see Tables 7 and 8 of Experimental Examples 6 and 7).

Therefore, the N2-(2-methoxyphenyl)pyrimidine derivative represented by formula 1 of the present invention was confirmed to have an excellent activity to inhibit ALK activity and cancer cell specific toxicity, so that it can be effectively used as a composition for the prevention or treatment of such cancers as non-small cell lung cancer, neuroblastoma, inflammatory myelofibroblastoma, rhabdomyosarcoma, myofibroblastoma, breast cancer, stomach cancer, lung cancer, and melanoma.

The compound represented by formula 1 of the present invention can be administered orally or parenterally in various formulations at the time of clinical administration. The formulations can be prepared by mixing the compound of the invention with generally used diluents or excipients such as fillers, extenders, binders, wetting agents, disintegrants, and surfactants.

The formulations for oral administration are exemplified by tablets, pills, powders, granules, capsules, and troches (candy type), etc. Such solid preparations are prepared by mixing one or more compounds of the present invention with one or more excipients such as starch, calcium carbonate, sucrose, lactose and gelatin. Except for the simple excipients, lubricants, for example magnesium stearate, talc, etc, can be used. Liquid formulations for oral administrations are suspensions, solutions (medicines dissolved or dispersed in water or organic solvents), emulsions or syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The effective dosage of the compound of the present invention can be adjusted according to age, weight, and gender of patient, administration pathway, health condition, severity of disease, etc. For example, the effective dosage is generally 0.001-100 mg/kg/day, and preferably 0.01-35 mg/kg/day. Based on an adult patient weighing 70 kg, the effective dosage is generally 0.07-7000 mg/day, and preferably 0.7-2500 mg/day, which can be administered 1-several times a day or the dosage can be divided and administered several times a day at a regular interval according to the judgment of a doctor or a pharmacist.

In addition, the present invention provides a health functional food composition comprising the N2-(2-methoxyphenyl)pyrimidine derivative represented by formula 1, the optical isomer thereof, or the pharmaceutically acceptable salt of the same as an active ingredient for the prevention or improvement of cancer.

Particularly, the food comprising the N2-(2-methoxyphenyl)pyrimidine derivative represented by formula 1, the optical isomer thereof, or the pharmaceutically acceptable salt of the same as an active ingredient herein is not limited. For example, the compound of the present invention can be added to drinks, meats, sausages, breads, biscuits, rice cakes, chocolates, candies, snacks, cookies, pizza, ramyuns, flour products, gums, dairy products including ice cream, soups, beverages, vitamin complex, milk products, and milk-processing products, and in a wide sense, almost every food applicable in the production of health food can be included. The compound of the present invention can be added as it is or as mixed with other food components according to the conventional method.

The N2-(2-methoxyphenyl)pyrimidine derivative represented by formula 1 of the present invention was confirmed to have an excellent activity to inhibit ALK activity, so that it can be effectively used as a health functional food composition for the prevention or improvement of such cancers as non-small cell lung cancer, neuroblastoma, inflammatory myelofibroblastoma, rhabdomyosarcoma, myofibroblastoma, breast cancer, stomach cancer, lung cancer, and melanoma.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1: Preparation of N-((1-(3-amino-4-methoxyphenyl)cyclopentyl)methyl)-2,2,2-trifluoroacetamide

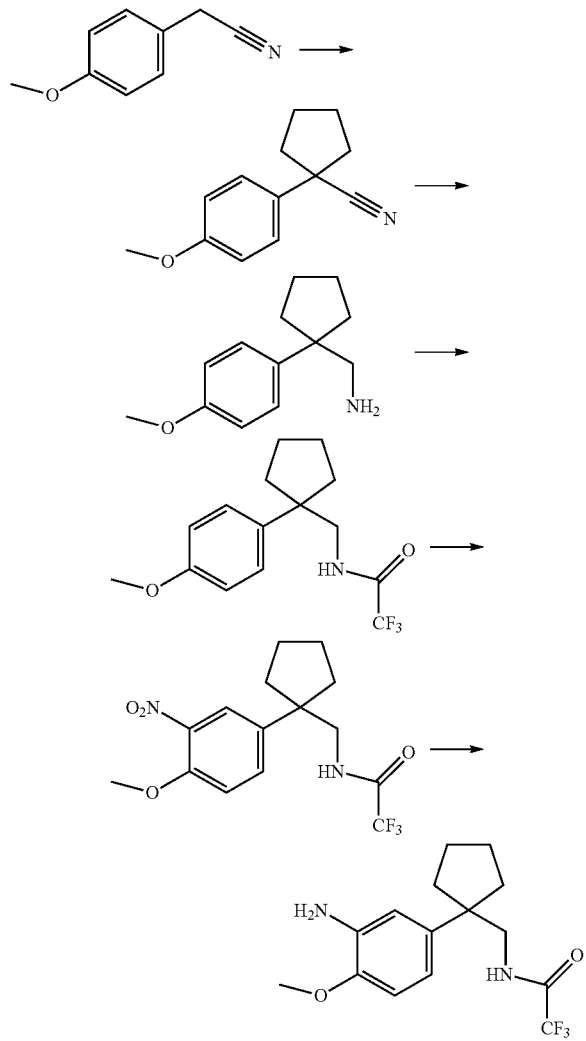

Step 1: Preparation of 1-(4-methoxyphenyl)cyclopentane-1-carbonitrile

Sodium hydride (2.85 g, 71.34 mmol) was dissolved in dimethylformamide (50 ml), to which 2-(4-methoxyphenyl)acetonitrile (5.0 g, 33.97 mmol) and 1,4-dibromobutane (8.80 g, 40.77 mmol) were loaded at 0° C. The reaction mixture was stirred at room temperature for 2 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 1-(4-methoxyphenyl)cyclopentane-1-carbonitrile as a white solid (5.10 g, 25.3 mmol, yield: 75%).
$^1$H-NMR (300 MHz, CDCl$_3$) δ 7.36 (d, J=8.7 Hz, 2H), 7.36 (d, J=9.0 Hz, 2H), 3.81 (s, 3H), 2.44-2.46 (m, 2H), 1.91-2.04 (m, 6H); LC/MS 202.1[M+H$^+$].

Step 2: Purification of (1-(4-methoxyphenyl)cyclopentyl)methaneamine 1-(4-methoxyphenyl)cyclopentane-1-carbonitrile prepared in step 1 was dissolved in diethylether (5 ml). This mixed solution was added to diethylether (50 ml) containing lithium aluminum hydride (1.89 g, 49.97 mmol) dissolved therein at 0° C. The reaction mixture was stirred at room temperature for 4 hours. Water and 2 N sodium hydroxide aqueous solution were added thereto at 0° C. The reaction mixture was stirred for 20 minutes and the produced solid was filtered. The filtrate was dried over sodium sulfate, and then filtered. The solvent was eliminated by distillation under reduced pressure. Then, purification was performed by silica gel column chromatography (eluent: methanol/dichloromethane, 1/10) to give the target compound (1-(4-methoxyphenyl)cyclopentyl)methaneamine as a yellow solid (4.3 g, 20.944 mmol, yield: 83%).
$^1$H-NMR (300 MHz, CDCl$_3$) δ 7.21 (d, J=7.8 Hz, 2H), 6.87 (d, J=7.8 Hz, 2H), 4.74 (br, 2H), 3.79 (s, 3H), 2.85 (s, 2H), 1.94 (br, 4H), 1.70-1.73 (m. 4H); LC/MS 206.10 [M+H$^+$].

Step 3: Preparation of 2,2,2-trifluoro-N-((1-(4-methoxyphenyl)cyclopentyl)methyl)acetamide (1-(4-methoxyphenyl)cyclopentyl)methaneamine (4.5 g, 21.92 mmol) prepared in step 2 was dissolved in dichloromethane (50 ml), to which anhydrous trifluoroacetic acid (5.5 g, 26.30 mmol) and triethylamine (7.6 ml, 54.79 mmol) were loaded at 0° C. The reaction mixture was stirred at room temperature for 2 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-((1-(4-methoxyphenyl)cyclopentyl)methyl)acetamide as a white solid (5.1 g, 16.926 mmol, yield: 77%).
$^1$H-NMR (300 MHz, CDCl$_3$) δ 7.19 (d, J=9.0 Hz, 2H), 6.90 (d, J=8.7 Hz, 2H), 5.89 (br, 1H), 3.81 (s, 3H), 3.44 (d, J=6.3 Hz, 2H), 1.60-1.89 (m, 8H); LC/MS 206.10[M+H$^+$].

Step 4: Preparation of 2,2,2-trifluoro-N-((1-(4-methoxy-3-nitrophenyl)cyclopentyl)methyl)acetamide 2,2,2-trifluoro-N-((1-(4-methoxyphenyl)cyclopentyl)methyl)acetamide (5.0 g, 16.59 mmol) prepared in step 3 was dissolved in trifluoroacetic acid (50 ml), to which trifluoroacetic acid (12.5 ml) solution containing concentrated nitric acid (1.05 g, 16.59 mmol) dissolved therein was added at 0° C. The reaction mixture was stirred at 0° C. for 2 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-((1-(4-methoxy-3-nitrophenyl)cyclopentyl)methyl)acetamide as a yellow solid (4.1 g, 11.839 mmol, yield: 72%).
$^1$H-NMR (300 MHz, CDCl$_3$) δ 7.75 (d, J=1.5 Hz, 1H), 7.46 (d, J=8.7 Hz, 1H), 7.09 (d, J=8.4 Hz, 1H), 6.09 (br, 1H), 3.96 (s, 3H), 3.50 (d, J=6.6 Hz, 2H), 1.68-2.04 (m, 8H); LC/MS 346.92 [M+H$^+$].

Step 5: Preparation of N-((1-(3-amino-4-methoxyphenyl)cyclopentyl)methyl)-2,2,2-trifluoroacetamide 2,2,2-trifluoro-N-((1-(4-methoxy-3-nitrophenyl)cyclopentyl)methyl)acetamide (300 mg, 0.89 mmol) prepared in step 4 was dissolved in methanol (5 ml), to which 10 weight % Pd/C (30 mg) was added. The mixture was stirred for 4 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/1) to give the target compound N-((1-(3-amino-4-methoxyphenyl)cyclopentyl)methyl)-2,2,2-trifluoroacetamide as a white solid (242 mg, 0.765 mmol, yield: 88%).

$^1$H-NMR (300 MHz, CDCl$_3$) δ 6.75 (d, J=8.4 Hz, 1H), 6.58-6.62 (m, 2H), 5.98 (br, 1H), 3.85 (s, 3H), 3.79 (br, 2H), 3.40 (d, J=6.0 Hz, 2H), 1.75-1.85 (m, 8H) LC/MS 316.46 [M+H$^+$], 632.90 [2M+H$^+$].

Preparative Example 2: Preparation of N-((1-(3-amino-4-methoxyphenyl)cyclohexyl)methyl)-2,2,2-trifluoroacetamide

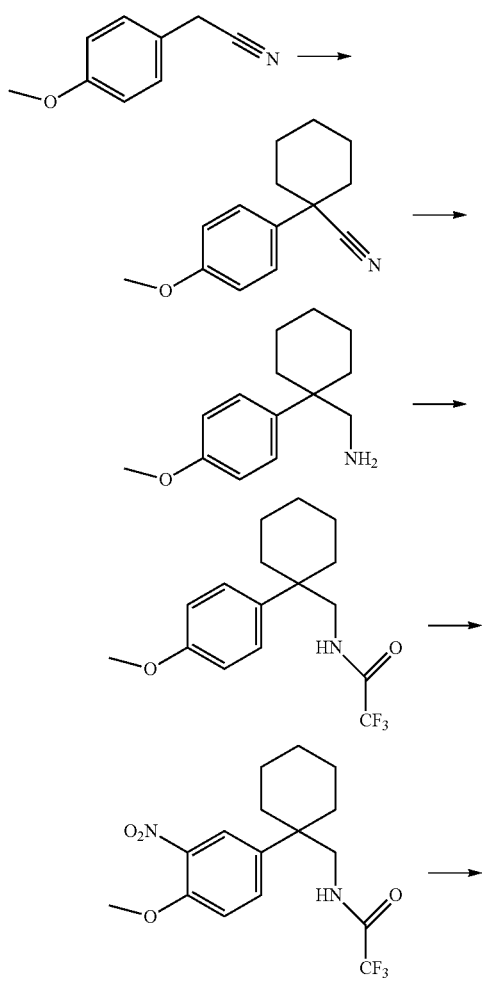

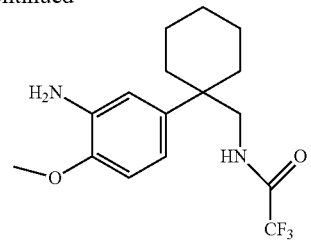

Step 1: Preparation of 1-(4-methoxyphenyl)cyclohexanecarbonitrile

Sodium hydride (2.85 g, 71.3 mmol) was dissolved in dimethylformamide (50 mL), to which 2-(4-methoxyphenyl)acetonitrile (5.0 g, 33.97 mmol) and 1,5-dibromopentane (9.37 g, 40.77 mmol) were loaded at 0° C. The reaction mixture was stirred at room temperature for 2 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 1-(4-methoxyphenyl)cyclohexanecarbonitrile as a white solid (5.2 g, 24.152 mmol, yield: 71%).

$^1$H-NMR (300 MHz, CDCl$_3$) δ 7.40 (d, J=9.0 Hz, 2H), 6.91 (d, J=8.7 Hz, 2H), 3.81 (s, 3H), 2.12-2.16 (m, 2H), 1.58-1.85 (m, 7H), 1.24-1.28 (m, 1H); LC/MS 216.1 [M+H$^+$].

Step 2: Preparation of (1-(4-methoxyphenyl)cyclohexyl)methaneamine

Lithium aluminum hydride (1.79 g, 47.38 mmol) was dissolved in diethylether (51 mL), to which diethylether (5 mL) solution containing 1-(4-methoxyphenyl)cyclopentane-1-carbonitrile (5.1 g, 23.69 mmol) prepared in step 1 was added at 0° C. The reaction mixture was stirred at room temperature for 4 hours. Water and 2 N sodium hydroxide aqueous solution were added thereto at 0° C. The reaction mixture was stirred for 20 minutes and the produced solid was filtered. The filtrate was dried over sodium sulfate, and then filtered. The solvent was eliminated by distillation under reduced pressure. Then, purification was performed by silica gel column chromatography (eluent: methanol/dichloromethane, 1/10) to give the target compound (1-(4-methoxyphenyl)cyclohexyl)methaneamine as a yellow solid (4.5 g, 20.517 mmol, yield: 87%).

$^1$H-NMR (300 MHz, CDCl$_3$) δ 7.24 (d, J=9.0 Hz, 2H), 6.89 (d, J=8.7 Hz, 2H), 3.80 (s, 3H), 2.65 (s, 2H), 2.06-2.11 (m, 2H), 1.35-1.53 (m, 8H); LC/MS 220.03 [M+H$^+$].

Step 3: Preparation of 2,2,2-trifluoro-N-((1-(4-methoxyphenyl)cyclohexyl)methyl)acetamide (1-(4-methoxyphenyl)cyclohexyl)methaneamine (4.5 g, 20.52 mmol) prepared in step 2 was dissolved in dichloromethane (45 mL), to which anhydrous trifluoroacetic acid (5.2 g, 24.62 mmol) and triethylamine (7.1 mL, 51.29 mmol) were added at 0° C. The reaction mixture was stirred at room temperature for 2 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-((1-(4-methoxyphenyl)cyclohexyl)methyl)acetamide as a white solid (5.5 g, 17.441 mmol, yield: 85%).

$^1$H-NMR (300 MHz, CDCl$_3$) δ 7.25 (d, J=9.3 Hz, 2H), 6.93 (d, J=8.7 Hz, 2H), 5.81 (br, 1H), 3.82 (s, 3H), 3.40 (d, J=6.3 Hz, 2H), 2.04-2.17 (m, 2H), 1.38-1.66 (m, 8H); LC/MS 316.06 [M+H$^+$].

Step 4: Preparation of 2,2,2-trifluoro-N-((1-(4-methoxy-3-nitrophenyl)cyclohexyl)methyl)acetamide 2,2,2-trifluoro-N-((1-(4-methoxyphenyl)cyclohexyl) methyl)acetamide (5.3 g, 16.79 mmol) prepared in step 3 was dissolved in trifluoroacetic acid (50 ml), to which trifluoroacetic acid (12.5 ml) solution containing concentrated nitric acid (1.05 g, 16.59 mmol) dissolved therein was added at 0° C. The reaction mixture was stirred at 0° C. for 2 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-((1-(4-methoxy-3-nitrophenyl)cyclohexyl)methyl)acetamide as a yellow solid (4.3 g, 11.934 mmol, yield: 71%).

$^1$H-NMR (300 MHz, CDCl$_3$) δ 7.82 (d, J=2.4 Hz, 1H), 7.52 (dd, J=2.1 Hz, 8.7 Hz, 1H), 7.12 (d, J=9.0 Hz, 1H), 5.18 (s, 1H), 3.98 (s, 3H), 3.45 (d, J=6.6 Hz, 2H), 2.06-2.14 (m, 2H), 1.22-1.69 (m, 8H); LC/MS 360.87 [M+H$^+$], 720.78 [2M+H$^+$].

Step 5: Preparation of N-((1-(3-amino-4-methoxyphenyl)cyclohexyl)methyl)-2,2,2-trifluoroacetamide 2,2,2-trifluoro-N-((1-(4-methoxy-3-nitrophenyl)cyclohexyl)methyl)acetamide (300 mg 0.837 mmol) prepared in step 4 was dissolved in methanol (5 ml), to which 10 weight % Pd/C (30 mg) was added. The mixture was stirred for 4 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/1) to give the target compound N-((1-(3-amino-4-methoxyphenyl)cyclohexyl)methyl)-2,2,2-trifluoroacetamide as a white solid (252 mg, 0.763 mmol, yield: 92%).

$^1$H-NMR (300 MHz, CDCl$_3$) δ 6.78 (d, J=8.4 Hz, 1H), 6.65-6.69 (m, 2H), 5.85 (br, 1H), 3.86 (s, 3H), 3.79 (br, 2H), 3.37 (d, J=6.0 Hz, 2H), 1.99-2.05 (m, 2H), 1.40-1.56 (m, 8H); LC/MS 330.48 [M+H+], 660.84 [2M+H$^+$].

Preparative Example 3: Preparation of N-(1-(3-amino-4-methoxybenzyl)cyclopropyl)-2,2,2-trifluoroacetamide

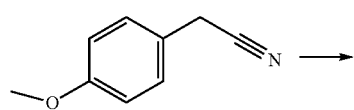

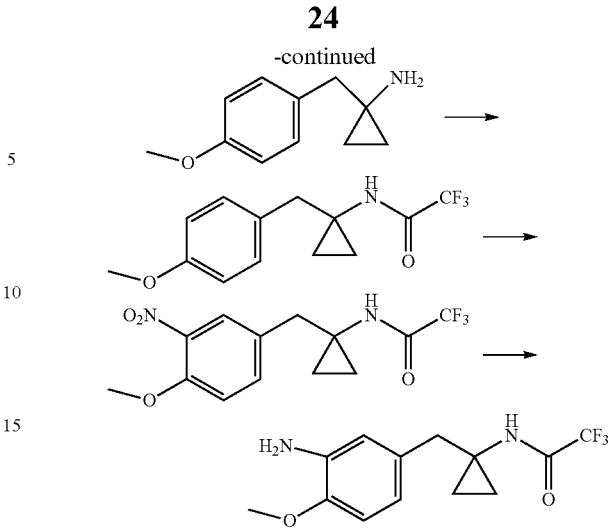

Step 1: Preparation of 1-(4-methoxybenzyl)cyclopropane-1-amine 2-(4-methoxyphenyl)acetonitrile (4.0 g, 27.18 mmol) was dissolved in tetrahydrofuran/ether (30 mL/30 mL), to which titanium isopropoxide (8.19 g, 54.36 mmol) was added at 0° C. Then, 3 M ethylmagnesium bromide (18.1 mL, 54.36 mmol) was added thereto at room temperature. The reaction mixture was stirred for 1 hour. Boron trifluoride diethyl ether (7.71 g, 54.36 mmol) was added to the reaction mixture, followed by stirring at room temperature for 1 hour. 2 N sodium hydroxide solution was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 1-(4-methoxybenzyl)cyclopropane-1-amine as a colorless oil (2.1 g, 11.84 mmol, yield: 44%).

$^1$H-NMR (300 MHz, CDCl$_3$) δ 7.17 (d, J=8.4 Hz, 2H), 6.86 (d, J=8.7 Hz, 2H), 3.79 (s, 3H), 2.66 (s, 2H), 1.45 (br, 2H), 0.58-0.62 (m, 4H); LC/MS 177.9.

Step 2: Preparation of 2,2,2-trifluoro-N-(1-(4-methoxybenzyl)cyclopropyl)acetamide 1-(4-methoxybenzyl)cyclopropane-1-amine (1.0 g, 5.64 mmol) was dissolved in dichloromethane (10 mL), to which anhydrous trifluoroacetic acid (1.42 g, 6.77 mmol) and triethylamine (1.96 mL, 14.10 mmol) were added at 0° C. The reaction mixture was stirred at room temperature for 2 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-(1-(4-methoxybenzyl)cyclopropyl)acetamide as a white solid (1.21 g, 4.43 mmol, yield: 65%).

$^1$H-NMR (300 MHz, CDCl$_3$) δ 7.08 (d, J=8.4 Hz, 2H), 6.85 (d, J=8.7 Hz, 2H), 6.35 (br, 1H), 3.79 (s, 3H), 2.86 (s, 2H), 0.89-0.95 (m, 4H); LC/MS 274.0.

Step 3: Preparation of 2,2,2-trifluoro-N-(1-(4-methoxy-3-nitrobenzyl)cyclopropyl)acetamide 2,2,2-trifluoro-N-(1-(4-methoxybenzyl)cyclopropyl)acetamide (1.0 g, 3.65 mmol) prepared in step 1 was dissolved in trifluoroacetic acid (10 mL), to which trifluoroacetic acid (1.0 mL) solution containing concentrated nitric acid (0.42 g, 4.03 mmol) dissolved therein was added at 0° C. The reaction mixture was stirred at 0° C. for 2 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-(1-(4-methoxy-3-nitrobenzyl)cyclopropyl)acetamide as a yellow solid (718 mg, 2.26 mmol, yield: 62%).

$^1$H-NMR (300 MHz, CDCl$_3$) δ 7.67 (s, 1H), 7.32 (d, J=8.4 Hz, 1H), 7.04 (d, J=2.1 Hz, 8.4 Hz, 1H), 6.38 (s, br, 1H), 3.96 (s, 3H), 2.95 (s, 2H), 0.95 (s, 4H); LC/MS: 319.0 [M+H$^+$].

Step 4: Preparation of N-(1-(3-amino-4-methoxybenzyl)cyclopropyl)-2,2,2-trifluoroacetamide 2,2,2-trifluoro-N-(1-(4-methoxy-3-nitrobenzyl)cyclopropyl)acetamide (200 mg 0.837 mmol) prepared in step 3 was dissolved in methanol (5 ml), to which 10 weight % Pd/C (20 mg) was added. The mixture was stirred for 4 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/1) to give the target compound N-(1-(3-amino-4-methoxybenzyl)cyclopropyl)-2,2,2-trifluoroacetamide as a white solid (150 mg, 0.520 mmol, yield: 83%).

$^1$H-NMR (300 MHz, CDCl$_3$) δ 6.70-6.73 (m, 1H), 6.48-6.52 (m, 2H), 3.83 (s, 3H), 3.77 (br, 2H), 2.77 (d, J=1.8 Hz, 2H), 0.89 (br, 2H), 0.86 (br, 2H); LC/MS 289.1 [M+H$^+$].

Preparative Example 4: Preparation of N-(3-amino-4-methoxyphenethyl)-2,2,2-trifluoroacetamide

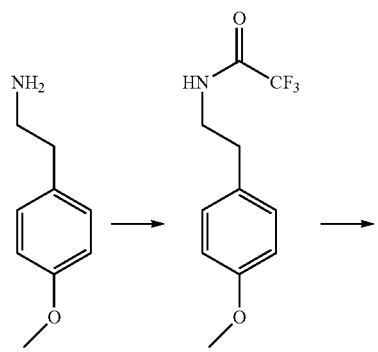

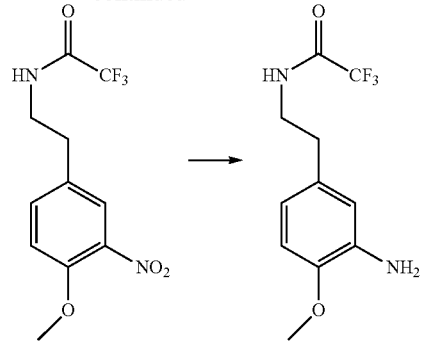

Step 1: Preparation of 2,2,2-trifluoro-N-(4-methoxyphenethyl)acetamide 4-methoxyphenethylamine (12.0 g, 79.36 mmol) was dissolved in dichloromethane (50 mL), to which trifluoroacetic anhydride (13.5 mL, 95.2 mmol) and triethylamine (27.6 mL, 198.4 mmol) were added at 0° C. The reaction mixture was stirred at room temperature for 3 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound 2,2,2-trifluoro-N-(4-methoxyphenethyl)acetamide as a white solid (19.0 g, 76.9 mmol, yield: 97%).

$^1$H-NMR (300 MHz, CDCl$_3$) δ 2.72 (t, J=7.2 Hz, 2H), 3.35-3.39 (m, 2H), 3.71 (s, 3H), 6.87 (d, J=8.4 Hz, 2H), 7.11 (d, J=8.7 Hz, 2H), 9.46 (s, 1H); LC/MS 248.30 [M+H$^+$].

Step 2: Preparation of 2,2,2-trifluoro-N-(4-methoxy-3-nitrophenethyl)acetamide 2,2,2-trifluoro-N-(4-methoxyphenethyl)acetamide (20.0 g, 80.89 mmol) prepared in step 1 was dissolved in trifluoroacetic acid (206 mL), to which concentrated nitric acid (5.09 g, 80.89 mmol) was added at 0° C. The reaction mixture was stirred at room temperature for 2 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound 2,2,2-trifluoro-N-(4-methoxy-3-nitrophenethyl)acetamide as a white solid (19.2 g, 65.7 mmol, yield: 81%).

$^1$H-NMR (300 MHz, CDCl$_3$) δ 2.82 (t, J=6.9 Hz, 2H), 3.42 (q, J=6.9, 12.9 Hz, 2H), 3.89 (s, 3H), 7.29 (d, J=8.7 Hz, 1H), 7.49 (dd, J=1.8, 8.4 Hz, 1H), 7.72 (d, J=1.8 Hz, 1H), 9.46 (s, 1H); LC/MS 293.28 [M+H$^+$], 585.44 [2M+H$^+$].

Step 3: Preparation of N-(3-amino-4-methoxyphenethyl)-2,2,2-trifluoroacetamide 2,2,2-trifluoro-N-(4-methoxy-3-nitrophenethyl)acetamide (100 mg, 0.34 mmol) prepared in step 2 was dissolved in methanol (2 ml), to which 10 weight % Pd/C (10 mg) was added. The mixture was stirred for 4 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/1) to give the target compound N-(3-amino-4-methoxyphenethyl)-2,2,2-trifluoroacetamide as a white solid (78 mg, yield: 88%).

$^1$H-NMR (300 MHz, CDCl$_3$) δ 6.73 (d, J=7.5 Hz, 1H), 6.51-6.53 (m, 2H), 6.34 (br, 1H), 3.84 (s, 3H), 3.48-3.57 (m, 4H), 2.71-2.76 (m, 2H); LC/MS 262.8 [M+H$^+$], 5.25.0 [2M+H$^+$].

Preparative Example 5: Preparation of 2-methoxy-5-(1-(piperidine-1-ylmethyl)cyclopentyl)aniline

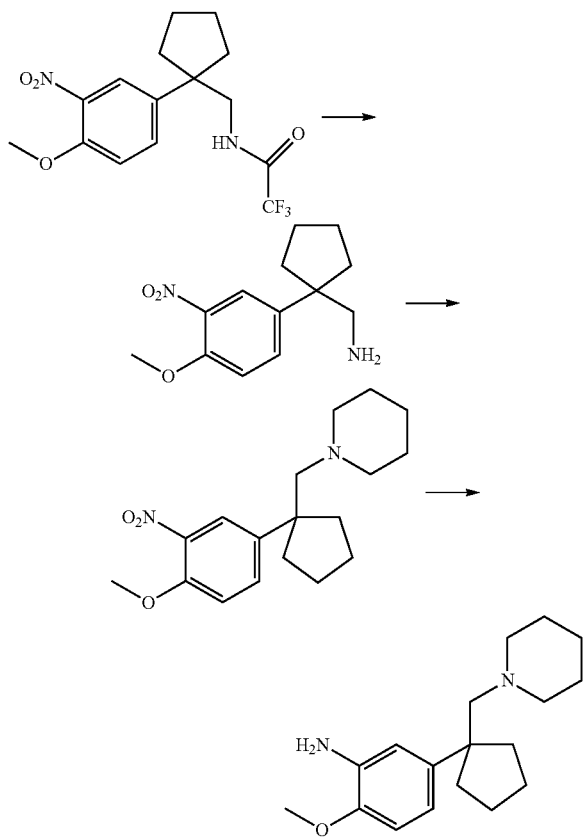

Step 1: Preparation of (1-(4-methoxy-3-nitrophenyl)cyclopentyl)methaneamine 2,2,2-trifluoro-N-((1-(4-methoxy-3-nitrophenyl)cyclopentyl)methyl)acetamide (600 mg, 1.74 mmol) was dissolved in ethanol (5 mL), to which potassium carbonate (2.39 g, 17.36 mmol) aqueous solution (2.5 mL) was added. The reaction mixture was stirred at 100° C. for 6 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/chloroform) to give the target compound (1-(4-methoxy-3-nitrophenyl)cyclopentyl)methaneamine as a white solid (350 mg, 1.398 mmol, yield: 81%).

$^1$H-NMR (300 MHz, CDCl$_3$) δ 7.76 (d, J=2.4 Hz, 1H), 7.47 (dd, J=2.1 Hz, 8.4 Hz, 1H), 7.05 (d, J=8.7 Hz, 1H), 3.95 (s, 3H), 2.75 (s, 2H), 1.72-1.96 (m, 8H), 1.01 (br, 2H); LC/MS 250.9 [M+H$^+$], 500.9 [2M+H$^+$].

Step 2: Preparation of 1-((1-(4-methoxy-3-nitrophenyl)cyclopentyl)methyl)piperidine (1-(4-methoxy-3-nitrophenyl)cyclopentyl)methaneamine (100 mg, 0.39 mmol) prepared in step 1 was dissolved in acetonitrile (1 mL), to which 1,5-dibromopentane (92 mg, 0.39 mmol) and potassium carbonate (110 mg, 0.79 mmol) were added. The reaction mixture was stirred at 80° C. for 15 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 1-((1-(4-methoxy-3-nitrophenyl)cyclopentyl)methyl)piperidine as a yellow solid (92 mg, 0.289 mmol, yield: 72%).

$^1$H-NMR (300 MHz, CDCl$_3$) δ 7.83 (d, J=2.4 Hz, 1H), 7.49 (dd, J=2.4 Hz, 9.0 Hz, 1H), 6.97 (d, J=9.0 Hz, 1H), 3.94 (s, 3H), 2.28 (s, 2H), 1.99-2.11 (m, 6H), 1.63-1.73 (m, 6H), 1.27-1.37 (m, 6H); LC/MS 318.8 [M+H$^+$].

Step 3: Preparation of 2-methoxy-5-(1-(piperidine-1-ylmethyl)cyclopentyl)aniline 1-((1-(4-methoxy-3-nitrophenyl)cyclopentyl)methyl)piperidine (70 mg, 0.22 mmol) prepared in step 2 was dissolved in methanol (2 ml), to which 10 weight % Pd/C (7 mg) was added. The mixture was stirred for 4 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/1) to give the target compound 2-methoxy-5-(1-(piperidine-1-ylmethyl)cyclopentyl)aniline as a yellow solid (52 mg, 0.180 mmol, yield: 83%).

$^1$H-NMR (300 MHz, CDCl$_3$) δ 6.42-6.72 (m, 3H), 3.82 (s, 3H), 3.65 (br, 2H), 2.29 (s, 2H), 2.10-2.12 (m, 4H), 1.93-1.97 (m, 2H), 1.64-1.77 (m, 6H), 1.27-1.41 (m, 6H); LC/MS 289.2 [M+H$^+$].

Preparative Example 6: Preparation of 2-methoxy-5-(1-(morpholinomethyl)cyclopentyl)aniline

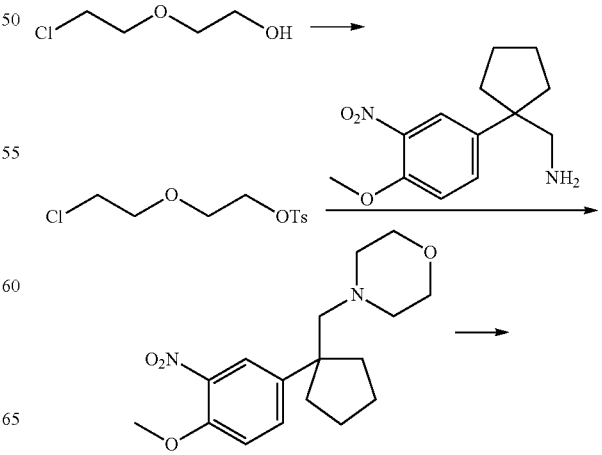

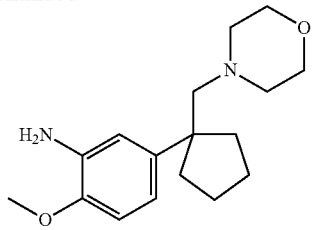

Step 1: Preparation of 2-(2-chloroethoxy)ethyl 4-methylbenzenesulfonate 2-(2-chloroethoxy)ethane-1-ol (2.00 g, 16.1 mmol) was dissolved in dichloromethane (20 mL), to which tosyl chloride (3.70 g, 19.3 mmol) and triethylamine (56 mL, 40.14 mmol) were added at 0° C. The reaction mixture was stirred at room temperature for 2 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2-(2-chloroethoxy)ethyl 4-methylbenzenesulfonate as a colorless solution (4.0 g, 14.349 mmol, yield: 89%).

$^1$H-NMR (300 MHz, CDCl$_3$) δ 7.81 (d, J=8.1 Hz, 2H), 7.35 (d, J=8.7 Hz, 2H), 4.18 (t, J=4.8 Hz, 2H), 3.66-3.73 (m, 4H), 3.55 (t, J=6.09 Hz, 2H), 2.45 (s, 3H); LC/MS 278.9 [M+H$^+$].

Step 2: Preparation of 4-((1-(4-methoxy-3-nitrophenyl)cyclopentyl)methyl)morpholine 2-(2-chloroethoxy)ethyl 4-methylbenzenesulfonate (134 mg, 0.48 mmol) prepared in step 1 and potassium carbonate (165 mg, 1.19 mmol) were added to acetonitrile (1 mL) solution containing (1-(4-methoxy-3-nitrophenyl)cyclopentyl)methaneamine (100 mg, 0.39 mmol) dissolved therein. The reaction mixture was stirred at 80° C. for 15 hours. The reaction mixture was cooled to room temperature and water was added to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 4-((1-(4-methoxy-3-nitrophenyl)cyclopentyl)methyl)morpholine as a yellow solid (98 mg, 0.306 mmol, yield: 77%).

$^1$H-NMR (300 MHz, CDCl$_3$) δ 7.82 (s, 1H), 7.49 (dd, J=1.2 Hz, 8.4 Hz, 1H), 6.99 (d, J=8.7 Hz, 1H), 3.94 (s, 3H), 3.53 (t, J=3.9 Hz, 4H), 2.37 (s, 2H), 2.17 (t, J=3.9 Hz, 4H), 1.99-2.03 (m, 2H), 1.71-1.81 (m, 6H); LC/MS 320.8 [M+H$^+$].

Step 3: Preparation of 2-methoxy-5-(1-(morpholinomethyl)cyclopentyl)aniline 4-((1-(4-methoxy-3-nitrophenyl)cyclopentyl)methyl)morpholine (85 mg, 0.27 mmol) prepared in step 2 was dissolved in methanol (2 ml), to which 10 weight % Pd/C (9 mg) was added. The mixture was stirred for 4 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/1) to give the target compound 2-methoxy-5-(1-(morpholinomethyl)cyclopentyl)aniline as a yellow solid (71 mg, 0.244 mmol, yield: 92%).

$^1$H-NMR (300 MHz, CDCl$_3$) δ 6.66-6.69 (m, 3H), 3.82 (s, 3H), 3.71 (br, 2H), 3.52 (t, J=4.5 Hz, 4H), 2.34 (s, 2H), 2.14 (t, J=4.5 Hz, 4H), 1.93-1.97 (m, 2H), 1.66-1.78 (m, 6H); LC/MS 291.1 [M+H$^+$].

Preparative Example 7: Preparation of 2-methoxy-5-(2-(piperidine-1-yl)ethyl)aniline

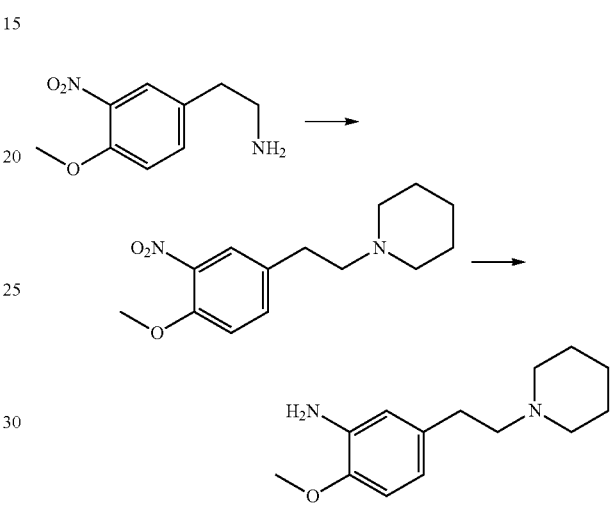

Step 1: Preparation of 1-(4-methoxy-3-nitrophenethyl)piperidine (4-methoxy-3-nitrophenyl)methaneamine (0.10 g, 0.51 mmol) was dissolved in acetonitrile (2 mL), to which 1,5-dibromopentane (140 mg, 0.61 mmol) and potassium carbonate (276 g, 2.00 mmol) were added. The reaction mixture was stirred at 100° C. for 15 hours. The reaction mixture was cooled to room temperature and water was added to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 1-(4-methoxy-3-nitrophenethyl)piperidine as a colorless solution (0.098 g, 0.371 mmol, yield: 73%).

$^1$H-NMR (300 MHz, CDCl$_3$) δ 7.70 (d, J=2.1 Hz, 1H), 7.38 (dd, J=2.1, 8.4 Hz, 1H), 6.99 (d, J=8.4 Hz, 1H), 3.94 (s, 3H), 2.77-2.82 (m, 2H), 2.50-2.56 (m, 2H), 2.45 (br, 4H), 1.58-1.63 (m, 4H), 1.45-1.47 (m, 2H); LC/MS 265.1 [M+H$^+$].

Step 2: Preparation of 2-methoxy-5-(2-(piperidine-1-yl)ethyl)aniline 1-(4-methoxy-3-nitrophenethyl)piperidine (60 mg, 0.25 mmol) prepared in step 1 was dissolved in ethylacetate (2 mL), to which 10 weight % Pd/C (7 mg) was added. The mixture was stirred for 15 hours under a hydrogen gas balloon. The solid generated in the reaction mixture was filtered with celite, which was washed with ethylacetate. The solvent was eliminated by distillation under reduced pressure. Then, purification was performed by silica gel column chromatography (eluent: ethylacetate/hexane, 2/1) to give the target compound 2-methoxy-5-(2-(piperidine-1-yl)ethyl) aniline as a yellow solid (0.043 g, 0.183 mmol, yield: 75%).

$^1$H-NMR (300 MHz, CDCl$_3$) δ 6.69 (d, J=8.1 Hz, 1H), 6.53-6.57 (m, 2H), 3.82 (br, 2H), 3.81 (s, 3H), 2.67-2.72 (m, 2H), 2.48-2.56 (m, 6H), 1.59-1.67 (m, 4H), 1.45-1.47 (m, 2H); LC/MS 235.1 [M+H$^+$].

Preparative Example 8: Preparation of 2-methoxy-5-(2-morpholinoethyl)aniline

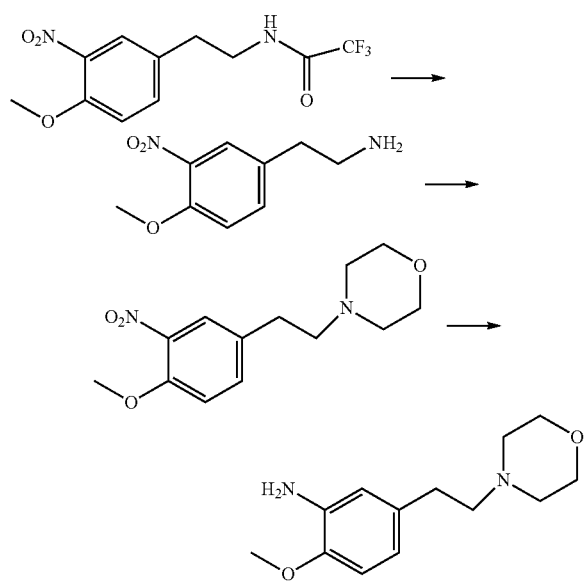

Step 1: Preparation of 2-(4-methoxy-3-nitrophenyl)ethane-1-amine 2,2,2-trifluoro-N-(4-methoxy-3-nitrophenyl)ethane-1-amine (3.0 g, 10.3 mmol) was dissolved in ethanol (15 mL), to which potassium carbonate (5.7 g, 41.1 mmol) aqueous solution (15 mL) was added. The reaction mixture was stirred at 90° C. for 5 hours. The reaction mixture was distilled under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound 2-(4-methoxy-3-nitrophenyl)ethane-1-amine as a yellow solid (1.2 g, 6.12 mmol, yield: 60%).

$^1$H-NMR (300 MHz, CDCl$_3$) δ 7.70 (d, J=2.1 Hz, 1H), 7.39 (dd, J=2.4, 8.7 Hz, 1H), 7.00 (d, J=8.7 Hz, 1H), 3.95 (s, 3H), 2.97 (t, J=6.9 Hz, 2H), 2.75 (t, J=6.9 Hz, 2H), 1.48 (br, 2H); LC/MS 197.2 [M+H$^+$].

Step 2: Preparation of 4-(4-methoxy-3-nitrophenethyl)morpholine 2-(4-methoxy-3-nitrophenyl)ethane-1-amine (0.10 g, 0.51 mmol) prepared in step 1 was dissolved in acetonitrile (2 mL), to which 2-(2-chloroethoxy)ethyl 4-methylbenzenesulfonate (0.17 g, 0.61 mmol) and potassium carbonate (276 g, 2.00 mmol) were added. The reaction mixture was stirred at 100° C. for 15 hours. The reaction mixture was cooled to room temperature and water was added to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 4-(4-methoxy-3-nitrophenethyl)morpholine as a yellow solution (0.92 g, 0.345 mmol, yield: 68%).

$^1$H-NMR (300 MHz, CDCl$_3$) δ 7.71 (d, J=2.1 Hz, 1H), 7.39 (dd, J=2.4, 8.7 Hz, 1H), 7.00 (d, J=8.4 Hz, 1H), 3.94 (s, 3H), 3.73 (t, J=4.8 Hz, 4H), 2.76-2.82 (m, 2H), 2.49-2.61 (m, 6H); LC/MS 266.8 [M+H$^+$].

Step 3: Preparation of 2-methoxy-5-(2-morpholinoethyl)aniline 4-(4-methoxy-3-nitrophenethyl)morpholine (0.065 g, 0.244 mmol) was dissolved in ethylacetate (2 mL), to which 10 weight % Pd/C (7 mg) was added. The mixture was stirred for 15 hours under a hydrogen gas balloon. The solid generated in the reaction mixture was filtered with celite, which was washed with ethylacetate. The solvent was eliminated by distillation under reduced pressure. Then, purification was performed by silica gel column chromatography (eluent: ethylacetate/hexane, 2/1) to give the target compound 2-methoxy-5-(2-morpholinoethyl)aniline as a yellow solid (0.042 g, 0.178 mmol, yield: 73%).

$^1$H-NMR (300 MHz, CDCl$_3$) δ 7.70 (d, J=7.8 Hz, 1H), 6.53-6.57 (m, 2H), 3.82 (s, 3H), 3.78 (br, 2H), 3.75 (t, 4H), 2.64-2.71 (m, 2H), 2.53-2.59 (m, 6H); LC/MS 237.1 [M+H$^+$].

Preparative Example 9: Preparation of N-(3-amino-4-methoxybenzyl)-2,2,2-trifluoroacetamide

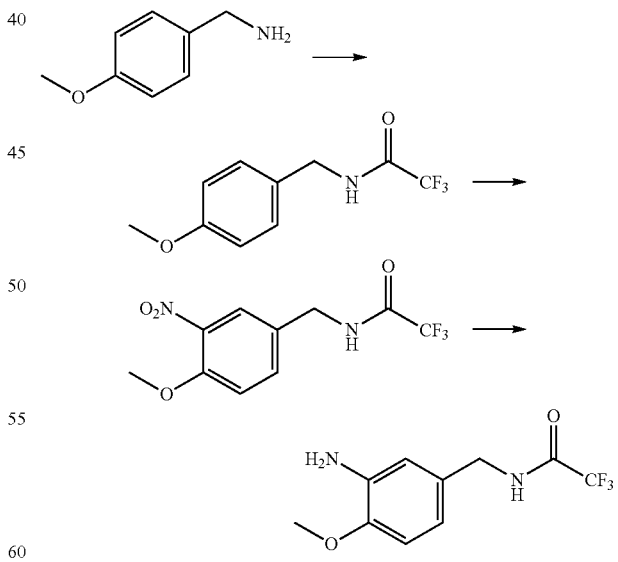

Step 1: Preparation of 2,2,2-trifluoro-N-(4-methoxybenzyl)acetamide 4-methoxybenzylamine (2.0 g, 14.58 mmol) was dissolved in dichloromethane (20 mL), to which anhydrous trifluoroacetic acid (3.7 g, 17.49 mmol) and triethylamine (7.1 mL, 51.29 mmol) were added at 0° C. The reaction mixture was stirred at room temperature for 2 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-(4-methoxybenzyl)acetamide as a white solid (3.0 g, 12.87 mmol, yield: 88%).

$^1$H-NMR (300 MHz, CDCl$_3$) δ 7.22 (d, J=8.4 Hz, 2H), 6.90 (d, J=8.4 Hz, 2H), 6.53 (br, 1H), 4.46 (d, J=5.7 Hz, 2H), 3.81 (s, 3H)

Step 2: Preparation of 2,2,2-trifluoro-N-(4-methoxy-3-nitrobenzyl)acetamide 2,2,2-trifluoro-N-(4-methoxybenzyl)acetamide (2.5 g, 10.72 mmol) prepared in step 1 was dissolved in trifluoroacetic acid (20 mL), to which trifluoroacetic acid (5 mL) solution containing concentrated nitric acid (1.23 g, 11.79 mmol) dissolved therein was added at 0° C. The reaction mixture was stirred at room temperature for 2 hours. The reaction mixture was distilled under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-(4-methoxy-3-nitrobenzyl)acetamide as a yellow solid (1.8 g, 6.47 mmol, yield: 60%).

$^1$H-NMR (300 MHz, CDCl$_3$) δ 7.79 (d, J=2.1 Hz, 1H), 7.53 (dd, J=8.7, 2.1 Hz, 1H), 7.09 (d, J=8.1 Hz, 1H), 6.76 (br, 1H), 4.52 (d, J=6.0 Hz, 2H), 3.97 (s, 3H); LC/MS 279.1 [M+H$^+$].

Step 3: Preparation of N-(3-amino-4-methoxybenzyl)-2,2,2-trifluoroacetamide 2,2,2-trifluoro-N-(4-methoxy-3-nitrobenzyl)acetamide (1.0 g, 3.59 mmol) prepared in step 2 was dissolved in ethylacetate (10 mL), to which 10 weight % Pd/C (0.1 g) was added. The mixture was stirred for 2 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/1) to give the target compound N-(3-amino-4-methoxybenzyl)-2,2,2-trifluoroacetamide as a white solid (0.81 g, 3.26 mmol, yield: 89%).

$^1$H-NMR (300 MHz, CDCl$_3$) δ 6.74 (d, J=8.71 Hz, 1H), 6.63-6.65 (m, 2H), 4.39 (d, J=5.4 Hz, 2H), 3.86 (s, 3H) 3.26 (br, 2H); LC/MS 249.1 [M+H$^+$].

Preparative Example 10: Preparation of 2,5-dichloro-N-(4-fluoro-2-(isopropylsulfonyl)phenyl)pyrimidine-4-amine

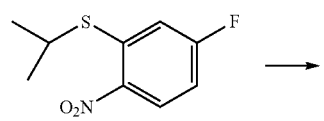

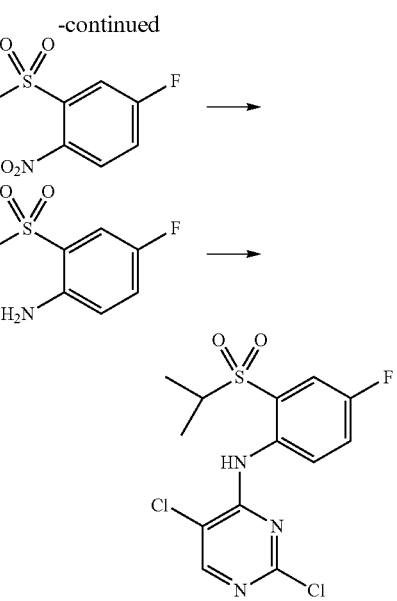

Step 1: Preparation of (5-fluoro-2-nitrophenyl)(isopropyl)sulfane 2,4-difluoronitrobenzene (2.00 g, 12.57 mmol) was dissolved in dimethylformamide (150 mL), to which 2-propanethiol (0.86 g, 11.31 mmol) and potassium carbonate (4.34 g, 31.43 mmol) were added. The reaction mixture was stirred at room temperature for 15 hours. Sodium hydroxide was added thereto to terminate the reaction, followed by extraction twice with ethylacetate/hexane (1/4). The extracted organic layer was washed with water and brine, dried over sodium sulfate, filtered, and concentrated under reduced pressure. Then, purification was performed by MPLC (medium pressure liquid chromatography) to give the target compound (5-fluoro-2-nitrophenyl) (isopropyl)sulfane (1.70 g, 7.90 mmol, yield: 63%, about 10% of minor included).

$^1$H-NMR (300 MHz, CDCl$_3$) δ 8.27-8.22 (m, 1H), 7.15-7.08 (m, 1H), 6.95-6.89 (m, 1H), 3.57-3.46 (m, 1H), 1.44 (d, J=6.0 Hz, 6H); EI/Ms 215 [H$^+$].

Step 2: Preparation of 4-fluoro-2-(isopropylsulfonyl)-1-nitrobenzene (5-fluoro-2-nitrophenyl) (isopropyl)sulfane (1.70 g, 6.16 mmol) prepared in step 1 was dissolved in dichloromethane (60 mL), to which m-CPBA (m-chloroperoxybenzoic acid, 70%) (3.49 g, 14.16 mmol) was added at 0° C. The reaction mixture was stirred at room temperature for 16 hours. Upon completion of the reaction, a new spot was formed under (5-fluoro-2-nitrophenyl) (isopropyl)sulfane, which was confirmed by TLC. The resulting solid was filtered and washed three times with sodium bicarbonate (aq.). The solid was washed with water and brine. The organic layer was dried over sodium sulfate and concentrated under reduced pressure. Then, purification was performed by MPLC to give the target compound 4-fluoro-2-(isopropylsulfonyl)-1-nitrobenzene (1.20 g, 4.85 mmol, yield: 90%).

$^1$H-NMR (300 MHz, CDCl$_3$) δ 8.26-8.21 (m, 1H), 7.88-7.83 (m, 2H), 3.32-3.23 (m, 1H), 1.36 (d, J=6.0 Hz, 6H).; EI/Ms 247 [H+].

Step 3: Preparation of 4-fluoro-2-(isopropylsulfonyl) aniline 4-fluoro-2-(isopropylsulfonyl)-1-nitrobenzene (3.00 g, 12.13 mmol) prepared in step 2 was dissolved in ethanol, to which 10 weight % Pd/C (0.30 g) was added. The mixture was stirred at room temperature for 15 hours while purging hydrogen gas. Pd/C was filtered and concentrated under reduced pressure. Then, purification was performed by MPLC to give the target compound 4-fluoro-2-(isopropylsulfonyl) aniline (1.00 g, 4.60 mmol, yield: 57%).

$^1$H-NMR (300 MHz, CDCl$_3$) δ 9.83 (br, s, 1H), 8.62-8.57 (m, 1H), 7.66-7.63 (m, 1H), 7.48 (m, 1H), 3.28-3.18 (m, 1H), 1.34 (d, J=6.9 Hz, 6H); EI/Ms 217[H+].

Step 4: Preparation of 2,5-dichloro-N-(4-fluoro-2-(isopropylsulfonyl)phenyl)pyrimidine-4-amine 2,4,5-trichloropyrimidine (1.21 g, 6.58 mmol) was dissolved in DMSO (dimethylformamide, 80 mL), to which sodium hydride (0.29 g, 7.23 mmol) was added at 0° C. And 4-fluoro-2-(isopropylsulfonyl) aniline (1.00 g, 4.60 mmol) prepared in step 3 was added thereto, which was stirred at room temperature for 15 hours. Water was added thereto to terminate the reaction, followed by neutralization with 1 N HCl. Upon completion of the reaction, a new spot was formed under 2,4,5-trichloropyrimidine, which was confirmed by TLC. The reactant was extracted with ethylacetate. The ethylacetate layer was washed with water and brine, dried over sodium sulfate, and concentrated under reduced pressure. Then, purification was performed by MPLC to give the target compound 2,5-dichloro-N-(4-fluoro-2-(isopropylsulfonyl)phenyl)pyrimidine-4-amine (0.40 g, 1.10 mmol, yield: 17%).

$^1$H-NMR (300 MHz, CDCl$_3$) δ 9.83 (br, s, 1H), 8.62-8.57 (m, 1H), 7.66-7.63 (m, 1H), 7.48 (m, 1H), 3.28-3.18 (m, 1H), 1.34 (d, J=6.9 Hz, 6H); EI/MS 363 [H+].

Preparative Example 11: Preparation of 2,5-dichloro-N-(5-fluoro-2-(isopropylsulfonyl)phenyl)pyrimidine-4-amine

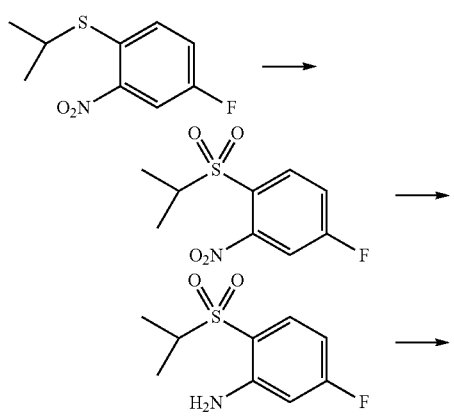

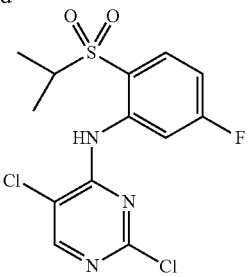

Step 1: Preparation of (4-fluoro-2-nitrophenyl)(isopropyl)sulfane 2,5-difluoronitrobenzene (5.00 g, 31.43 mmol) was dissolved in dimethylformamide, to which potassium carbonate (8.69 g, 62.86 mmol) and 2-propanethiol (0.30 mL, 5.66 mmol) were added, followed by reaction at room temperature for 15 hours. Sodium hydroxide was added thereto to terminate the reaction, followed by extraction twice with ethylacetate/hexane (1/4). The extracted organic layer was washed with water and brine, dried over sodium sulfate, filtered, and concentrated under reduced pressure to give the target compound (4-fluoro-2-nitrophenyl) (isopropyl)sulfane (6.00 g, 27.88 mmol, yield: 89%).

$^1$H-NMR (300 MHz, CDCl$_3$) δ 7.83-7.79 (m, 1H), 7.51-7.46 (m, 1H), 7.39-7.27 (m, 1H), 3.57-3.48 (m, 1H) 1.38 (d, J=6.9 Hz, 6H); EI/Ms 215 [H+].

Step 2: Preparation of 4-fluoro-2-(isopropylsulfonyl)-1-nitrobenzene (4-fluoro-2-nitrophenyl)(isopropyl)sulfane (6.00 g, 27.88 mmol) prepared in step 1 was dissolved in dichloromethane (100 mL), to which m-CPBA (70%) (10.58 g, 61.32 mmol) was added at 0° C. The reaction mixture was stirred at room temperature overnight. Upon completion of the reaction, a new spot was formed under the starting material, which was confirmed by TLC. The resulting solid was filtered and washed with sodium bicarbonate (aq.). The solid was washed with water and brine. The organic layer was dried over magnesium sulfate and concentrated under reduced pressure. Then, purification was performed by MPLC to give the target compound 4-fluoro-2-(isopropylsulfonyl)-1-nitrobenzene (3.40 g, 13.75 mmol, yield: 49%).

$^1$H-NMR (300 MHz, CDCl$_3$) δ 8.16-8.12 (m, 1H), 7.56-7.53 (m, 1H), 7.49-7.43 (m, 1H), 4.00-3.91 (m, 1H), 1.42 (d, J=6.9 Hz, 6H); EI/Ms 248 [H$^+$].

Step 3: Preparation of 2-fluoro-6-(isopropylsulfonyl)aniline 4-fluoro-2-(isopropylsulfonyl)-1-nitrobenzene (3.40 g, 13.75 mmol) prepared in step 2 was dissolved in methanol (100 ml), to which zinc (4.50 g, 68.76 mmol), ammonium formate (4.15 g, 68.76 mmol), and 10 weight % Pd/C (0.30 g) were added. The mixture was stirred at room temperature for 2 hours. Upon completion of the reaction, a new spot was formed under the starting material, which was confirmed by TLC. Pd/C was filtered and the reaction mixture was concentrated under reduced pressure. Then, purification was performed by MPLC to give the target compound 2-fluoro-6-(isopropylsulfonyl)aniline (2.10 g, 9.67 mmol, yield: 76%).

¹H-NMR (300 MHz, CDCl₃) δ 7.46-7.43 (m, 1H), 7.23-7.17 (m, 1H), 6.77-6.70 (m, 1H), 5.17 (br, s, 2H), 3.37-3.28 (m, 1H), 1.33 (d, J=6.9 Hz, 6H); EI/MS 217 [H⁺].

Step 4: Preparation of 2,5-dichloro-N-(5-fluoro-2-(isopropylsulfonyl)phenyl)pyrimidine-4-amine 2,4,5-trichloropyrimidine (2.05 g, 11.18 mmol) was dissolved in dimethylformamide (100 mL), to which sodium hydride (60%, 0.54 g, 7.82 mmol) was added at 0° C. 2-fluoro-6-(isopropylsulfonyl)aniline (1.70 g, 22.36 mmol) prepared in step 3 was added thereto, which was stirred at room temperature for 14 hours. Water was added thereto to terminate the reaction, followed by neutralization with 1 N HCl. Upon completion of the reaction, a new spot was formed under the starting material, which was confirmed by TLC. The reaction mixture was extracted with ethylacetate. The ethylacetate layer was washed with water and brine, dried over sodium sulfate, and concentrated under reduced pressure. Then, purification was performed by MPLC to give the target compound 2,5-dichloro-N-(5-fluoro-2-(isopropylsulfonyl)phenyl)pyrimidine-4-amine (1.10 g, 3.02 mmol, yield: 27%).

¹H-NMR (300 MHz, CDCl₃) δ 8.56 (s, 1H), 8.29 (s, 1H), 7.80-7.78 (m, 1H), 7.55-7.47 (m, 2H), 3.11-3.01 (m, 1H), 1.27 (d, J=6.9 Hz, 6H); LC/MS 365 [M+H⁺].

Preparative Example 12: Preparation of 2,5-dichloro-N-(2-fluoro-6-(isopropylsulfonyl)phenyl)pyrimidine-4-amine

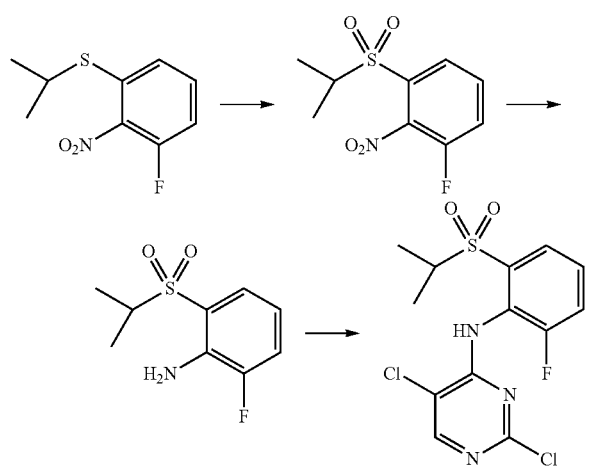

Step 1: Preparation of (5-fluoro-2-nitrophenyl)(isopropyl)sulfane 2,6-difluoronitrobenzene (5.00 g, 31.43 mmol) was dissolved in dimethylformamide, to which potassium carbonate (8.69 g, 62.86 mmol) and 2-propanethiol (0.30 mL, 5.66 mmol) were added, followed by reaction at 50° C. for 15 hours. Upon completion of the reaction, the reaction mixture was cooled to room temperature. Sodium hydroxide (aq.) was added thereto to terminate the reaction, followed by extraction twice with ethylacetate/hexane (1:4). The extracted organic layer was washed 3 times with water and brine, dried over sodium sulfate, and concentrated under reduced pressure to give the target compound (5-fluoro-2-nitrophenyl)(isopropyl)sulfane (5.20 g, 27.41 mmol, yield: 77%). Without any additional purification process, the reaction of step 2 was carried out.

¹H-NMR (300 MHz, CDCl₃) δ 7.46-7.39 (m, 1H), 7.34-7.31 (m, 1H), 7.15-7.08 (m, 1H), 3.52-3.43 (m, 1H), 1.32 (d, J=6.6 Hz, 6H); EI/MS 215 [H⁺].

Step 2: Preparation of 1-fluoro-3-(isopropylsulfonyl)-2-nitrobenzene (5-fluoro-2-nitrophenyl)(isopropyl)sulfane (5.20 g, 24.15 mmol) prepared in step 1 was dissolved in dichloromethane (100 mL), to which m-CPBA (70%) (12.51 g, 50.73 mmol) was added at 0° C. The reaction mixture was stirred at room temperature overnight. Upon completion of the reaction, a new spot was formed under the starting material, which was confirmed by TLC. The resulting solid was filtered and washed twice with sodium bicarbonate (aq.). The solid was washed with water and brine. The organic layer was dried over sodium sulfate and concentrated under reduced pressure. Then, purification was performed by MPLC to give the target compound 1-fluoro-3-(isopropylsulfonyl)-2-nitrobenzene (3.20 g, 12.94 mmol, yield: 54%).

¹H-NMR (300 MHz, CDCl₃) δ 8.16-8.12 (m, 1H), 7.56-7.53 (m, 1H), 7.49-7.43 (m, 1H), 4.00-3.91 (m, 1H), 1.42 (d, J=6.9 Hz, 6H); EI/Ms 248 [H⁺].

Step 3: Preparation of 2-fluoro-6-(isopropylsulfonyl)aniline 1-fluoro-3-(isopropylsulfonyl)-2-nitrobenzene (3.00 g, 12.13 mmol) prepared in step 2 was dissolved in ethylacetate (50 mL), to which 10 weight % Pd/C (0.30 g) was added. The mixture was stirred at room temperature for 16 hours while purging hydrogen gas. Pd/C was filtered and the reaction mixture was concentrated under reduced pressure. Then, purification was performed by MPLC to give the target compound 2-fluoro-6-(isopropylsulfonyl)aniline (2.50 g, 11.97 mmol, yield: 95%).

¹H-NMR (300 MHz, CDCl₃) δ 7.43-7.41 (m, 1H), 7.21-7.15 (m, 1H), 6.72-6.71 (m, 1H), 5.17 (br, s, 2H), 3.33-3.29 (m, 1H), 1.31 (d, J=6.6 Hz, 6H); EI/Ms 217 [H⁺].

Step 4: Preparation of 2,5-dichloro-N-(2-fluoro-6-(isopropylsulfonyl)phenyl)pyrimidine-4-amine 2,4,5-trichloropyrimidine (0.30 g, 1.64 mmol) was dissolved in dimethylformamide (40 mL), to which sodium hydride (60%, 0.13 g, 3.29 mmol) was added at 0° C. 2-fluoro-6-(isopropylsulfonyl)aniline (0.25 g, 1.15 mmol) prepared in step 3 was added thereto, followed by stirring at room temperature for 14 hours. Upon completion of the reaction, a new spot was formed under 2,4,5-trichloropyrimidine, which was confirmed by TLC. Water was added thereto to terminate the reaction, followed by neutralization with 1 N HCl. The reaction mixture was extracted with ethylacetate. The ethylacetate layer was washed with water and brine, dried over sodium sulfate, and concentrated under reduced pressure. Then, purification was performed by MPLC to give the target compound 2,5-dichloro-N-(2-fluoro-6-(isopropylsulfonyl)phenyl)pyrimidine-4-amine (0.20 g, 0.55 mmol, yield: 33%).

¹H-NMR (300 MHz, CDCl₃) δ 8.55 (s, 1H), 8.29 (s, 1H), 7.80-7.78 (m, 1H), 7.52-7.47 (m, 2H), 3.08-3.03 (m, 1H), 1.27 (d, J=6.9 Hz, 6H); EI/MS 217 [H⁺].

Preparative Example 13: Preparation of N-(2-(3-amino-4-methoxyphenyl)-2-methylpropyl)-2,2,2-trifluoroacetamide

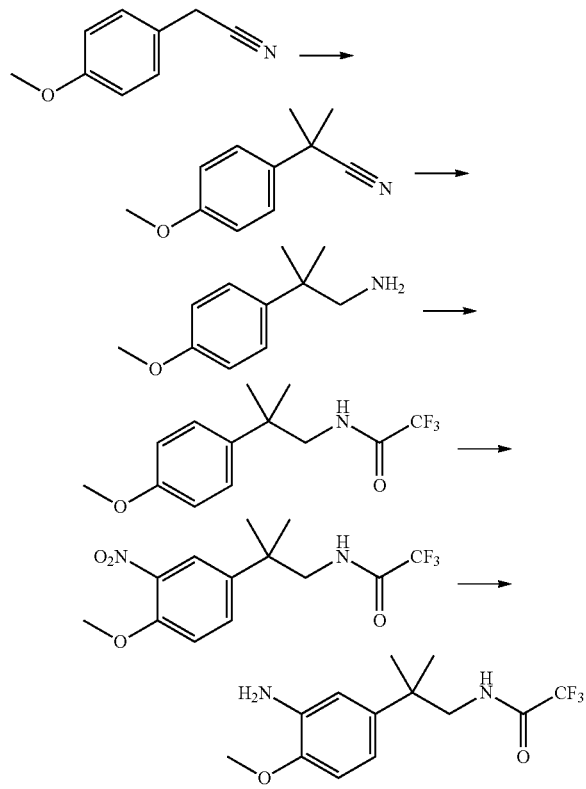

Step 1: Preparation of 2-(4-methoxyphenyl)-2-methylpropanenitrile

Sodium-tert-butoxide (13.06 g, 135.89 mmol) was added to dimethylformamide (30 mL) and tetrahydrofuran (30 mL), to which 2-(4-methoxyphenyl)acetonitrile (5.00 g, 33.97 mmol) was added at 5° C. Methyliodide (8.44 mL, 135.89 mmol) was added thereto at 5° C., followed by stirring at 10° C. for 4 hours. The reaction mixture was cooled in an ice bath and added with 2 N HCl. Upon completion of the reaction, a new spot was formed under the starting material, which was confirmed by TLC. The reaction mixture was extracted with ethylacetate. The ethylacetate layer was washed with water and brine, dried over sodium sulfate, and concentrated under reduced pressure. Then, purification was performed by MPLC to give the target compound 2-(4-methoxyphenyl)-2-methylpropanenitrile (4.00 g, 22.83 mmol, yield: 67%).

$^{1}$H-NMR (300 MHz, CDCl$_3$) δ 7.40 (d, J=6.0 Hz, 2H), 6.92 (d, J=6.0 Hz, 2H), 3.82 (s, 3H), 1.70 (s, 6H); EI/MS 161 [M+].

In step 1, 2-(4-methoxyphenyl)propanenitrile was obtained in addition to the compound 2-(4-methoxyphenyl)-2-methylpropanenitrile.

$^{1}$H-NMR (300 MHz, CDCl$_3$) δ 7.96-7.93 (m, 1H), 7.40-7.37 (m, 1H), 6.92-6.88 (m, 2H), 3.85-3.82 (m, 3H), 1.71 (s, 3H); EI/MS 175 [M+].

Step 2: Preparation of 2-(4-methoxyphenyl)-2-methylpropane-1-amine 2-(4-methoxyphenyl)-2-methylpropanenitrile (2.00 g, 11.41 mmol) prepared in step 1 was dissolved in diethylether (100 mL), and the temperature was lowered to 0° C. Lithium aluminum hydride (0.52 g, 13.70 mmol) was added thereto, followed by stirring at room temperature for 4 hours. Upon completion of the reaction, a new spot was formed under the starting material, which was confirmed by TLC. The reaction mixture was cooled in an ice bath. 2 N sodium hydroxide was added to terminate the reaction, followed by separating the diethylether layer. The water layer was extracted twice with ethylacetate, followed by washing with water and brine. The organic layer was dried over sodium sulfate and concentrated under reduced pressure. Then, purification was performed by MPLC to give the target compound 2-(4-methoxyphenyl)-2-methylpropane-1-amine (1.75 g, 9.76 mmol, yield: 86%).

$^{1}$H-NMR (300 MHz, CDCl$_3$) δ 7.27 (d, J=6.0 Hz, 2H), 6.89 (d, J=6.0 Hz, 2H), 3.80 (s, 3H), 2.76 (s, 2H), 1.28 (s, 6H); EI/MS 179 [M+].

Step 3: Preparation of 2-(4-methoxyphenyl)-2-methylpropane-1-amine 2-(4-methoxyphenyl)-2-methylpropane-1-amine (1.70 g, 9.48 mmol) prepared in step 2 was dissolved in dichloromethane (100 mL), to which triethanolamine (3.96 mL, 28.44 mmol) was added at 0° C. Lithium aluminum hydride (0.52 g, 13.70 mmol) was added thereto, followed by stirring at room temperature for 4 hours. Upon completion of the reaction, a new spot was formed under the starting material, which was confirmed by TLC. The reaction mixture was cooled in an ice bath. 2 N sodium hydroxide was added to terminate the reaction, followed by separating the diethylether layer. The water layer was extracted twice with ethylacetate, followed by washing with water and brine. The organic layer was dried over sodium sulfate and concentrated under reduced pressure. Then, purification was performed by MPLC to give the target compound 2-(4-methoxyphenyl)-2-methylpropane-1-amine (1.90 g, 6.90 mmol, yield: 73%).

$^{1}$H-NMR (300 MHz, CDCl$_3$) δ 7.28 (d, J=8.4 Hz, 2H), 6.92 (d, J=8.7 Hz, 2H), 5.86 (br, s, 1H), 3.82 (s, 3H), 3.51 (d, J=6.0 Hz, 2H), 1.35 (s, 6H); EI/MS 275 [M+].

Step 4: Preparation of 2,2,2-trifluoro-N-(2-(4-methoxy-3-nitrophenyl)-2-methylpropyl)acetamide 2-(4-methoxyphenyl)-2-methylpropane-1-amine (1.90 g, 6.90 mmol) prepared in step 3 was dissolved in acetonitrile (50 mL), to which trifluoroacetic acid (3.84 mL, 27.61 mmol) was added. The temperature was lowered to −10° C. Potassium nitrate (0.59 g, 6.90 mmol) was slowly added thereto, followed by stirring. Upon completion of the reaction, a new spot was formed under the starting material, which was confirmed by TLC. Water was added thereto to terminate the reaction, followed by neutralization with potassium carbonate. The water layer was extracted twice with ethylacetate. The ethylacetate layer was washed with water and brine, dried over sodium sulfate, and concentrated under reduced pressure. Then, purification was performed by MPLC to give the target compound 2,2,2-trifluoro-N-(2-(4-methoxy-3-nitrophenyl)-2-methylpropyl)acetamide (2.00 g, 6.24 mmol, yield: 91%).

$^1$H-NMR (300 MHz, CDCl$_3$) δ 7.84 (d, J=2.4 Hz, 1H), 7.56 (dd, J=6.0, 2.4 Hz, 1H), 7.11 (d, J=6.0 Hz, 1H), 6.03 (br, s, 1H), 3.97 (s, 3H), 3.55-3.53 (m, 2H), 1.39 (s, 6H); LC/MS 321 [M+H$^+$].

Step 5: Preparation of N-(2-(3-amino-4-methoxyphenyl)-2-methylpropyl)-2,2,2-trifluoroacetamide N-(2-(3-amino-4-methoxyphenyl)-2-methylpropyl)-2,2,2-trifluoroacetamide (2.00 g, 6.24 mmol) was dissolved in ethanol (100 mL), to which 10 weight % Pd/C (0.20 g) was added. The mixture was stirred at room temperature overnight while purging hydrogen gas. Upon completion of the reaction, a new spot was formed under the starting material, which was confirmed by TLC. 10 weight was filtered and the reaction mixture was concentrated under reduced pressure and dried to give the target compound N-(2-(3-amino-4-methoxyphenyl)-2-methylpropyl)-2,2,2-trifluoroacetamide (1.25 g, 4.31 mmol, yield: 69%).
$^1$H-NMR (300 MHz, CDCl$_3$) δ 6.77-6.75 (m, 1H), 6.70-6.64 (m, 2H), 5.91 (br, s, 1H), 3.86-3.84 (m, 5H), 3.48-3.46 (m, 2H), 1.26 (s, 6H); LC/MS 290 [M+H$^+$].

Preparative Example 13: Preparation of N-(3-(3-amino-4-methoxyphenyl)propyl)-2,2,2-trifluoroacetamide trifluoroethanone

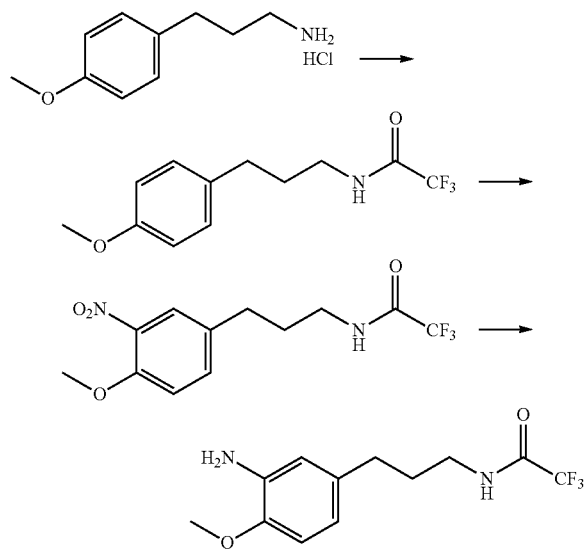

Step 1: Preparation of 2,2,2-trifluoro-N-(3-(4-methoxyphenyl)propyl)acetamide 3-(4-methoxyphenyl)propane-1-amine hydrochloride (2.0 g, 9.9 mmol) was dissolved in dichloromethane (20 mL), to which anhydrous trifluoroacetic acid (2.0 g, 11.96 mmol) and triethylamine (4.13 ml, 29.8 mmol) were added at 0° C. The reaction mixture was stirred at room temperature for 2 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-(3-(4-methoxyphenyl)propyl)acetamide as a white solid (2.3 g, 8.80 mmol, yield: 89%).
$^1$H-NMR (300 MHz, CDCl$_3$) δ 7.09 (d, J=8.1 Hz, 2H), 6.84 (d, J=8.4 Hz, 2H), 6.25 (br, 1H), 3.79 (s, 3H), 3.8 (q, J=6.6 Hz, 2H), 2.63 (t, J=7.2 Hz, 2H), 1.89 (pent, J=7.2 Hz, 2H); LC/MS 262.1 [M+H+].

Step 2: Preparation of 2,2,2-trifluoro-N-(3-(4-methoxy-3-nitrophenyl)propyl)acetamide 2,2,2-trifluoro-N-(3-(4-methoxyphenyl)propyl)acetamide (2.0 g, 7.66 mmol) prepared in step 1 was dissolved in trifluoroacetic acid (20 mL), to which trifluoroacetic acid (10 mL) solution containing concentrated nitric acid (0.88 g, 8.42 mmol) dissolved therein was added at 0° C. The reaction mixture was stirred at room temperature for 2 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 2,2,2-trifluoro-N-(3-(4-methoxy-3-nitrophenyl)propyl)acetamide as a yellow solid (2.02 g, 6.59 mmol, yield: 86%)
$^1$H-NMR (300 MHz, CDCl$_3$) δ 7.68 (d, J=2.1 Hz, 1H), 7.37 (dd, J=2.4, 8.7 Hz, 1H), 7.03 (d, J=8.7 Hz, 1H), 6.55 (br, 1H), 3.94 (s, 3H), 3.8 (q, J=6.9 Hz, 2H), 2.63 (t, J=7.5 Hz, 2H), 1.89 (pent, J=7.5 Hz, 2H); LC/MS 307.2 [M+H$^+$].

Step 3: Preparation of N-(3-(3-amino-4-methoxyphenyl)propyl)-2,2,2-trifluoroacetamide trifluoroethanone 2,2,2-trifluoro-N-(3-(4-methoxy-3-nitrophenyl)propyl)acetamide (2.0 g, 6.53 mmol) prepared in step 2 was dissolved in methanol (20 mL), to which 10 weight % Pd/C (0.20 g, 10%) was added. The mixture was stirred at room temperature for 4 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/1) to give the target compound N-(3-(3-amino-4-methoxyphenyl)propyl)-2,2,2-trifluoroacetamide trifluoroethanone as a yellow solid (1.6 g, 5.79 mmol, yield: 89%).
$^1$H-NMR (300 MHz, CDCl$_3$) δ 6.70 (d, J=8.1 Hz, 1H), 6.50-6.53 (m, 2H), 6.34 (br, 1H), 3.82 (s, 3H), 3.78 (br, 2H), 3.35 (q, J=7.2 Hz, 2H), 1.86 (pent, J=6.9 Hz, 2H); LC/MS 277.1 [M+H$^+$], 553.3 [2M+H$^+$].

Preparative Example 15: Preparation of 2-(3-amino-4-methoxyphenyl) acetonitrile

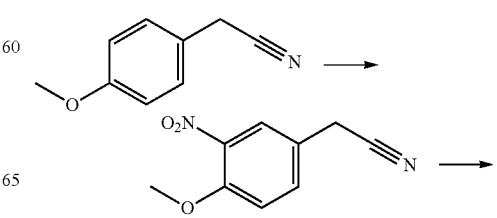

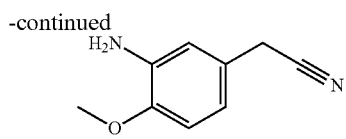

Step 1: Preparation of 2-(4-methoxy-3-nitrophenyl)acetonitrile 2-(4-methoxyphenyl)acetonitrile (0.20 g, 1.36 mmol) was dissolved in acetonitrile (10 mL), to which trifluoroacetic acid (0.76 mL, 5.44 mmol) was added. The temperature thereof was lowered to −10° C. Potassium nitrate (0.12 g, 1.360.61 mmol) was slowly added thereto, followed by stirring. Upon completion of the reaction, a new spot was formed under the starting material, which was confirmed by TLC. Water was added thereto to terminate the reaction, followed by neutralization with potassium carbonate. The water layer was extracted twice with ethylacetate. The ethylacetate layer was washed with water and brine, dried over sodium sulfate, and concentrated under reduced pressure. Then, purification was performed by MPLC to give the target compound 2-(4-methoxy-3-nitrophenyl)acetonitrile (1.80 g, 9.37 mmol, yield: 69%).

$^1$H-NMR (300 MHz, CDCl$_3$) δ 7.83 (s, 1H), 7.57 (dd, J=8.7, 2.4 Hz, 1H), 7.15 (d, J=8.7 Hz, 1H), 3.99 (s, 3H), 3.77 (s, 2H); LC/MS 192 [M+H$^+$].

Step 2: Preparation of 2-(3-amino-4-methoxyphenyl)acetonitrile 2-(4-methoxy-3-nitrophenyl)acetonitrile (1.80 g, 9.37 mmol) prepared in step 1 was dissolved in ethanol (10 mL), to which 10 weight % Pd/C (0.94 g, 0.94 mmol) was added. The mixture was stirred while purging hydrogen gas. Upon completion of the reaction, a new spot was formed under the starting material, which was confirmed by TLC. Water was added thereto to terminate the reaction, followed by neutralization with potassium carbonate. The water layer was extracted twice with ethylacetate. The ethylacetate layer was washed with water and brine, dried over sodium sulfate, and concentrated under reduced pressure. Then, purification was performed by MPLC to give the target compound 2-(3-amino-4-methoxyphenyl)acetonitrile (1.30 g, 8.32 mmol, yield: 89%).

$^1$H-NMR (300 MHz, CDCl$_3$) δ 6.75-6.73 (m, 1H), 6.65-6.62 (m, 2H), 3.84 (s, 3H), 3.61 (s, 2H); LC/MS 163 [M+H$^+$].

Preparative Example 16: Preparation of 2-(3-amino-4-methoxyphenyl) acetic acid

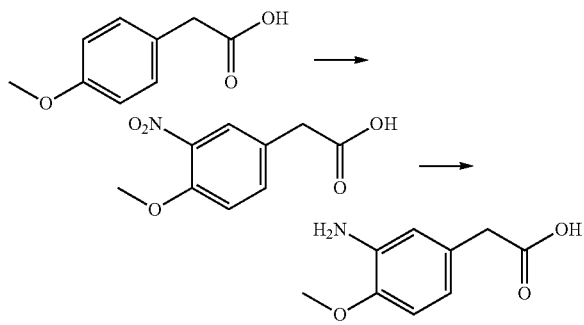

Step 1: Preparation of 2-(4-methoxy-3-nitrophenyl)acetic acid 4-methoxyphenylacetic acid (5.00 g, 30.09 mmol) was dissolved in acetonitrile (450 mL), to which trifluoroacetic acid (16.73 mL, 120.36 mmol) was added. The temperature thereof was lowered to −10° C. Potassium nitrate (2.56 g, 30.09 mmol) was slowly added thereto, followed by stirring. Upon completion of the reaction, a new spot was formed under the starting material, which was confirmed by TLC. Water was added thereto to terminate the reaction, followed by neutralization with potassium carbonate. The water layer was extracted twice with ethylacetate. The ethylacetate layer was washed with water and brine, dried over sodium sulfate, and concentrated under reduced pressure. Then, recrystallization was performed by using MC/Hex (methylchloride/hexane) to give the target compound 2-(4-methoxy-3-nitrophenyl)acetic acid (4.30 g, 20.36 mmol, yield: 68%).

$^1$H-NMR (300 MHz, CDCl$_3$) δ 7.81 (s, 1H), 7.50-7.47 (m, 1H), 7.08 (d, J=8.7 Hz, 1H), 3.96 (s, 3H), 3.67 (s, 2H); LC/MS 212 [M+H$^+$].

Step 2: Preparation of 2-(3-amino-4-methoxyphenyl)acetic acid 2-(4-methoxy-3-nitrophenyl)acetic acid (1.30 g, 6.16 mmol) prepared in step 1 was dissolved in methanol (150 mL), to which 10 weight % Pd/C (0.62 g, 0.62 mmol) was added. The mixture was stirred at room temperature for 15 hours while purging hydrogen gas. Upon completion of the reaction, a new spot was formed under the starting material, which was confirmed by TLC. 10 weight % Pd/C was filtered and the reaction mixture was concentrated under reduced pressure. Then, purification was performed by MPLC to give the target compound 2-(3-amino-4-methoxyphenyl)acetic acid (1.00 g, 5.52 mmol, yield: 90%).

$^1$H-NMR (300 MHz, CDCl$_3$) δ 6.74-6.72 (m, 1H), 6.65-6.62 (m, 2H), 4.67 (br, s, 3H), 3.83 (s, 3H), 3.50 (s, 2H); LC/MS 182 [M+H$^+$].

Preparative Example 17: Preparation of 2,2,2-trifluoro-1-(piperazine-1-yl)ethane-1-one

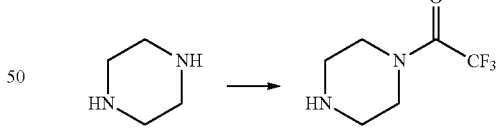

Piperazine (5.05 g, 58 mmol) was dissolved in dichloromethane (50 mL), to which anhydrous trifluoroacetic acid (1.2 g, 5.8 mmol) was added at 0° C. The reaction mixture was stirred at room temperature for 4 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound 2,2,2-trifluoro-1-(piperazine-1-yl)ethane-1-one as a white solid (200 mg, 1.10 mmol, yield: 2%).

$^1$H-NMR (300 MHz, CDCl$_3$) δ 3.64-3.68 (m, 1H), 3.59 (br, 2H), 2.91-2.94 (m, 4H), 1.91 (br, 1H)

Preparative Example 18: Preparation of N-(5-amino-2-bromo-4-methoxyphenethyl)-2,2,2-trifluoroacetamide

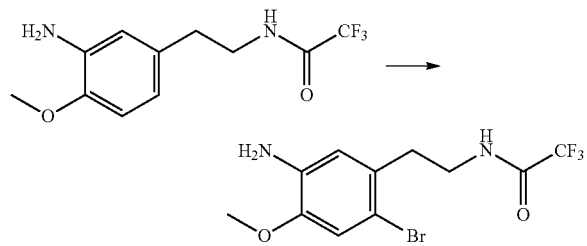

N-(3-amino-4-methoxyphenethyl)-2,2,2-trifluoroacetamide (5.0 g, 19 mmol) was dissolved in methanol (25 mL), followed by stirring. N-bromosuccinimide (3.7 g, 21 mmol) was dissolved in 4 mL of dimethylformamide, which was added to the solution prepared above at 0° C. The reaction mixture was stirred at room temperature for 2 hours. Thiosodium sulfate (aq.) was added thereto to terminate the reaction, followed by extraction with ethylacetate. The organic layer was washed with brine, dried over magnesium sulfate, and concentrated under reduced pressure. Then, purification was performed by silica gel column chromatography (eluent: ethylacetate/hexane, 1/2) to give the target compound N-(5-amino-2-bromo-4-methoxyphenethyl)-2,2,2-trifluoroacetamide as a white solid (4.7 g, 14 mmol, yield: 72%).

$^1$H-NMR (300 MHz, CDCl$_3$) δ 6.94 (s, 1H), 6.57 (s, 1H), 6.37 (s, br, 1H), 3.86 (s, 3H), 3.59 (q, J=6.9 Hz, 2H), 2.89 (t, J=6.3 Hz, 1H); LC/MS 341.00 [M+H$^+$].

Preparative Example 19: Preparation of N-(5-amino-4-methoxy-2-(1-methyl-1H-pyrazole-4-yl)phenethyl)-2,2,2-trifluoroacetamide

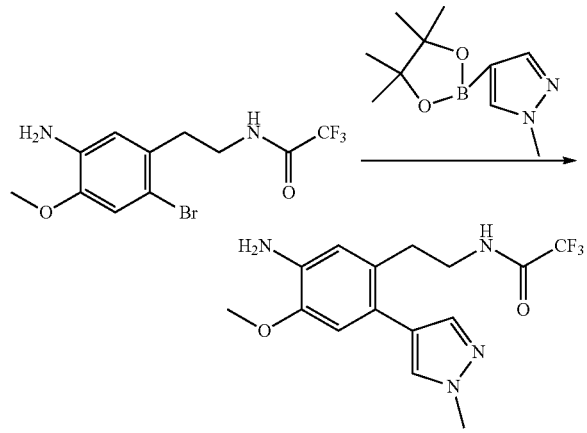

N-(5-amino-2-bromo-4-methoxyphenethyl)-2,2,2-trifluoroacetamide (100 mg, 0.30 mmol) was dissolved in n-butanol (3 mL), to which 1-methylpyrazoleboronicacidpinacolester (61 mg, 0.3 mmol), SPhos (16.0 mg, 0.04 mmol), sodium carbonate (155 mg, 1.47 mmol), and Pd$_2$(dba)$_3$ (tris(dibenzylideneacetone)dipalladium(0), 16.0 mg, 0.02 mmol) were added while stirring. Gas was eliminated from the reaction mixture, followed by heating at 115° C. overnight. The reaction mixture was filtered with celite, washed with dichloromethane, concentrated under reduced pressure, and extracted with ethylacetate. The organic layer was washed with brine, dried over magnesium sulfate, filtered, and concentrated under reduced pressure. Then, purification was performed by silica gel column chromatography (eluent: ethylacetate/hexane, 1/1) to give the target compound (5-amino-4-methoxy-2-(1-methyl-1H-pyrazole-4-yl)phenethyl)-2,2,2-trifluoroacetamide as a brown oil (30.0 mg, 0.09 mmol, yield: 15%).

$^1$H-NMR (300 MHz, CDCl$_3$) δ 7.48 (s, 1H), 7.41 (s, 1H), 6.68 (s, 1H), 6.58 (s, 1H), 6.23 (s, br, 1H), 3.96 (s, 3H), 3.84 (s, 1H), 3.44 (q, J=7.2 Hz, 2H), 2.84 (t, J=7.2 Hz 2H)

Preparative Example 20: Preparation of 2-(4-amino-5-methoxy-2-methylphenyl) acetonitrile

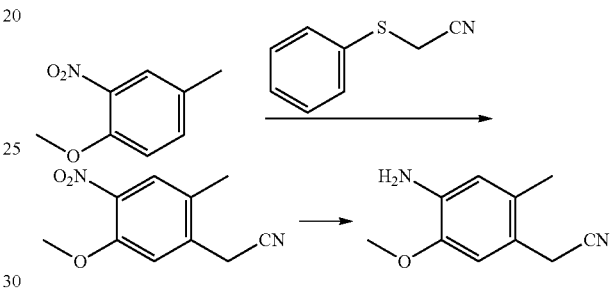

Step 1: Preparation of 2-(4-nitro-5-methoxy-2-methylphenyl) acetonitrile

Sodium hydroxide (5.74 g, 144 mmol) was dissolved in anhydrous dimethylsulfoxide (15.0 mL), to which anhydrous dimethylsulfoxide (15.0 mL) solution containing 4-methyl-2-nitroanisole (2.40 g, 14.4 mmol) and phenylthioacetonitrile (2.14 g, 14.4 mmol) dissolved therein was added at 30° C., followed by stirring at room temperature for one hour. Ice and 6 N HCl aqueous solution were added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 2/3) to give the target compound 2-(4-nitro-5-methoxy-2-methylphenyl) acetonitrile as a yellow solid (2.31 g, 11.2 mmol, yield; 78%).

$^1$H-NMR (300 MHz, CDCl$_3$) δ 7.75 (s, 1H), 7.16 (s, 1H), 4.00 (s, 3H), 3.75 (s, 2H), 2.33 (s, 3H); LC/MS 207.1 [M+H$^+$].

Step 2: Preparation of 2-(4-amino-5-methoxy-2-methylphenyl) acetonitrile 2-(4-nitro-5-methoxy-2-methylphenyl) acetonitrile (450 mg, 2.18 mmol) prepared in step 1 was dissolved in methanol (25 mL), to which 10 weight % Pd/C (45.0 mg, 0.422 mmol) was added. The mixture was stirred for 2 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/3) to give the target compound 2-(4-amino-5-methoxy-2-methylphenyl) acetonitrile as a white solid (350 mg, 1.98 mmol, yield: 91%).

$^1$H-NMR (300 MHz, CDCl$_3$) δ 6.76 (s, 1H), 6.57 (s, 1H), 3.87 (s, 3H), 3.79 (s, br, 2H), 3.59 (s, 2H), 2.21 (s, 3H); LC/MS 177.1 [M+H$^+$].

Preparative Example 21: Preparation of 2-(4-amino-5-methoxy-2-methylphenyl)-2-methylpropanenitrile

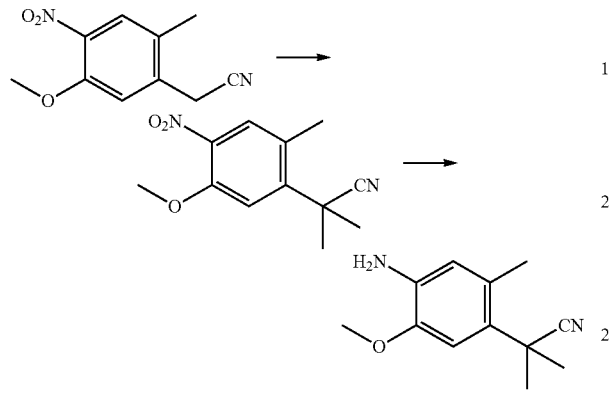

Step 1: Preparation of 2-(5-methoxy-2-methyl-4-nitrophenyl)-2-methylpropanenitrile Sodium hydride (0.804 g, 20.2 mmol) was dissolved in dimethylformamide (15 mL), to which dimethylformamide (10 mL) solution containing 2-(4-nitro-5-methoxy-2-methylphenyl) acetonitrile (1.66 g, 8.05 mmol) dissolved therein was added at ° C., followed by stirring for 20 minutes. Methyliodide (1.10 mL, 17.7 mmol) was added thereto, followed by stirring at room temperature for 8 hours. Ice was added thereto to terminate the reaction, followed by extraction twice with ethylacetate. The extracted organic layer was dried over sodium sulfate and then filtered. The solvent was eliminated by distillation under reduced pressure. The generated solid was recrystallized by using water to give the target compound 2-(5-methoxy-2-methyl-4-nitrophenyl)-2-methylpropanenitrile as a white solid (1.77 g, 7.57 mmol yield: 94%).

$^1$H-NMR (300 MHz, CDCl$_3$) δ 7.74 (s, 1H), 7.06 (s, 1H), 3.96 (s, 3H), 2.62 (s, 3H), 1.83 (s, 6H); LC/MS 235.10 [M+H$^+$].

Step 2: Preparation of 2-(4-amino-5-methoxy-2-methylphenyl)-2-methylpropanenitrile 2-(5-methoxy-2-methyl-4-nitrophenyl)-2-methylpropanenitrile (450 mg, 1.92 mmol) prepared in step 1 was dissolved in methanol (25 mL), to which 10 weight % Pd/C (45.0 mg, 0.422 mmol) was added. The mixture was stirred for 12 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/3) to give the target compound 2-(4-amino-5-methoxy-2-methylphenyl)-2-methylpropanenitrile as a white solid (350 mg, 1.71 mmol, yield: 89%).

$^1$H-NMR (300 MHz, CDCl$_3$) δ 6.75 (s, 1H), 6.59 (s, 1H), 3.86 (s, 3H), 3.78 (s, br, 2H), 2.51 (s, 3H), 1.78 (s, 6H); LC/MS 205.10 [M+H$^+$].

Preparative Example 22: Preparation of N-(2-(4-amino-5-methoxy-2-methylphenyl)propane-2-yl)-2,2,2-trifluoroacetamide

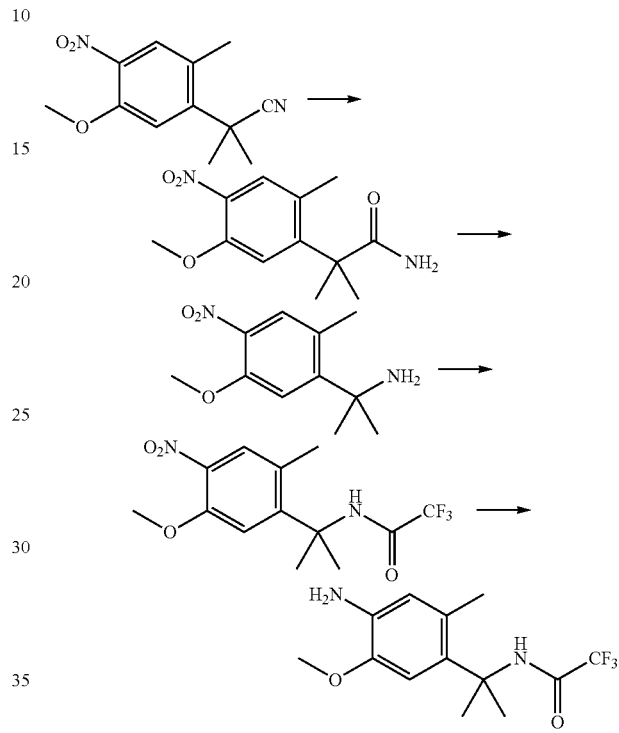

Step 1: Preparation of 2-(5-methoxy-2-methyl-4-nitrophenyl)-2-methylpropaneamide 2-(5-methoxy-2-methyl-4-nitrophenyl)-2-methylpropanenitrile (500 mg, 2.13 mmol) was dissolved in water (8 mL), to which sulfuric acid (7.00 mL) was added at room temperature. The reaction mixture was stirred at 100° C. for 4 hours. The reaction mixture was extracted twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound 2-(5-methoxy-2-methyl-4-nitrophenyl)-2-methylpropaneamide as a yellow solid (420 mg, 1.66 mmol, yield: 78%).

$^1$H-NMR (300 MHz, CDCl$_3$) δ 7.70 (s, 1H), 7.14 (s, 1H), 5.33 (s, br, 1H), 5.17 (s, br, 1H), 3.98 (s, 3H), 2.34 (s, 3H), 1.61 (s, 6H); LC/MS 253.1 [M+H$^+$].

Step 2: Preparation of 2-(5-methoxy-2-methyl-4-nitrophenyl)propane-2-amine 2-(5-methoxy-2-methyl-4-nitrophenyl)-2-methylpropaneamide (100 mg, 0.396 mmol) prepared in step 1 was dissolved in acetonitrile/water (1/1, 2 mL), to which bistrifluoroacetoxyiodobenzene (171 mg, 0.396 mmol) was added at room temperature, followed by stirring for 12 hours. The reaction mixture was diluted with water (5 mL) and sodium hydrogen carbonate (5 mL) and extracted twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound 2-(5-methoxy-2-methyl-4-nitrophenyl)propane-2-amine as a white solid (80.0 mg, 0.356 mmol, yield: 89%).

$^1$H-NMR (300 MHz, CDCl$_3$) δ 7.68 (s, 1H), 7.45 (s, 1H), 3.96 (s, 3H), 2.57 (s, 3H), 1.58 (s, 6H), 1.54 (s, br, 2H); LC/MS 225.1 [M+H$^+$].

Step 3: Preparation of 2,2,2-trifluoro-N-(2-(5-methoxy-2-methyl-4-nitrophenyl)propane-2-yl)acetamide 2-(5-methoxy-2-methyl-4-nitrophenyl)propane-2-amine (80.0 mg, 0.356 mmol) prepared in step 2 was dissolved in dichloromethane (5 mL), to which anhydrous trifluoroacetic acid (89.9 mg, 0.428 mmol) and triethylamine (90.1 mg, 0.892 mmol) were added at 0° C. The reaction mixture was stirred at room temperature for 30 minutes. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 2/3) to give the target compound 2,2,2-trifluoro-N-(2-(5-methoxy-2-methyl-4-nitrophenyl)propane-2-yl)acetamide as a white solid (95.0 mg, 0.296 mmol, yield: 83%).

$^1$H-NMR (300 MHz, CDCl$_3$) δ 7.69 (s, 1H), 7.09 (s, 1H), 6.47 (s, br, 1H), 3.96 (s, 3H), 2.41 (s, 2H), 1.83 (s, 6H); LC/MS 321.1 [M+H$^+$].

Step 4: Preparation of N-(2-(4-amino-5-methoxy-2-methylphenyl)propane-2-yl)-2,2,2-trifluoroacetamide 2,2,2-trifluoro-N-(2-(5-methoxy-2-methyl-4-nitrophenyl)propane-2-yl)acetamide (95.0 mg, 0.296 mmol) prepared in step 3 was dissolved in methanol (10 mL), to which 10 weight % Pd/C (10.0 mg, 0.094 mmol) was added. The mixture was stirred for 2 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/3) to give the target compound N-(2-(4-amino-5-methoxy-2-methylphenyl)propane-2-yl)-2,2,2-trifluoroacetamide as a white solid (54.0 mg, 0.186 mmol, yield: 63%).

$^1$H-NMR (300 MHz, CDCl$_3$) δ 6.82 (s, 1H), 6.53 (s, 1H), 6.36 (s, br, 1H), 3.84 (s, 3H), 3.73 (s, br, 2H), 2.33 (s, 3H), 1.83 (s, 6H); LC/MS 291.1 [M+H$^+$].

Preparative Example 23: Preparation of N-(2-(4-amino-5-methoxy-2-methylphenyl)propane-2-yl)formamide

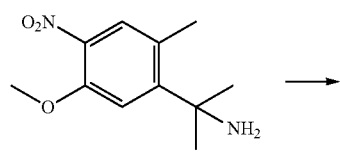

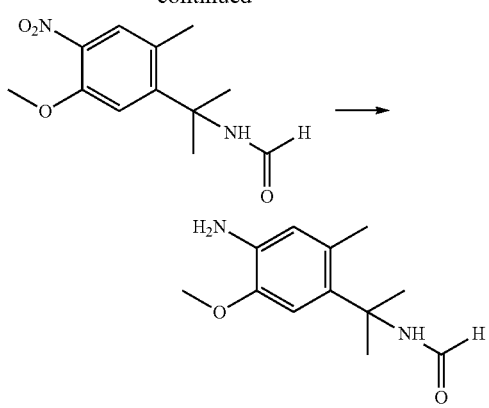

Step 1: Preparation of N-(2-(5-methoxy-2-methyl-4-nitrophenyl)propane-2-yl)formamide 2-(5-methoxy-2-methyl-4-nitrophenyl)propane-2-amine (250 mg, 1.11 mmol) was dissolved in ethylformate (10 mL), followed by reflux-stirring at 65° C. for 12 hours. The solvent was eliminated by distillation under reduced pressure. Then, purification was performed by silica gel column chromatography (eluent: methanol/dichloromethane, 1/9) to give the target compound N-(2-(5-methoxy-2-methyl-4-nitrophenyl)propane-2-yl)formamide as a white solid (220 mg, 0.872 mmol, yield: 78%).

$^1$H-NMR (300 MHz, CDCl$_3$) δ 8.15 (s, 0.6H), 8.01-7.96 (m, 0.3H), 7.73 (s, 0.4H) 7.70 (s, 0.6H), 7.15 (s, 1H), 6.10-6.06 (m, 0.3H), 5.73 (s, br, 0.6H), 3.99 (s, 1H), 3.98 (s, 2H), 2.49 (s, 1H), 2.46 (s, 2H), 1.80 (s, 4H), 1.78 (s, 2H); LC/MS 253.1 [M+H$^+$].

Step 2: Preparation of N-(2-(4-amino-5-methoxy-2-methylphenyl)propane-2-yl)formamide N-(2-(5-methoxy-2-methyl-4-nitrophenyl)propane-2-yl)formamide (220 mg, 0.872 mmol) prepared in step 1 was dissolved in methanol (25 mL), to which 10 weight % Pd/C (25.0 mg, 0.234 mmol) was added. The mixture was stirred for 4 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/3) to give the target compound N-(2-(4-amino-5-methoxy-2-methylphenyl)propane-2-yl)formamide as a white solid (170 mg, 0.764 mmol, yield: 87%).

$^1$H-NMR (300 MHz, CDCl$_3$) δ 8.11 (s, 0.3H), 8.00-7.96 (m, 0.7H), 6.82 (s, 1H), 6.53 (s, 1H), 5.92-5.88 (m, 0.6H), 5.56 (s, br, 0.3H), 3.83 (s, 3H), 3.73 (s, br, 2H), 2.37 (s, 1H), 2.33 (s, 2H), 1.80 (s, 2H), 1.69 (s, 4H); LC/MS 223.2 [M+H$^+$].

Preparative Example 24: Preparation of N-(2-(4-amino-5-methoxy-[1,1'-biphenyl]-2-yl)ethyl)-2,2,2-trifluoroacetamide

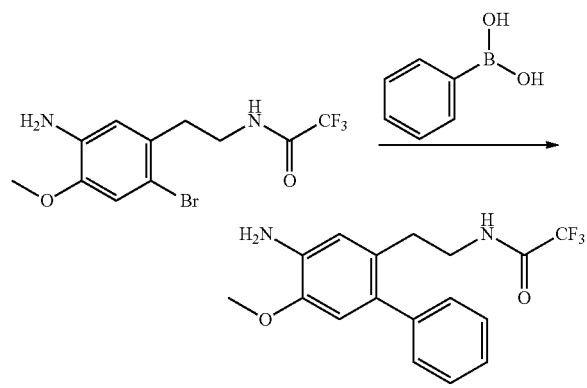

N-(2-bromo-4-methoxy-5-nitrophenethyl)-2,2,2-trifluoroacetamide (200 mg, 0.59 mmol) was dissolved in n-butanol (7 mL), to which phenylboronic acid (286 mg, 2.35 mmol), SPhos (16.0 mg, 0.04 mmol), sodium carbonate (310 mg, 2.93 mmol), and $Pd_2(dba)_3$ (16.0 mg, 0.02 mmol) were added while stirring. Gas was eliminated from the reaction mixture, followed by heating at 115° C. overnight. The reaction mixture was filtered with celite, washed with dichloromethane, concentrated under reduced pressure, and extracted with ethylacetate. The organic layer was washed with brine, dried over magnesium sulfate, filtered, and concentrated under reduced pressure. Then, column chromatography was performed by using ethylacetate/hexane (4/1) to give the target compound N-(2-(4-amino-5-methoxy-[1,1'-biphenyl]-2-yl)ethyl)-2,2,2-trifluoroacetamide (185 mg, 0.32 mmol, yield: 93%).

Preparative Example 25: Preparation of N-(4-amino-5-methoxy-2-methylbenzyl)-2,2,2-trifluoroacetamide

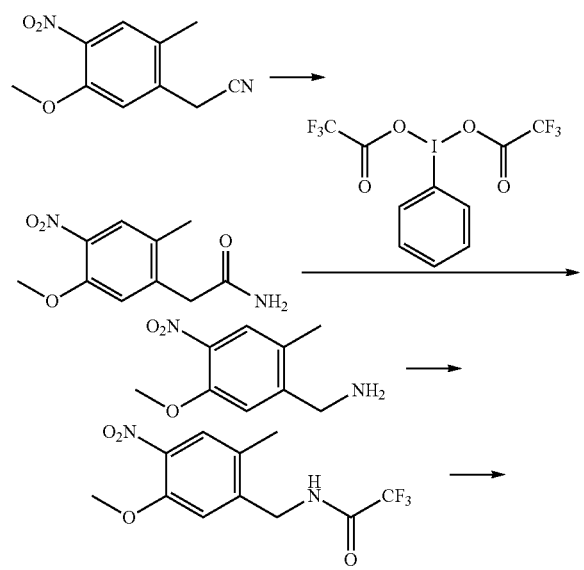

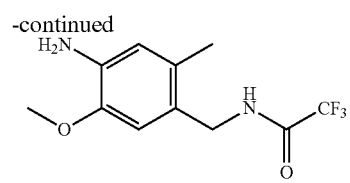

Step 1: Preparation of 2-(5-methoxy-2-methyl-4-nitrophenyl)acetamide 2-(5-methoxy-2-methyl-4-nitrophenyl)acetonitrile (900 mg, 4.36 mmol) was dissolved in HCl (10.0 mL) at room temperature. The reaction mixture was stirred at 30° C. for 48 hours. The reaction mixture was diluted with water, followed by extraction with ethylacetate (150 ml). The extracted organic layer was concentrated under reduced pressure. Then, purification was performed by recrystallization to give the target compound 2-(5-methoxy-2-methyl-4-nitrophenyl)acetamide as a white solid (690 mg, 3.08 mmol, yield: 70%).

$^1$H-NMR (300 MHz, $CDCl_3$) δ 7.75 (s, 1H), 6.97 (s, 1H), 5.52 (s, br, 1H), 5.37 (s, br, 1H), 3.97 (s, 3H), 3.64 (s, 2H), 2.33 (s, 3H); LC/MS 224.9 [M+H$^+$].

Step 2: Preparation of (5-methoxy-2-methyl-4-nitrophenyl)methaneamine 2-(5-methoxy-2-methyl-4-nitrophenyl)acetamide (600 mg, 2.68 mmol) prepared in step 1 was dissolved in acetonitrile/water (1:1), which was added to [bis(trifluoroacetoxy)iodo]benzene (1151 mg, 2.675 mmol), followed by stirring for 12 hours. The reaction mixture was diluted with water (5.0 ml), to which sodium hydrogen carbonate solution was added, followed by extraction with ethylacetate (15 ml). The extracted organic layer was concentrated under reduced pressure. Then, column chromatography was performed (eluent: methanol/methylchloride, 1/9) to give the target compound (5-methoxy-2-methyl-4-nitrophenyl)methaneamine as a yellow solid (400 mg, 2.04 mmol, yield: 76%).

$^1$H-NMR (300 MHz, $CDCl_3$) δ 7.69 (s, 1H), 7.24 (s, 1H), 3.97 (s, 3H), 3.90 (s, 2H), 2.26 (s, 3H), 1.49 (s, br, 2H); LC/MS 197.1 [M+H$^+$].

Step 3: Preparation of 2,2,2-trifluoro-N-(5-methoxy-2-methyl-4-nitrobenzyl)acetamide (5-methoxy-2-methyl-4-nitrophenyl)methaneamine (150 mg, 0.764 mmol) was dissolved in dichloromethane (15.0 ml) and trifluoroaceticanhydride (193 mg, 0.917 mmol), to which triethylamine (193 mg, 1.91 mmol) was added. The reaction mixture was stirred at room temperature for 30 minutes. Water (5.0 ml) was added thereto to terminate the reaction, followed by extraction twice with dichloromethane (10 ml). The extracted organic layer was washed with water and brine, and dried over sodium sulfate. The solvent was eliminated by distillation under reduced pressure. Then, purification was performed by silica gel column chromatography (eluent: ethylacetate/hexane, 2/3) to give the target compound 2,2,2-trifluoro-N-(5-methoxy-2-methyl-4-nitrobenzyl)acetamide as a white solid (150 mg, 0.581 mmol, yield: 76%).

$^1$H-NMR (300 MHz, $CDCl_3$) δ 7.70 (s, 1H), 6.96 (s, 1H), 6.53 (s, br, 1H), 4.56 (d, J=5.9 Hz, 2H), 3.93 (s, 3H), 2.32 (s, 2H); LC/MS 293.0 [M+H$^+$].

Step 4: Preparation of N-(4-amino-5-methoxy-2-methylbenzyl)-2,2,2-trifluoroacetamide 2,2,2-trifluoro-N-(5-methoxy-2-methyl-4-nitrobenzyl)acetamide (150 mg, 0.513 mmol) prepared in step 3 was dissolved in methanol (20.0 mL), to which 10 weight % Pd/C (15.0 mg, 0.140 mmol) was added. The mixture was stirred at room temperature for 2 hours under a hydrogen gas balloon. The reaction mixture was filtered with celite. The solvent was eliminated by distillation under reduced pressure. Then, purification was performed by silica gel column chromatography (eluent: acetate/hexane, 3/7) to give the target compound N-(4-amino-5-methoxy-2-methylbenzyl)-2,2,2-trifluoroacetamide as a white solid (110 mg, 0.419 mmol, yield: 82%).

$^1$H-NMR (300 MHz, CDCl$_3$) δ 6.67 (s, 1H), 6.58 (s, 1H), 6.25 (s, br, 1H), 3.85 (s, 3H), 3.83 (s, br, 2H), 2.21 (s, 3H); LC/MS 263.1 [M+H$^+$].

Preparative Example 26: Preparation of N-(4-amino-5-methoxy-2-methylbenzyl) formamide

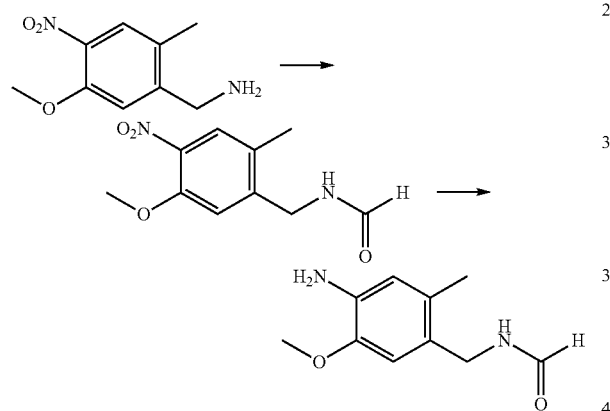

Step 1: Preparation of N-(5-methoxy-2-methyl-4-nitrobenzyl)formamide (5-methoxy-2-methyl-4-nitrocyclohexyl)methaneamine (250 mg, 1.27 mmol) was dissolved in ethylformate (10 mL), followed by reflux-stirring at 65° C. for 4 hours. The solvent was eliminated by distillation under reduced pressure. Then, purification was performed by silica gel column chromatography (eluent: methanol/dichloromethane, 1/9) to give the target compound N-(5-methoxy-2-methyl-4-nitrobenzyl)formamide as a white solid (150 mg, 0.669 mmol, yield: 52%).

1H NMR (300 MHz, CDCl3) 8.33 (s, 1H), 7.68 (s, 1H), 6.99 (s, 1H), 5.88 (s, br, 1H), 4.50 (d, J=6.0 Hz, 2H) 3.93 (s, 3H), 2.31 (s, 3H); LC/MS 225.1 [M+H$^+$].

Step 2: Preparation of N-(4-amino-5-methoxy-2-methylbenzyl) formamide

N-(5-methoxy-2-methyl-4-nitrobenzyl)formamide (150 mg, 0.668 mmol) prepared in step 1 was dissolved in methanol (15 mL), to which 10 weight % Pd/C (15.0 mg, 0.140 mmol) was added. The mixture was stirred for 5 hours under a hydrogen gas balloon. The solid generated in the reaction mixture was filtered with celite, which was washed with methanol. The solvent was eliminated by distillation under reduced pressure. Then, purification was performed by silica gel column chromatography (eluent: ethylacetate/hexane, 2/3) to give the target compound N-(4-amino-5-methoxy-2-methylbenzyl) formamide as a white solid (110 mg, 0.566 mmol, yield: 85%).

1H NMR (300 MHz, CDCl3) 8.20 (s, 1H), 6.67 (s, 1H), 6.54 (s, 1H), 5.53 (s, br, 1H), 4.37 (d, J=5.30 Hz, 2H) 3.82 (s, 3H), 3.75 (s, br, 2H), 2.19 (s, 3H); LC/MS 194.1 [M+H$^+$].

Example 1: Preparation of N2-(5-(1-(aminomethyl)cyclopentyl)-2-methoxyphenyl)-5-chloro-N4-(2-(isopropylsulfonyl)phenyl)pyrimidine-2,4-diamine

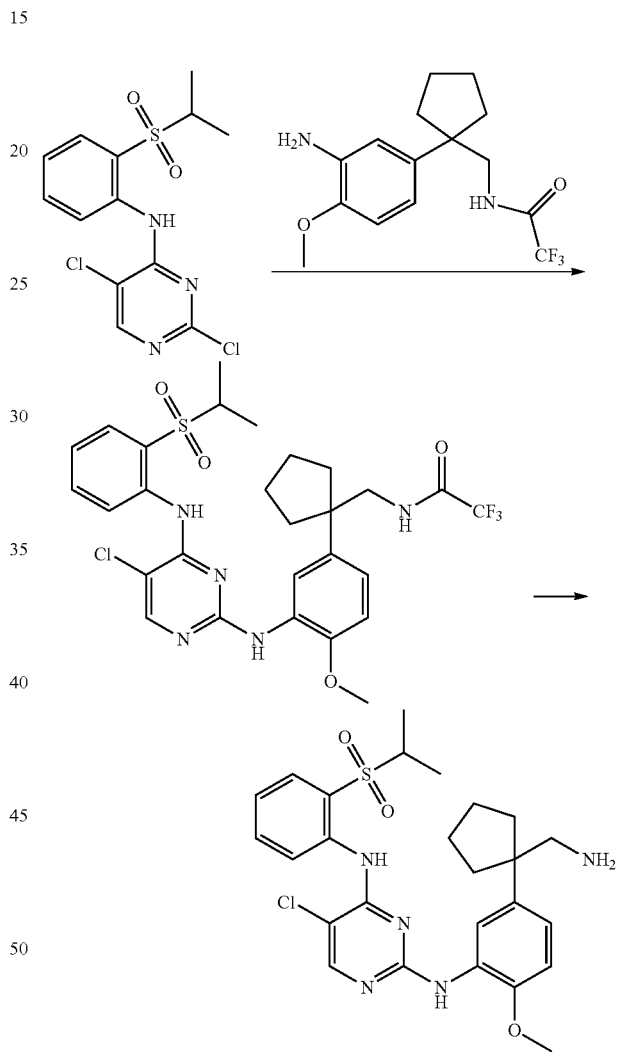

Step 1: Preparation of N-((1-(3-((5-chloro-4-((2-(isopropylsulfonyl)phenyl)amino)pyrimidine-2-yl)amino)-4-methoxyphenyl)cyclopentyl)methyl)-2,2,2-trifluoroacetamide 2,5-dichloro-N-(2-(isopropylsulfonyl)phenyl)pyrimidine-4-amine (75 mg, 0.22 mmol) was dissolved in 0.08 M HCl.ethoxyethanol (0.1 mL), to which the compound (75 mg, 0.24 mmol) prepared in preparative example 1 was added, followed by stirring at 80° C. for 15 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound N-((1-(3-((5-chloro-4-((2-(isopropylsulfonyl)phenyl)amino)pyrimidine-2-yl)amino)-4-methoxyphenyl)cyclopentyl)methyl)-2,2,2-trifluoroacetamide as a white solid (81 mg, 0.129 mmol, yield: 60%).

$^1$H-NMR (300 MHz, CDCl$_3$) δ 9.26 (s, 1H), 8.48 (d, J=8.4 Hz, 1H), 8.29 (s, 1H), 8.18 (s, 1H), 7.93 (d, J=8.1 Hz, 1H), 7.59-7.65 (m, 1H), 7.53 (s, 1H), 7.23-7.28 (m, 1H), 6.82-6.88 (m, 2H), 6.01 (br, 1H), 3.92 (s, 3H), 3.36 (d, J=5.7 Hz, 2H), 3.27 (sept J=6.9 Hz, 1H), 1.32 (d J=6.9 Hz, 6H); LC/MS 626.0 [M+H$^+$].

Step 2: Preparation of N2-(5-(1-(aminomethyl)cyclopentyl)-2-methoxyphenyl)-5-chloro-N4-(2-(isopropylsulfonyl)phenyl)pyrimidine-2,4-diamine N-((1-(3-((5-chloro-4-((2-(isopropylsulfonyl)phenyl)amino)pyrimidine-2-yl)amino)-4-methoxyphenyl)cyclopentyl)methyl)-2,2,2-trifluoroacetamide (60 mg, 0.09 mmol) was dissolved in ethanol (2 mL), to which potassium carbonate (132 mg, 0.96 mmol) aqueous solution (1 mL) was added, followed by stirring at 100° C. for 15 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(5-(1-(aminomethyl)cyclopentyl)-2-methoxyphenyl)-5-chloro-N4-(2-(isopropylsulfonyl)phenyl)pyrimidine-2,4-diamine as a white solid (49 mg, 0.092 mmol, yield: 98%).

$^1$H-NMR (300 MHz, CDCl$_3$) δ 9.47 (br, 1H), 8.45 (d, J=8.1 Hz, 1H), 8.19 (s, 2H), 7.91 (d, J=8.1 Hz, 1H), 7.58-7.63 (m, 1H), 7.51 (s, 1H), 7.21-7.27 (m, 1H), 6.81-6.88 (m, 2H), 3.89 (s, 3H), 3.28 (sept J=6.9 Hz, 1H), 2.61 (s, 2H), 1.60-1.69 (m, 8H), 1.32 (d, J=6.9 Hz, 6H); LC/MS 530.0 [M+H$^+$].

Example 2: Preparation of N2-(5-(1-(aminomethyl)cyclohexyl)-2-methoxyphenyl)-5-chloro-N4-(2-(isopropylsulfonyl)phenyl)pyrimidine-2,4-diamine

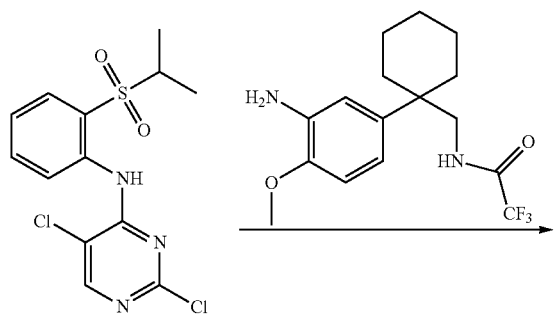

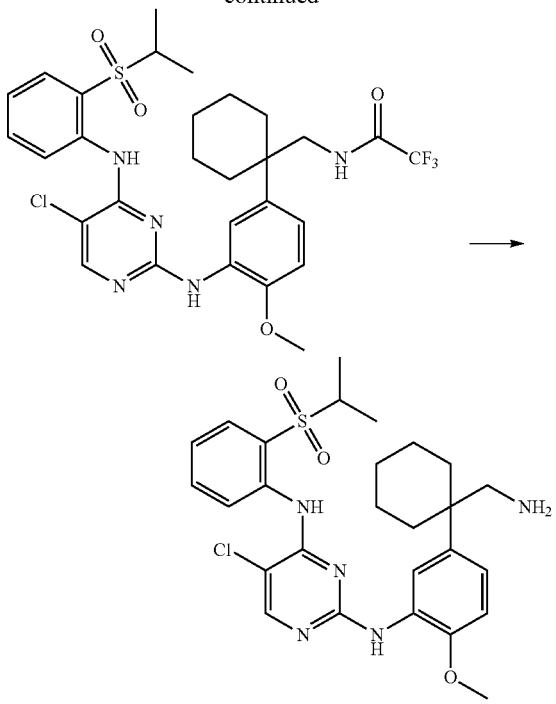

Step 1: Preparation of N-((1-(3-((5-chloro-4-((2-(isopropylsulfonyl)phenyl)amino)pyrimidine-2-yl)amino)-4-methoxyphenyl)cyclohexyl)methyl)-2,2,2-trifluoroacetamide 2,5-dichloro-N-(2-(isopropylsulfonyl)phenyl)pyrimidine-4-amine (75 mg, 0.22 mmol) was dissolved in 0.08 M HCl.ethoxyethanol (0.1 mL), to which the compound (75 mg, 0.24 mmol) prepared in preparative example 2 was added, followed by stirring at 80° C. for 15 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound N-((1-(3-((5-chloro-4-((2-(isopropylsulfonyl)phenyl)amino)pyrimidine-2-yl)amino)-4-methoxyphenyl)cyclohexyl)methyl)-2,2,2-trifluoroacetamide as a white solid (89 mg, 0.139 mmol, yield: 64%).

$^1$H-NMR (300 MHz, CDCl$_3$) δ 9.54 (s, 1H), 8.51 (d, J=8.1 Hz, 1H), 8.39 (s, 1H), 8.18 (s, 1H), 7.92 (d, J=7.8 Hz, 1H), 7.61-7.66 (m, 1H), 7.53 (s, 1H), 7.24-7.28 (m, 1H), 6.90 (br, 2H), 5.89 (br, 1H), 3.93 (s, 3H), 3.37 (d, J=5.1 Hz, 2H), 3.26 (sept J=6.9 Hz, 1H), 1.91 (br, 2H), 1.51-1.64 (m, 4H), 1.40 (br, 4H), 1.32 (d, J=6.9 Hz, 6H); LC/MS 640.0 [M+H$^+$].

Step 2: Preparation of N2-(5-(1-(aminomethyl)cyclohexyl)-2-methoxyphenyl)-5-chloro-N4-(2-(isopropylsulfonyl)phenyl)pyrimidine-2,4-diamine N-((1-(3-((5-chloro-4-((2-(isopropylsulfonyl)phenyl)amino)pyrimidine-2-yl)amino)-4-methoxyphenyl)cyclohexyl)methyl)-2,2,2-trifluoroacetamide (75 mg, 0.12 mmol) prepared in step 1 was dissolved in ethanol (2 mL), to which potassium carbonate (162 mg, 1.17 mmol) aqueous solution (1 mL) was added, followed by stirring at 100° C. for 15 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(5-(1-(aminomethyl)cyclohexyl)-2-methoxyphenyl)-5-chloro-N4-(2-(isopropylsulfonyl)phenyl)pyrimidine-2,4-diamine as a white solid (49 mg, 0.092 mmol, yield: 98%).

¹H-NMR (300 MHz, CDCl₃) δ 9.51 (br, 1H), 8.49 (d, J=8.1 Hz, 1H), 8.28 (s, 1H), 8.19 (s, 1H), 7.91 (d, J=8.1 Hz, 1H), 7.63 (t, J=7.8 Hz, 1H), 7.51 (s, 1H), 7.22-7.27 (m, 1H), 6.85-6.94 (m, 2H), 3.89 (s, 3H), 3.28 (sept J=6.9 Hz, 1H), 2.62 (s, 2H), 1.89 (br, 2H), 1.41-1.44 (m, 6H), 1.32 (d, J=6.9 Hz, 6H), 1.10 (br, 2H); LC/MS 544 [M+H⁺].

Example 3: Preparation of N2-(5-((1-aminocyclopropyl)methyl)-2-methoxyphenyl)-5-chloro-N4-(2-(isopropylsulfonyl)phenyl)pyrimidine-2,4-diamine

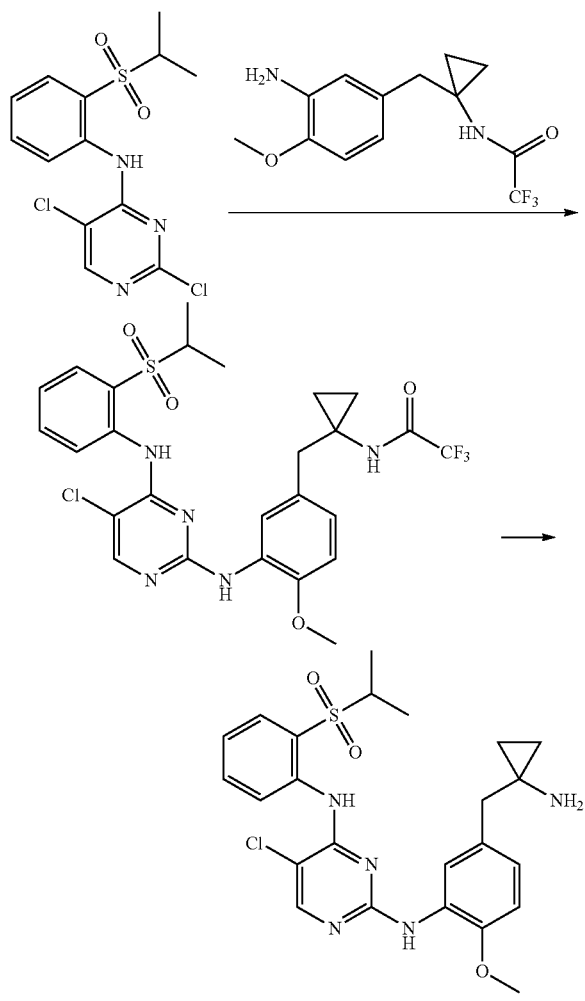

Step 1: Preparation of N-(1-(3-((5-chloro-4-((2-(isopropylsulfonyl)phenyl)amino)pyrimidine-2-yl)amino)-4-methoxybenzyl)cyclopropyl)-2,2,2-trifluoroacetamide 2,5-dichloro-N-(2-(isopropylsulfonyl)phenyl)pyrimidine-4-amine (75 mg, 0.22 mmol) was dissolved in 0.08 M HCl.ethoxyethanol (0.1 mL), to which the compound (75 mg, 0.24 mmol) prepared in preparative example 3 was added, followed by stirring at 80° C. for 15 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound N-(1-(3-((5-chloro-4-((2-(isopropylsulfonyl)phenyl)amino)pyrimidine-2-yl)amino)-4-methoxybenzyl)cyclopropyl)-2,2,2-trifluoroacetamide as a white solid (46 mg, 0.077 mmol, yield: 37%).

¹H-NMR (300 MHz, CDCl₃) δ 9.59 (s, 1H), 8.54 (d, J=7.5 Hz, 1H), 8.18 (d, J=10.2 Hz, 2H), 7.94 (d, J=7.8 Hz, 1H), 7.58-7.65 (m, 2H), 7.26-7.29 (m, 2H), 6.83 (d, J=7.8 Hz, 1H), 6.74 (d, J=7.8 Hz, 1H), 6.35 (s, 1H), 3.91 (s, 3H), 3.27 (sept J=6.9 Hz, 1H), 2.79 (s, 2H), 1.58 (s, 2H), 1.33 (d, J=6.9 Hz, 6H), 0.79 (br, 2H), 0.73 (br, 2H); LC/MS 598.0 [M+H⁺].

Step 2: Preparation of N2-(5-((1-aminocyclopropyl)methyl)-2-methoxyphenyl)-5-chloro-N4-(2-(isopropylsulfonyl)phenyl)pyrimidine-2,4-diamine N-(1-(3-((5-chloro-4-((2-(isopropylsulfonyl)phenyl)amino)pyrimidine-2-yl)amino)-4-methoxybenzyl)cyclopropyl)-2,2,2-trifluoroacetamide (35 mg, 0.06 mmol) prepared in step 1 was dissolved in ethanol (2 mL), to which potassium carbonate (81 mg, 0.56 mmol) aqueous solution (1 mL) was added, followed by stirring at 100° C. for 15 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(5-((1-aminocyclopropyl)methyl)-2-methoxyphenyl)-5-chloro-N4-(2-(isopropylsulfonyl)phenyl)pyrimidine-2,4-diamine as a white solid (16 mg, 0.032 mmol, yield: 55%).

¹H-NMR (300 MHz, CDCl₃) δ 9.54 (s, 1H), 8.52 (d, J=8.1 Hz, 1H), 8.20 (d, J=11.1 Hz, 2H), 7.94 (d, J=8.1 Hz, 1H), 7.60-7.63 (m, 2H), 7.26-7.29 (m, 2H), 6.84 (s, 2H), 3.90 (s, 3H), 3.26 (sept J=6.9 Hz, 1H), 2.59 (s, 2H), 1.46 (br, 2H), 1.32 (d, J=6.9 Hz, 6H), 0.49 (br, 2H), 0.32 (br, 2H); LC/MS 502.0 [M+H⁺].

Example 4: Preparation of N2-(5-(2-aminoethyl)-2-methoxyphenyl)-5-chloro-N4-(2-(isopropylsulfonyl)phenyl) pyrimidine-2,4-diamine

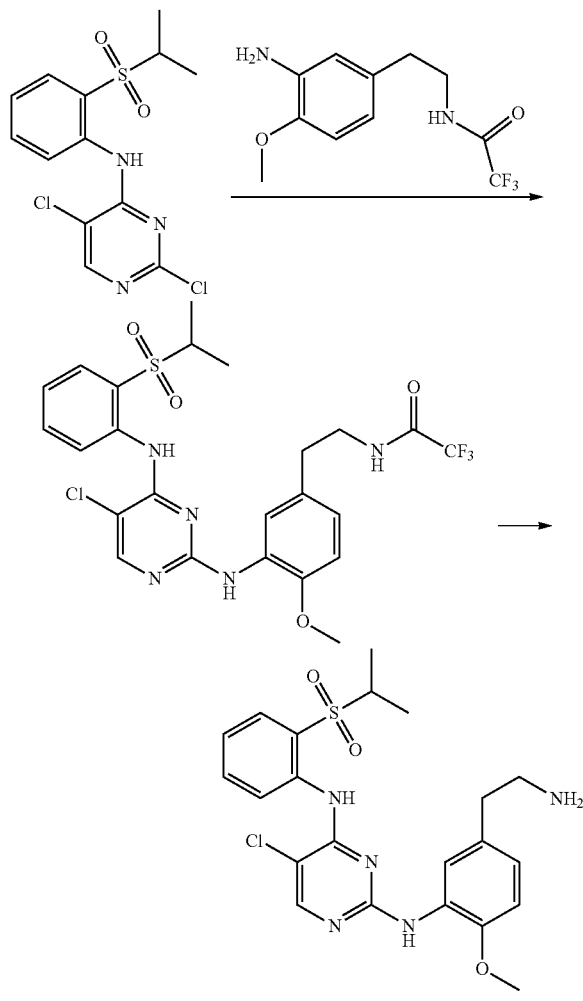

Step 1: Preparation of N-(3-((5-chloro-4-((2-(isopropylsulfonyl)phenyl)amino)pyrimidine-2-yl)amino)-4-methoxyphenethyl)-2,2,2-trifluoroacetamide 2,5-dichloro-N-(2-(isopropylsulfonyl)phenyl)pyrimidine-4-amine (50 mg, 0.14 mmol) was dissolved in 0.08 M HCl.ethoxyethanol (0.1 mL), to which the compound (42 mg, 0.16 mmol) prepared in preparative example 4 was added, followed by stirring at 80° C. for 15 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound N-(3-((5-chloro-4-((2-(isopropylsulfonyl)phenyl)amino)pyrimidine-2-yl)amino)-4-methoxyphenethyl)-2,2,2-trifluoroacetamide as a white solid (54 mg, 0.129 mmol, yield: 66%).

$^1$H-NMR (300 MHz, CDCl$_3$) δ 9.56 (s, 1H), 8.53 (d, J=8.1 Hz, 1H), 8.21 (s, 1H), 8.18 (s, 1H), 7.94 (d, J=7.5 Hz, 1H), 7.59-7.67 (m, 2H), 7.27 (br, 1H), 6.84 (d, J=6.6 Hz, 1H), 6.77 (d, J=8.1 Hz, 1H), 6.27 (br, 1H), 3.91 (s, 3H), 3.47-3.49 (m, 2H), 3.27 (hept, J=6.9 Hz, 1H), 2.76 (br, 2H), 1.32 (d, J=6.9 Hz, 6H; LC/MS 571.7 [M+H$^+$].

Step 2: Preparation of N2-(5-(2-aminoethyl)-2-methoxyphenyl)-5-chloro-N4-(2-(isopropylsulfonyl)phenyl) pyrimidine-2,4-diamine N-(3-((5-chloro-4-((2-(isopropylsulfonyl)phenyl)amino)pyrimidine-2-yl)amino)-4-methoxyphenethyl)-2,2,2-trifluoroacetamide (50 mg, 0.09 mmol) prepared in step 1 was dissolved in ethanol (2 mL), to which potassium carbonate (121 mg, 0.87 mmol) aqueous solution (1 mL) was added, followed by stirring at 100° C. for 15 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(5-(2-aminoethyl)-2-methoxyphenyl)-5-chloro-N4-(2-(isopropylsulfonyl)phenyl)pyrimidine-2,4-diamine as a white solid (35 mg, 0.092 mmol, yield: 85%).

$^1$H-NMR (300 MHz, CDCl$_3$) δ 9.49 (br, 1H), 8.53 (d, J=8.4 Hz, 1H), 8.18 (s, 1H), 8.13 (s, 1H), 7.93 (d, J=8.1 Hz, 1H), 7.66 (t, J=7.8 Hz, 1H), 7.59 (s, 1H), 7.26-7.30 (m, 1H), 6.81 (br, 2H), 3.88 (s, 3H), 3.26 (hept, J=6.9 Hz, 1H), 2.81 (t, J=6.9 Hz, 2H), 2.61 (t, J=6.9 Hz, 2H), 1.31 (d, J=6.9 Hz, 6H), 1.20 (br, 2H); LC/MS 475.9 [M+H$^+$], 951.3 [2M+H$^+$].

Example 5: Preparation of 5-chloro-N4-(2-(isopropylsulfonyl)phenyl-N2-(2-methoxy-5-(1-(piperidine-1-ylmethyl)cyclopentyl) phenyl)pyrimidine-2,4-diamine

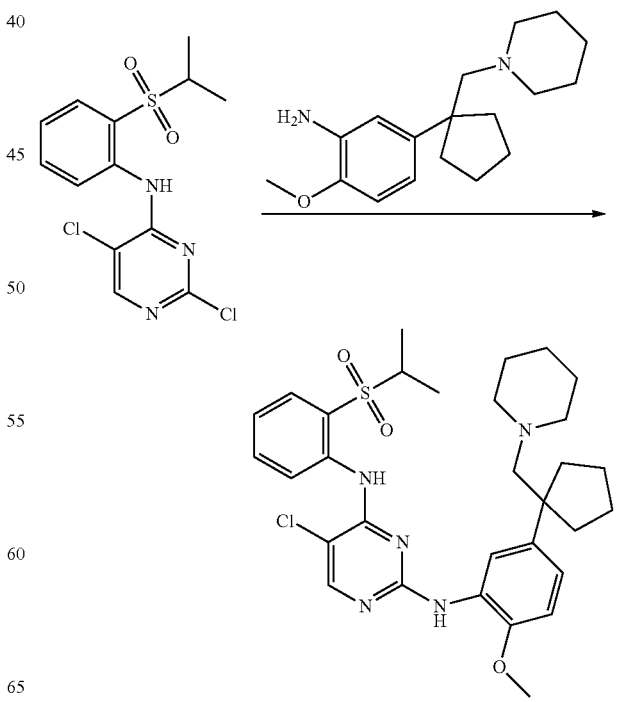

2,5-dichloro-N-(2-(isopropylsulfonyl)phenyl)pyrimidine-4-amine (50 mg, 0.14 mmol) was dissolved in 0.08 M HCl.ethoxyethanol (0.1 mL), to which the compound (46 mg, 0.16 mmol) prepared in preparative example 5 was added, followed by stirring at 80° C. for 15 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound 5-chloro-N4-(2-(isopropylsulfonyl)phenyl-N2-(2-methoxy-5-(1-(piperidine-1-ylmethyl)cyclopentyl) phenyl)pyrimidine-2,4-diamine as a white solid (33 mg, 0.055 mmol, yield: 33%).

$^1$H-NMR (300 MHz, CDCl$_3$) δ 9.47 (s, 1H), 8.46 (d, J=8.4 Hz, 1H), 8.18 (s, 1H), 8.10 (br, 1H), 7.90 (dd, J=1.2 Hz, 8.1 Hz, 1H), 7.58 (t, J=7.5 Hz, 1H), 7.44 (s, 1H), 7.22 (t, J=7.8 Hz, 1H), 6.94 (dd, J=2.1 Hz, 8.4 Hz, 1H), 6.78 (d, J=8.4 Hz, 1H), 3.87 (s, 3H), 3.28 (sept, J=6.6 Hz, 1H), 2.23 (s, 2H), 2.08 (br, 4H), 1.79 (br, 3H), 1.57 (br, 7H), 1.34-1.40 (m, 3H), 1.32 (d, J=6.6 Hz, 6H), 1.21-1.25 (m, 3H); LC/MS 598.3 [M+H$^+$].

Example 6: Preparation of 5-chloro-N4-(2-(isopropylsulfonyl)phenyl)-N2-(2-methoxy-5-(1-(morpholinomethyl)cyclopentyl)phenyl)pyrimidine-2,4-diamine

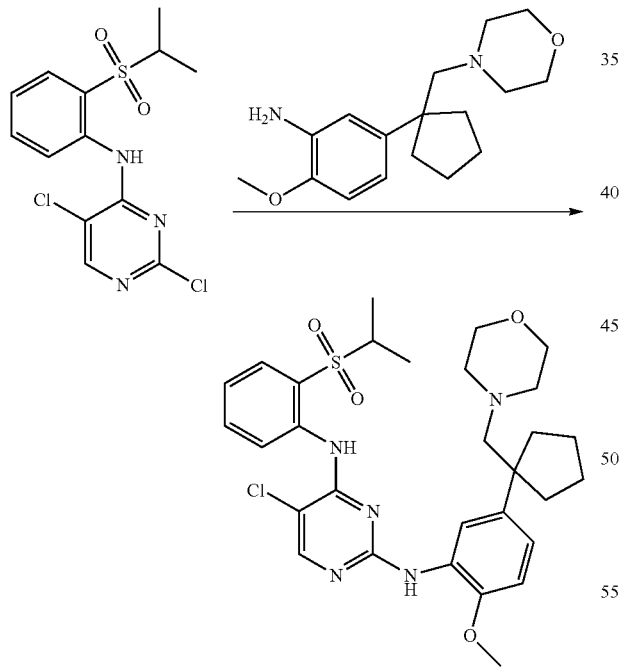

2,5-dichloro-N-(2-(isopropylsulfonyl)phenyl)pyrimidine-4-amine (50 mg, 0.14 mmol) was dissolved in 0.08 M HCl.ethoxyethanol (0.1 mL), to which the compound (46 mg, 0.16 mmol) prepared in preparative example 6 was added, followed by stirring at 100° C. for 24 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound 5-chloro-N4-(2-(isopropylsulfonyl)phenyl)-N2-(2-methoxy-5-(1-(morpholinomethyl)cyclopentyl)phenyl)pyrimidine-2,4-diamine as a white solid (26 mg, 0.043 mmol, yield: 30%).

$^1$H-NMR (300 MHz, CDCl$_3$) δ 9.49 (s, 1H), 8.49 (d, J=8.4 Hz, 1H), 8.19 (s, 1H), 8.17 (br, 1H), 7.90 (d, J=7.8 Hz, 1H), 7.59 (t, J=7.5 Hz, 1H), 7.43 (s, 1H), 7.23 (t, J=7.8 Hz, 1H), 6.99 (dd, J=1.8 Hz, 8.4 Hz, 1H), 6.78 (d, J=8.4 Hz, 1H), 3.87 (s, 3H), 3.49 (t, J=4.5 Hz, 4H), 3.28 (sept, J=6.6 Hz, 1H), 2.30 (s, 2H), 2.12 (t, J=4.5 Hz, 4H), 1.61-1.84 (m, 8H), 1.32 (d, J=6.6 Hz, 6H); LC/MS 600.1 [M+H$^+$].

Example 7: Preparation of N-(3-(5-chloro-4-(2-(isopropylsulfonyl)phenylamino)pyrimidine-2-ylamino)-4-methoxyphenethyl)acetamide

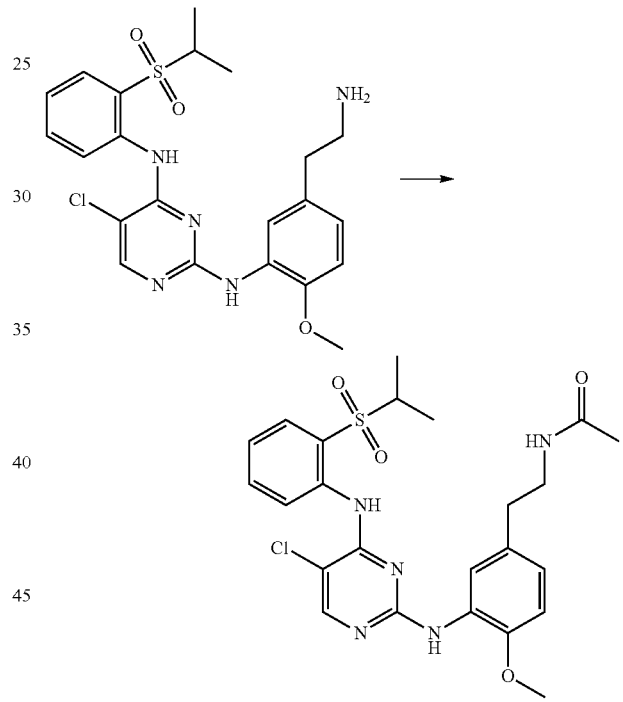

2,5-dichloro-N-(2-(isopropylsulfonyl)phenyl)pyrimidine-4-amine (50.0 mg, 0.105 mmol) was dissolved in dichloromethane (1 mL), to which trimethylamine (11 mg, 0.11 mmol) and acetic anhydride (11 mg, 0.11 mmol) were added, followed by stirring at room temperature for 3 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: dichloromethane/methanol, 10/1) to give the target compound N-(3-(5-chloro-4-(2-(isopropylsulfonyl)phenylamino)pyrimidine-2-ylamino)-4-methoxyphenethyl)acetamide as a white solid (47 mg, 0.091 mmol, yield: 87%).

$^1$H-NMR (300 MHz, CDCl$_3$) δ 9.57 (s, 1H), 8.57-8.54 (m, 1H), 8.20-8.18 (m, 2H), 7.96-7.94 (m, 1H), 7.67-7.28 (m,

2H), 6.84-6.82 (m, 2H), 5.42-5.36 (m, 1H), 3.92 (s, 3H), 3.40 (s, 2H), 3.28-3.26 (m, 1H), 2.71-2.70 (m, 2H), 2.25 (s, 1H), 1.94 (s, 3H), 1.32 (s, 6H)

Example 8: Preparation of N-(3-(5-chloro-4-(2-(isopropylsulfonyl)phenylamino)pyrimidine-2-ylamino)-4-methoxyphenethyl) methanesulfonamide

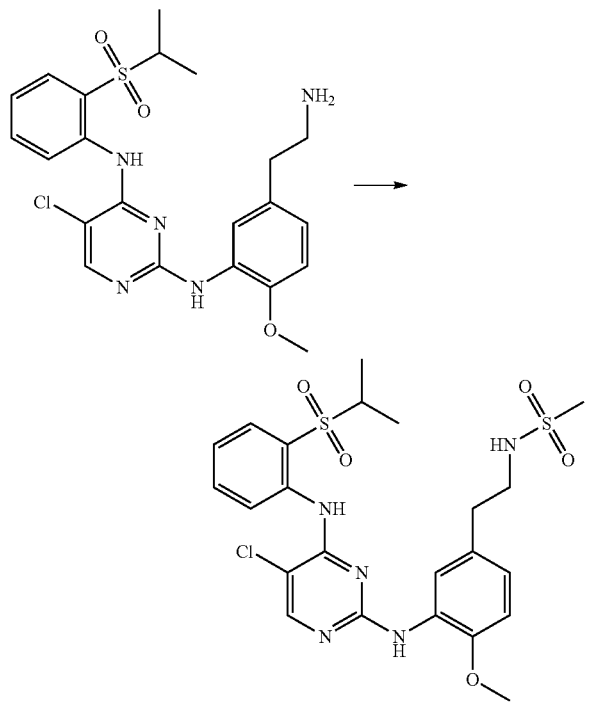

2,5-dichloro-N-(2-(isopropylsulfonyl)phenyl)pyrimidine-4-amine (50.0 mg, 0.105 mmol) was dissolved in dichloromethane (1 mL), to which methanesulfonylchloride (13 mg, 0.12 mmol) was added at 0° C. Trimethylamine (11 mg, 0.11 mmol) was added thereto, followed by stirring at room temperature for 6 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: dichloromethane/methanol, 10/1) to give the target compound N-(3-(5-chloro-4-(2-(isopropylsulfonyl)phenylamino)pyrimidine-2-ylamino)-4-methoxyphenethyl) methanesulfonamide as a white solid (55 mg, 0.10 mmol, yield: 95%).

$^1$H-NMR (300 MHz, CDCl$_3$) δ d 9.55 (s, 1H), 8.54 (d, J=8.4 Hz, 1H), 8.19 (s, 1H), 7.95 (d, J=7.8 Hz, 1H) 7.69 (t, J=7.8 Hz, 1H), 7.57 (s, 1H), 6.8-6.78 (m, 1H), 3.90 (s, 3H), 3.32-3.24 (m, 3H), 2.82 (s, 3H), 2.77 (t, J=6.3 Hz, 2H), 1.33 (d, J=6.9 Hz, 6H)

Example 9: Preparation of 5-chloro-N2-(5-(2-(dimethylamino)ethyl)-2-methoxyphenyl)-N4-(2-(isopropylsulfonyl)phenyl)pyrimidine-2,4-diamine

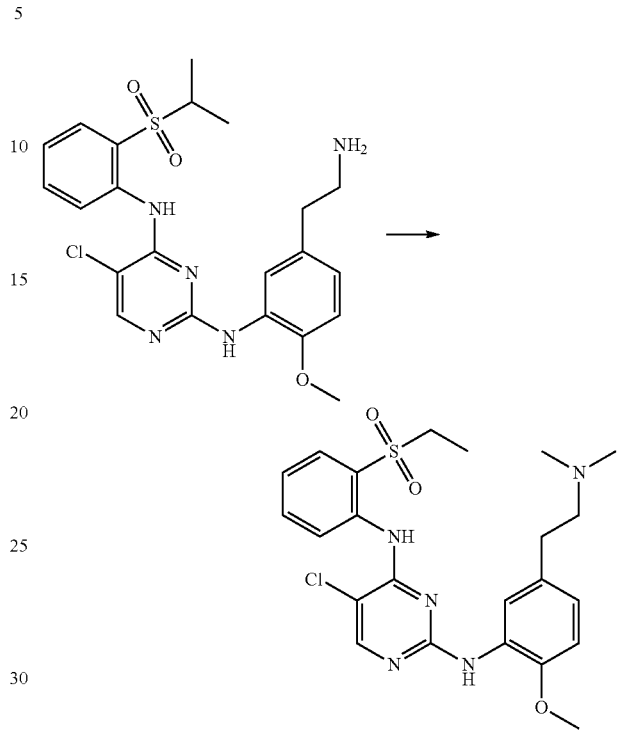

2,5-dichloro-N-(2-(isopropylsulfonyl)phenyl)pyrimidine-4-amine (50.0 mg, 0.105 mmol) was dissolved in tetrahydrofuran (1 mL), to which trimethylamine (21 mg, 0.21 mmol) and methyliodide (15 mg, 0.105 mmol) were added. The reaction mixture was reflux-stirred for 4 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: dichloromethane/methanol, 10/1) to give the target compounds 5-chloro-N2-(5-(2-(dimethylamino)ethyl)-2-methoxyphenyl)-N4-(2-(isopropylsulfonyl)phenyl)pyrimidine-2,4-diamine (Rf 0.6; mg, 0.020 mmol, yield: 19%) and 5-chloro-N4-(2-(isopropylsulfonyl)phenyl)-N2-(2-methoxy-5-(2-(methylamino)ethyl)phenyl)pyrimidine-2,4-diamine (Rf 0.7; 27 mg, 0.055 mmol, yield: 52%) as white solids.

The following NMR and LC/MS data are the values obtained from 5-chloro-N2-(5-(2-(dimethylamino)ethyl)-2-methoxyphenyl)-N4-(2-(isopropylsulfonyl)phenyl)pyrimidine-2,4-diamine.

$^1$H-NMR (300 MHz, CDCl$_3$) δ d 9.55 (s, 1H), 8.54 (d, J=8.7 Hz, 1H), 8.16 (d, J=6.3 Hz, 2H), 7.87 (d, J=7.8 Hz, 1H), 7.63-7.58 (m, 1H), 7.46 (s, 1H), 3.83 (s, 3H), 3.61-3.59 (m, 1H), 2.62 (s, 6H), 1.64 (d, J=9.6 Hz, 6H)

Example 10: Preparation of 5-chloro-N4-(2-(isopropylsulfonyl)phenyl)-N2-(2-methoxy-5-(2-(methylamino)ethyl)phenyl)pyrimidine-2,4-diamine

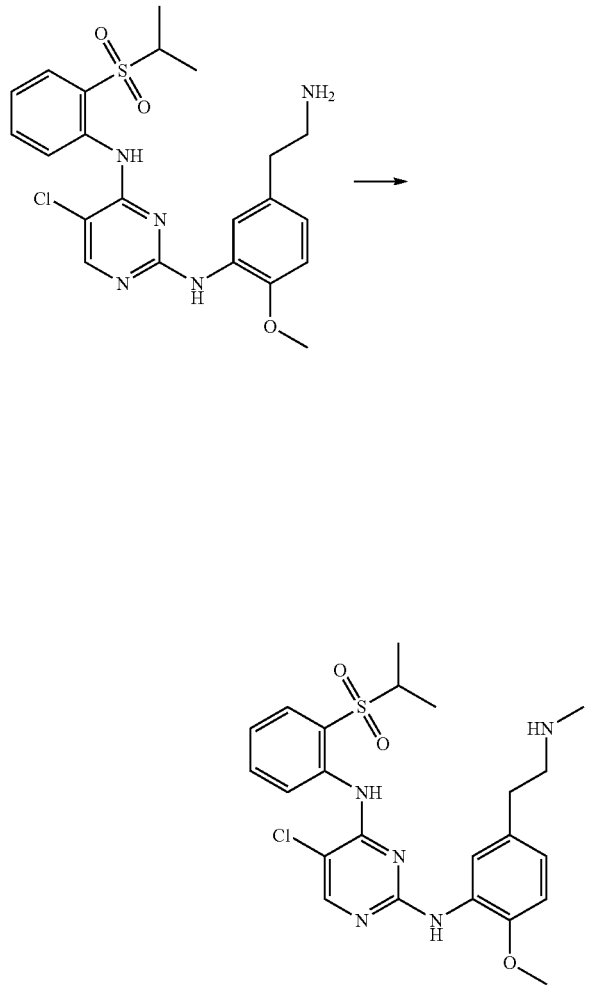

Example 10 was performed in the same manner as described in Example 9. As a result, the target compounds 5-chloro-N4-(2-(isopropylsulfonyl)phenyl)-N2-(2-methoxy-5-(2-(methylamino)ethyl)phenyl)pyrimidine-2,4-diamine (Rf 0.7; 27 mg, 0.055 mmol, yield: 52%) and 5-chloro-N2-(5-(2-(dimethylamino)ethyl)-2-methoxyphenyl)-N4-(2-(isopropylsulfonyl)phenyl)pyrimidine-2,4-diamine (Rf 0.6; 10 mg, 0.020 mmol, yield: 19%), the compound prepared in Example 9, were obtained.

The following NMR and LC/MS data are the values obtained from 5-chloro-N4-(2-(isopropylsulfonyl)phenyl)-N2-(2-methoxy-5-(2-(methylamino)ethyl)phenyl)pyrimidine-2,4-diamine.

$^1$H-NMR (300 MHz, CDCl$_3$) δ 9.55-9.49 (m, 1H), 8.50-8.47 (m, 1H), 8.12 (s, 2H), 7.87-7.84 (s, 1H), 7.64-7.59 (m, 1H), 7.43 (s, 1H), 6.85-6.75 (m, 2H), 3.81 (s, 3H), 3.63 (br, s, 4H), 3.22-3.18 (m, 1H), 3.07 (s, 3H), 2.63 (s, 1H), 2.57 (s, 2H), 2.10 (s, 1H), 2.01-1.95 (m, 1H), 1.25-1.23 (d, J=6.3 Hz, 6H).

Example 11: Preparation of N2-(5-(2-(benzylamino)ethyl)-2-methoxyphenyl)-5-chloro-N4-(2-(isopropylsulfonyl)phenyl)pyrimidine-2,4-diamine

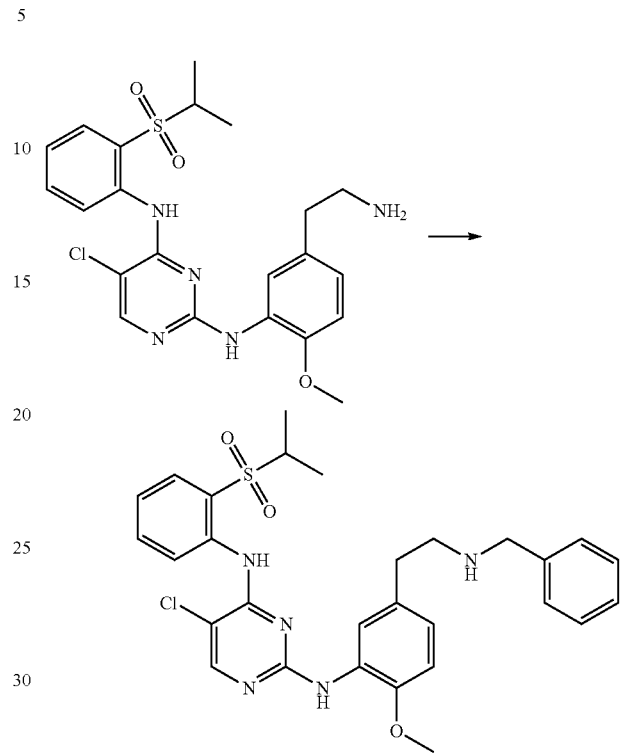

2,5-dichloro-N-(2-(isopropylsulfonyl)phenyl)pyrimidine-4-amine (50.0 mg, 0.105 mmol) was dissolved in dichloromethane (2 mL), to which sodium sulfate (15 mg, 0.11 mmol) and benzaldehyde (10 mg, 0.090 mmol) were added, followed by stirring at room temperature for 4 hours. The solid generated in the mixture was filtered, and the solvent was distillated under reduced pressure. The mixture was dissolved in methanol (2 mL), to which sodium borohydride was added, followed by stirring for 1 hour. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: dichloromethane/methanol, 10/1) to give the target compound N2-(5-(2-(benzylamino)ethyl)-2-methoxyphenyl)-5-chloro-N4-(2-(isopropylsulfonyl)phenyl)pyrimidine-2,4-diamine as a white solid (28 mg, 0.49 mmol, yield: 47%).

$^1$H-NMR (300 MHz, CDCl$_3$) δ 9.53 (m, 1H), 8.56 (d, J=8.1 Hz, 1H), 8.14 (s, 2H), 7.92 (dd, J=7.8 Hz, 7.5 Hz, 1H), 7.68-7.65 (m, 1H), 7.55 (s, 1H), 7.32-7.30 (m, 4H), 6.8 (s, 2H), 3.87 (s, 3H), 3.80 (s, 2H), 3.28-3.18 (m, 1H), 2.82 (s, 4H), 1.31 (d, J=6.9H z, 6H); LC/MS (ESI) m/z 566.3 [M+H]$^+$

Example 12: Preparation of N-(3-(5-chloro-4-(2-(isopropylsulfonyl)phenylamino)pyrimidine-2-ylamino)-4-methoxyphenethyl)-2-phenylacetamide

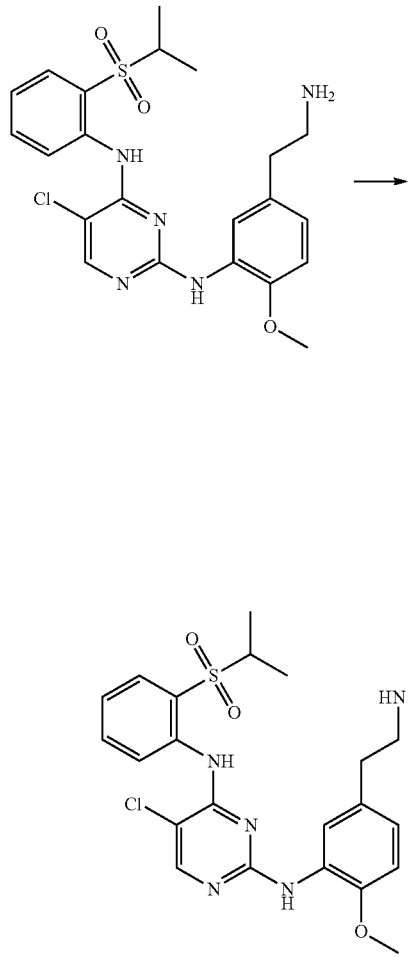

N2-(5-(2-aminoethyl)-2-methoxyphenyl)-5-chloro-N4-(2-(isopropylsulfonyl)phenyl)pyrimidine-2,4-diamine (50.0 mg, 0.105 mmol) was dissolved in dichloromethane (2 mL), to which trimethylamine (16 mg, 0.16 mmol) and phenylacetylchloride (16 mg, 0.11 mmol) were added at 0° C., followed by stirring at room temperature for 4 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: dichloromethane/methanol, 10/1) to give the target compound N-(3-(5-chloro-4-(2-(isopropylsulfonyl)phenylamino)pyrimidine-2-ylamino)-4-methoxyphenethyl)-2-phenylacetamide as a white solid (36 mg, 0.49 mmol, yield: 58%).

$^1$H-NMR (300 MHz, CDCl$_3$) δ 9.49 (s, 1H), 8.44 (d, J=8.1 Hz, 1H), 8.17 (s, 1H), 8.02 (s, 1H), 7.89 (dd, J=8.1, 7.8 Hz, 1H), 7.59 (s, 2H), 7.16-7.14 (m, 3H), 6.75 (d, J=8.1 Hz, 1H), 6.62-6.59 (m, 1H), 5.28-5.26 (m, 1H), 3.88 (s, 3H), 3.50 (s, 2H), 3.33-3.21 (m, 3H), 2.59-2.54 (m, 2H), 1.30 (d, J=6.6 Hz, 6H); LC/MS (ESI) m/z 594.12 [M+H]$^+$

Example 13: Preparation of 5-chloro-N2-(5-(2-(ethylamino)ethyl)-2-methoxyphenyl)-N4-(2-(isopropylsulfonyl)phenyl)pyrimidine-2,4-diamine

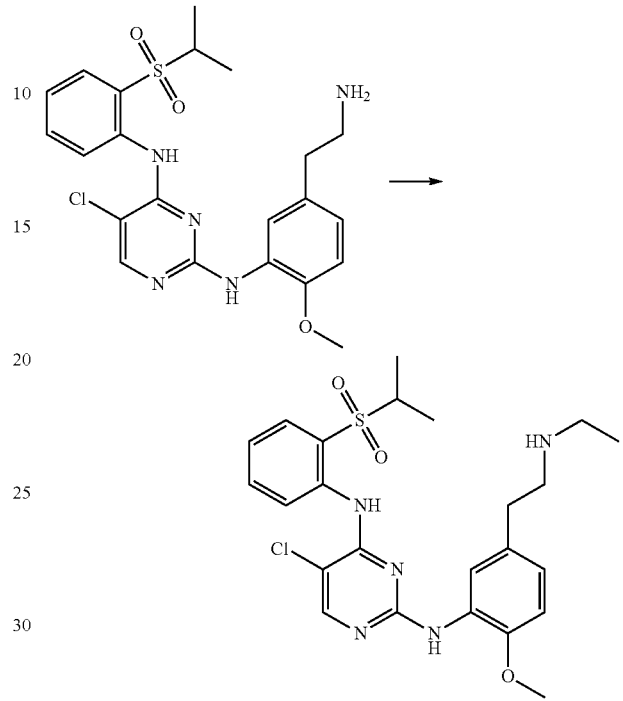

2,5-dichloro-N-(2-(isopropylsulfonyl)phenyl)pyrimidine-4-amine (67.0 mg, 0.180 mmol) was dissolved in tetrahydrofuran (2.7 mL), to which trimethylamine (103 mg, 0.798 mmol) and ethyliodide (133 mg, 0.795 mmol) were added, followed by stirring at room temperature for 4 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: dichloromethane/methanol, 10/1) to give the target compounds 5-chloro-N2-(5-(2-(ethylamino)ethyl)-2-methoxyphenyl)-N4-(2-(isopropylsulfonyl)phenyl)pyrimidine-2,4-diamine (Rf 0.6; 19.8 mg, 0.0393 mmol, yield: 22%) and 5-chloro-N2-(5-(2-(diethylamino)ethyl)-2-methoxyphenyl)-N4-(2-(isopropylsulfonyl)phenyl)pyrimidine-2,4-diamine (Rf 0.7; 18.0 mg, 0.0338 mmol, yield: 19%) as white solids.

The following NMR and LC/MS data are the values obtained from 5-chloro-N2-(5-(2-(ethylamino)ethyl)-2-methoxyphenyl)-N4-(2-(isopropylsulfonyl)phenyl)pyrimidine-2,4-diamine.

$^1$H-NMR (300 MHz, CDCl$_3$) δ 9.62 (s, 1H), 8.60 (d, J=4.8 Hz, 1H), 8.23 (d, J=6.9 Hz, 2H), 7.94 (d, J=4.2 Hz, 1H), 7.74-7.71 (m, 1H), 7.52 (s, 1H), 7.36-7.33 (m, 1H), 6.95 (d, J=4.8 Hz, 1H), 6.86 (d, J=4.8 Hz, 1H), 3.90 (s, 3H), 3.69 (s, 1H), 3.29-3.26 (m, 1H), 3.24 (d, J=3 Hz, 4H), 3.13 (d, J=4.5 Hz, 2H), 1.54 (t, J=4.2 Hz, 3H), 1.34 (d, J=3.9 Hz, 6H); LC/MS (ESI) m/z 504 [M+H]$^+$.

Example 14: Preparation of 5-chloro-N2-(5-(2-(di-ethylamino)ethyl)-2-methoxyphenyl)-N4-(2-(isopropylsulfonyl)phenyl)pyrimidine-2,4-diamine Example 15: Preparation of 5-chloro-N2-(5-(2-(isopropylamino)ethyl)-2-methoxyphenyl)-N4-(2-(isopropylsulfonyl)phenyl)pyrimidine-2,4-diamine

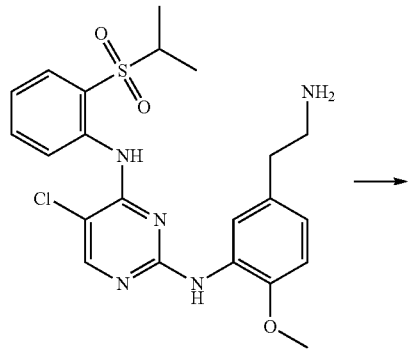

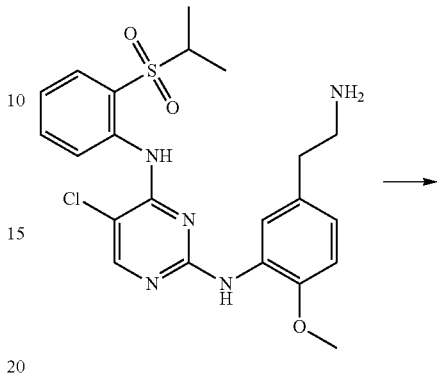

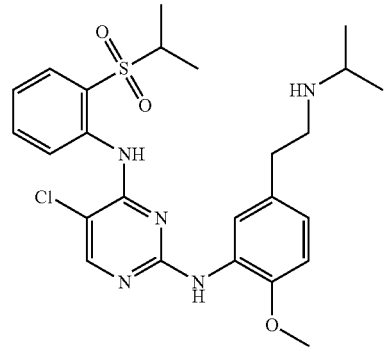

Example 14 was performed in the same manner as described in Example 13. As a result, the target compounds 5-chloro-N2-(5-(2-(diethylamino)ethyl)-2-methoxyphenyl)-N4-(2-(isopropylsulfonyl)phenyl)pyrimidine-2,4-diamine (Rf 0.7; 18.0 mg, 0.0338 mmol, yield: 19%) and 5-chloro-N2-(5-(2-(ethylamino)ethyl)-2-methoxyphenyl)-N4-(2-(isopropylsulfonyl)phenyl)pyrimidine-2,4-diamine (Rf 0.6; 19.8 mg, 0.0393 mmol, yield: 22%), the compound prepared in Example 13, were obtained.

The following NMR and LC/MS data are the values obtained from 5-chloro-N2-(5-(2-(diethylamino)ethyl)-2-methoxyphenyl)-N4-(2-(isopropylsulfonyl)phenyl)pyrimidine-2,4-diamine.

$^1$H-NMR (300 MHz, CDCl$_3$) δ 9.67 (s, 1H), 8.65 (d, J=5.1 Hz, 1H), 8.27 (s, 1H), 8.23 (s, 1H), 7.96 (dd, J=4.8 Hz, 4.5 Hz, 1H), 7.71-7.69 (m, 1H), 7.34 (s, 1H), 6.94 (dd, J=5.1 Hz, 6.88 (d, J=5.1 Hz, 1H), 3.93 (s, 3H), 3.69-3.61 (m, 4H), 3.32-3.27 (m, 1H), 3.18 (d, J=3.9 Hz, 5H), 1.46-1.43 (m, 6H), 1.36 (d, J=4.2 Hz, 6H); LC/MS (ESI) m/z 532 [M+H]$^+$.

2,5-dichloro-N-(2-(isopropylsulfonyl)phenyl)pyrimidine-4-amine (50.0 mg, 0.105 mmol) was dissolved in dimethylformamide (1 mL), to which cesium hydroxide-water (103 mg, 0.210 mmol) and 2-bromopropane (133 mg, 0.105 mmol) were added, followed by stirring at room temperature for 48 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: dichloromethane/methanol, 10/1) to give the target compound 5-chloro-N2-(5-(2-(isopropylamino)ethyl)-2-methoxyphenyl)-N4-(2-(isopropylsulfonyl)phenyl)pyrimidine-2,4-diamine as a white solid (8.0 mg, 0.015 mmol, yield: 15%).

$^1$H-NMR (300 MHz, CDCl$_3$) δ 9.57 (s, 1H), 8.60 (d, J=8.1 Hz, 1H), 8.20 (s, 1H), 8.16 (s, 1H), 7.92 (dd, J=1.2 Hz, 8.1 Hz), 7.73-7.68 (m, 1H), 7.50 (s, 1H), 7.32 (d, J=7.2 Hz, 1H), 6.88-6.79 (m, 2H), 3.87 (s, 3H)

Example 16: Preparation of 1-(3-(5-chloro-4-(2-(isopropylsulfonyl)phenylamino)pyrimidine-2-ylamino)-4-methoxyphenethyl)-3-ethylurea

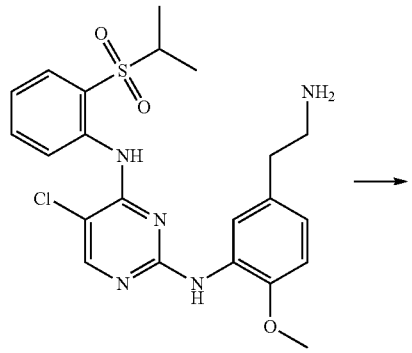

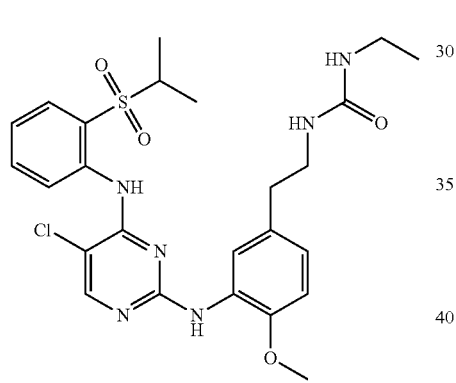

2,5-dichloro-N-(2-(isopropylsulfonyl)phenyl)pyrimidine-4-amine (50.0 mg, 0.105 mmol) was dissolved in dichloromethane (1 mL), to which triethylamine (16 mg, 0.16 mmol) and ethylisocyanate (9.1 mg, 0.16 mmol) were added at 0° C., followed by stirring at room temperature for 18 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate) to give the target compound 1-(3-(5-chloro-4-(2-(isopropylsulfonyl)phenylamino)pyrimidine-2-ylamino)-4-methoxyphenethyl)-3-ethylurea as a white solid (20 mg, 0.037 mmol, yield: 35%).

$^1$H-NMR (300 MHz, CDCl$_3$) δ 9.46 (s, 1H), 8.46 (d, J=8.4 Hz, 1H), 8.09 (d, J=9 Hz, 2H), 7.87 (dd, J=1.2 Hz, 7.8 Hz, 1H), 7.61-7.49 (m, 1H), 7.49 (s, 1H), 6.77-6.70 (m, 2H), 4.10-4.03 (m, 2H), 3.81 (s, 1H), 3.28-3.20 (m, 2H), 3.18 (d, J=6.9 Hz, 1H), 3.13-3.02 (m, 2H), 2.62-2.58 (m, 2H), 1.53 (s, 1H), 1.25 (d, J=6.9 Hz, 6H), 1.03-0.98 (m, 3H); LC/MS (ESI) m/z 547.0 [M+H]$^+$

Example 17: Preparation of 1-(3-(5-chloro-4-(2-(isopropylsulfonyl)phenylamino)pyrimidine-2-ylamino)-4-methoxyphenethyl)-3-cyclohexylurea

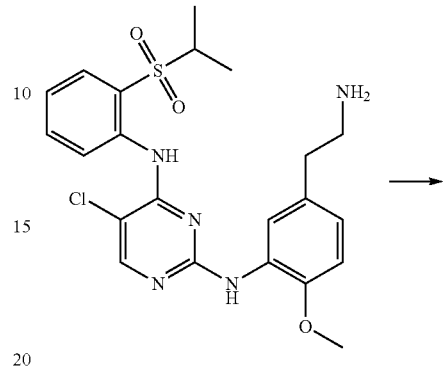

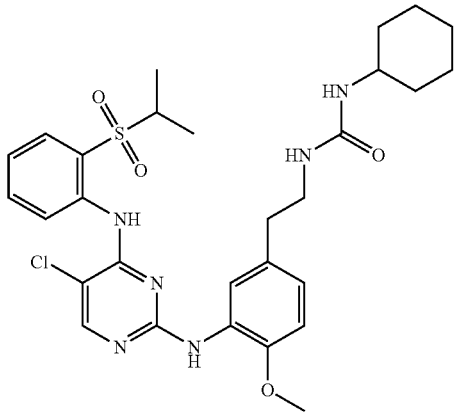

2,5-dichloro-N-(2-(isopropylsulfonyl)phenyl)pyrimidine-4-amine (50.0 mg, 0.105 mmol) was dissolved in dichloromethane (1 mL), to which triethylamine (16 mg, 0.16 mmol) and cyclohexylisocyanate (12.5 mg, 0.100 mmol) were added at 0° C., followed by stirring at room temperature for 18 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 5/1) to give the target compound 1-(3-(5-chloro-4-(2-(isopropylsulfonyl)phenylamino)pyrimidine-2-ylamino)-4-methoxyphenethyl)-3-cyclohexylurea as a white solid (48 mg, 0.080 mmol, yield: 76%).

$^1$H-NMR (300 MHz, CDCl$_3$) δ 9.53 (s, 1H), 8.53 (d, J=8.4 Hz, 1H), 8.17 (d, J=12.3 Hz, 2H), 7.93 (d, J=7.8 Hz, 1H), 7.67-7.62 (m, 1H), 7.58 (s, 1H), 7.29-7.24 (m, 1H), 6.84-6.77 (m, 1H), 4.17-4.08 (m, 3H), 3.88 (s, 1H), 3.33-3.19 (m, 3H), 2.69 (t, J=6.6 Hz, 2H), 1.87-1.84 (m, 2H), 1.68-1.55 (m, 4H), 1.32 (d, J=6.9 Hz, 6H), 1.25-1.08 (m, 4H); LC/MS (ESI) m/z 603.1 [M+H]$^+$.

Example 18: Preparation of 1-(3-(5-chloro-4-(2-(isopropylsulfonyl)phenylamino)pyrimidine-2-ylamino)-4-methoxyphenethyl)-3-phenylurea

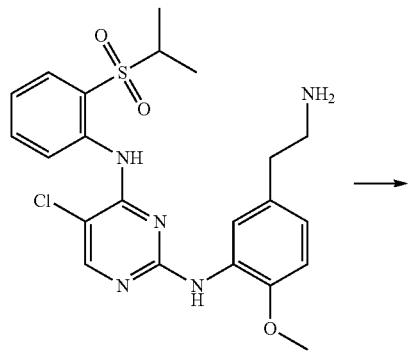

Example 19: Preparation of 1-(3-(5-chloro-4-(2-(isopropylsulfonyl)phenylamino)pyrimidine-2-ylamino)-4-methoxyphenethyl)-3-methylthiourea

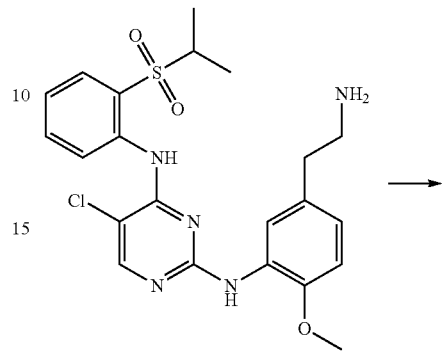

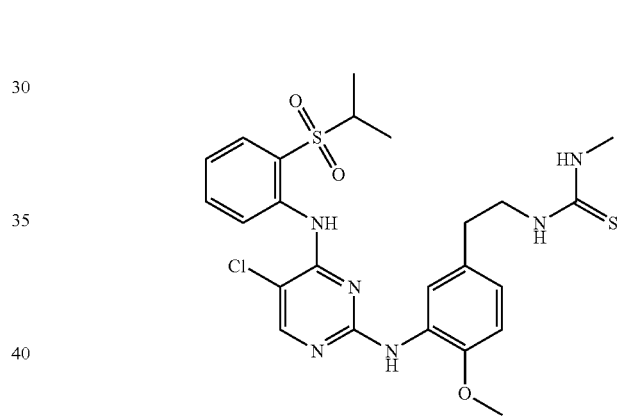

2,5-dichloro-N-(2-(isopropylsulfonyl)phenyl)pyrimidine-4-amine (50.0 mg, 0.105 mmol) was dissolved in dichloromethane (1 mL), to which triethylamine (16 mg, 0.16 mmol) and phenylisocyanate (12 mg, 0.10 mmol) were added at 0° C., followed by stirring at room temperature for 18 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 1-(3-(5-chloro-4-(2-(isopropylsulfonyl)phenylamino)pyrimidine-2-ylamino)-4-methoxyphenethyl)-3-phenylurea as a white solid (36 mg, 0.042 mmol, yield: 42%).

$^1$H-NMR (300 MHz, CDCl$_3$) δ 9.51 (s, 1H), 8.50 (d, J=8.4 Hz, 1H), 8.13 (s, 1H), 7.91 (dd, J=1.2 Hz, 7.8 Hz, 1H), 7.67-7.61 (m, 1H), 7.56 (s, 1H), 7.24-7.17 (m, 4H), 7.05-7.01 (m, 1H), 6.79 (s, 2H), 6.42 (s, 1H), 4.80-4.76 (m, 1H), 4.15-4.08 (m, 1H), 3.86 (s, 3H), 3.41-3.35 (m, 1H), 3.27-3.18 (m, 1H), 2.71 (t, J=6.6 Hz, 2H), 1.68 (s, 1H), 1.30 (d, J=6.9 Hz, 6H), 1.25-1.23 (m, 1H); LC/MS (ESI) m/z 597.0 [M+H]$^+$.

2,5-dichloro-N-(2-(isopropylsulfonyl)phenyl)pyrimidine-4-amine (50.0 mg, 0.105 mmol) was dissolved in dichloromethane (1 mL), to which triethylamine (16 mg, 0.16 mmol) and methylisothiocyanate (7.3 mg, 0.10 mmol) were added at 0° C., followed by stirring at room temperature for 18 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound 1-(3-(5-chloro-4-(2-(isopropylsulfonyl)phenylamino)pyrimidine-2-ylamino)-4-methoxyphenethyl)-3-methylthiourea as a white solid (35 mg, 0.060 mmol, yield: 60%).

$^1$H-NMR (300 MHz, CDCl$_3$) δ 9.48 (s, 1H), 8.48 (d, J=8.4 Hz, 1H), 8.12 (d, J=4.8 Hz, 2H), 7.87 (d, J=7.8 Hz, 1H), 7.61 (t, J=7.5 Hz, 1H), 7.50 (s, 1H), 6.75 (br, s, 2H), 5.67-5.62 (m, 1H), 5.51 (br, s, 1H), 4.08-4.01 (m, 1H), 3.82 (s, 3H), 3.569-3.55 (m, 2H), 3.24-3.14 (m, 1H), 2.81 (d, J=4.2 Hz, 3H), 2.74 (t, J=6.6 Hz, 2H), 1.97 (s, 1H), 1.26 (d, J=6.6 Hz, 6H; LC/MS (ESI) m/z 550.9 [M+H]$^+$.

Example 20: Preparation of 1-benzyl-3-(3-(5-chloro-4-(2-(isopropylsulfonyl)phenylamino)pyrimidine-2-ylamino)-4-methoxyphenethyl)thiourea

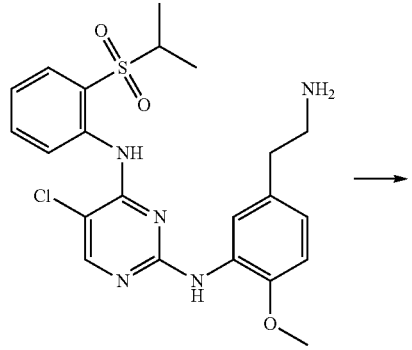

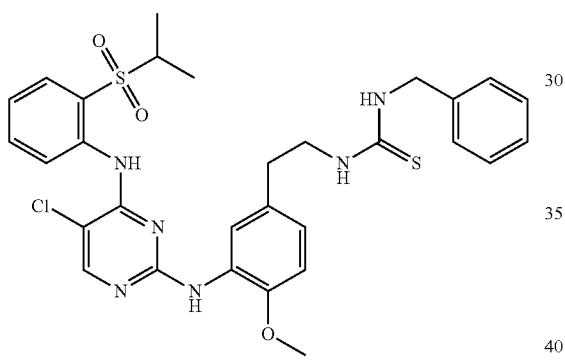

2,5-dichloro-N-(2-(isopropylsulfonyl)phenyl)pyrimidine-4-amine (50.0 mg, 0.105 mmol) was dissolved in dichloromethane (1 mL), to which triethylamine (16 mg, 0.16 mmol) and benzylisothiocyanate (15 mg, 0.10 mmol) were added at 0° C., followed by stirring at room temperature for 18 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate) to give the target compound 1-benzyl-3-(3-(5-chloro-4-(2-(isopropylsulfonyl)phenylamino)pyrimidine-2-ylamino)-4-methoxyphenethyl)thiourea as a white solid (28 mg, 0.043 mmol, yield: 43%).

$^1$H-NMR (300 MHz, CDCl$_3$) δ 9.56 (s, 1H), 8.52 (d, J=4.8 Hz, 1H), 8.16 (d, J=4.5 Hz, 2H), 7.95 (dd, J=0.9, 4.8 Hz, 1H), 7.66-7.65 (m, 1H), 7.58 (s, 1H), 7.31-7.28 (m, 3H), 7.22 (d, J=4.2 Hz, 2H), 6.81 (d, J=4.8 Hz, 1H), 6.75-6.74 (m, 1H), 4.50 (br, s, 2H), 4.16 (m, 1H), 3.91 (s, 3H), 3.61 (br, s, 2H), 3.29-3.24 (m, 1H), 2.77 (t, J=3.9 Hz, 2H), 1.62 (br, s, 1H), 1.33 (d, J=4.2 Hz, 6H), 1.29-1.26 (m, 2H); LC/MS (ESI) m/z 627.0 [M+H]$^+$.

Example 21: Preparation of 5-chloro-N4-(2-(isopropylsulfonyl)phenyl)-N2-(2-methoxy-5-(2-(piperidine-1-yl)ethyl)phenyl)pyrimidine-2,4-diamine

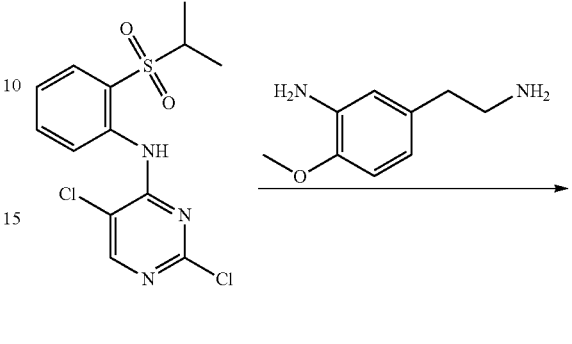

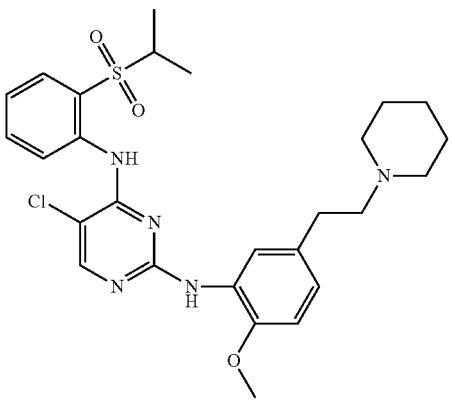

2,5-dichloro-N-(2-(isopropylsulfonyl)phenyl)pyrimidine-4-amine (50 mg, 0.14 mmol) was dissolved in 0.08 M HCl.ethoxyethanol (0.1 mL), to which the compound (0.04 g, 0.16 mmol) prepared in preparative example 7 was added, followed by stirring at 100° C. for 15 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound 5-chloro-N4-(2-(isopropylsulfonyl)phenyl)-N2-(2-methoxy-5-(2-(piperidine-1-yl)ethyl)phenyl)pyrimidine-2,4-diamine as a white solid (0.036 g, 0.066 mmol, yield: 46%).

$^1$H-NMR (300 MHz, CDCl$_3$) δ 9.54 (s, 1H), 8.57 (d, J=8.4 Hz, 1H), 8.18 (s, 1H), 8.13 (s, 1H), 7.92 (d, J=7.8 Hz, 1H), 7.67 (t, J=7.5 Hz, 1H), 7.57 (s, 1H), 7.23-7.28 (m, 1H), 6.82 (s, 2H), 3.88 (s, 3H), 3.26 (sept, J=6.9 Hz, 1H), 2.66-2.71 (m, 2H), 2.36-2.46 (m, 6H), 1.58-1.62 (m, 4H), 1.44-1.45 (m, 2H), 1.32 (d, J=6.9 Hz, 6H); LC/MS 544.0 [M+H$^+$].

Example 22: Preparation of 5-chloro-N4-(2-(isopropylsulfonyl)phenyl)-N2-(2-methoxy-5-(2-morpholinoethyl)phenyl)pyrimidine-2,4-diamine Example 23: Preparation of 1-(3-(5-chloro-4-(2-(isopropylsulfonyl)phenylamino)pyrimidine-2-ylamino)-4-methoxyphenethyl)-3-ethylthiourea

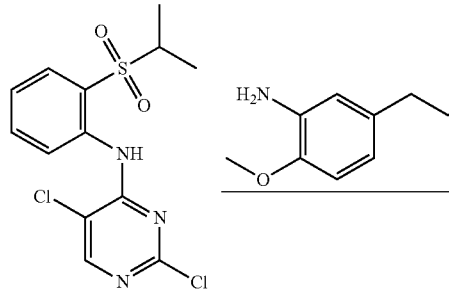
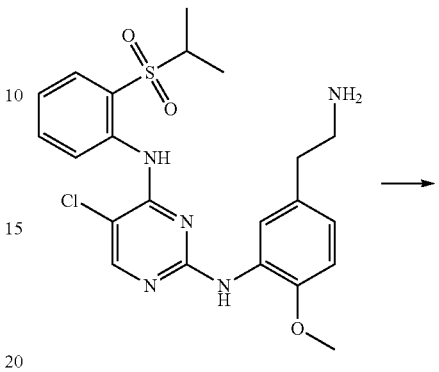

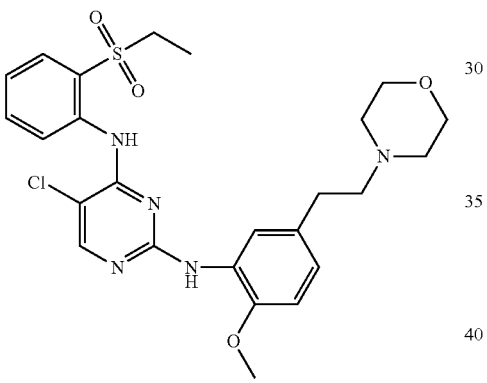
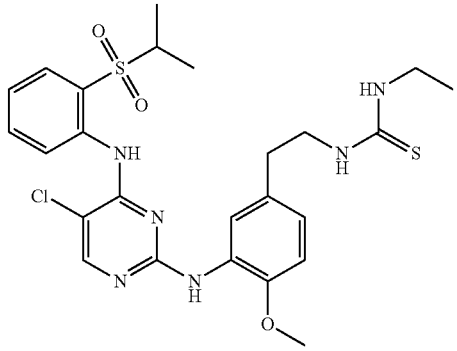

2,5-dichloro-N-(2-(isopropylsulfonyl)phenyl)pyrimidine-4-amine (50 mg, 0.14 mmol) was dissolved in 0.08 M HCl.ethoxyethanol (0.1 mL), to which the compound (0.04 g, 0.16 mmol) prepared in preparative example 8 was added, followed by stirring at 100° C. for 15 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound 5-chloro-N4-(2-(isopropylsulfonyl)phenyl)-N2-(2-methoxy-5-(2-morpholinoethyl)phenyl)pyrimidine-2,4-diamine as a white solid (0.038 g, 0.069 mmol, yield: 48%).

$^1$H-NMR (300 MHz, CDCl$_3$) δ 9.56 (s, 1H), 8.59 (d, J=8.4 Hz, 1H), 8.18 (s, 1H), 8.15 (s, 1H), 7.92 (dd, J=1.5, 8.1 Hz, 1H), 7.67 (t, J=7.2 Hz, 1H), 7.57 (s, 1H), 7.23-7.27 (m, 1H), 6.82 (s, 2H), 3.88 (s, 3H), 3.71-3.79 (m, 4H), 3.26 (sept, J=6.9 Hz, 1H), 2.66-2.72 (m, 2H), 2.44-2.59 (m, 6H), 1.32 (d, J=6.9 Hz, 6H); LC/MS 546.1 [M+H$^+$].

2,5-dichloro-N-(2-(isopropylsulfonyl)phenyl)pyrimidine-4-amine (50.0 mg, 0.105 mmol) was dissolved in dichloromethane (1 mL), to which triethylamine (16 mg, 0.16 mmol) and ethylisothiocyanate (8.7 mg, 0.10 mmol) were added at 0° C., followed by stirring at room temperature for 18 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound 1-(3-(5-chloro-4-(2-(isopropylsulfonyl)phenylamino)pyrimidine-2-ylamino)-4-methoxyphenethyl)-3-ethylthiourea as a white solid (36.5 mg, 0.060 mmol, yield: 60%).

$^1$H-NMR (300 MHz, CDCl$_3$) δ 9.58 (s, 1H), 8.57 (d, J=4.8 Hz, 1H), 8.22 (d, J=6 Hz, 2H), 7.96 (dd, J=0.6, 4.8 Hz, 1H), 7.70-7.66 (m, 1H), 7.60 (s, 1H), 6.87-6.81 (m, 2H), 4.16-4.12 (m, 1H), 3.92 (s, 1H), 3.66-3.65 (m, 2H), 3.31-3.26 (m, 2H), 2.83-2.80 (m, 2H), 1.60 (br, s, 1H), 1.35 (d, J=4.2 Hz, 6H), 1.29 (t, J=4.2 Hz, 1H), 1.17-1.14 (m, 3H); LC/MS (ESI) m/z 565.0 [M+H]$^+$.

Example 24: Preparation of 3-(3-(5-chloro-4-(2-(isopropylsulfonyl)phenylamino)pyrimidine-2-ylamino)-4-methoxyphenethylamino)propanoate

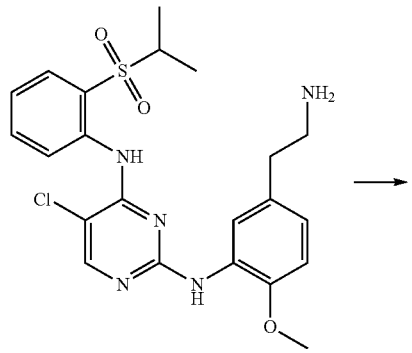

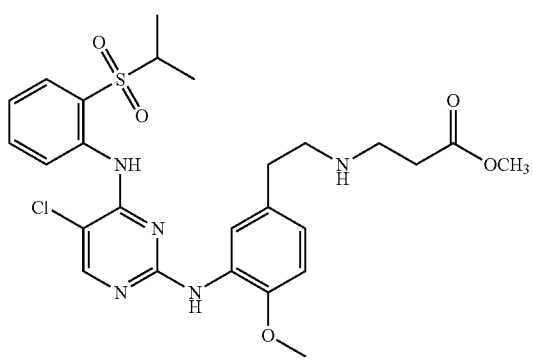

2,5-dichloro-N-(2-(isopropylsulfonyl)phenyl)pyrimidine-4-amine (50.0 mg, 0.105 mmol) was dissolved in methanol (1 mL), to which methyl acrylate (8.6 mg, 0.10 mmol) was added at 0° C., followed by stirring at room temperature for 18 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound methyl 3-(3-(5-chloro-4-(2-(isopropylsulfonyl)phenylamino)pyrimidine-2-ylamino)-4-methoxyphenethylamino)propanoate as a yellow oil (17.8 mg, 0.030 mmol, yield: 30%).

$^1$H-NMR (300 MHz, CDCl$_3$) δ 9.55 (s, 1H)), 8.57 (d, J=8.7 Hz, 1H), 8.18 (s, 2H), 7.94 (d, J=0.9, 8.4 Hz, 1H), 7.72-7.66 (m, 1H), 7.55 (s, 1H), 6.84 (s, 2H), 3.89 (s, 3H), 3.67 (s, 3H), 3.05-2.94 (m, 7H), 2.78 (s, 2H), 1.33 (d, J=6.9 Hz, 6H), 1.23-1.20 (m, 2H); LC/MS (ESI) m/z 564.0 [M+H]$^+$.

Example 25: Preparation of 5-chloro-N4-(2-(isopropylsulfonyl)phenyl)-N2-(2-methoxy-5-(2-(pyrimidine-2-ylamino)ethyl)phenyl)pyrimidine-2,4-diamine

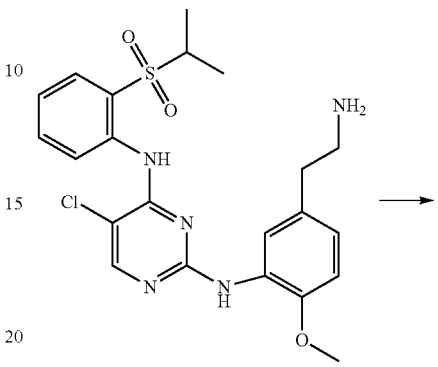

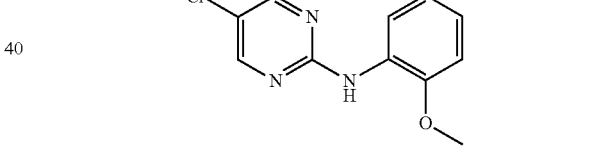

2,5-dichloro-N-(2-(isopropylsulfonyl)phenyl)pyrimidine-4-amine (50.0 mg, 0.105 mmol) was dissolved in isopropanol (1 mL), to which potassium carbonate (26 mg, 0.19 mmol) and 2-chloropyrimidine (11 mg, 0.10 mmol) were added at 0° C., followed by stirring at 110° C. for 45 minutes in a microwave reactor. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound 5-chloro-N4-(2-(isopropylsulfonyl)phenyl)-N2-(2-methoxy-5-(2-(pyrimidine-2-ylamino)ethyl)phenyl)pyrimidine-2,4-diamine as a white solid (31 mg, yield: 59%).

$^1$H-NMR (300 MHz, CDCl$_3$) δ 9.47 (s, 1H), 8.52 (d, J=8.4 Hz, 1H), 8.25-8.24 (m, 2H), 8.18 (s, 1H), 7.92 (d, J=7.8 Hz, 1H), 7.66-7.60 (m, 2H), 6.82 (s, 2H), 6.51 (br, s, 1H), 5.05-5.01 (m, 1H), 3.88 (s, 3H), 3.65-3.63 (m, 1H), 3.54-3.52 (m, 2H), 3.28-3.22 (m, 1H), 2.79-2.74 (m, 2H), 1.30 (d, J=6.9 Hz, 6H); LC/MS (ESI) m/z 556.1 [M+H]$^+$.

Example 26: Preparation of methyl 2-(3-(5-chloro-4-(2-(isopropylsulfonyl)phenylamino)pyrimidine-2-ylamino)-4-methoxyphenethylamino)acetate

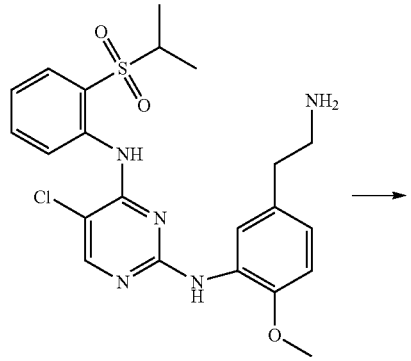

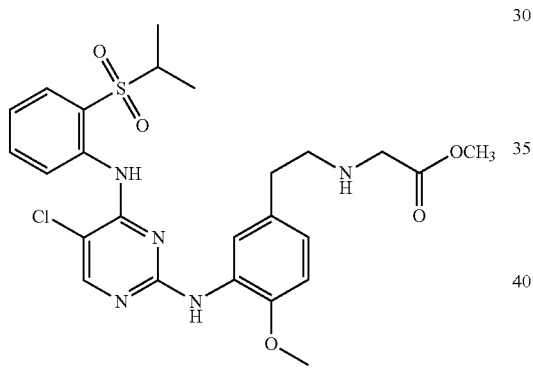

2,5-dichloro-N-(2-(isopropylsulfonyl)phenyl)pyrimidine-4-amine (50.0 mg, 0.105 mmol) was dissolved in tetrahydrofuran (1 mL), to which methylbromoacetate (15 mg, 0.10 mmol) and triethylamine (10 mg, 0.10 mmol) were added at 0° C., followed by stirring at room temperature for 4 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound methyl 2-(3-(5-chloro-4-(2-(isopropylsulfonyl)phenylamino)pyrimidine-2-ylamino)-4-methoxyphenethylamino)acetate as a white solid (28 mg, yield: 49%).

$^1$H-NMR (300 MHz, CDCl$_3$) δ 9.52 (s, 1H), 8.56 (d, J=8.4 Hz, 1H), 8.17 (s, 1H), 8.14 (s, 1H), 7.94 (d, J=7.8 Hz, 1H), 7.73-7.64 (m, 2H), 7.56-7.51 (m, 1H), 6.82 (s, 2H), 3.88 (s, 3H), 3.70 (s, 3H), 3.37 (s, 2H), 3.28-3.21 (m, 1H), 2.77 (d, J=6.3 Hz, 2H), 2.71 (d, J=6.0 Hz, 2H), 1.32 (d, J=6.9 Hz, 6H), 0.89-0.83 (m, 4H)

Example 27: Preparation of 2-(3-(5-chloro-4-(2-(isopropylsulfonyl)phenylamino)pyrimidine-2-ylamino)-4-methoxyphenethylamino)acetic acid

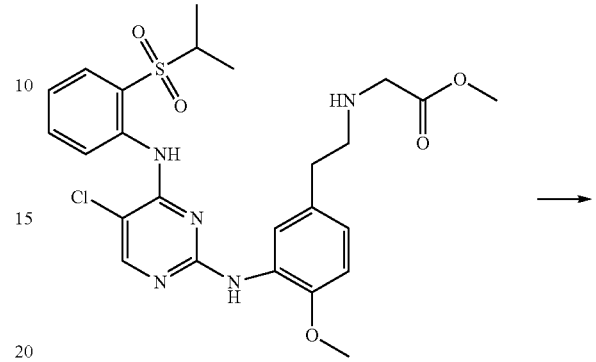

Methyl 2-(3-(5-chloro-4-(2-(isopropylsulfonyl)phenylamino)pyrimidine-2-ylamino)-4-methoxyphenethylamino)acetate (15 mg, 0.027 mmol) was dissolved in ethylacetate, to which water was added, followed by reflux-stirring for 12 hours. The reaction mixture was concentrated, to which isopropanol was added. The reaction mixture was washed with isopropanol, filtered, and concentrated. As a result, the target compound 2-(3-(5-chloro-4-(2-(isopropylsulfonyl)phenylamino)pyrimidine-2-ylamino)-4-methoxyphenethylamino)acetic acid was obtained as a white solid (4 mg, yield: 29%).

$^1$H-NMR (300 MHz, CDCl$_3$) δ 9.50 (s, 1H), 8.52 (br, s, 1H), 8.18-8.00 (m, 1H), 7.99-7.94 (m, 1H), 7.82-7.79 (m, 1H), 7.64-7.60 (m, 1H), 6.83-6.66 (m, 2H), 3.90-3.55 (m, 5H), 3.20-3.02 (m, 5H), 2.04 (s, 1H), 1.31 (d, J=21 Hz, 6H); LC/MS (ESI) m/z 535.8 [M+H]$^+$.

Example 28: Preparation of N-(3-((5-chloro-4-((2-(isopropylsulfonyl)phenyl)amino)pyrimidine-2-yl)amino)-4-methoxybenzyl)-2,2,2-trifluoroacetamide

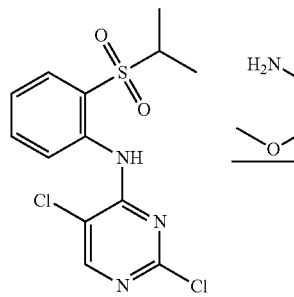 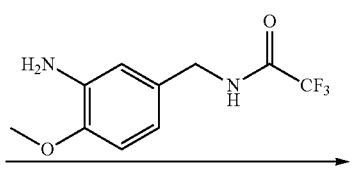 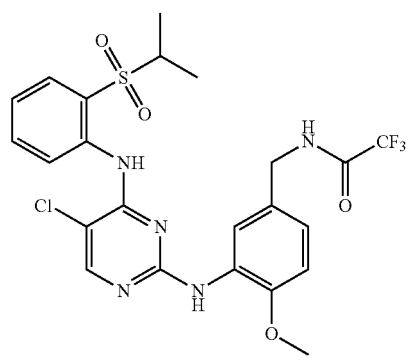

2,5-dichloro-N-(2-(isopropylsulfonyl)phenyl)pyrimidine-4-amine/2,5-dichloro-N-(2-(isopropylsulfonyl)phenyl)pyrimidine-4-amine (50 mg, 0.14 mmol) was dissolved in 0.08 M HCl.ethoxyethanol (1 mL), to which the compound (0.04 g, 0.16 mmol) prepared in preparative example 9 was added, followed by stirring at 80° C. for 15 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound N-(3-((5-chloro-4-((2-(isopropylsulfonyl)phenyl)amino)pyrimidine-2-yl)amino)-4-methoxybenzyl)-2,2,2-trifluoroacetamide as a white solid (0.055 g, 0.098 mmol, yield: 69%).

$^1$H-NMR (300 MHz, CDCl$_3$) δ 9.56 (s, 1H), 8.51 (d, J=8.4 Hz, 1H), 8.29 (s, 1H), 8.16 (s, 1H), 7.91 (d, J=7.8 Hz, 1H), 7.65 (t, J=7.8 Hz, 1H), 7.59 (s, 1H), 7.28 (t, J=7.5 Hz, 1H), 6.84-6.91 (m, 2H), 6.54 (br, 1H), 4.37 (d, J=5.4 Hz, 2H), 3.91 (s, 3H), 3.24 (sept, J=6.9 Hz, 1H), 1.30 (d, J=6.9 Hz, 6H); LC/MS 558.4 [M+H+].

Example 29: Preparation of N2-(5-(aminomethyl)-2-methoxyphenyl)-5-chloro-N4-(2-(isopropylsulfonyl)phenyl)pyrimidine-2,4-diamine

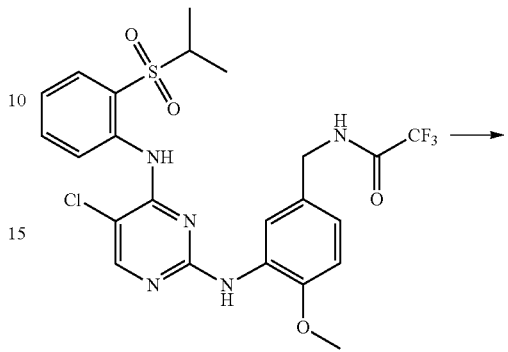 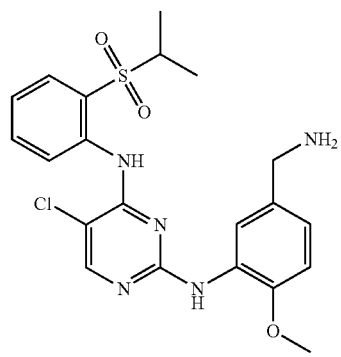

The compound (40 mg, 0.07 mmol) prepared in example 28 was dissolved in ethanol (2 mL), to which potassium carbonate (180 mg, 0.72 mmol) aqueous solution (0.05 mL) was added, followed by stirring at 90° C. for 1 hour. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(5-(aminomethyl)-2-methoxyphenyl)-5-chloro-N4-(2-(isopropylsulfonyl)phenyl)pyrimidine-2,4-diamine as a white solid (0.02 g, 0.04 mmol, yield: 61%).

$^1$H-NMR (300 MHz, CDCl$_3$) δ 8.44 (d, J=8.1 Hz, 1H), 8.15 (s, 1H), 7.89-7.93 (m, 2H), 7.67 (t, J=6.9 Hz, 1H), 7.36 (t, J=6.9 Hz, 1H), 6.94-7.03 (m, 2H), 3.87 (s, 3H), 3.59 (s, 2H), 3.33 (sept, J=6.9 Hz, 1H), 1.24 (d, J=6.9 Hz, 6H); LC/MS 462.3 [M+H+].

Example 30: Preparation of N-(3-(5-chloro-4-(2-(isopropylsulfonyl)phenylamino)pyrimidine-2-ylamino)-4-methoxyphenethyl)-2,2,2-trifluoroacetamide

Example 31: Preparation of N2-(5-(2-aminoethyl)-2-isopropoxyphenyl)-5-chloro-N4-(2-(isopropylsulfonyl)phenyl)pyrimidine-2,4-diamine

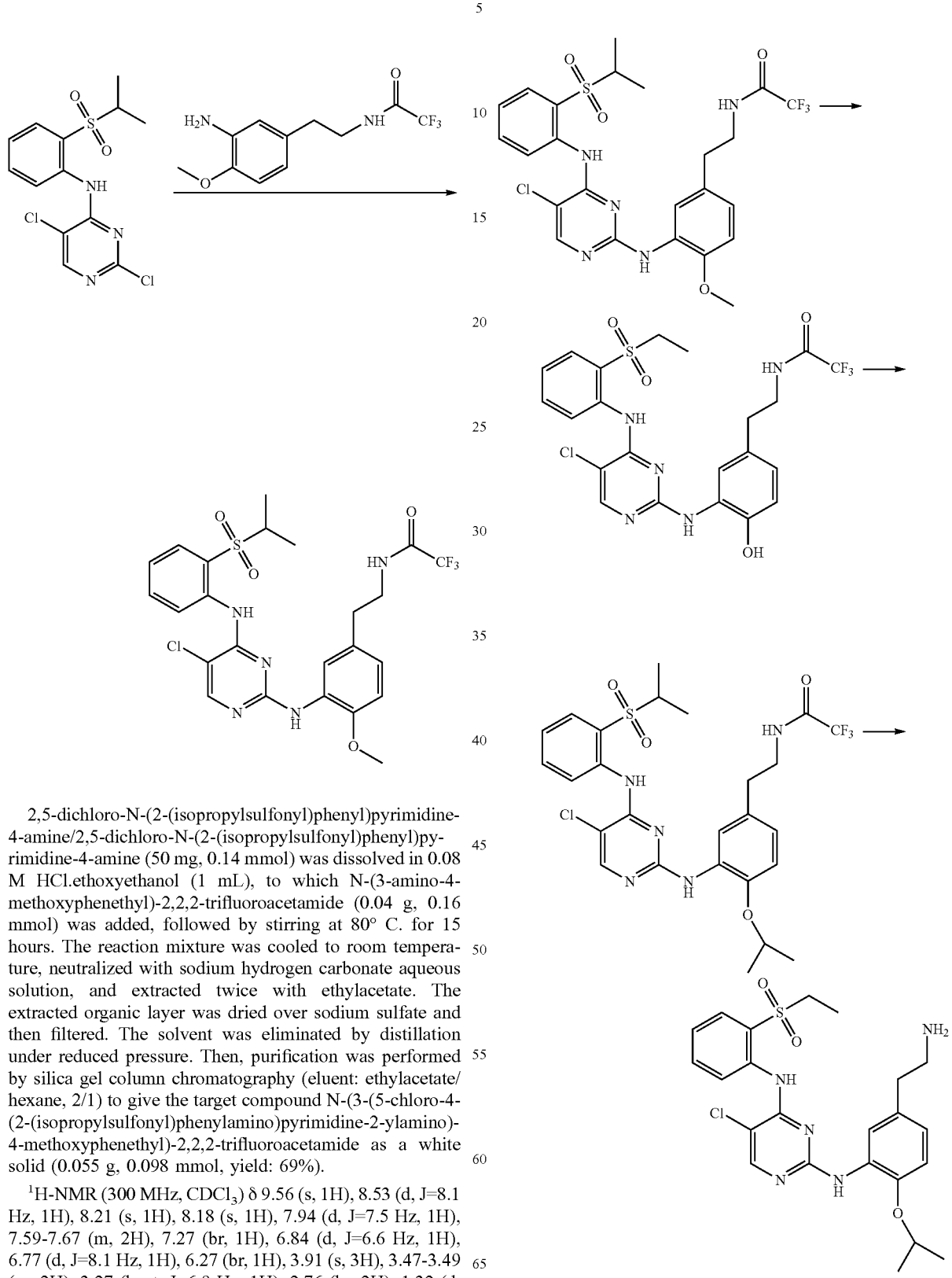

2,5-dichloro-N-(2-(isopropylsulfonyl)phenyl)pyrimidine-4-amine/2,5-dichloro-N-(2-(isopropylsulfonyl)phenyl)pyrimidine-4-amine (50 mg, 0.14 mmol) was dissolved in 0.08 M HCl.ethoxyethanol (1 mL), to which N-(3-amino-4-methoxyphenethyl)-2,2,2-trifluoroacetamide (0.04 g, 0.16 mmol) was added, followed by stirring at 80° C. for 15 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound N-(3-(5-chloro-4-(2-(isopropylsulfonyl)phenylamino)pyrimidine-2-ylamino)-4-methoxyphenethyl)-2,2,2-trifluoroacetamide as a white solid (0.055 g, 0.098 mmol, yield: 69%).

$^1$H-NMR (300 MHz, CDCl$_3$) δ 9.56 (s, 1H), 8.53 (d, J=8.1 Hz, 1H), 8.21 (s, 1H), 8.18 (s, 1H), 7.94 (d, J=7.5 Hz, 1H), 7.59-7.67 (m, 2H), 7.27 (br, 1H), 6.84 (d, J=6.6 Hz, 1H), 6.77 (d, J=8.1 Hz, 1H), 6.27 (br, 1H), 3.91 (s, 3H), 3.47-3.49 (m, 2H), 3.27 (hept, J=6.9 Hz, 1H), 2.76 (br, 2H), 1.32 (d, J=6.9 Hz, 6H; LC/MS 571.7 [M+H+].

Step 1: Preparation of N-(3-((5-chloro-4-((2-(iso-propylsulfonyl)phenyl)amino)pyrimidine-2-yl)amino)-4-hydroxyphenethyl)-2,2,2-trifluoroacetamide The compound (0.45 g, 0.79 mmol) prepared in example was dissolved in dichloromethane (5 mL), to which borontribromide (0.59 g, 2.36 mmol) was added at 0° C., followed by stirring at room temperature for 4 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound N-(3-((5-chloro-4-((2-(isopropylsulfonyl)phenyl)amino)pyrimidine-2-yl)amino)-4-hydroxyphenethyl)-2,2,2-trifluoroacetamide as a white solid (0.22 g, 0.394 mmol, yield: 50%).

$^1$H-NMR (300 MHz, CDCl$_3$) δ 9.66 (br, 1H), 9.44-9.47 (m, 2H), 8.53 (d, J=7.2 Hz, 1H), 8.24-8.25 (m, 2H), 7.80 (d, J=8.1 Hz, 1H), 7.64 (t, J=7.2 Hz, 1H), 7.50 (s, 1H), 7.31 (t, J=7.8 Hz, 1H), 6.72-6.81 (m, 2H), 3.44 (sept, J=6.9 Hz, 1H), 3.24-3.29 (m, 2H), 2.61 (t, J=7.5 Hz, 2H), 1.14 (d, J=6.9 Hz, 6H); LC/MS 558.0 [M+H$^+$].

Step 2: Preparation of N-(3-((4-chloro-3-((2-(iso-propylsulfonyl)phenyl)amino)phenyl)amino)-4-isopropoxyphenethyl)-2,2,2-trifluoroacetamide N-(3-((5-chloro-4-((2-(isopropylsulfonyl)phenyl)amino)pyrimidine-2-yl)amino)-4-hydroxyphenethyl)-2,2,2-trifluoroacetamide (0.10 g, 0.18 mmol) prepared in step 1 was dissolved in dichloromethane (1 mL), to which isopropanol (13 mg, 0.22 mmol), triphenylphosphine (0.071 g, 0.27 mmol), and diethylazodicarboxylate (0.055 g, 0.27 mmol) were added, followed by stirring at room temperature for 4 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: ethylacetate/hexane, 1/1) to give the target compound N-(3-((4-chloro-3-((2-(isopropylsulfonyl)phenyl)amino)phenyl)amino)-4-isopropoxyphenethyl)-2,2,2-trifluoroacetamide as a white solid (0.082 g, 0.137 mmol, yield: 76%).

$^1$H-NMR (300 MHz, CDCl$_3$) δ 9.55 (br, 1H), 8.52 (d, J=8.1 Hz, 1H), 8.18-8.19 (m, 2H), 7.94 (d, J=8.1 Hz, 1H), 7.59-7.66 (m, 2H), 7.26-7.29 (m, 2H), 6.85 (d, J=8.4 Hz, 1H), 6.85 (d, J=8.1 Hz, 1H), 3.58 (sept, J=6.0 Hz, 1H), 3.45 (q, J=6.9 Hz, 2H), 3.27 (sept, J=6.9 Hz, 1H), 2.72 (t, J=6.6 Hz, 2H), 1.39 (d, J=6.0 Hz, 6H), 1.32 (d, J=6.9 Hz, 6H); LC/MS 600.1 [M+H$^+$].

Step 3: Preparation of N2-(5-(2-aminoethyl)-2-isopropoxyphenyl)-5-chloro-N4-(2-(isopropylsulfonyl)phenyl)pyrimidine-2,4-diamine N-(3-((4-chloro-3-((2-(isopropylsulfonyl)phenyl)amino)phenyl)amino)-4-isopropoxyphenethyl)-2,2,2-trifluoroacetamide (0.05 g, 0.08 mmol) prepared in step 2 was dissolved in ethanol (5 mL), to which potassium carbonate (0.05 g, 0.33 mmol) aqueous solution (1 mL) was added, followed by stirring at 90° C. for 2 hours. The reaction mixture was distilled under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(5-(2-aminoethyl)-2-isopropoxyphenyl)-5-chloro-N4-(2-(isopropylsulfonyl)phenyl)pyrimidine-2,4-diamine as a white solid (0.032 g, 0.063 mmol, yield: 76%).

$^1$H-NMR (300 MHz, CDCl$_3$) δ 9.49 (br, 1H), 8.53 (d, J=7.8 Hz, 1H), 8.18 (s, 1H), 8.13 (s, 1H), 7.94 (dd, J=7.8, 1.2 Hz, 1H), 7.62-7.68 (m, 2H), 7.28-7.31 (m, 1H), 6.83 (d, J=8.4 Hz, 1H), 6.76 (dd, J=8.1, 1.8 Hz, 1H), 3.57 (sept, J=6.0 Hz, 1H), 3.27 (sept, J=6.9 Hz, 1H), 2.79 (t, J=6.9 Hz, 2H), 2.59 (t, J=6.9 Hz, 2H), 1.57 (s, 1H), 1.38 (d, J=6.0 Hz, 6H), 1.32 (d, J=6.9 Hz, 6H); LC/MS 504.0 [M+H$^+$].

Example 32: Preparation of N2-(5-(2-aminoethyl)-2-methoxyphenyl)-5-chloro-N4-(4-fluoro-2-(isopropylsulfonyl)phenyl)pyrimidine-2,4-diamine

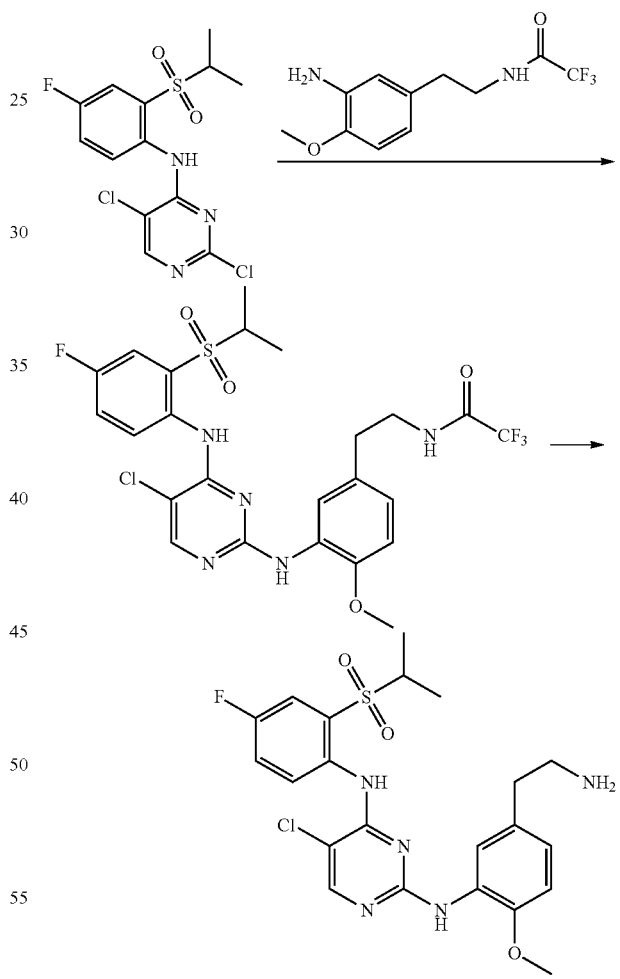

Step 1: Preparation of N-(3-((5-chloro-4-((5-fluoro-2-(isopropylsulfonyl)phenyl)amino)pyrimidine-2-yl)amino)-4-methoxyphenethyl)-2,2,2-trifluoroacetamide The compound (39.9 mg, 0.19 mmol) prepared in preparative example 9 and the compound (A, 70 mg, 0.19 mmol) prepared in preparative example 10 were dissolved in 0.08 M HCl.ethoxyethanol (2.5 mL), followed by stirring at 100° C. for 18 hours. Upon completion of the reaction, a new spot was formed under the starting material, which was confirmed by TLC. Water was added thereto to terminate the reaction, followed by neutralization with 1 N HCl. The reaction mixture was extracted with ethylacetate. The ethylacetate layer was washed with water and brine, dried over sodium sulfate, and concentrated under reduced pressure. Then, purification was performed by MPLC to give the target compound N-(3-((5-chloro-4-((5-fluoro-2-(isopropylsulfonyl)phenyl)amino)pyrimidine-2-yl)amino)-4-methoxyphenethyl)-2,2,2-trifluoroacetamide (20 mg, 0.03 mmol, yield: 18%).

$^1$H-NMR (300 MHz, CDCl$_3$) δ 8.18-8.16 (m, 2H), 7.95 (s, 1H), 7.85-8.82 (m, 1H), 7.61 (s, 1H), 7.51-7.44 (m, 2H), 6.81 (m, 1H), 6.71 (m, 1H), 3.87-7.84 (m, 3H), 3.46-3.39 (m, 2H), 3.15-3.10 (m, 1H), 2.61-2.57 (m, 2H), 1.25 (d, J=6.9 Hz, 6H); LC/MS 590 [M+H$^+$].

Step 2: Preparation of N2-(5-(2-aminoethyl)-2-methoxyphenyl)-5-chloro-N4-(4-fluoro-2-(isopropylsulfonyl)phenyl)pyrimidine-2,4-diamine N-(3-((5-chloro-4-((5-fluoro-2-(isopropylsulfonyl)phenyl)amino)pyrimidine-2-yl)amino)-4-methoxyphenethyl)-2,2,2-trifluoroacetamide (40.0 mg, 0.07 mmol) prepared in step 1 and potassium carbonate (37.5 mg, 0.27 mmol) were dissolved in ethanol/water (3/1, 5 mL), followed by stirring at 90° C. for 3 hours. Upon completion of the reaction, a new spot was formed under the starting material, which was confirmed by TLC. Ethanol was concentrated under reduced pressure, which was dissolved in ethylacetate. The reaction mixture was washed with water. The organic layer was dried over sodium sulfate and concentrated under reduced pressure. As a result, the target compound N2-(5-(2-aminoethyl)-2-methoxyphenyl)-5-chloro-N4-(4-fluoro-2-(isopropylsulfonyl)phenyl)pyrimidine-2,4-diamine was obtained (12 mg, 0.02 mmol, yield: 35%).

$^1$H-NMR (300 MHz, CDCl$_3$) δ 9.25 (s, 1H), 8.50-8.46 (m, 1H), 8.18 (s, 1H), 8.08 (s, 1H), 7.68-7.66 (m, 1H), 7.57 (s, 1H), 7.40 (m, 1H), 6.82 (m, 2H), 3.89 (s, 3H), 3.29-3.25 (m, 1H), 2.84-2.82 (m, 2H), 2.64-2.60 (m, 2H), 1.34 (d, J=6.9 Hz, 6H); LC/MS 494 [M+H$^+$].

Example 33: Preparation of N2-(5-(2-aminoethyl)-2-methoxyphenyl)-5-chloro-N4-(5-fluoro-2-(isopropylsulfonyl)phenyl)pyrimidine-2,4-diaminehydrochloride

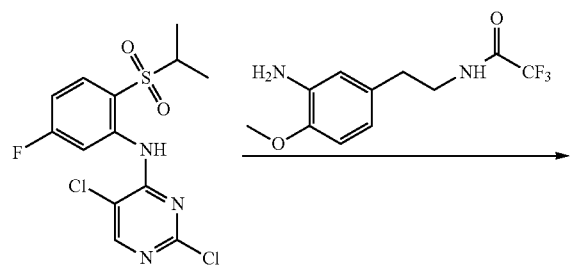

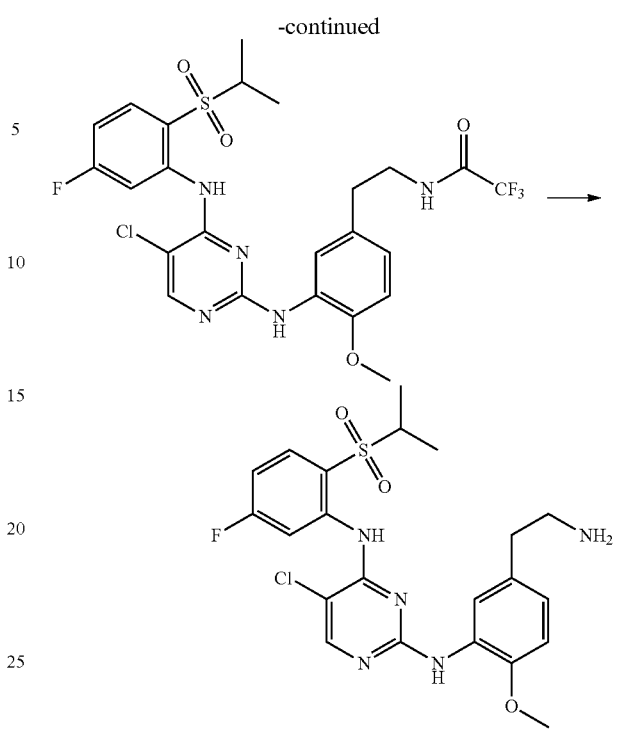

Step 1: Preparation of N-(3-((5-chloro-4-((5-fluoro-2-(isopropylsulfonyl)phenyl)amino)pyrimidine-2-yl)amino)-4-methoxyphenethyl)-2,2,2-trifluoroacetamide The compound (28.8 mg, 0.11 mmol) prepared in preparative example 9 and the compound (50 mg, 0.14 mmol) prepared in preparative example 11 were dissolved in 0.08 M HCl.ethoxyethanol (1 mL), followed by stirring at 100° C. for 18 hours. Upon completion of the reaction, a new spot was formed under the starting material, which was confirmed by TLC. Water was added thereto to terminate the reaction, followed by neutralization with 1 N HCl. The reaction mixture was extracted with ethylacetate. The ethylacetate layer was washed with water and brine, dried over sodium sulfate, and concentrated under reduced pressure. Then, purification was performed by MPLC to give the target compound N-(3-((5-chloro-4-((5-fluoro-2-(isopropylsulfonyl)phenyl)amino)pyrimidine-2-yl)amino)-4-methoxyphenethyl)-2,2,2-trifluoroacetamide (13 mg, 0.02 mmol, yield: 16%).

$^1$H-NMR (300 MHz, CDCl$_3$) δ 8.18-8.16 (m, 2H), 7.95 (s, 1H), 7.85-8.82 (m, 1H), 7.61 (s, 1H), 7.51-7.44 (m, 2H), 6.81 (m, 1H), 6.71 (m, 1H), 3.87-7.84 (m, 3H), 3.46-3.39 (m, 2H), 3.15-3.10 (m, 1H), 2.61-2.57 (m, 2H), 1.25 (d, J=6.9 Hz, 6H); LC/MS 590 [M+H$^+$].

Step 2: Preparation of N2-(5-(2-aminoethyl)-2-methoxyphenyl)-5-chloro-N4-(5-fluoro-2-(isopropylsulfonyl)phenyl)pyrimidine-2,4-diaminehydrochloride The compound (13.0 mg, 0.02 mmol) prepared in step 1 was dissolved in ethanol (2 mL), to which water (0.5 mL) containing potassium carbonate (11.0 mg, 0.08 mmol) dissolved therein was added, followed by stirring at 90° C. for 3 hours. Upon completion of the reaction, a new spot was formed under the starting material, which was confirmed by TLC. Ethanol was concentrated under reduced pressure, which was dissolved in MC. The reaction mixture was washed with water and brine. The MC layer was dried over sodium sulfate and concentrated under reduced pressure. Ether was added thereto. 4 M HCl.dioxane was also added thereto, followed by stirring for 1 hour. The generated solid was filtered and dried. As a result, the target compound N2-(5-(2-aminoethyl)-2-methoxyphenyl)-5-chloro-N4-(5-fluoro-2-(isopropylsulfonyl)phenyl)pyrimidine-2,4-diaminehydrochloride was obtained (5 mg, 0.01 mmol, yield: 51%).

$^1$H-NMR (300 MHz, CDCl$_3$) δ 8.20 (s, 1H), 7.96-7.94 (m, 1H), 7.73-7.70 (m, 2H), 7.55 (s, 1H), 6.99-6.96 (m, 2H), 3.87 (s, 3H), 3.47-3.43 (m, 1H), 3.07-3.04 (m, 2H), 3.73-3.70 (m, 2H), 1.26 (d, J=18.5 Hz, 6H) LC/MS 494 [M+H$^+$].

Example 34: Preparation of N2-(5-(2-aminoethyl)-2-methoxyphenyl)-5-chloro-N4-(2-fluoro-6-(isopropylsulfonyl)phenyl)pyrimidine-2,4-diaminehydrochloride

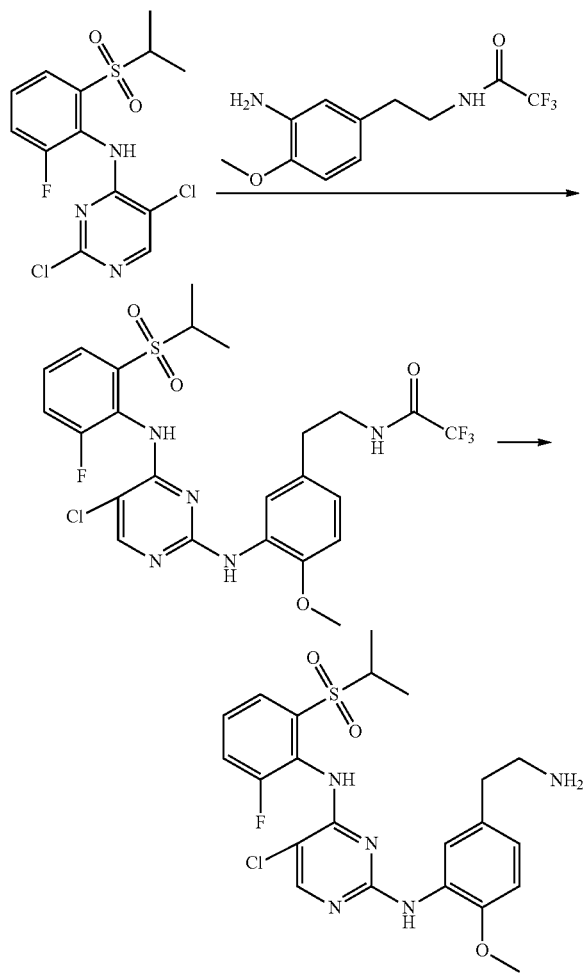

Step 1: Preparation of N-(3-((5-chloro-4-((2-fluoro-6-(isopropylsulfonyl)phenyl)amino)pyrimidine-2-yl)amino)-4-methoxyphenethyl)-2,2,2-trifluoroacetamide The compound (28.8 mg, 0.11 mmol) prepared in preparative example 9 and the compound (50 mg, 0.14 mmol) prepared in preparative example 12 were dissolved in 0.08 M HCl.ethoxyethanol (1 mL), followed by stirring at 100° C. for 18 hours. Upon completion of the reaction, a new spot was formed under the starting material, which was confirmed by TLC. Water was added thereto to terminate the reaction, followed by neutralization with 1 N HCl. The reaction mixture was extracted with ethylacetate. The ethylacetate layer was washed with water and brine, dried over sodium sulfate, and concentrated under reduced pressure. Then, purification was performed by MPLC to give the target compound N-(3-((5-chloro-4-((2-fluoro-6-(isopropylsulfonyl)phenyl)amino)pyrimidine-2-yl)amino)-4-methoxyphenethyl)-2,2,2-trifluoroacetamide (12 mg, 0.02 mmol, yield: 15%).

$^1$H-NMR (300 MHz, CDCl$_3$) δ 8.18-8.16 (m, 2H), 7.95 (s, 1H), 7.84-8.82 (m, 1H), 7.61 (s, 1H), 7.53-7.44 (m, 2H), 6.81 (m, 1H), 6.71 (m, 1H), 3.87-7.84 (m, 3H), 3.43-3.42 (m, 2H), 3.15-3.10 (m, 1H), 2.61-2.57 (m, 2H), 1.25 (d, J=6.9 Hz, 6H); LC/MS 590 [M+H$^+$].

Step 2: Preparation of N2-(5-(2-aminoethyl)-2-methoxyphenyl)-5-chloro-N4-(2-fluoro-6-(isopropylsulfonyl)phenyl)pyrimidine-2,4-diaminehydrochloride N-(3-((5-chloro-4-((2-fluoro-6-(isopropylsulfonyl)phenyl)amino)pyrimidine-2-yl)amino)-4-methoxyphenethyl)-2,2,2-trifluoroacetamide (12.0 mg, 0.02 mmol) prepared in step 1 was dissolved in ethanol (2 mL), to which water (0.5 mL) containing potassium carbonate (11.0 mg, 0.08 mmol) dissolved therein was added, followed by stirring at 90° C. for 3 hours. Upon completion of the reaction, a new spot was formed under the starting material, which was confirmed by TLC. Ethanol was concentrated under reduced pressure, which was dissolved in MC. The reaction mixture was washed with water and brine. The MC layer was dried over sodium sulfate and concentrated under reduced pressure. Ether was added thereto. 4 M HCl.dioxane was also added thereto, followed by stirring for 1 hour. The generated solid was filtered and dried. As a result, the target compound N2-(5-(2-aminoethyl)-2-methoxyphenyl)-5-chloro-N4-(2-fluoro-6-(isopropylsulfonyl)phenyl)pyrimidine-2,4-diaminehydrochloride was obtained (6 mg, 0.01 mmol, yield: 61%).

$^1$H-NMR (300 MHz, CDCl$_3$) δ 8.25 (s, 1H), 7.98-7.96 (m, 1H), 7.78-7.70 (m, 2H), 7.34 (s, 1H), 7.09-7.07 (m, 1H), 7.03-7.01 (m, 1H), 3.87 (s, 3H), 3.47-3.44 (m, 1H), 3.08-3.05 (m, 2H), 2.75-2.73 (m, 2H), 1.27 (d, J=17 Hz, 6H); LC/MS 494 [M+H$^+$].

Example 35: Preparation of N2-(5-(1-amino-2-methylpropane-2-yl)-2-methoxyphenyl)-5-chloro-N4-(2-(isopropylsulfonyl)phenyl)pyrimidine-2,4-diamine

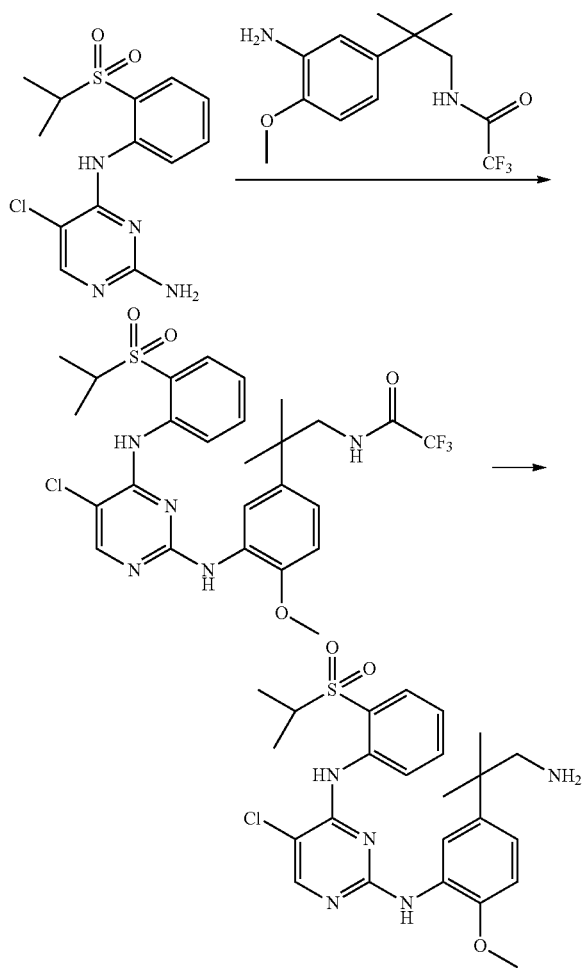

Step 1: Preparation of N-(2-(3-((5-chloro-4-((4-fluoro-2-(isopropylsulfonyl)phenyl)amino)pyrimidine-2-yl)amino)-4-methoxyphenyl)-2-methylpropyl)-2,2,2-trifluoroacetamide 2,5-dichloro-N-(2-(isopropylsulfonyl)phenyl)pyrimidine-4-amine/2,5-dichloro-N-(2-(isopropylsulfonyl)phenyl)pyrimidine-4-amine (70 mg, 0.29 mmol) and the compound (67.0 mg, 0.23 mmol) prepared in preparative example 13 were dissolved in 0.08 M HCl.ethoxyethanol (3 mL), followed by stirring at 100° C. for 18 hours. Upon completion of the reaction, a new spot was formed under the starting material, which was confirmed by TLC. Water was added thereto to terminate the reaction, followed by neutralization with sodium hydrogen carbonate aqueous solution. The reaction mixture was extracted with ethylacetate. The ethylacetate layer was washed with water and brine, dried over sodium sulfate, and concentrated under reduced pressure. Then, purification was performed by MPLC and recrystallization was also performed by using MC/Hex to give the target compound N-(2-(3-((5-chloro-4-((4-fluoro-2-(isopropylsulfonyl)phenyl)amino)pyrimidine-2-yl)amino)-4-methoxyphenyl)-2-methylpropyl)-2,2,2-trifluoroacetamide (32 mg, 0.05 mmol, yield: 23%).

$^1$H-NMR (300 MHz, CDCl$_3$) δ 9.54 (s, 1H), 8.51 (d, J=7.8 Hz, 1H), 8.36 (s, 1H), 8.19 (s, 1H), 7.94 (d, J=8.1 Hz, 1H), 7.65-7.60 (m, 1H), 7.53 (s, 1H), 7.28-7.23 (m, 1H), 6.94-6.85 (m, 2H), 6.01 (br, s, 1H), 3.92 (s, 3H), 3.44 (d, J=6.0 Hz, 2H), 3.29-3.25 (m, 1H), 1.33 (d, J=6.9 Hz, 6H), 1.24 (s, 6H); LC/MS 600 [M+H$^+$].

Step 2: Preparation of N2-(5-(1-amino-2-methylpropane-2-yl)-2-methoxyphenyl)-5-chloro-N4-(2-(isopropylsulfonyl)phenyl)pyrimidine-2,4-diamine N-(2-(3-((5-chloro-4-((4-fluoro-2-(isopropylsulfonyl)phenyl)amino)pyrimidine-2-yl)amino)-4-methoxyphenyl)-2-methylpropyl)-2,2,2-trifluoroacetamide (32 mg, 0.05 mmol) prepared in step 1 was dissolved in ethanol (3 mL), to which water (1.5 mL) containing potassium carbonate (29.5 mg, 0.21 mmol) dissolved therein was added, followed by stirring at 90° C. for 3 hours. Upon completion of the reaction, a new spot was formed under the starting material, which was confirmed by TLC. Ethanol was concentrated under reduced pressure. Water was added thereto, followed by extraction with ethylacetate. The ethylacetate layer was washed with water and brine, dried over sodium sulfate, and concentrated under reduced pressure. Ether was added thereto. 4 M HCl.dioxane was also added thereto, followed by stirring for 1 hour. The generated solid was filtered and dried. As a result, the target compound N2-(5-(1-amino-2-methylpropane-2-yl)-2-methoxyphenyl)-5-chloro-N4-(2-(isopropylsulfonyl)phenyl)pyrimidine-2,4-diamine was obtained (17 mg, 0.03 mmol, yield: 68%).

$^1$H-NMR (300 MHz, CDCl$_3$) δ 8.35 (m, 1H), 8.18 (s, 1H), 7.99-7.96 (m, 1H), 7.70-7.68 (m, 1H), 7.53-7.40 (m, 3H), 7.19-7.16 (m, 1H), 3.87 (s, 3H), 3.44-3.40 (m, 1H), 1.35 (s, 6H), 1.28 (d, J=6.6 Hz, 6H); LC/MS 505 [M+H$^+$].

Example 36: Preparation of N2-(5-(1-amino-2-methylpropane-2-yl)-2-methoxyphenyl)-5-chloro-N4-(4-fluoro-2-(isopropylsulfonyl)phenyl)pyrimidine-2,4-diamine

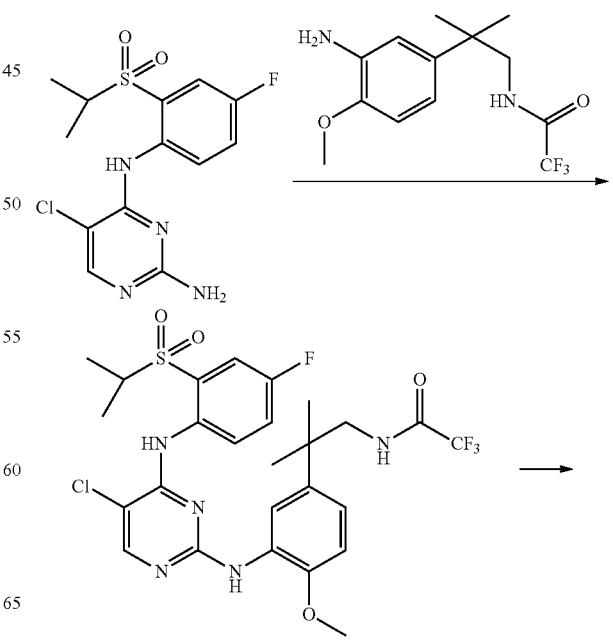

95

-continued

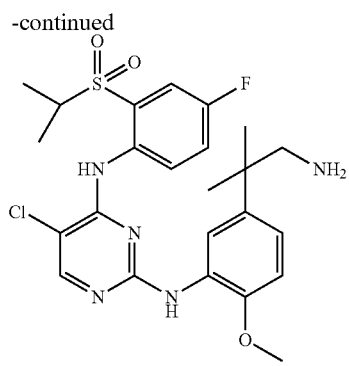

Step 1: Preparation of N-(2-(3-((5-chloro-4-((4-fluoro-2-(isopropylsulfonyl)phenyl)amino)pyrimidine-2-yl)amino)-4-methoxyphenyl)-2-methylpropyl)-2,2,2-trifluoroacetamide The compound (70 mg, 0.19 mmol) prepared in preparative example 10 and the compound (44.6 mg, 0.15 mmol) prepared in preparative example 13 were dissolved in 0.08 M HCl.ethoxyethanol (2.5 mL), followed by stirring at 100° C. for 18 hours. Upon completion of the reaction, a new spot was formed under the starting material, which was confirmed by TLC. Water was added thereto to terminate the reaction, followed by neutralization with 1 N HCl. The reaction mixture was extracted with ethylacetate. The ethylacetate layer was washed with water and brine, dried over sodium sulfate, and concentrated under reduced pressure. Then, purification was performed by MPLC and recrystallization was also performed by MC/Hex to give the target compound N-(2-(3-((5-chloro-4-((4-fluoro-2-(isopropylsulfonyl)phenyl)amino)pyrimidine-2-yl)amino)-4-methoxyphenyl)-2-methylpropyl)-2,2,2-trifluoroacetamide (37 mg, 0.06 mmol, yield: 32%).

$^1$H-NMR (300 MHz, CDCl$_3$) δ 9.32 (s, 1H), 8.50-8.45 (m, 1H), 8.35 (s, 1H), 8.18 (s, 1H), 7.67 (dd, J=8.1, 3.0 Hz, 1H), 7.47 (s, 1H), 7.39-7.32 (m, 1H), 6.95-6.86 (m, 2H), 6.05 (br, s, 1H), 3.92 (s, 3H), 3.47 (d, J=5.7 Hz, 2H), 3.32-3.23 (m, 1H), 1.34 (d, J=6.9 Hz, 6H), 1.27 (s, 6H); LC/MS 618 [M+H$^+$].

Step 2: Preparation of N2-(5-(1-amino-2-methylpropane-2-yl)-2-methoxyphenyl)-5-chloro-N4-(4-fluoro-2-(isopropylsulfonyl)phenyl)pyrimidine-2,4-diamine N-(2-(3-((5-chloro-4-((4-fluoro-2-(isopropylsulfonyl)phenyl)amino)pyrimidine-2-yl)amino)-4-methoxyphenyl)-2-methylpropyl)-2,2,2-trifluoroacetamide (37.0 mg, 0.06 mmol) prepared in step 1 was dissolved in ethanol (2 mL), to which water (0.5 mL) containing potassium carbonate (33.1 mg, 0.248 mmol) dissolved therein was added, followed by stirring at 9° C. for 3 hours. Upon completion of the reaction, a new spot was formed under the starting material, which was confirmed by TLC. Ethanol was concentrated under reduced pressure, which was dissolved in MC. The reaction mixture was washed with water and brine. The MC layer was dried over sodium sulfate and concentrated under reduced pressure. Ether was added thereto. 4 M HCl.dioxane was also added thereto, followed by stirring for 1 hour. The generated solid was filtered and dried. As a result, the target compound N2-(5-(1-amino-2-methylpropane-2-yl)-2-methoxyphenyl)-5-chloro-N4-(4-fluoro-2-

96

(isopropylsulfonyl)phenyl)pyrimidine-2,4-diamine was obtained (20 mg, 0.04 mmol, yield: 65%).

$^1$H-NMR (300 MHz, CDCl$_3$) δ 8.29 (br, s, 1H), 8.21 (s, 1H), 7.78 (dd, J=51.5, 26.5 Hz, 1H), 7.55 (s, 1H), 7.50-7.47 (m, 2H), 7.22-7.20 (m, 1H), 3.90 (s, 3H), 3.50 (m, 1H), 3.16 (m, 2H), 1.40 (s, 6H), 1.32 (d, J=50 Hz, 6H); LC/MS 522 [M+H$^+$].

Example 37: Preparation of N2-(5-(1-amino-2-methylpropane-2-yl)-2-methoxyphenyl)-5-chloro-N4-(5-fluoro-2-(isopropylsulfonyl)phenyl)pyrimidine-2,4-diamine

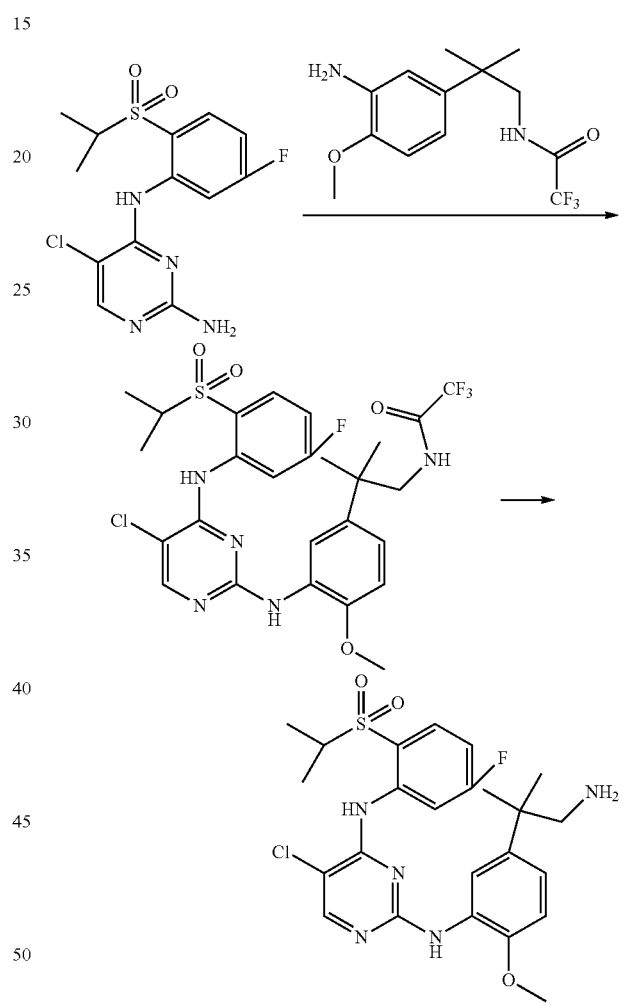

Step 1: Preparation of N-(2-(3-((5-chloro-4-((5-fluoro-2-(isopropylsulfonyl)phenyl)amino)pyrimidine-2-yl)amino)-4-methoxyphenyl)-2-methylpropyl)-2,2,2-trifluoroacetamide The compound (70 mg, 0.19 mmol) prepared in preparative example 11 and the compound (44.63 mg, 0.15 mmol) prepared in preparative example 13 were dissolved in 0.08 M HCl.ethoxyethanol (2.5 mL), followed by stirring at 100° C. for 18 hours. Upon completion of the reaction, a new spot was formed under the starting material, which was confirmed by TLC. Water was added thereto to terminate the reaction, followed by neutralization with 1 N HCl. The reaction mixture was extracted with ethylacetate. The ethylacetate layer was washed with water and brine, dried over sodium sulfate, and concentrated under reduced pressure. Then, purification was performed by MPLC and recrystallization was also performed by MC/Hex to give the target compound N-(2-(3-((5-chloro-4-((5-fluoro-2-(isopropylsulfonyl)phenyl)amino)pyrimidine-2-yl)amino)-4-methoxyphenyl)-2-methylpropyl)-2,2,2-trifluoroacetamide (20 mg, 0.03 mmol, yield: 17%).

¹H-NMR (300 MHz, CDCl₃) δ 8.31-8.27 (m, 2H), 8.17 (s, 1H), 7.82-7.80 (m, 1H), 7.49-7.44 (m, 3H), 6.85-6.81 (m, 2H), 5.98 (br, s, 1H), 3.88 (s, 3H), 3.41-3.38 (m, 2H), 3.16-3.12 (m, 1H), 1.29 (d, J=6.9 Hz, 6H), 1.21 (s, 6H); LC/MS 619 [M+H⁺].

Step 2: Preparation of N2-(5-(1-amino-2-methylpropane-2-yl)-2-methoxyphenyl)-5-chloro-N4-(5-fluoro-2-(isopropylsulfonyl)phenyl)pyrimidine-2,4-diamine N-(2-(3-((5-chloro-4-((5-fluoro-2-(isopropylsulfonyl)phenyl)amino)pyrimidine-2-yl)amino)-4-methoxyphenyl)-2-methylpropyl)-2,2,2-trifluoroacetamide (12.0 mg, 0.02 mmol) prepared in step 1 was dissolved in ethanol (2 mL), to which water (0.5 mL) containing potassium carbonate (11.0 mg, 0.08 mmol) dissolved therein was added, followed by stirring at 90° C. for 3 hours. Upon completion of the reaction, a new spot was formed under the starting material, which was confirmed by TLC. Ethanol was concentrated under reduced pressure, which was dissolved in MC. The reaction mixture was washed with water and brine. The MC layer was dried over sodium sulfate and concentrated under reduced pressure. Ether was added thereto. 4 M HCl.dioxane was also added thereto, followed by stirring for 1 hour. The generated solid was filtered and dried. As a result, the target compound N2-(5-(1-amino-2-methylpropane-2-yl)-2-methoxyphenyl)-5-chloro-N4-(5-fluoro-2-(isopropylsulfonyl)phenyl)pyrimidine-2,4-diamine was obtained (12 mg, 0.02 mmol, yield: 80%).

¹H-NMR (300 MHz, CDCl₃) δ 8.19 (s, 1H), 7.90-7.89 (m, 1H), 7.74-7.69 (m, 2H), 7.41-7.38 (m, 2H), 7.13-7.11 (m, 1H), 3.87 (s, 3H), 3.45 (m, 1H), 3.11 (m, 2H), 1.36 (s, 6H), 1.28 (d, J=60.5 Hz, 6H); LC/MS 522 [M+H⁺].

Example 38: Preparation of N2-(5-(1-amino-2-methylpropane-2-yl)-2-methoxyphenyl)-5-chloro-N4-(2-fluoro-6-(isopropylsulfonyl)phenyl)pyrimidine-2,4-diamine

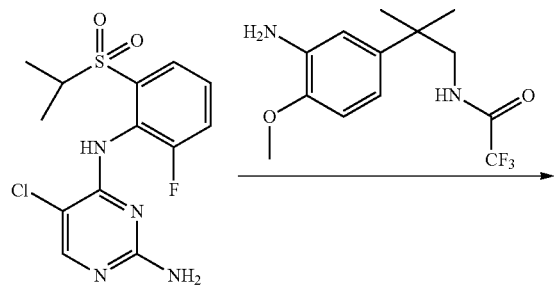

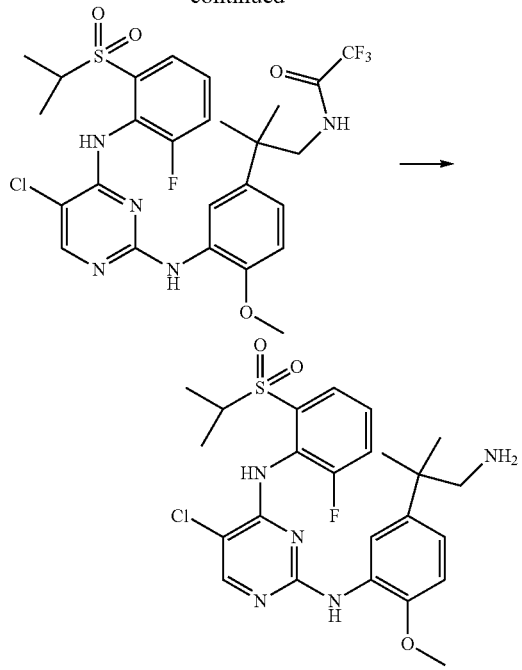

Step 1: Preparation of N-(2-(3-((5-chloro-4-((2-fluoro-6-(isopropylsulfonyl)phenyl)amino)pyrimidine-2-yl)amino)-4-methoxyphenyl)-2-methylpropyl)-2,2,2-trifluoroacetamide The compound (70 mg, 0.19 mmol) prepared in preparative example 12 and the compound (44.63 mg, 0.15 mmol) prepared in preparative example 13 were dissolved in 0.08 M HCl.ethoxyethanol (2.5 mL), followed by stirring at 100° C. for 18 hours. Upon completion of the reaction, a new spot was formed under the starting material, which was confirmed by TLC. Water was added thereto to terminate the reaction, followed by neutralization with 1 N HCl. The reaction mixture was extracted with ethylacetate. The ethylacetate layer was washed with water and brine, dried over sodium sulfate, and concentrated under reduced pressure. Then, purification was performed by MPLC and recrystallization was also performed by MC/Hex to give the target compound N-(2-(3-((5-chloro-4-((2-fluoro-6-(isopropylsulfonyl)phenyl)amino)pyrimidine-2-yl)amino)-4-methoxyphenyl)-2-methylpropyl)-2,2,2-trifluoroacetamide (19 mg, 0.03 mmol, yield: 16%).

¹H-NMR (300 MHz, CDCl₃) δ 8.31-8.27 (m, 2H), 8.17 (s, 1H), 7.82-7.80 (m, 1H), 7.49-7.42 (m, 3H), 6.85-6.81 (m, 2H), 5.98 (br, s, 1H), 3.88 (s, 3H), 3.41-3.39 (m, 2H), 3.17-3.12 (m, 1H), 1.29 (d, J=6.9 Hz, 6H), 1.21 (s, 6H); LC/MS 619 [M+H⁺].

Step 2: Preparation of N2-(5-(1-amino-2-methylpropane-2-yl)-2-methoxyphenyl)-5-chloro-N4-(2-fluoro-6-(isopropylsulfonyl)phenyl)pyrimidine-2,4-diamine N-(2-(3-((5-chloro-4-((2-fluoro-6-(isopropylsulfonyl)phenyl)amino)pyrimidine-2-yl)amino)-4-methoxyphenyl)-2-methylpropyl)-2,2,2-trifluoroacetamide (19.0 mg, 0.03 mmol) prepared in step 1 was dissolved in ethanol (2 mL), to which water (0.5 mL) containing potassium carbonate (17.0 mg, 0.12 mmol) dissolved therein was added, followed by stirring at 90° C. for 3 hours. Upon completion of the reaction, a new spot was formed under the starting material, which was confirmed by TLC. Ethanol was concentrated under reduced pressure, which was dissolved in MC. The reaction mixture was washed with water and brine. The MC layer was dried over sodium sulfate and concentrated under reduced pressure. Ether was added thereto. 4 M HCl.dioxane was also added thereto, followed by stirring for 1 hour. The generated solid was filtered and dried. As a result, the target compound N2-(5-(1-amino-2-methylpropane-2-yl)-2-methoxyphenyl)-5-chloro-N4-(2-fluoro-6-(isopropylsulfonyl)phenyl)pyrimidine-2,4-diamine was obtained (13 mg, 0.02 mmol, yield: 83%).

$^1$H-NMR (300 MHz, CDCl$_3$) δ 8.18 (s, 1H), 7.90-7.89 (m, 1H), 7.74-7.67 (m, 2H), 7.45 (s, 1H), 7.37-7.35 (m, 1H), 7.11-7.10 (m, 1H), 3.87 (s, 3H), 3.45 (m, 1H), 3.10 (m, 2H), 1.35 (s, 6H), 1.28 (d, J=60.5 Hz, 6H) LC/MS 522 [M+H$^+$].

Example 39: Preparation of 2,2'-(3-(5-chloro-4-(2-(isopropylsulfonyl)phenylamino)pyrimidine-2-ylamino)-4-methoxyphenethylazeindiyl)diethanol 2,5-dichloro-N-(2-(isopropylsulfonyl)phenyl)pyrimidine-4-amine (50.0 mg, 0.105 mmol) was dissolved in dimethylformamide (1 mL), to which cesium carbonate (85 mg, 0.26 mmol) and bromoethanol (19 mg, 0.16 mmol) were added at 0° C., followed by stirring at room temperature for 18 hours. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound 2,2'-(3-(5-chloro-4-(2-(isopropylsulfonyl)phenylamino)pyrimidine-2-ylamino)-4-methoxyphenethylazeindiyl)diethanol as a white solid (13 mg, yield: 24%).

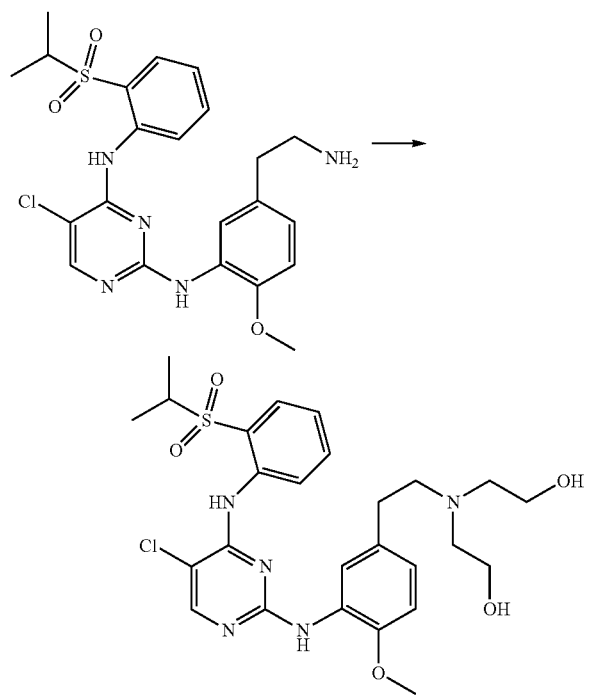

$^1$H-NMR (300 MHz, CDCl$_3$) δ 9.54 (s, 1H), 8.55 (d, J=4.8 Hz, 8.21 (s, 1H), 8.16 (s, 1H), 7.96 (d, J=4.8 Hz, 1H), 7.68-7.65 (m, 1H), 7.61 (s, 1H), 6.86-6.80 (m, 2H), 4.77 (br, s, 1H), 4.20 (s, 2H), 3.91 (s, 3H), 3.80 (s, 2H), 3.35 (d, J=3.6 Hz, 2H), 3.32-3.27 (m, 1H), 2.72-2.69 (m, 2H), 2.32-2.31 (m, 1H), 1.34 (d, J=3.9 Hz, 6H); LC/MS (ESI) m/z 563.8 [M+H]$^+$.

Example 40: Preparation of N-(3-(3-((5-chloro-4-((2-(isopropylsulfonyl)phenyl)amino)pyrimidine-2-yl)amino)-4-methoxyphenyl)propyl)-2,2,2-trifluoroacetamide

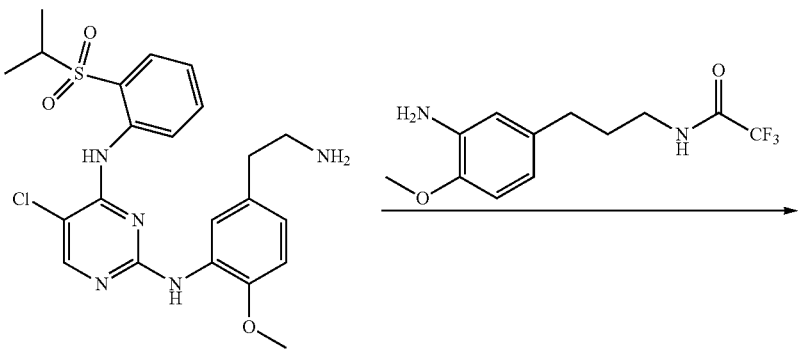

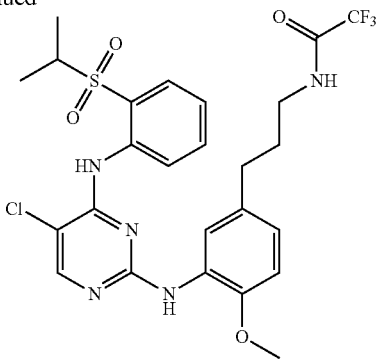

2,5-dichloro-N-(2-(isopropylsulfonyl)phenyl) pyrimidine-4-amine (100 mg, 0.29 mmol) was dissolved in 0.08M HCl.ethoxyethanol (1 mL), to which the compound (80 mg, 0.29 mmol) prepared in preparative example 14 was added, followed by stirring at 80° C. for 15 hours. The temperature of the reaction temperature was lowered to room temperature. The reaction mixture was neutralized with sodium hydrogen carbonate aqueous solution, followed by extraction twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/1) to give the target compound N-(3-(3-((5-chloro-4-((2-(isopropylsulfonyl)phenyl)amino)pyrimidine-2-yl)amino)-4-methoxyphenyl)propyl)-2,2,2-trifluoroacetamide as a white solid (0.48 g, 0.82 mmol, yield: 59%).

$^1$H-NMR (300 MHz, CDCl$_3$) δ 9.54 (s, 1H), 8.55 (d, J=8.7 Hz, 1H), 8.18 (s, 1H), 8.14 (s, 1H), 7.93 (d, J=8.1 Hz, 1H), 7.65 (t, J=7.2 Hz, 1H), 7.57 (s, 1H), 7.26-7.31 (m, 1H), 6.76-6.84 (m, 2H), 6.24 (br, 1H), 3.89 (s, 3H), 3.22-3.35 (m, 3H), 2.58 (t, J=7.2 Hz, 2H), 1.80 (pent, J=7.5 Hz, 2H), 1.31 (d, J=6.9 Hz, 6H); LC/MS 586.2 [M+H$^+$].

Example 41: Preparation of N2-(5-(3-aminopropyl)-2-methoxyphenyl)-5-chloro-N4-(2-(isopropylsulfonyl)phenyl)pyrimidine-2,4-diamine

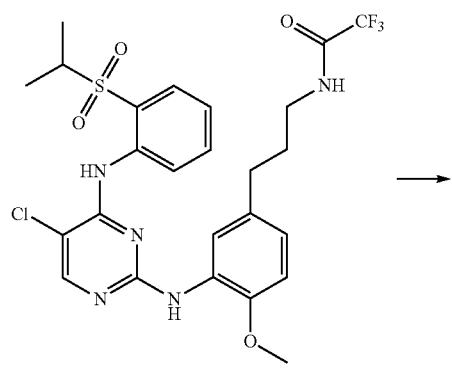

→

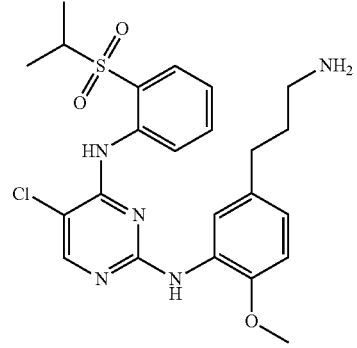

N-(3-(3-((5-chloro-4-((2-(isopropylsulfonyl)phenyl)amino)pyrimidine-2-yl)amino)-4-methoxyphenyl)propyl)-2,2,2-trifluoroacetamide (0.1 g, 0.17 mmol) prepared in example 40 was dissolved in ethanol (2 mL), to which potassium carbonate (90 mg, 0.68 mmol) aqueous solution (1 mL), followed by stirring at 90° C. for 2 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(5-(3-aminopropyl)-2-methoxyphenyl)-5-chloro-N4-(2-(isopropylsulfonyl)phenyl)pyrimidine-2,4-diamine as a white solid (32 mg, 0.065 mmol, yield: 76%).

$^1$H-NMR (300 MHz, CDCl$_3$) δ 9.49 (br, 1H), 8.53 (d, J=8.4 Hz, 1H), 8.18 (s, 1H), 8.12 (s, 1H), 7.93 (d, J=7.8 Hz, 1H), 7.59-7.67 (m, 2H), 7.24-7.28 (m, 1H), 6.79 (s, 2H), 3.88 (s, 3H), 3.26 (sept, J=6.9 Hz, 1H), 2.65 (t, J=6.6 Hz, 2H), 2.52 (t, J=7.5 Hz, 2H), 1.63 (pent, J=7.5 Hz, 2H), 1.31 (d, J=6.9 Hz, 6H); LC/MS 490.2 [M+H$^+$].

Example 42: Preparation of 2-(3-((5-chloro-4-((2-(isopropylsulfonyl)phenyl)amino)pyrimidine-2-yl)amino)-4-methoxyphenyl)acetamide

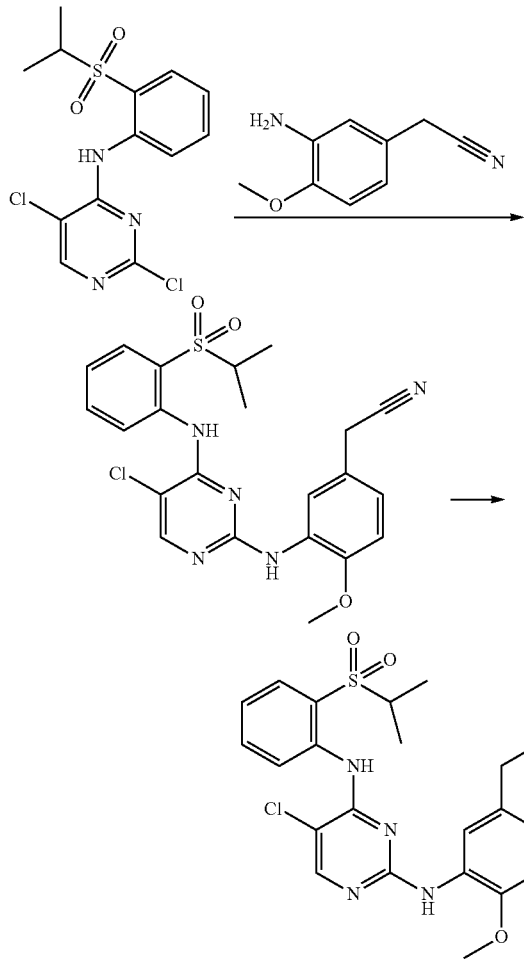

Step 1: Preparation of 2-(3-((5-chloro-4-((2-(isopropylsulfonyl)phenyl)amino)pyrimidine-2-yl)amino)-4-methoxyphenyl)acetonitrile 2,5-dichloro-N-(2-(isopropylsulfonyl)phenyl)pyrimidine-4-amine (373.6 mg, 1.08 mmol) and the compound (140.0 mg, 0.86 mmol) prepared in preparative example 15 were dissolved in 0.08 M HCl.ethoxyethanol (10 mL), followed by stirring at 90° C. Upon completion of the reaction, a new spot was formed under the starting material, which was confirmed by TLC. Water was added thereto to terminate the reaction, followed by neutralization with sodium hydrogen carbonate. The water layer was extracted twice with ethylacetate. The ethylacetate layer was washed with water and brine, dried over sodium sulfate, and concentrated under reduced pressure. Then, purification was performed by MPLC to give the target compound 2-(3-((5-chloro-4-((2-(isopropylsulfonyl)phenyl)amino)pyrimidine-2-yl)amino)-4-methoxyphenyl)acetonitrile (0.60 mg, 1.27 mmol, yield: 55%).

$^1$H-NMR (300 MHz, CDCl$_3$) δ 9.54 (s, 1H), 8.49 (d, J=8.4 Hz, 1H), 8.29 (s, 1H), 8.20 (s, 1H), 7.97-7.94 (m, 1H), 7.70-7.63 (m, 2H), 7.34-7.29 (m, 1H), 6.95-6.85 (m, 2H), 3.92 (s, 3H), 3.55 (s, 2H), 3.28-3.24 (m, 1H), 1.33 (d, J=6.9 Hz, 6H); LC/MS 472 [M+H$^+$].

Step 2: Preparation of 2-(3-((5-chloro-4-((2-(isopropylsulfonyl)phenyl)amino)pyrimidine-2-yl)amino)-4-methoxyphenyl)acetamide 2-(4-methoxyphenyl)acetonitrile (20 mg, 0.14 mmol), acetaldoxime (39.2 g, 0.41 mmol), and Cu$^{II}$-4A (20 mg) were dissolved in methanol (2 mL), followed by stirring at 80° C. for 15 hours. The generated solid was filtered, which was washed with methanol. The reaction mixture was concentrated under reduced pressure and the solvent was filtered. Then, purification was performed by MPLC to give the target compound 2-(3-((5-chloro-4-((2-(isopropylsulfonyl)phenyl)amino)pyrimidine-2-yl)amino)-4-methoxyphenyl)acetamide (13 mg, 0.03 mmol, yield: 66%).

$^1$H-NMR (300 MHz, CDCl$_3$) δ 9.53 (s, 1H), 8.50-8.47 (m, 1H), 8.25 (s, 1H), 7.95-7.93 (m, 1H), 7.68-7.65 (m, 2H), 7.31-7.26 (m, 1H), 6.87 (m, 2H), 5.41-5.33 (m, 2H), 3.92 (s, 3H), 3.44 (s, 2H), 3.26-3.25 (m, 1H), 1.32 (d, J=6.9 Hz, 6H); LC/MS 490 [M+H$^+$].

Example 43: Preparation of 2-ethoxyethyl 2-(3-((5-chloro-4-((2-(isopropylsulfonyl)phenyl)amino)pyrimidine-2-yl)amino)-4-methoxyphenyl)acetate

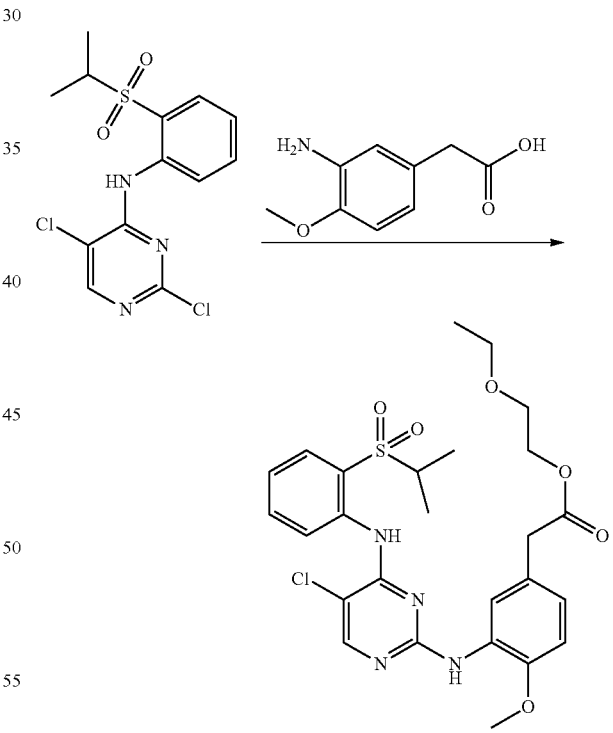

2,5-dichloro-N-(2-(isopropylsulfonyl)phenyl)pyrimidine-4-amine (0.81 g, 2.35 mmol) and the compound (0.34 g, 1.88 mmol) prepared in preparative example 16 were dissolved in 0.08 M HCl.ethoxyethanol (15 mL), followed by stirring at 90° C. Upon completion of the reaction, a new spot was formed under the starting material, which was confirmed by TLC. Water was added thereto to terminate the reaction, and the water layer was extracted twice with ethylacetate. The ethylacetate layer was washed with water and brine, dried over sodium sulfate, and concentrated under reduced pressure. Then, purification was performed by MPLC to give the target compound 2-ethoxyethyl 2-(3-((5-chloro-4-((2-(isopropylsulfonyl)phenyl)amino)pyrimidine-2-yl)amino)-4-methoxyphenyl)acetate (460 mg, 0.82 mmol, yield: 35%).

$^1$H-NMR (300 MHz, CDCl$_3$) δ 9.48 (s, 1H), 8.52 (d, J=8.4 Hz, 1H), 8.20-8.17 (m, 2H), 7.94 (d, J=8.4 Hz, 1H), 7.72-7.67 (m, 1H), 7.61 (s, 1H), 7.31-7.28 (m, 1H), 6.92-6.82 (m, 2H), 4.24-4.21 (m, 2H), 3.89 (s, 3H), 3.64-3.61 (m, 2H), 3.54-3.47 (m, 4H), 3.30-3.21 (m, 1H), 1.33 (d, J=6.9 Hz, 6H); LC/MS 563 [M+H$^+$].

Example 44: Preparation of 2-(3-((5-chloro-4-((2-(isopropylsulfonyl)phenyl)amino)pyrimidine-2-yl)amino)-4-methoxyphenyl)acetic acid Method 1

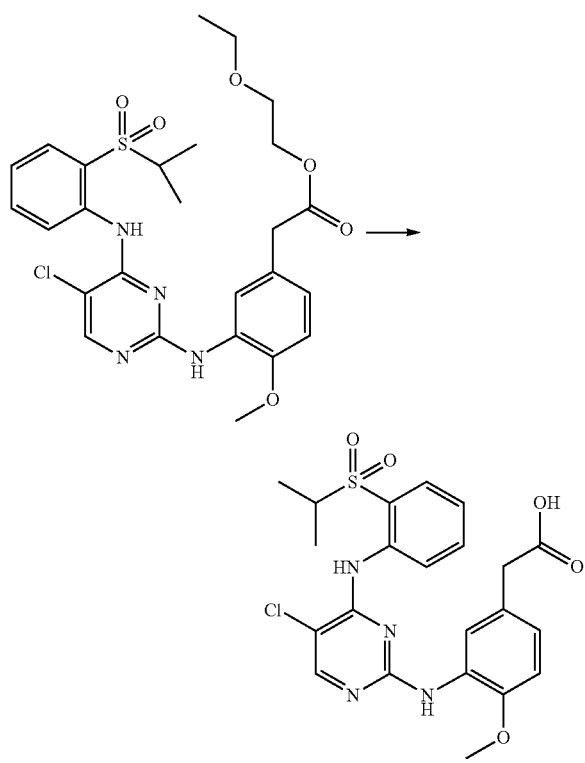

The compound (0.40 g, 0.71 mmol) prepared in example 43 was dissolved in methanol (120 mL), to which sodium hydroxide (0.37 g, 14.20 mmol) and water (40 mL) were added, followed by reaction. Upon completion of the reaction, the reaction mixture was dissolved in MC, which was acidized to pH 3 with concentrated hydrochloric acid. The organic layer was washed with water and brine, dried over sodium sulfate, and concentrated under reduced pressure. Then, recrystallization was performed by MC/Hex to give the target compound 2-(3-((5-chloro-4-((2-(isopropylsulfonyl)phenyl)amino)pyrimidine-2-yl)amino)-4-methoxyphenyl)acetic acid (0.21 g, 0.43 mmol, yield: 60%)

$^1$H-NMR (300 MHz, CDCl$_3$) δ 9.52 (s, 1H), 8.48 (d, J=7.8 Hz, 1H), 8.17 (m, 2H), 7.94 (d, J=7.8 Hz, 1H), 7.74-7.66 (m, 2H), 7.31-7.28 (m, 1H), 6.90-6.87 (m, 2H), 3.90 (s, 3H), 3.49 (m, 2H), 3.24-3.18 (m, 1H), 1.31 (d, J=6.9 Hz, 6H); LC/MS 491 [M+H$^+$].

Method 2

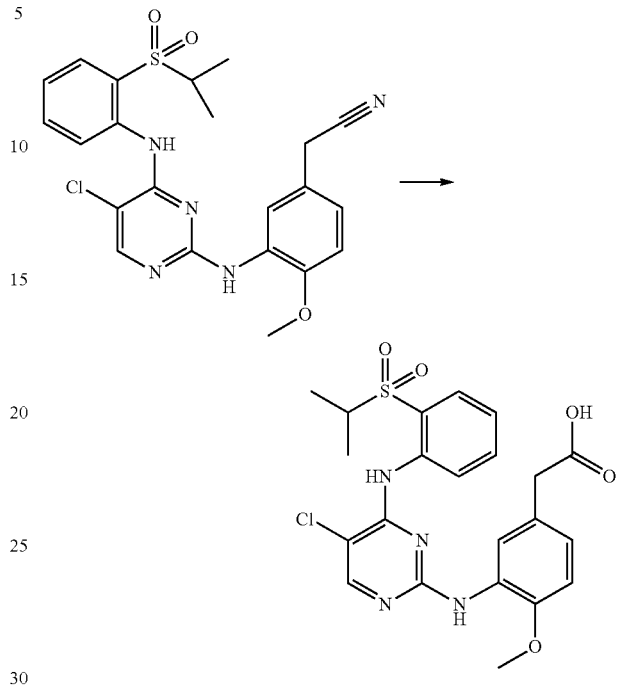

2-(3-((5-chloro-4-((2-(isopropylsulfonyl)phenyl)amino)pyrimidine-2-yl)amino)-4-methoxyphenyl)acetonitrile (100 mg, 0.20 mmol) was dissolved in 1,4-dioxane, to which sulfuric acid (0.21 mL, 2.00 mmol) was added. The temperature thereof was raised to 10° C., followed by reaction for 3 days. Upon completion of the reaction, the reaction mixture was concentrated under reduced pressure, diluted with water, extracted with ethylacetate, washed with sodium hydrogen carbonate, water and brine, and dried over sodium carbonate. As a result, the target compound 2-(3-((5-chloro-4-((2-(isopropylsulfonyl)phenyl)amino)pyrimidine-2-yl)amino)-4-methoxyphenyl)acetic acid was obtained (45 mg, 0.09 mmol, yield: 45%).

$^1$H-NMR (300 MHz, CDCl$_3$) δ 9.52 (s, 1H), 8.48 (d, J=7.8 Hz, 1H), 8.17 (m, 2H), 7.94 (d, J=7.8 Hz, 1H), 7.74 7 66 (m, 2H), 7.31-7 28 (m, 1H), 6.90-6.87 (m, 2H), 3.90 (s, 3H), 3.49 (m, 2H), 3.24-3.18 (m, 1H), 1.31 (d, J=6.9 Hz, 6H); LC/MS 491 [M+H$^+$].

Example 45: Preparation of 2-(3-((5-chloro-4-((2-(isopropylsulfonyl)phenyl)amino)pyrimidine-2-yl)amino)-4-methoxyphenyl)-1-morpholinoethane-1-one

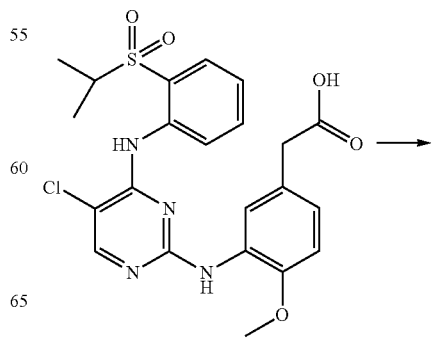

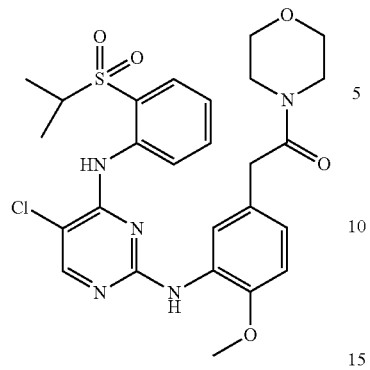

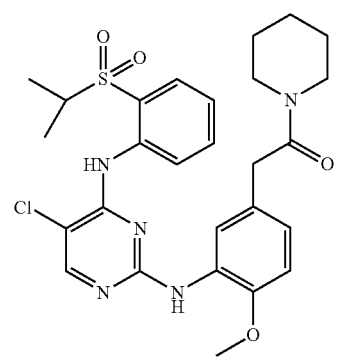

2-(3-(5-chloro-4-(2-(isopropylsulfonyl)phenylamino)pyrimidine-2-ylamino)-4-methoxyphenyl)acetic acid (100 mg, 0.20 mmol) was dissolved in dichloroethane (15 mL), to which EDCI (1-ethyl-3-(3-dimethylaminopropyl)carbodiimide; 47.4 mg, 0.31 mmol) and DMAP (4-dimethylaminopyridine; cat. 2.4 mg, 0.02 mmol) were added. Then, morpholine (0.026 mL, 0.31 mmol) was added thereto, followed by stirring at room temperature overnight. Water was added thereto to terminate the reaction. The reaction mixture was washed with water and brine, and dried over magnesium sulfate. Then, purification was performed by MPLC to give the target compound 2-(3-((5-chloro-4-((2-(isopropylsulfonyl)phenyl)amino)pyrimidine-2-yl)amino)-4-methoxyphenyl)-1-morpholinoethane-1-one (45 mg, 0.08 mmol, yield: 63.0%).

$^1$H-NMR (300 MHz, CDCl$_3$) δ 9.56 (s, 1H), 8.59-8.56 (m, 1H), 8.20-8.17 (m, 2H), 7.94-7.92 (m, 1H), 7.69-7.64 (m, 1H), 7.56 (s, 1H), 7.26 (m, 1H), 6.85 (m, 2H), 3.90 (s, 3H), 3.64-3.61 (m, 6H), 3.50 (m, 2H), 3.41 (m, 2H), 3.28-3.23 (m, 1H), 1.33 (d, J=6.6 Hz, 6H) LC/MS (ESI) m/z 504.2 [M+H$^+$].

Example 46: Preparation of 2-(3-((5-chloro-4-((2-(isopropylsulfonyl)phenyl)amino)pyrimidine-2-yl)amino)-4-methoxyphenyl)-1-(piperidine-1-yl)ethane-1-one 2-(3-(5-chloro-4-(2-(isopropylsulfonyl)phenylamino)pyrimidine-2-ylamino)-4-methoxyphenyl)acetic acid (100 mg, 0.20 mmol) was dissolved in dichloroethane (15 mL), to which EDCI (47.4 mg, 0.31 mmol) and DMAP (cat. 2.4 mg, 0.02 mmol) were added. Then, morpholine (0.026 mL, 0.31 mmol) was added thereto, followed by reaction at room temperature. Water was added thereto to terminate the reaction. The reaction mixture was washed with water and brine, and dried over magnesium sulfate. Then, purification was performed by MPLC to give the target compound 2-(3-((5-chloro-4-((2-(isopropylsulfonyl)phenyl)amino)pyrimidine-2-yl)amino)-4-methoxyphenyl)-1-(piperidine-1-yl)ethane-1-one (26 mg, 0.05 mmol, yield: 36%).

$^1$H-NMR (300 MHz, CDCl$_3$) δ 9.53 (s, 1H), 8.57-8.55 (m, 1H), 8.17 (s, 2H), 7.94-7.91 (m, 1H), 7.70-7.64 (m, 1H), 7.56 (s, 1H), 7.27-7.23 (m, 1H), 6.85 (m, 2H), 3.89 (s, 3H), 3.58-3.55 (m, 4H), 3.30-3.34 (m, 2H), 3.28-3.21 (m, 1H), 1.50-1.56 (m, 4H), 1.37-1.31 (m, 2H), 1.33 (d, J=6.9 Hz, 6H); LC/MS (ESI) m/z 559 [M+H$^+$].

Example 47: Preparation of 2-(3-((5-chloro-4-((2-(isopropylsulfonyl)phenyl)amino)pyrimidine-2-yl)amino)-4-methoxyphenyl)-N-(hydroxymethyl)acetamide

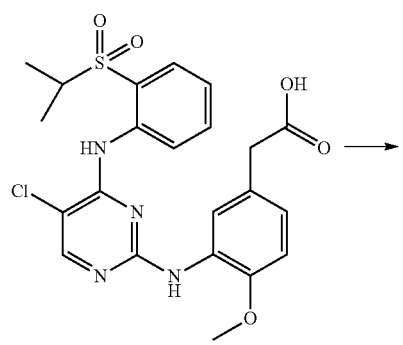

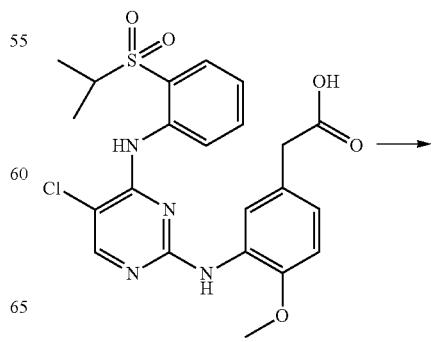

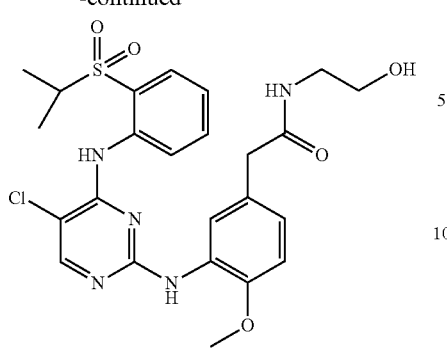

2-(3-(5-chloro-4-(2-(isopropylsulfonyl)phenylamino)pyrimidine-2-ylamino)-4-methoxyphenyl)acetic acid (100 mg, 0.20 mmol) was dissolved in dichloroethane (15 mL), to which EDCI (47.4 mg, 0.31 mmol) and DMAP (cat. 2.4 mg, 0.02 mmol) were added. Then, ethanolamine (0.019 mL, 0.31 mmol) was added thereto, followed by reaction at room temperature. Water was added thereto to terminate the reaction. The reaction mixture was washed with water and brine, and dried over magnesium sulfate. Then, purification was performed by MPLC to give the target compound 2-(3-((5-chloro-4-((2-(isopropylsulfonyl)phenyl)amino)pyrimidine-2-yl)amino)-4-methoxyphenyl)-N-(hydroxymethyl)acetamide (50 mg, 0.010 mmol, yield: 72%).

$^1$H-NMR (300 MHz, CDCl$_3$) δ 9.57 (s, 1H), 8.53-8.51 (m, 1H), 8.20-8.17 (m, 2H), 7.95-7.92 (m, 1H), 7.70-7.65 (m, 1H), 7.59 (s, 1H), 7.33-7.26 (m, 1H), 6.87 (m, 2H), 5.90 (br, s, 1H), 3.92 (s, 3H), 3.66 (m, 2H), 3.48 (m, 2H), 3.36-3.34 (m, 2H), 3.27-3.22 (m, 1H), 2.81 (br, s, 1H), 1.33 (d, J=6.6 Hz, 6H); LC/MS (ESI) m/z 504.2 [M+H$^+$].

Example 48: Preparation of 2-(3-((5-chloro-4-((2-(isopropylsulfonyl)phenyl)amino)pyrimidine-2-yl)amino)-4-methoxyphenyl)-1-(piperazine-1-yl) ethane-1-one

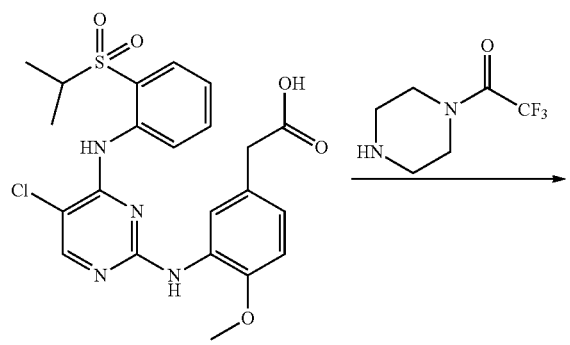

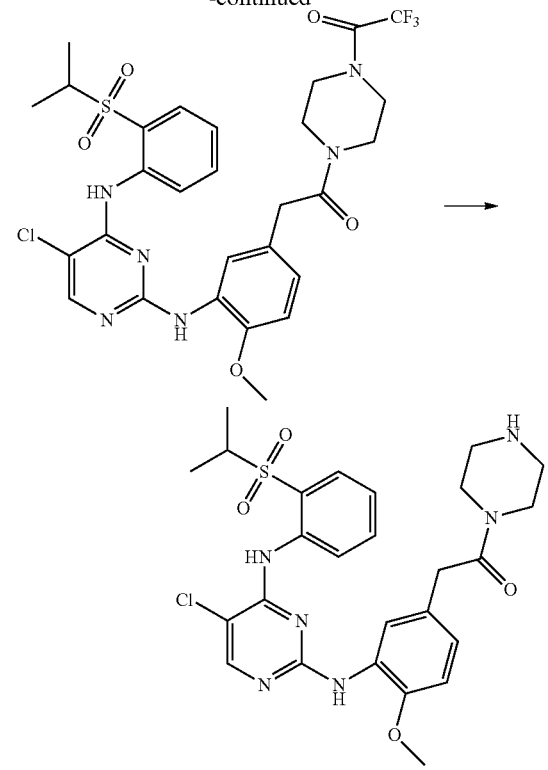

Step 1: Preparation of 1-(4-(2-(3-((5-chloro-4-((2-(isopropylsulfonyl)phenyl)amino)pyrimidine-2-yl)amino)-4-methoxyphenyl)acetyl)piperazine-1-yl)-2,2,2-trifluoroethane-1-one 2-(3-(5-chloro-4-(2-(isopropylsulfonyl)phenylamino)pyrimidine-2-ylamino)-4-methoxyphenyl)acetic acid (1000 mg, 0.204 mmol) and the compound (45 mg, 0.24 mmol) prepared in preparative example 17 were dissolved in dichloromethane (2 mL), to which EDCI.HCl (59 mg, 0.31 mmol) and DMAP (2 mg) were added, followed by stirring at room temperature for 15 hours. Water was added thereto to terminate the reaction, followed by extraction twice with dichloromethane. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound 1-(4-(2-(3-((5-chloro-4-((2-(isopropylsulfonyl)phenyl)amino)pyrimidine-2-yl)amino)-4-methoxyphenyl)acetyl)piperazine-1-yl)-2,2,2-trifluoroethane-1-one as a white solid (95 mg, yield: 71%).

$^1$H-NMR (300 MHz, CDCl$_3$) δ 9.59 (s, 1H), 8.58 (d, J=8.1 Hz, 1H), 8.24 (s, 1H), 8.16 (s, 1H), 7.93 (d, J=7.5 Hz, 1H), 7.67 (t, J=7.5 Hz, 1H), 7.55 (s, 1H), 7.23-7.29 (m, 1H), 3.90 (s, 3H), 3.67 (br, 5H), 3.39-3.55 (m, 5H), 3.25 (hept, J=6.9 Hz, 1H), 1.32 (d, J=6.9 Hz, 6H); LC/MS 655.3 [M+H]$^+$.

Step 2: Preparation of 2-(3-((5-chloro-4-((2-(isopropylsulfonyl)phenyl)amino)pyrimidine-2-yl)amino)-4-methoxyphenyl)-1-(piperazine-1-yl)ethane-1-one 1-(4-(2-(3-((5-chloro-4-((2-(isopropylsulfonyl)phenyl)amino)pyrimidine-2-yl)amino)-4-methoxyphenyl)acetyl)piperazine-1-yl)-2,2,2-trifluoroethane-1-one (50 mg, 0.076 mmol) prepared in step 1 was dissolved in ethanol (2 mL), to which potassium carbonate (42 mg, 0.31 mmol) aqueous solution (1 mL) was added, followed by stirring at 9° C. for 10 minutes. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound 2-(3-((5-chloro-4-((2-(isopropylsulfonyl)phenyl)amino)pyrimidine-2-yl)amino)-4-methoxyphenyl)-1-(piperazine-1-yl)ethane-1-one as a white solid (35 mg, yield: 83%).

$^1$H-NMR (300 MHz, CDCl$_3$) δ 9.54 (s, 1H), 8.56 (d, J=8.4 Hz, 1H), 8.18 (br, 2H), 7.92 (d, J=7.8 Hz, 1H), 7.67 (t, J=7.8 Hz, 1H), 7.56 (s, 1H), 7.23-7.28 (m, 1H), 6.85 (s, 2H), 3.89 (s, 3H), 3.59 (br, 4 h), 3.83 (br, 2H), 3.26 (hept, J=6.6 Hz, 1H), 2.82 (br, 2H), 2.69 (br, 2H), 1.32 (d, J=6.6 Hz, 6H); LC/MS 559.2 [M+H]$^+$.

Example 49: Preparation of 2-(3-((5-chloro-4-((2-(isopropylsulfonyl)phenyl)amino)pyrimidine-2-yl)amino)-4-methoxyphenyl)-N-(pyridine-4-yl)acetamide

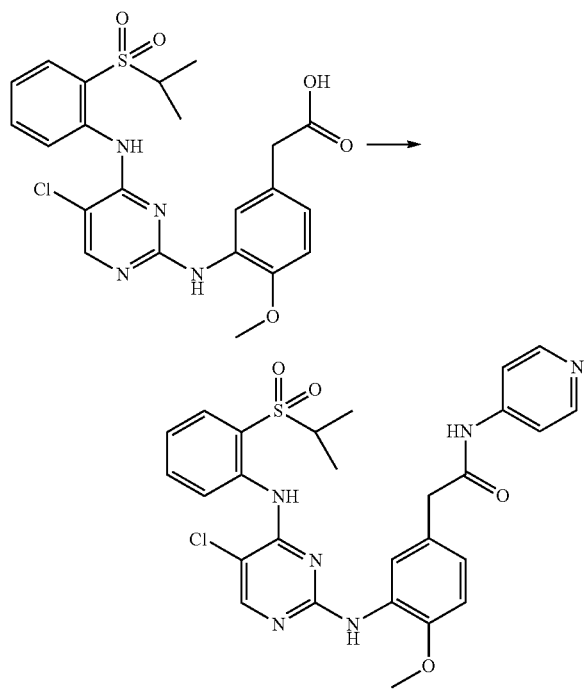

2-(3-(5-chloro-4-(2-(isopropylsulfonyl)phenylamino)pyrimidine-2-ylamino)-4-methoxyphenyl)acetic acid (100 mg, 0.20 mmol) was dissolved in dichloroethane (15 mL), to which EDCI (47.4 mg, 0.31 mmol) and DMAP (cat. 2.4 mg, 0.02 mmol) were added. Then, aminopyridine (0.019 mL, 0.31 mmol) was added thereto, followed by reaction at room temperature. Water was added thereto to terminate the reaction. The reaction mixture was washed with water and brine, and dried over magnesium sulfate. Then, purification was performed by MPLC to give the target compound 2-(3-((5-chloro-4-((2-(isopropylsulfonyl)phenyl)amino)pyrimidine-2-yl)amino)-4-methoxyphenyl)-N-(pyridine-4-yl)acetamide (35 mg, 0.06 mmol, yield: 31%).

$^1$H-NMR (300 MHz, CDCl$_3$) δ 9.53 (s, 1H), 8.49-8.41 (m, 3H), 8.30 (s, 1H), 8.16 (s, 1H), 7.93-7.91 (m, 1H), 7.67-7.61 (m, 2H), 7.41-7.36 (m, 3H), 7.26 (m, 1H), 6.91 (s, 2H), 3.94 (s, 3H), 3.62 (s, 2H), 3.20-3.17 (m, 1H), 1.28 (m, 6H); LC/MS (ESI) m/z 548 [M+H$^+$].

Example 50: Preparation of 2-(3-((5-chloro-4-((2-(isopropylsulfonyl)phenyl)amino)pyrimidine-2-yl)amino)-4-methoxyphenyl)-N-phenylacetamide

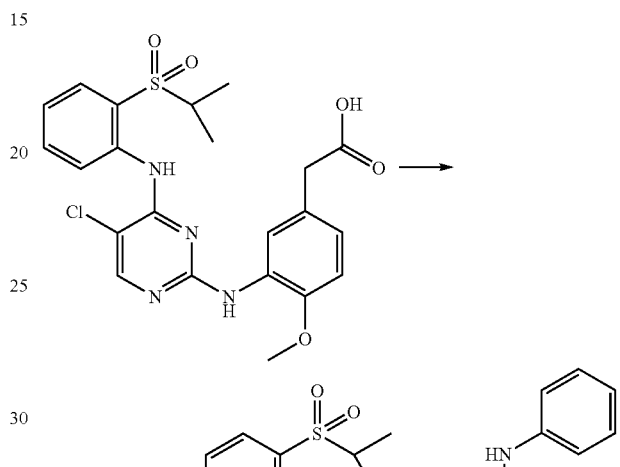

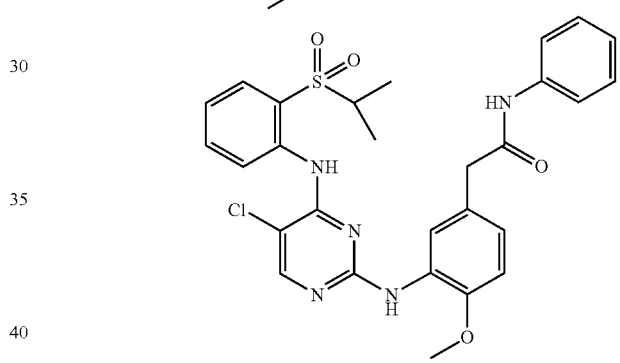

2-(3-(5-chloro-4-(2-(isopropylsulfonyl)phenylamino)pyrimidine-2-ylamino)-4-methoxyphenyl)acetic acid (100 mg, 0.20 mmol) was dissolved in dichloroethane (15 mL), to which EDCI (47.4 mg, 0.31 mmol) and triethanolamine (0.06 mL, 0.31 mmol) were added. Then, aminopyridine (0.019 mL, 0.31 mmol) was added thereto, followed by reaction at room temperature. Water was added thereto to terminate the reaction. The reaction mixture was washed with water and brine, and dried over magnesium sulfate. Then, purification was performed by MPLC to give the target compound 2-(3-((5-chloro-4-((2-(isopropylsulfonyl)phenyl)amino)pyrimidine-2-yl)amino)-4-methoxyphenyl)-N-phenylacetamide (34 mg, 0.06 mmol, yield: 28%).

$^1$H-NMR (300 MHz, CDCl$_3$) δ 9.48 (s, 1H), 8.46-8.43 (m, 1H), 8.30 (s, 1H), 8.16 (s, 1H), 7.92-7.90 (m, 1H), 7.69-7.62 (m, 2H), 7.39-7.37 (m, 2H), 7.32-7.23 (m, 2H), 7.13 (br, s, 1H), 7.09-7.04 (m, 1H), 6.91 (s, 2H), 3.94 (s, 3H), 3.57 (s, 2H), 3.19-3.12 (m, 1H), 1.26 (d, J=6.6 Hz, 6H); LC/MS (ESI) m/z 565 [M+H$^+$].

Example 51: Preparation of N2-(5-(2-aminoethyl)-4-bromo-2-methoxyphenyl)-5-chloro-N4-(2-(isopropylsulfonyl)phenyl)pyrimidine-2,4-diamine

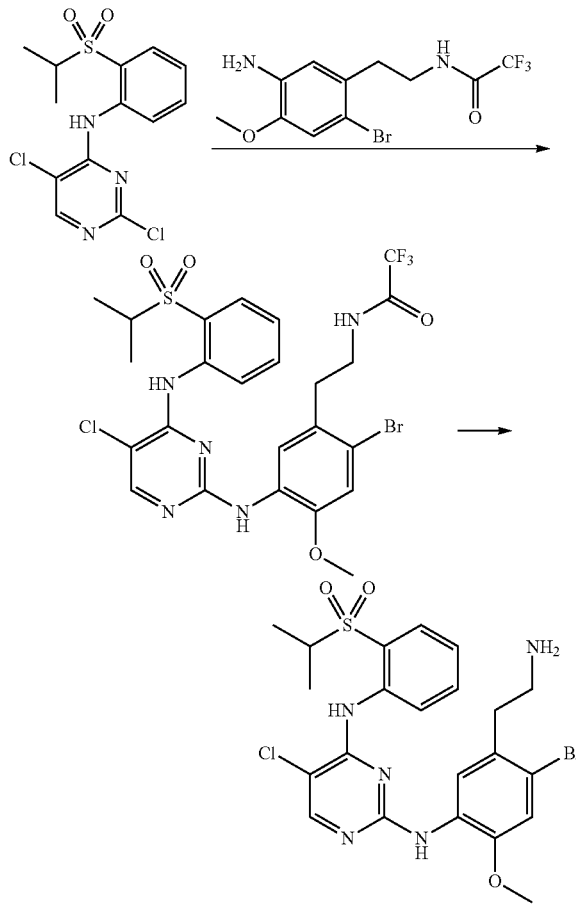

Step 1: Preparation of N-(2-bromo-5-((5-chloro-4-((2-(isopropylsulfonyl)phenyl)amino)pyrimidine-2-yl)amino)-4-methoxyphenethyl)-2,2,2-trifluoroacetamide N-(2-bromo-5-((5-chloro-4-((2-(isopropylsulfonyl)phenyl)amino)pyrimidine-2-yl)amino)-4-methoxyphenethyl)-2,2,2-trifluoroacetamide (50 mg, 0.14 mmol) and 2,5-dichloro-N-(2-(isopropylsulfonyl)phenyl) pyrimidine-4-amine (60.0 mg, 0.17 mmol) were added to 0.08 M HCl.ethoxyethanol (1.6 mL), which was heated at 90° C. overnight. Ethoxyethanol was removed from the reaction mixture. Sodium hydrogen carbonate aqueous solution was added thereto, followed by extraction with ethylacetate. The organic layer was washed with brine, dried over magnesium sulfate, filtered, and concentrated under reduced pressure. Then, column chromatography was performed (eluent: ethylacetate/hexane, 1/2) to give the target compound N-(2-bromo-5-((5-chloro-4-((2-(isopropylsulfonyl)phenyl)amino)pyrimidine-2-yl)amino)-4-methoxyphenethyl)-2,2,2-trifluoroacetamide as a yellow solid (48.0 mg, 0.07 mmol, yield: 52%).

$^1$H-NMR (300 MHz, CDCl$_3$) δ 9.62 (s, 1H), 8.51 (d, J=8.4 Hz, 1H), 8.30 (s, 1H), 8.20 (s, 1H), 7.96 (dd, J=7.8, 1.2 Hz, 1H), 7.67 (t, J=7.2 Hz, 1H), 7.50 (s, 1H), 7.32 (t, J=6.9 Hz, 1H), 7.07 (s, 1H), 6.33 (s, 1H), 3.93 (s, 3H), 3.58-3.50 (m, 2H), 3.33-3.24 (m, 2H), 2.92 (t, J=6.9 Hz, 2H), 1.34 (d, J=6.9 Hz, 6H); LC/MS 650.00 [M+H$^+$].

Step 2: Preparation of N2-(5-(2-aminoethyl)-4-bromo-2-methoxyphenyl)-5-chloro-N4-(2-(isopropylsulfonyl)phenyl)pyrimidine-2,4-diamine N-(2-bromo-5-((5-chloro-4-((2-(isopropylsulfonyl)phenyl)amino)pyrimidine-2-yl)amino)-4-methoxyphenethyl)-2,2,2-trifluoroacetamide (30.0 mg, 0.06 mmol) prepared in step 1 was dissolved in tetrahydrofuran (2 mL), to which water (1 mL) containing lithium hydroxide dissolved therein and methanol (1 mL) were added, followed by stirring at room temperature for 4 hours. The reaction mixture was extracted with ethylacetate, washed with brine, dried over magnesium sulfate, filtered, and concentrated under reduced pressure. Then, column chromatography was performed (eluent: ethylacetate/hexane, 3/1) to give the target compound N2-(5-(2-aminoethyl)-4-bromo-2-methoxyphenyl)-5-chloro-N4-(2-(isopropylsulfonyl)phenyl)pyrimidine-2,4-diamine as a yellow solid (13 mg, 0.02 mmol, yield: 32%).

$^1$H-NMR (300 MHz, CDCl$_3$) δ 9.54 (s, 1H), 8.50 (d, J=8.7 Hz, 1H), 8.21 (s, 1H), 8.17 (s, 1H), 7.93 (dd, J=7.8, 1.5 Hz, 1H), 7.66 (t, J=1.2 Hz, 1H), 7.45 (s, 1H), 7.30 (d, J=7.2 Hz, 1H), 7.03 (s, 1H), 3.88 (s, 1H), 3.29-3.20 (m, 1H), 2.87 (d, J=5.7 Hz, 2H), 2.81 (d, J=6.3 Hz, 2H), 1.30 (d, J=6.9 Hz, 6H); LC/MS 554.06 [M+H$^+$].

Example 52: Preparation of N2-(5-(2-aminoethyl)-2-methoxy-4-(1-methyl-1H-pyrazole-4-yl)phenyl)-5-chloro-N4-(2-(isopropylsulfonyl)phenyl)pyrimidine-2,4-diamine

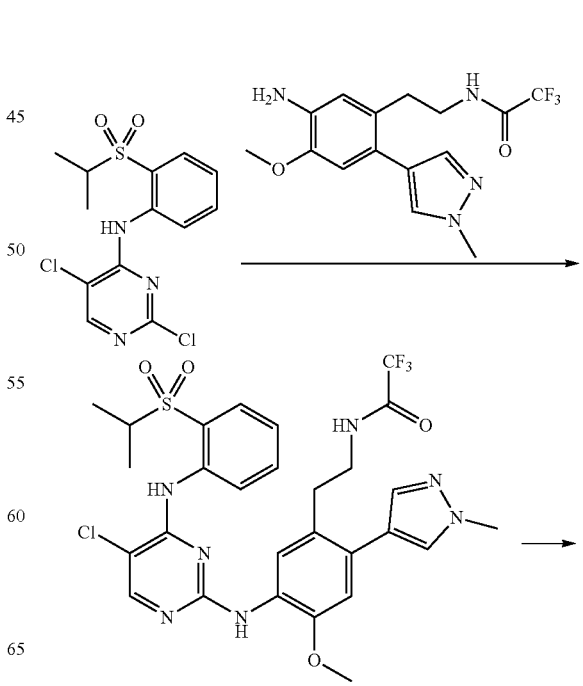

-continued

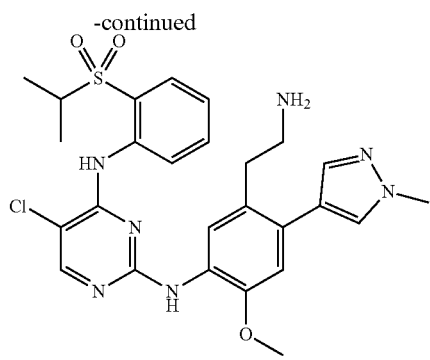

Step 1: Preparation of N-(5-(5-chloro-4-(2-(isopropylsulfonyl)phenylamino)pyrimidine-2-ylamino)-4-methoxy-2-(1-methyl-1H-pyrazole-4-yl)phenethyl)-2,2,2-trifluoroacetamide The compound (30 mg, 0.09 mmol) prepared in preparative example 19 and 2,5-dichloro-N-(2-(isopropylsulfonyl)phenyl) pyrimidine-4-amine (36.0 mg, 0.11 mmol) were dissolved in 0.08 M HCl.ethoxyethanol (1.6 mL), which was heated at 100° C. overnight. Ethoxyethanol was removed from the reaction mixture, followed by extraction with ethylacetate. The organic layer was washed with brine, dried over magnesium sulfate, filtered, and concentrated under reduced pressure. Then, purification was performed by silica gel column chromatography (eluent: ethylacetate/hexane, 4/1) to give the target compound N-(5-(5-chloro-4-(2-(isopropylsulfonyl)phenylamino)pyrimidine-2-ylamino)-4-methoxy-2-(1-methyl-1H-pyrazole-4-yl)phenethyl)-2,2,2-trifluoroacetamide (30.0 mg, 0.05 mmol, yield: 53%).

$^1$H-NMR (300 MHz, CDCl$_3$) δ 9.61 (s, 1H), 8.58 (d, J=8.1 Hz, 1H), 8.28 (s, 1H), 8.21 (s, 1H), 7.96 (d, J=7.8 Hz, 1H), 7.68 (t, J=7.8 Hz, 1H), 7.59 (s, 1H), 7.55 (s, 1H), 7.50 (s, 1H), 7.28 (t, J=6.6 Hz, 1H), 6.82 (s, 1H), 6.24 (s, 1H), 4.00 (s, 3H), 3.93 (s, 3H), 3.40-3.52 (m, 2H), 2.89 (t, J=6.9 Hz, 2H), 2.15 (s, 1H), 1.35 (d, J=6.9 Hz, 6H)

Step 2: Preparation of N2-(5-(2-aminoethyl)-2-methoxy-4-(1-methyl-1H-pyrazole-4-yl)phenyl)-5-chloro-N4-(2-(isopropylsulfonyl)phenyl)pyrimidine-2,4-diamine N-(5-(5-chloro-4-(2-(isopropylsulfonyl)phenylamino)pyrimidine-2-ylamino)-4-methoxy-2-(1-methyl-1H-pyrazole-4-yl)phenethyl)-2,2,2-trifluoroacetamide (30.0 mg, 0.05 mmol) prepared in step 1 was dissolved in tetrahydrofuran (1 mL), to which water (0.5 mL) containing lithium hydroxide dissolved therein was added, followed by stirring at room temperature for 3 hours with methanol (0.5 mL). The reaction mixture was extracted twice ethylacetate. The organic layer was washed with brine, dried over magnesium sulfate, filtered, and concentrated under reduced pressure. Then, purification was performed by silica gel column chromatography (eluent: ethylacetate/hexane, 3/1) to give the target compound N2-(5-(2-aminoethyl)-2-methoxy-4-(1-methyl-1H-pyrazole-4-yl)phenyl)-5-chloro-N4-(2-(isopropylsulfonyl)phenyl)pyrimidine-2,4-diamine (7.00 mg, 0.01 mmol, yield: 27%).

$^1$H-NMR (300 MHz, CDCl$_3$) δ 8.23 (s, 2H), 8.03 (d, J=7.8 Hz, 1H), 7.90 (s, 1H), 7.79-7.65 (m, 2H), 7.56 (t, J=7.5 Hz, 1H), 7.40 (s, 1H), 7.06 (s, 1H), 4.00 (s, 3H), 3.86 (s, 3H), 3.53-3.36 (m, 1H), 2.98 (s, 4H), 1.27 (d, J=5.4 Hz, 6H); LC/MS 556.2 [M+H+].

Example 53: Preparation of 2-(4-((5-chloro-4-((2-(isopropylsulfonyl)phenyl)amino)pyrimidine-2-yl)amino)-5-methoxy-2-methylphenyl)acetonitrile

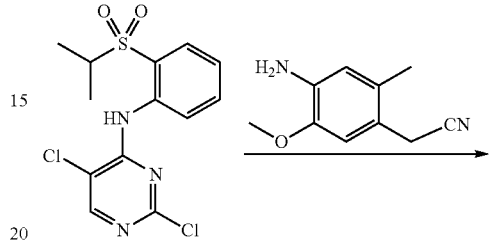

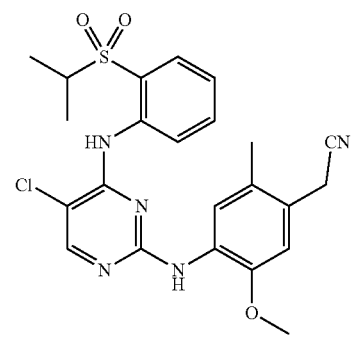

2,5-dichloro-N-(2-(isopropylsulfonyl)phenyl)pyrimidine-4-amine (472 mg, 1.36 mmol) was dissolved in 0.08 M HCl.ethoxyethanol (1.0 mL), to which the compound (200 mg, 1.13 mmol) prepared in preparative example 20 was added, followed by stirring at 80° C. for 12 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound 2-(4-((5-chloro-4-((2-(isopropylsulfonyl)phenyl)amino)pyrimidine-2-yl)amino)-5-methoxy-2-methylphenyl)acetonitrile as a white solid (450 mg, 0.926 mmol, yield: 81%).

$^1$H-NMR (300 MHz, CDCl$_3$) δ 9.53 (s, br, 1H), 8.53 (d, J=8.3 Hz, 1H), 8.18 (s, 1H), 8.13 (s, 1H), 7.94 (d, J=7.9 Hz, 1H), 7.64 (t, J=8.4 Hz, 1H), 7.55 (s, br, 1H), 7.28 (t, J=7.8 Hz, 1H), 6.86 (s, 1H), 3.91 (s, 3H), 3.63 (s, 2H), 3.26 (sept, J=6.9 Hz, 1H), 2.17 (s, 3H), 1.31 (d, J=6.9 Hz, 6H); LC/MS 485.9 [M+H$^+$].

Example 54: Preparation of 2-(4-((5-chloro-4-((2-(isopropylsulfonyl)phenyl)amino)pyrimidine-2-yl)amino)-5-methoxy-2-methylphenyl)-2-methylpropanenitrile

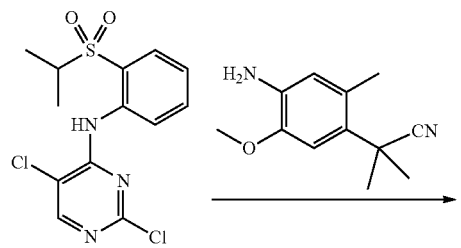

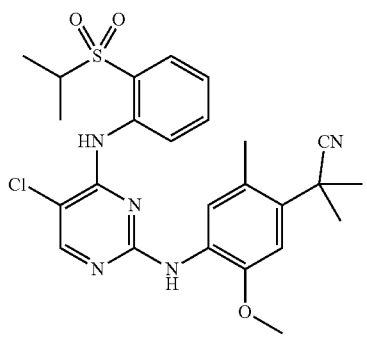

2,5-dichloro-N-(2-(isopropylsulfonyl)phenyl)pyrimidine-4-amine (472 mg, 1.36 mmol) was dissolved in 0.08 M HCl.ethoxyethanol (1.0 mL), to which the compound (200 mg, 0.979 mmol) prepared in preparative example 21 was added, followed by stirring at 80° C. for 12 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound 2-(4-((5-chloro-4-((2-(isopropylsulfonyl)phenyl)amino)pyrimidine-2-yl)amino)-5-methoxy-2-methylphenyl)-2-methylpropanenitrile as a white solid (433 mg, 0.875 mmol, yield: 86%).

$^1$H-NMR (300 MHz, CDCl$_3$) δ 9.53 (s, br, 1H), 8.52 (d, J=8.3 Hz, 1H), 8.18 (s, 1H), 8.12 (s, 1H), 7.94 (d, J=7.9 Hz, 1H), 7.66 (t, J=7.3 Hz, 1H), 7.53 (s, br, 1H), 7.28 (t, J=7.8 Hz, 1H), 6.83 (s, 1H), 3.90 (s, 3H), 3.26 (sept, J=6.9 Hz, 1H), 2.44 (s, 3H), 1.79 (s, 6H), 1.32 (d, J=6.9 Hz, 6H); LC/MS 513.8 [M+H$^+$].

Example 55: Preparation of N2-(4-(2-aminoethyl)-2-methoxy-5-methylphenyl)-5-chloro-N4-(2-(isopropylsulfonyl)phenyl)pyrimidine-2,4-diamine

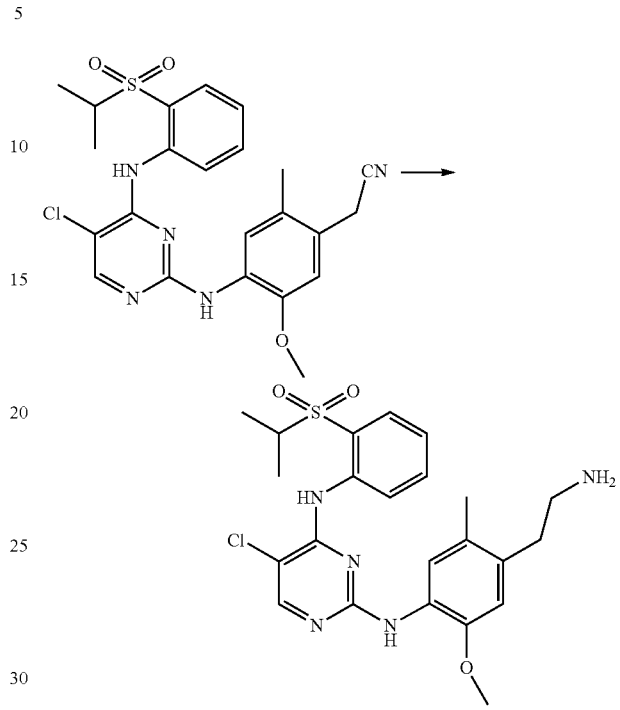

2-(4-((5-chloro-4-((2-(isopropylsulfonyl)phenyl)amino)pyrimidine-2-yl)amino)-5-methoxy-2-methylphenyl)acetonitrile (200 mg, 0.411 mmol) was dissolved in tetrahydrofuran (2 mL), to which 1.0 M BH$_3$/THF (boran/tetrahydrofuran; 177 mg, 2.06 mmol) was added at 0° C., followed by stirring at room temperature for 12 hours. Methanol was added thereto to terminate the reaction, which was distillated under reduced pressure. 1.5 N HCl (25.0 mL) was added thereto, followed by extraction twice with ethylacetate. The water layer was basified with sodium hydroxide aqueous solution, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound N2-(4-(2-aminoethyl)-2-methoxy-5-methylphenyl)-5-chloro-N4-(2-(isopropylsulfonyl)phenyl)pyrimidine-2,4-diamine as a yellow solid (90.0 mg, 0.185 mmol, yield: 45%).

$^1$H-NMR (300 MHz, CDCl$_3$) δ 9.51 (s, br, 1H), 8.57 (d, J=8.3 Hz, 1H), 8.15 (s, 1H), 8.01 (s, 1H), 7.92 (d, J=7.9 Hz, 1H), 7.63 (t, J=8.4 Hz, 1H), 7.48 (s, br, 1H), 7.26 (t, J=6.5 Hz, 1H), 6.69 (s, 1H), 3.87 (s, 3H), 3.25 (sept, J=6.9 Hz, 1H), 2.94 (t, J=6.7 Hz, 2H), 2.75 (t, J=7.0 Hz, 2H), 2.17 (s, 5H), 1.31 (d, J=6.9 Hz, 6H); LC/MS 489.8 [M+H$^+$].

Example 56: Preparation of N2-(4-(1-amino-2-methylpropane-2-yl)-2-methoxy-5-methylphenyl)-5-chloro-N4-(2-(isopropylsulfonyl)phenyl)pyrimidine-2,4-diamine

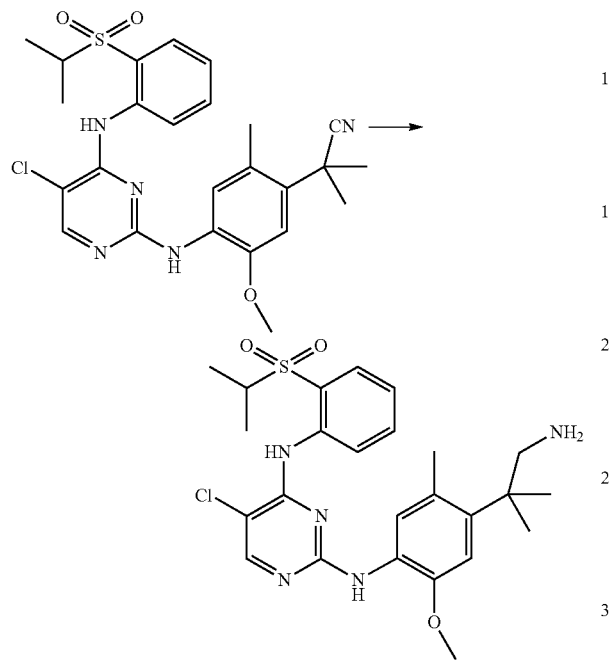

2-(4-((5-chloro-4-((2-(isopropylsulfonyl)phenyl)amino)pyrimidine-2-yl)amino)-5-methoxy-2-methylphenyl)-2-methylpropanenitrile (100 mg, 0.194 mmol) was dissolved in tetrahydrofuran (2 mL), to which 1.0 M BH₃/THF (boran/tetrahydrofuran; 83.6 mg, 0.972 mmol) was added at 0° C., followed by stirring at room temperature for 12 hours. Methanol was added thereto to terminate the reaction, which was distillated under reduced pressure. 1.5 N HCl (15 mL) was added thereto, followed by extraction twice with ethylacetate. The water layer was basified with sodium hydroxide aqueous solution, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound N2-(4-(1-amino-2-methylpropane-2-yl)-2-methoxy-5-methylphenyl)-5-chloro-N4-(2-(isopropylsulfonyl)phenyl)pyrimidine-2,4-diamine as a white solid (45.0 mg, 0.087 mmol, yield: 45%).

¹H-NMR (300 MHz, CDCl₃) δ 9.51 (s, br, 1H), 8.57 (d, J=8.4 Hz, 1H), 8.16 (s, 1H), 7.99 (s, 1H), 7.93 (d, J=8.0 Hz, 1H), 7.63 (t, J=8.4 Hz, 1H), 7.46 (s, br, 1H), 7.26 (t, J=6.9 Hz, 1H), 6.87 (s, 1H), 3.88 (s, 3H), 3.26 (sept, J=6.9 Hz, 1H), 2.96 (s, 2H), 2.34 (s, 3H), 1.39 (s, 6H), 1.31 (d, J=6.9 Hz, 6H), 1.26 (s, br, 2H); LC/MS 517.7 [M+H⁺].

Example 57: Preparation of N2-(4-(2-aminopropane-2-yl)-2-methoxy-5-methylphenyl)-5-chloro-N4-(2-(isopropylsulfonyl)phenyl)pyrimidine-2,4-diamine

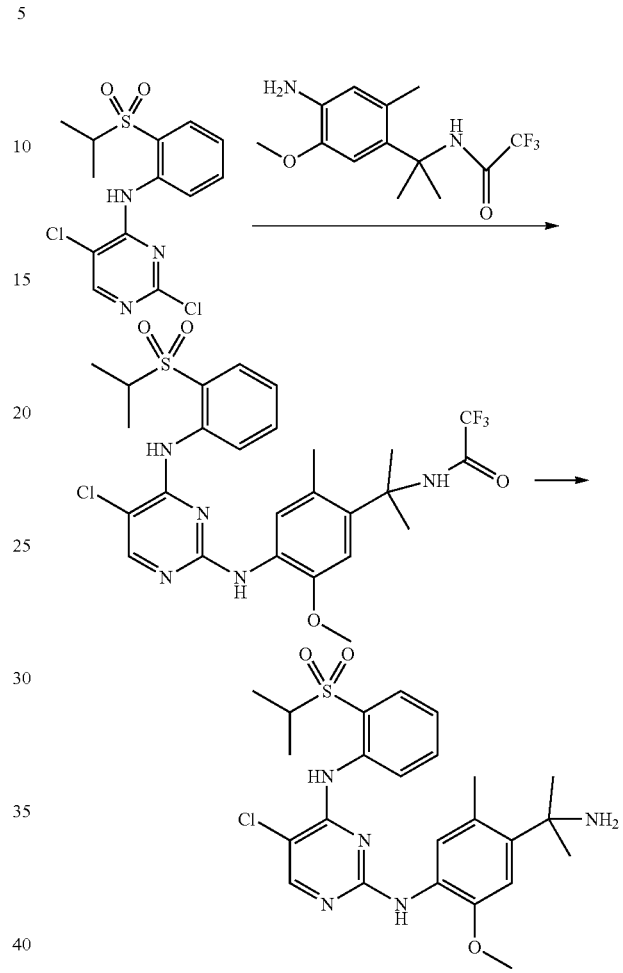

Step 1: Preparation of N-(2-(4-((5-chloro-4-((2-(isopropylsulfonyl)phenyl)amino)pyrimidine-2-yl)amino)-5-methoxy-2-methylphenyl)propane-2-yl)-2,2,2-trifluoroacetamide 2,5-dichloro-N-(2-(isopropylsulfonyl)phenyl)pyrimidine-4-amine (77.3 mg, 0.223 mmol) was dissolved in 0.08 M HCl.ethoxyethanol (0.5 mL), to which the compound (54.0 mg, 0.186 mmol) prepared in preparative example 22 was added, followed by stirring at 80° C. for 12 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/3) to give the target compound N-(2-(4-((5-chloro-4-((2-(isopropylsulfonyl)phenyl)amino)pyrimidine-2-yl)amino)-5-methoxy-2-methylphenyl)propane-2-yl)-2,2,2-trifluoroacetamide as a white solid (83.0 mg, 0.138 mmol, yield: 74%).

¹H-NMR (300 MHz, CDCl₃) δ 9.53 (s, br, 1H), 8.55 (d, J=8.4 Hz, 1H), 8.19 (s, 1H), 8.08 (s, 1H), 7.95 (d, J=7.9 Hz, 1H), 7.64 (t, J=8.5 Hz, 1H), 7.53 (s, br, 1H), 7.28 (t, J=8.5

Hz, 1H), 6.94 (s, 1H), 6.42 (s, br, 1H), 3.93 (s, 3H), 3.28 (sept, J=6.9 Hz, 1H), 2.29 (s, 1H), 1.87 (s, 6H), 1.34 (d, J=6.9 Hz, 6H); LC/MS 599.7 [M+H$^+$].

Step 2: Preparation of N2-(4-(2-aminopropane-2-yl)-2-methoxy-5-methylphenyl)-5-chloro-N4-(2-(isopropylsulfonyl)phenyl)pyrimidine-2,4-diamine N-(2-(4-((5-chloro-4-((2-(isopropylsulfonyl)phenyl) amino)pyrimidine-2-yl)amino)-5-methoxy-2-methylphenyl) propane-2-yl)-2,2,2-trifluoroacetamide (73.0 mg, 0.121 mmol) prepared in step 1 was dissolved in tetrahydrofuran (4.0 mL), methanol (2.0 mL) and water (1.0 mL), to which lithium hydroxide hydrate (127 mg, 3.03 mmol) was added, followed by stirring at 40° C. for 24 hours. The reaction mixture was distillated under reduced pressure, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(4-(2-aminopropane-2-yl)-2-methoxy-5-methylphenyl)-5-chloro-N4-(2-(isopropylsulfonyl)phenyl)pyrimidine-2,4-diamine as a white solid (25.0 mg, 0.049 mmol, yield: 40%).

$^1$H-NMR (300 MHz, CDCl$_3$) δ 9.50 (s, br, 1H), 8.57 (d, J=8.3 Hz, 1H), 8.16 (s, 1H), 8.00 (s, 1H), 7.93 (d, J=7.9 Hz, 1H), 7.63 (t, J=7.3 Hz, 1H), 7.48 (s, br, 1H), 7.26 (t, J=6.9 Hz, 1H), 7.15 (s, 1H), 3.89 (s, 3H), 3.26 (sept, J=6.9 Hz, 1H), 2.43 (s, 2H), 1.76 (s, br, 2H), 1.58 (s, 6H), 1.31 (d, J=6.9 Hz, 1H); LC/MS 504.0 [M+H$^+$].

Example 58: Preparation of 5-chloro-N2-(4-(2-(dimethylamino)ethyl)-2-methoxy-5-methylphenyl)-N4-(2-(isopropylsulfonyl)phenyl)pyrimidine-2,4-diamine

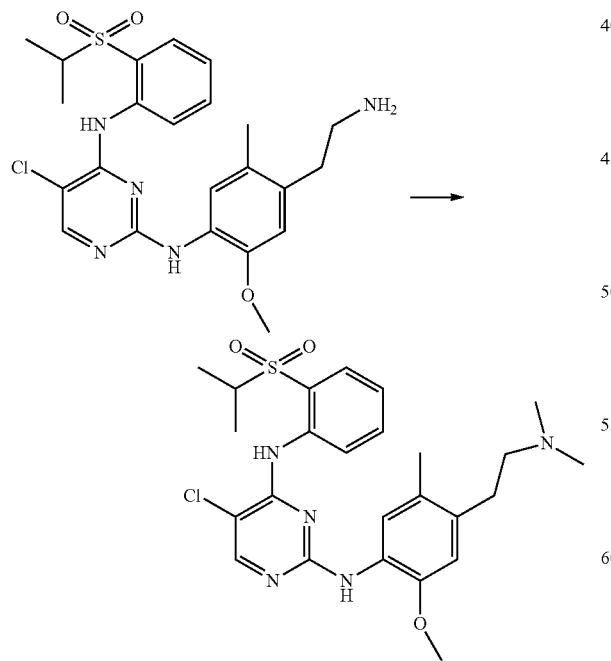

N2-(4-(2-aminoethyl)-2-methoxy-5-methylphenyl)-5-chloro-N4-(2-(isopropylsulfonyl)phenyl)pyrimidine-2,4-diamine (25.0 mg, 0.051 mmol) was dissolved in methanol (1.0 mL), to which acetic acid and formalin (35%) (4.37 mg, 0.051 mmol) were added at 0° C., followed by stirring at room temperature for 30 minutes. Sodiumcyanoborohydride (4.80 mg, 0.076 mmol) was added thereto, followed by stirring at room temperature for 30 minutes. Sodium hydrogen carbonate aqueous solution was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound 5-chloro-N2-(4-(2-(dimethylamino)ethyl)-2-methoxy-5-methylphenyl)-N4-(2-(isopropylsulfonyl)phenyl)pyrimidine-2,4-diamine as a white solid (20.0 mg, 0.039 mmol, yield: 77%).

$^1$H-NMR (300 MHz, CDCl$_3$) δ 9.53 (s, br, 1H), 8.58 (d, J=8.3 Hz, 1H), 8.18 (s, 1H), 8.05 (s, 1H), 7.95 (d, J=8.0 Hz, 1H), 7.66 (t, J=8.5 Hz, 1H), 7.51 (s, br, 1H), 7.29 (t, J=7.5 Hz, 1H), 6.73 (s, 1H), 3.90 (s, 3H), 3.28 (sept, J=6.9 Hz, 1H), 2.87-2.84 (m, 2H), 2.69-2.66 (m, 2H), 2.51 (s, 6H), 2.20 (s, 3H), 1.32 (d, J=6.9 Hz, 6H); LC/MS 518.0 [M+H$^+$].

Example 59: Preparation of N-(2-(4-((5-chloro-4-((2-(isopropylsulfonyl)phenyl)amino)pyrimidine-2-yl)amino)-5-methoxy-2-methylphenyl)-2-methylpropyl)formamide

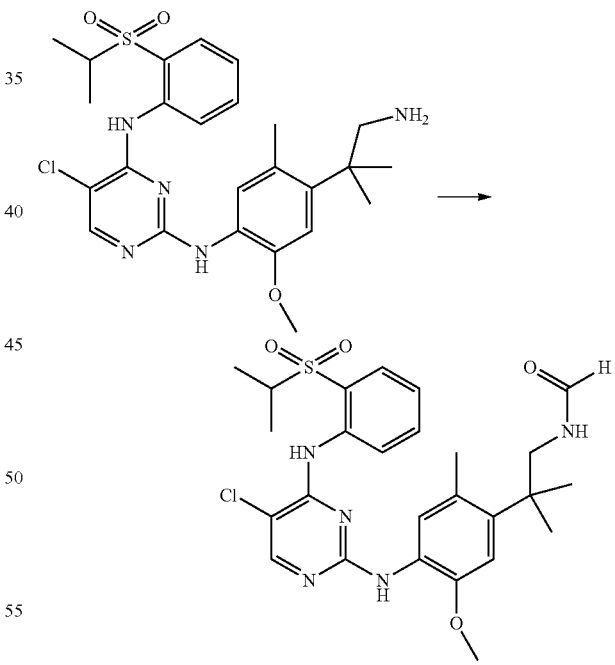

N2-(4-(1-amino-2-methylpropane-2-yl)-2-methoxy-5-methylphenyl)-5-chloro-N4-(2-(isopropylsulfonyl)phenyl) pyrimidine-2,4-diamine (80.0 mg, 0.154 mmol) was dissolved in ethylformate (3 mL), followed by reflux-stirring at 60° C. for 4 hours. The solvent was eliminated by distillation under reduced pressure. Then, purification was performed by silica gel column chromatography (eluent: methanol/ dichloromethane, 1/9) to give the target compound N-(2-(4-((5-chloro-4-((2-(isopropylsulfonyl)phenyl)amino)pyrimidine-2-yl)amino)-5-methoxy-2-methylphenyl)-2-methylpropyl)formamide as a white solid (80.0 mg, 0.146 mmol, yield: 94%).

$^1$H-NMR (300 MHz, CDCl$_3$) δ 9.54 (s, br, 0.7H), 9.51 (s, br, 0.2H), 8.56 (d, J=8.3 Hz, 1H), 8.16 (s, 1H), 8.11 (s, br, 1H), 8.04 (s, 1H), 7.93 (d, J=7.7 Hz, 1H), 7.63 (t, J=8.3 Hz, 1H), 7.48 (s, br, 1H), 7.26 (t, J=8.3 Hz, 1H), 6.86 (s, 0.8H), 6.78 (s, 0.2H), 5.20 (s, br, 1H), 3.88 (s, 2H), 3.87 (s, 1H), 3.67 (d, J=5.9 Hz, 1.6H), 3.48 (d, J=6.6 Hz, 0.4H), 3.26 (sept, J=6.9 Hz, 1H), 2.36 (s, 2.3H), 2.34 (s, 0.7H), 1.44 (s, 6H), 1.31 (d, J=6.9 Hz, 6H); LC/MS 546.0 [M+H$^+$].

Example 60: Preparation of 5-chloro-N4-(2-(isopropylsulfonyl)phenyl)-N2-(2-methoxy-5-methyl-4-(2-methyl-1-(methylamino)propane-2-yl)phenyl)pyrimidine-2,4-diamine

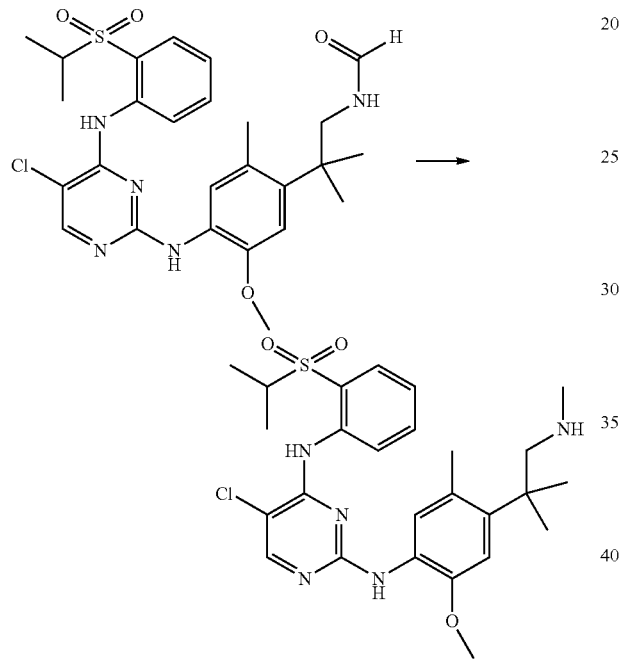

N-(2-(4-((5-chloro-4-((2-(isopropylsulfonyl)phenyl)amino)pyrimidine-2-yl)amino)-5-methoxy-2-methylphenyl)-2-methylpropyl)formamide (54.0 mg, 0.098 mmol) was dissolved in tetrahydrofuran (5.0 mL), to which lithium aluminum hydride (37.5 mg, 0.988 mmol) was added, followed by stirring at 60° C. for 12 hours. Water and sodium hydroxide aqueous solution were added thereto to terminate the reaction. The reaction mixture was filtered, and the filtrate was extracted twice with ethylacetate. The solvent was eliminated by distillation under reduced pressure. Then, purification was performed by silica gel column chromatography (eluent: methanol/dichloromethane, 1/9) to give the target compound 5-chloro-N4-(2-(isopropylsulfonyl)phenyl)-N2-(2-methoxy-5-methyl-4-(2-methyl-1-(methylamino)propane-2-yl)phenyl)pyrimidine-2,4-diamine as a white solid (10.0 mg, 0.018 mmol, yield: 20%).

$^1$H-NMR (300 MHz, CDCl$_3$) δ 9.51 (s, br, 1H), 8.57 (d, J=8.3 Hz, 1H), 8.16 (s, 1H), 7.97 (s, 1H), 7.92 (d, J=7.9, 1H), 7.63 (t J=7.2, 1H), 7.45 (s, br, 1H), 7.26 (t, J=7.2 Hz, 1H), 6.90 (s, 1H), 3.87 (s, 3H), 3.26 (sept, J=6.9 Hz, 1H), 2.85 (s, 2H), 2.39 (s, 3H), 2.34 (s, 3H), 1.45 (s, 6H), 1.31 (d, J=6.9 Hz, 6H), 1.25 (s, br, 1H); LC/MS 531.7 [M+H$^+$].

Example 61: Preparation of N-(2-(4-((5-chloro-4-((2-(isopropylsulfonyl)phenyl)amino)pyrimidine-2-yl)amino)-5-methoxy-2-methylphenyl)propane-2-yl)formamide

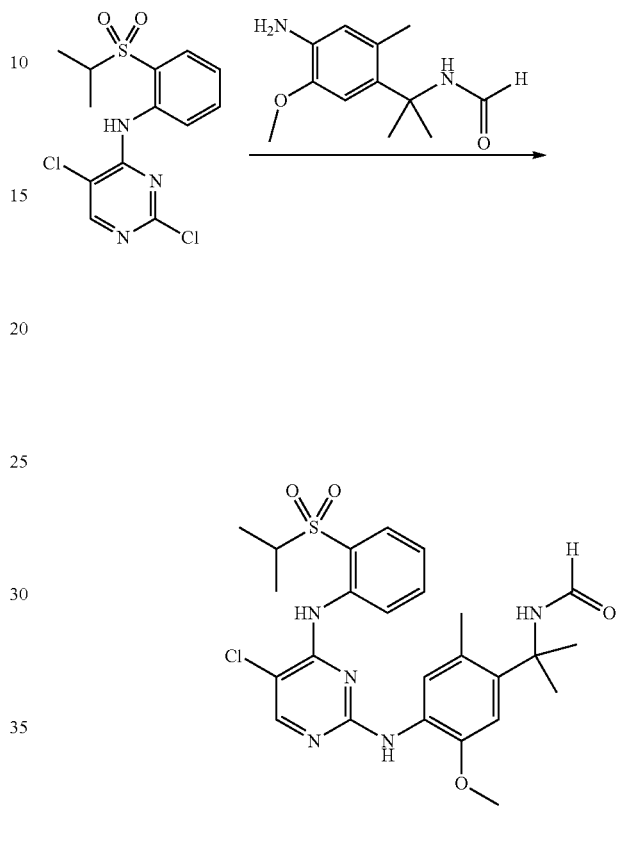

2,5-dichloro-N-(2-(isopropylsulfonyl)phenyl)pyrimidine-4-amine (280 mg, 0.809 mmol) was dissolved in 0.08 M HCl.ethoxyethanol (1 mL), to which the compound (150 mg, 0.674 mmol) prepared in preparative example 23 was added, followed by stirring at 80° C. for 12 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: ethylacetate/hexane, 2/3) to give the target compound N-(2-(4-((5-chloro-4-((2-(isopropylsulfonyl)phenyl)amino)pyrimidine-2-yl)amino)-5-methoxy-2-methylphenyl)propane-2-yl)formamide as a white solid (197 mg, 0.371 mmol, yield: 55%).

$^1$H-NMR (300 MHz, CDCl$_3$) δ 9.52 (s, br, 0.6H), 9.49 (s, br, 0.3H), 8.53 (t, J=7.7 Hz, 1H), 8.18 (s, 0.6H), 8.16 (s, 0.4H), 8.13 (s, 0.4H), 8.08 (s, 0.6H), 8.03-8.01 (m, 0.7H), 7.96 (s, 0.3H), 7.93 (d, J=8.0 Hz, 1H), 7.63 (t, J=7.7 Hz, 1H), 7.53 (s, br, 0.6H), 7.50 (s, br, 0.4H), 7.29-7.28 (m, 0.5H), 7.24-7.23 (m, 0.5H), 6.93 (s, 0.4H), 6.92 (s, 0.6H), 6.05-6.01 (m, 0.6H), 5.63 (s, br, 0.4H), 3.90 (s, 1.9H), 3.89 (s, 1.1H), 3.26 (sept, J=6.9 Hz, 1H), 2.32 (s, 1H), 2.29 (s, 2H), 1.81 (s, 2H), 1.73 (s, 4H), 1.31 (d, J=6.9 Hz, 6H); LC/MS 532.0 [M+H$^+$].

Example 62: Preparation of N-(4-((5-chloro-4-((2-(isopropylsulfonyl)phenyl)amino)pyrimidine-2-yl)amino)-5-methoxy-2-methylphenethyl)formamide

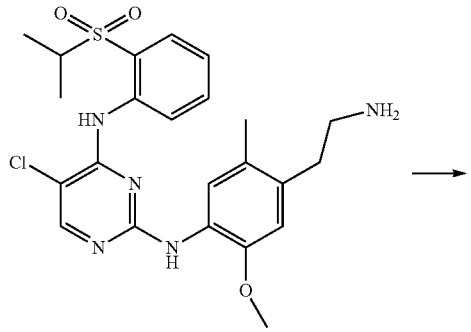

Example 63: Preparation of 5-chloro-N4-(2-(isopropylsulfonyl)phenyl)-N2-(2-methoxy-5-methyl-4-(2-(methylamino)ethyl)phenyl)pyrimidine-2,4-diamine

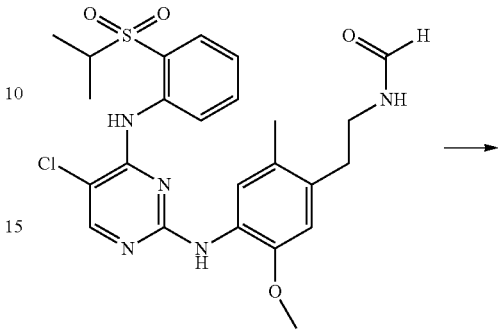

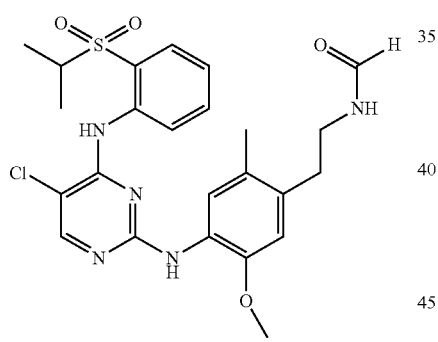

N2-(4-(2-aminoethyl)-2-methoxy-5-methylphenyl)-5-chloro-N4-(2-(isopropylsulfonyl)phenyl)pyrimidine-2,4-diamine (250 mg, 0.510 mmol) was dissolved in ethylformate (10 mL), followed by reflux-stirring at 60° C. for 4 hours. The solvent was eliminated by distillation under reduced pressure. Then, purification was performed by silica gel column chromatography (eluent: methanol/dichloromethane, 1/9) to give the target compound N-(4-((5-chloro-4-((2-(isopropylsulfonyl)phenyl)amino)pyrimidine-2-yl)amino)-5-methoxy-2-methylphenethyl)formamide as a white solid (200 mg, 0.386 mmol, yield: 76%).

$^1$H-NMR (300 MHz, CDCl$_3$) δ 9.52 (s, br, 1H), 8.57 (d, J=8.4 Hz, 1H), 8.18 (s, 1H), 8.16 (s, 1H), 8.06 (s, 1H), 7.93 (d, J=6.5 Hz, 1H), 7.63 (t, J=8.4 Hz, 1H), 7.49 (s, br, 1H), 7.29 (t, J=9.9 Hz, 1H), 6.68 (s, 0.8H), 6.61 (s, 0.2H), 5.54 (s, br, 1H), 3.87 (s, 3H), 3.53 (q, J=6.8 Hz, 1.7H), 3.44-0.342 (m, 0.4H), 3.26 (sept, J=6.9 Hz, 1H), 2.82 (t, J=7.2 Hz, 2H), 2.18 (s, 3H), 1.31 (d, J=6.9 Hz, 6H); LC/MS 517.7 [M+H$^+$].

N-(4-((5-chloro-4-((2-(isopropylsulfonyl)phenyl)amino)pyrimidine-2-yl)amino)-5-methoxy-2-methylphenethyl)formamide (180 mg, 0.347 mmol) was dissolved in tetrahydrofuran (15.0 mL), to which lithium aluminum hydride (132 mg, 3.47 mmol) was added, followed by stirring at 60° C. for 12 hours. Water and sodium hydroxide aqueous solution were added thereto to terminate the reaction. The reaction mixture was filtered, and the filtrate was extracted twice with ethylacetate. The solvent was eliminated by distillation under reduced pressure. Then, purification was performed by silica gel column chromatography (eluent: methanol/dichloromethane, 1/9) to give the target compound 5-chloro-N4-(2-(isopropylsulfonyl)phenyl)-N2-(2-methoxy-5-methyl-4-(2-(methylamino)ethyl)phenyl)pyrimidine-2,4-diamine as a white solid (30.0 mg, 0.059 mmol, yield: 17%).

$^1$H-NMR (300 MHz, CDCl$_3$) δ 9.51 (s, br, 1H), 8.57 (d, J=8.3 Hz, 1H), 8.16 (s, 1H), 8.00 (s, 1H), 7.92 (d, J=7.9 Hz, 1H), 7.63 (t, J=8.4 Hz, 1H), 7.48 (s, br, 1H), 7.26 (t, J=7.3 Hz, 1H), 6.70 (s, 1H), 3.86 (s, 3H), 3.26 (sept, J=6.9 Hz, 1H), 2.79 (s, 4H), 2.47 (s, 3H), 2.18 (s, 3H), 1.77 (s, br, 1H), 1.31 (d, J=6.9 Hz, 6H); LC/MS 504.0 [M+H$^+$].

Example 64: Preparation of 5-chloro-N4-(2-(isopropylsulfonyl)phenyl)-N2-(2-methoxy-5-methyl-4-(2-(methylamino)propane-2-yl)phenyl)pyrimidine-2,4-diamine

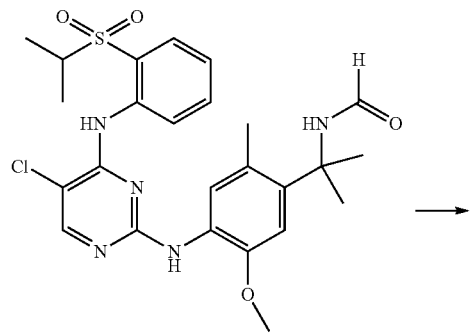

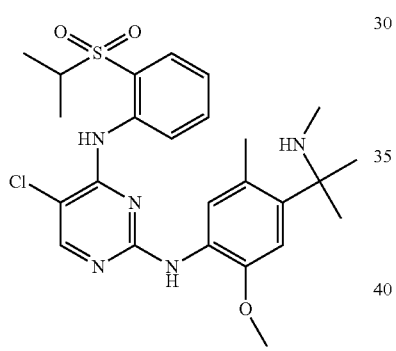

N-(2-(4-((5-chloro-4-((2-(isopropylsulfonyl)phenyl)amino)pyrimidine-2-yl)amino)-5-methoxy-2-methylphenyl)propane-2-yl)formamide (170 mg, 0.319 mmol) was dissolved in tetrahydrofuran (15.0 mL), to which lithium aluminum hydride (121 mg, 3.19 mmol) was added, followed by stirring at 60° C. for 12 hours. Water and sodium hydroxide aqueous solution were added thereto to terminate the reaction. The reaction mixture was filtered, and the filtrate was extracted twice with ethylacetate. The solvent was eliminated by distillation under reduced pressure. Then, purification was performed by silica gel column chromatography (eluent: methanol/dichloromethane, 1/9) to give the target compound 5-chloro-N4-(2-(isopropylsulfonyl)phenyl)-N2-(2-methoxy-5-methyl-4-(2-(methylamino)propane-2-yl)phenyl)pyrimidine-2,4-diamine as a yellow solid (45.0 mg, 0.086 mmol, yield: 27%).

$^1$H-NMR (300 MHz, CDCl$_3$) δ 9.51 (s, br, 1H), 8.57 (d, J=8.3 Hz, 1H), 8.16 (s, 1H), 7.98 (s, 1H), 7.93 (d, J=7.9 Hz, 1H), 7.63 (t, J=8.3 Hz, 1H), 7.48 (s, br, 1H), 7.26 (t, J=6.2 Hz, 1H), 6.93 (s, 1H), 3.88 (s, 3H), 3.26 (sept, J=6.9 Hz, 1H), 2.40 (s, 3H), 2.16 (s, 3H), 1.74 (s, br, 1H), 1.52 (s, 6H), 1.31 (d, J=6.9 Hz, 6H); LC/MS 520.0 [M+H$^+$].

Example 65: Preparation of 5-chloro-N2-(4-(1-(dimethylamino)-2-methylpropane-2-yl)-2-methoxy-5-methylphenyl)-N4-(2-(isopropylsulfonyl)phenyl)pyrimidine-2,4-diamine

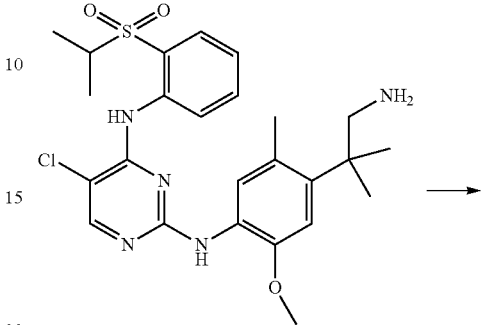

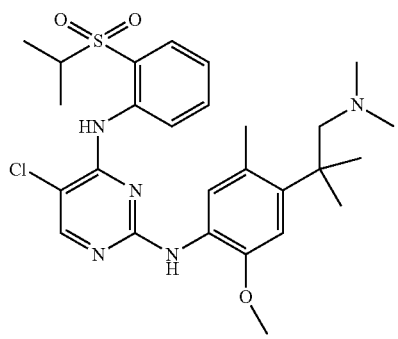

N2-(4-(1-amino-2-methylpropane-2-yl)-2-methoxy-5-methylphenyl)-5-chloro-N4-(2-(isopropylsulfonyl)phenyl)pyrimidine-2,4-diamine (40.0 mg, 0.077 mmol) and diisopropylethylamine (24.9 mg, 0.192 mmol) were dissolved in dimethylformamide (1.0 mL), to which methyliodide (21.9 mg, 0.154 mmol) was added, followed by stirring at 80° C. for 10 minutes in a microwave reactor. The spot of the starting material was disappeared, which was confirmed by TLC. Water (10 ml) was added thereto to terminate the reaction, followed by extraction twice with ethylacetate (15 ml). The organic layer was washed with brine. The solvent was eliminated by distillation under reduced pressure. Then, purification was performed by silica gel column chromatography (eluent: methanol/dichloromethane, 1/9) to give the target compound 5-chloro-N2-(4-(1-(dimethylamino)-2-methylpropane-2-yl)-2-methoxy-5-methylphenyl)-N4-(2-(isopropylsulfonyl)phenyl)pyrimidine-2,4-diamine as a yellow solid (20.0 mg, 0.036 mmol, yield: 47%).

$^1$H-NMR (300 MHz, CDCl$_3$) δ 9.49 (s, br, 1H), 8.57 (d, J=8.3 Hz, 1H), 8.15 (s, 1H), 7.95 (s, 1H), 7.92 (d, J=8.0 Hz, 1H), 7.63 (t, J=8.4 Hz, 1H), 7.46 (s, br, 1H), 7.26 (t, J=7.6 Hz, 1H), 6.94 (s, 1H), 3.88 (s, 3H), 3.26 (sept, J=6.9 Hz, 1H), 2.60 (s, 2H), 2.36 (s, 3H), 2.11 (s, 6H), 1.44 (s, 6H), 1.31 (d, J=6.9 Hz, 6H) LC/MS 546.6 [M+H$^+$].

Example 66: Preparation of 5-chloro-N2-(4-(2-(dimethylamino)propane-2-yl)-2-methoxy-5-methylphenyl)-N4-(2-(isopropylsulfonyl)phenyl)pyrimidine-2,4-diamine

Example 67: Preparation of N2-(2-(2-aminoethyl)-5-methoxybiphenyl-4-yl)-5-chloro-N4-(2-isopropylsulfonyl)phenyl)pyrimidine-2,4-diamine

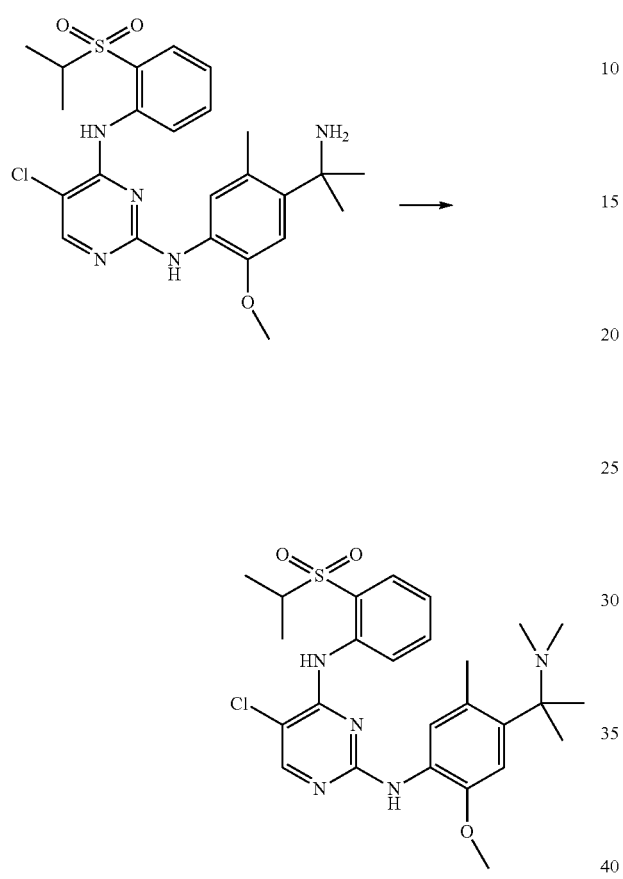

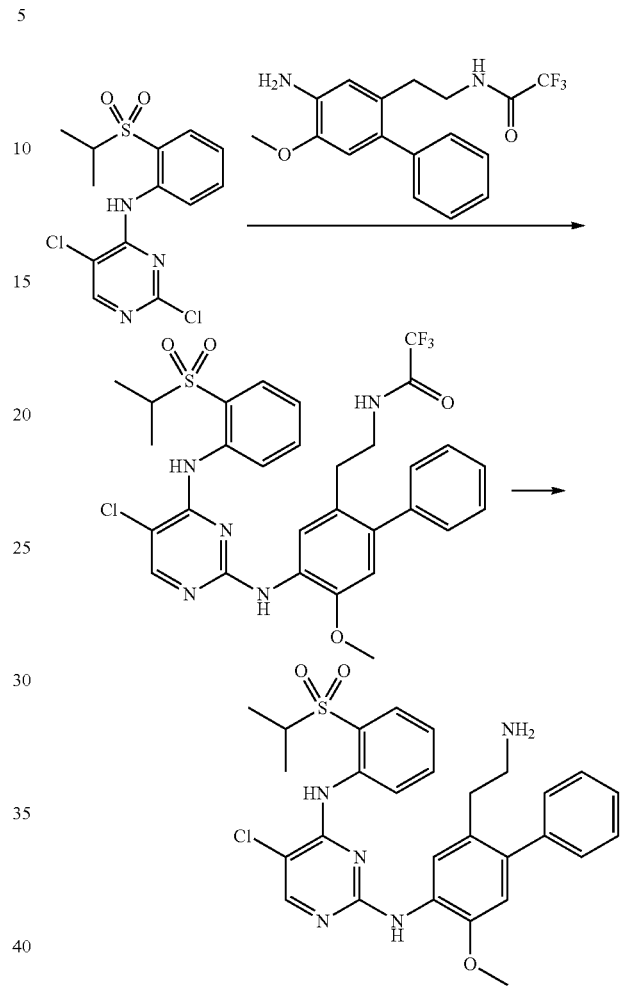

N2-(4-(2-aminopropane-2-yl)-2-methoxy-5-methylphenyl)-5-chloro-N4-(2-(isopropylsulfonyl)phenyl)pyrimidine-2,4-diamine (10.0 mg, 0.019 mmol) and dichloroethylamine (6.41 mg, 0.049 mmol) were dissolved in dimethylformamide (1.0 mL), to which methyliodide (5.63 mg, 0.039 mmol) was added, followed by stirring at 80° C. for 10 minutes in a microwave reactor. The spot of the starting material was disappeared, which was confirmed by TLC. Water (10 ml) was added thereto to terminate the reaction, followed by extraction twice with ethylacetate (15 ml). The organic layer was washed with brine. The solvent was eliminated by distillation under reduced pressure. Then, purification was performed by silica gel column chromatography (eluent: methanol/dichloromethane, 1/9) to give the target compound 5-chloro-N2-(4-(2-(dimethylamino)propane-2-yl)-2-methoxy-5-methylphenyl)-N4-(2-(isopropylsulfonyl)phenyl)pyrimidine-2,4-diamine as a yellow solid (20.0 mg, 0.036 mmol, yield: 47%).

$^1$H-NMR (300 MHz, CDCl$_3$) δ 9.50 (s, br, 1H), 8.59 (d, J=8.3 Hz, 1H), 8.15 (s, 1H), 7.93-7.90 (m, 2H), 7.63 (t, J=8.3 Hz, 1H), 7.46 (s, br, 1H), 7.24 (t, J=7.7 Hz, 1H), 6.91 (s, 1H), 3.86 (s, 3H), 3.26 (sept, J=6.9 Hz, 1H), 2.47 (s, 3H), 2.16 (s, 6H), 1.38 (s, 6H), 1.31 (d, J=6.9 Hz, 6H); LC/MS 532.1 [M+H$^+$].

Step 1: Preparation of N-(2-(4-(5-chloro-4-(2-(isopropylsulfonyl)phenylamino)pyrimidine-2-ylamino)-5-methoxybiphenyl-2-yl)ethyl)-2,2,2-trifluoroacetamide 2,5-dichloro-N-(2-(isopropylsulfonyl)phenyl)pyrimidine-4-amine (227 mg, 0.66 mmol) and the compound (185 mg, 0.55 mmol) prepared in preparative example 24 were dissolved in 0.08 M HCl.ethoxyethanol (1.6 mL), followed by stirring at 100° C. overnight. Ethoxyethanol was removed from the reaction mixture. The reaction mixture was extracted with ethylacetate. The organic layer was washed with brine, dried over magnesium sulfate, filtered, and concentrated under reduced pressure. Then, purification was performed by silica gel column chromatography (eluent: ethylacetate/hexane, 4/1) to give the target compound N-(2-(4-(5-chloro-4-(2-(isopropylsulfonyl)phenylamino)pyrimidine-2-ylamino)-5-methoxybiphenyl-2-yl)ethyl)-2,2,2-trifluoroacetamide as a yellow solid (150 mg, 0.23 mmol, yield: 50%).

$^1$H-NMR (300 MHz, CDCl$_3$) δ 9.59 (s, 1H), 8.56 (d, J=8.4 Hz, 1H), 8.29 (s, 1H), 8.20 (s, 1H), 7.93 (dd, J=7.9, 1.4 Hz, 1H), 7.66 (t, J=8.4 Hz, 1H), 7.60 (s, 1H), 7.46-7.37 (m, 3H), 7.31-7.23 (m, 2H), 6.77 (s, 1H), 5.99 (s, br, 1H), 3.90 (s, 3H), 3.28-3.22 (m, 3H), 2.77 (t, J=6.9 Hz, 2H), 1.33 (d, J=6.9 Hz, 6H); LC/MS 648.20 [M+H$^+$].

Step 2: Preparation of N2-(2-(2-aminoethyl)-5-methoxybiphenyl-4-yl)-5-chloro-N4-(2-isopropylsulfonyl)phenyl)pyrimidine-2,4-diamine N-(2-(4-(5-chloro-4-(2-(isopropylsulfonyl)phenylamino)pyrimidine-2-ylamino)-5-methoxybiphenyl-2-yl)ethyl)-2,2,2-trifluoroacetamide (100 mg, 0.15 mmol) prepared in step 1 was dissolved in tetrahydrofuran (1 mL), to which water (0.5 mL) containing lithium hydroxide dissolved therein was added, followed by stirring at room temperature for 3 hours with methanol (0.5 mL). The reaction mixture was extracted with ethylacetate. The organic layer was washed with brine, dried over magnesium sulfate, filtered, and concentrated under reduced pressure. Then, purification was performed by silica gel column chromatography (eluent: ethylacetate/hexane, 3/1) to give the target compound N2-(2-(2-aminoethyl)-5-methoxybiphenyl-4-yl)-5-chloro-N4-(2-isopropylsulfonyl)phenyl)pyrimidine-2,4-diamine (30 mg, 0.05 mmol, yield: 35%).

$^1$H-NMR (300 MHz, CDCl$_3$) δ 9.56 (s, 1H), 8.58 (d, J=8.4 Hz, 1H), 8.21 (s, 1H), 8.17 (s, 1H), 7.90 (d, J=7.8 Hz, 1H), 7.67 (t, J=8.4 Hz, 1H), 7.50 (s, 1H), 7.40-7.25 (m, 5H), 6.76 (s, 1H), 3.87 (s, 3H), 3.30-3.21 (m, 1H), 2.82 (d, J=6.0 Hz, 2H), 2.73 (s, 2H), 1.30 (d, J=6.9 Hz, 6H); LC/MS 552.20 [M+H$^+$].

Example 68: Preparation of N2-(4-(aminomethyl)-2-methoxy-5-methylphenyl)-5-chloro-N4-(2-(isopropylsulfonyl)phenyl)pyrimidine-2,4-diamine

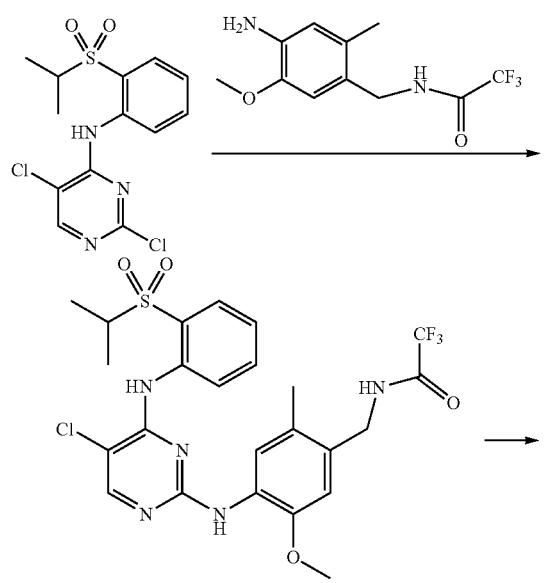

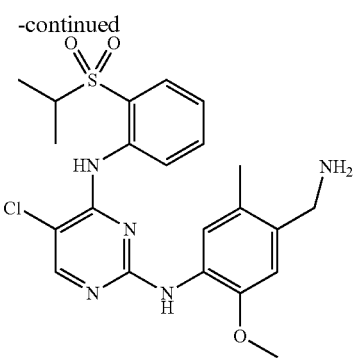

Step 1: Preparation of N-(4-((5-chloro-4-((2-(isopropylsulfonyl)phenyl)amino)pyrimidine-2-yl)amino)-5-methoxy-2-methylbenzyl)-2,2,2-trifluoroacetamide The compound (100 mg, 0.381 mmol) prepared in preparative example 25 and 2,5-dichloro-N-(2-(isopropylsulfonyl)phenyl)pyrimidine-4-amine (145 mg, 0.419 mmol) were dissolved in 0.08 M HCl.ethoxyethanol (1.0 mL) at room temperature, followed by stirring at 80° C. for 12 hours. The reaction mixture was added with sodium hydrogen carbonate, followed by extraction twice with ethylacetate (15 ml). The solvent was eliminated by distillation under reduced pressure. Then, purification was performed by column chromatography (eluent: ethylacetate/hexane, 3/7) to give the target compound N-(4-((5-chloro-4-((2-(isopropylsulfonyl)phenyl)amino)pyrimidine-2-yl)amino)-5-methoxy-2-methylbenzyl)-2,2,2-trifluoroacetamide as a white solid (180 mg, 0.314 mmol, yield: 82%).

$^1$H-NMR (300 MHz, CDCl$_3$) δ 9.54 (s, br, 1H), 8.53 (d, J=8.3 Hz, 1H), 8.18 (s, 1H), 8.14 (s, 1H), 7.93 (d, J=7.9 Hz, 1H), 7.64 (t, J=8.3 Hz, 1H), 7.55 (s, br, 1H), 7.27 (t, J=7.8 Hz, 1H), 6.76 (s, 1H), 6.29 (s, br, 1H), 4.48 (d, J=5.3 Hz, 2H), 3.89 (s, 3H), 3.25 (sept, J=6.9 Hz, 1H), 2.18 (s, 3H), 1.31 (d, J=6.9 Hz, 6H) LC/MS 572.1 [M+H$^+$].

Step 2: Preparation of N2-(4-(aminomethyl)-2-methoxy-5-methylphenyl)-5-chloro-N4-(2-(isopropylsulfonyl)phenyl)pyrimidine-2,4-diamine The compound (170 mg, 0.297 mmol) prepared in step 1 was dissolved in tetrahydrofuran (4.0 mL), methanol (2.0 mL), water (2.0 mL), and lithiumhydroxidemonohydrate (62.4 mg, 1.49 mmol) at room temperature, followed by stirring for 12 hours. Tetrahydrofuran and methanol were eliminated from the reaction mixture under reduced pressure. Water (15 ml) was added thereto to terminate the reaction, followed by extraction twice with ethylacetate (35 ml). The solvent was eliminated by distillation under reduced pressure. Then, purification was performed by column chromatography (eluent: methanol/dichloromethane, 1/9) to give the target compound N2-(4-(aminomethyl)-2-methoxy-5-methylphenyl)-5-chloro-N4-(2-(isopropylsulfonyl)phenyl)pyrimidine-2,4-diamine as a white solid (110 mg, 0.231 mmol, yield: 78%).

$^1$H-NMR (300 MHz, CDCl$_3$) δ 9.53 (s, br, 1H), 8.59 (d, J=8.3 Hz, 1H), 8.18 (s, 1H), 8.05 (s, 1H), 7.93 (d, J=7.8 Hz, 1H), 7.66 (t, J=8.5 Hz, 1H), 7.54 (s, br, 1H), 7.28 (t, J=8.4 Hz, 1H), 6.92 (s, 1H), 3.92 (s, 3H), 3.85 (s, 2H), 3.28 (sept, J=6.9 Hz, 1H), 2.21 (s, 3H), 1.68 (s, br, 2H), 1.32 (d, J=6.9 Hz, 6H); LC/MS 475.9 [M+H⁺].

Example 69: Preparation of 1-(4-((5-chloro-4-((2-(isopropylsulfonyl)phenyl)amino)pyrimidine-2-yl)amino)-5-methoxy-2-methylphenyl)-N,N,N-trimethylmethanealuminum iodide

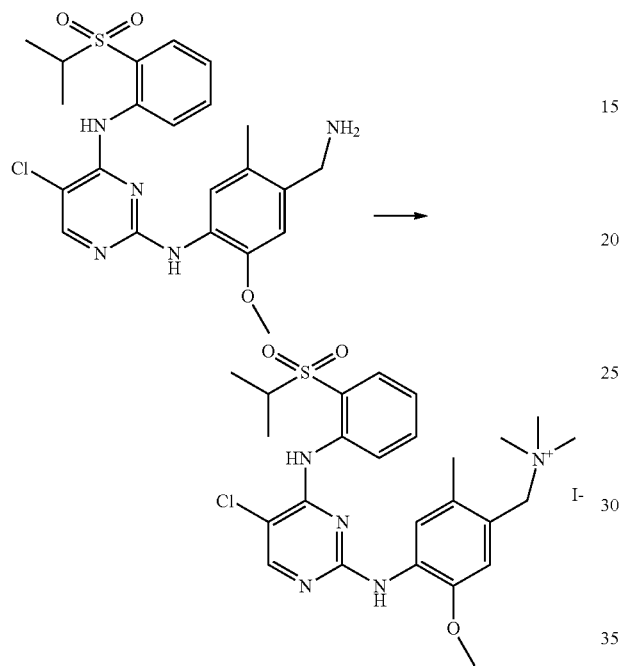

N2-(4-(aminomethyl)-2-methoxy-5-methylphenyl)-5-chloro-N4-(2-(isopropylsulfonyl)phenyl)pyrimidine-2,4-diamine (50.0 mg, 0.105 mmol) was dissolved in dimethylformamide (1 mL), to which diisopropylethylamine (33.9 mg, 0.262 mmol) and methyliodide (29.8 mg, 0.210 mmol) were added at room temperature, followed by stirring at 80° C. for 10 minutes in a microwave reactor. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound 1-(4-((5-chloro-4-((2-(isopropylsulfonyl)phenyl)amino)pyrimidine-2-yl)amino)-5-methoxy-2-methylphenyl)-N,N,N-trimethylmethanealuminum iodide as a white solid (20.0 mg, 0.030 mmol, yield: 29%).

¹H-NMR (300 MHz, CDCl₃) δ 9.58 (s, br, 1H), 8.52 (d, J=8.3 Hz, 1H), 8.26 (s, 1H), 8.18 (s, 1H), 7.93 (d, J=8.0 Hz, 1H), 7.69-7.66 (m, 2H), 7.42 (s, br, 1H), 7.31 (t, J=7.7 Hz, 1H), 5.06 (s, 2H), 3.99 (s, 3H), 3.44 (s, 9H), 3.29 (sept, J=6.9 Hz, 1H), 2.37 (s, 3H), 1.34 (d, J=6.9 Hz, 6H); LC/MS 518.0 [M+I-].

Example 70: Preparation of 5-chloro-N2-(4-((dimethylamino)methyl)-2-methoxy-5-methylphenyl)-N4-(2-(isopropylsulfonyl)phenyl)pyrimidine-2,4-diamine

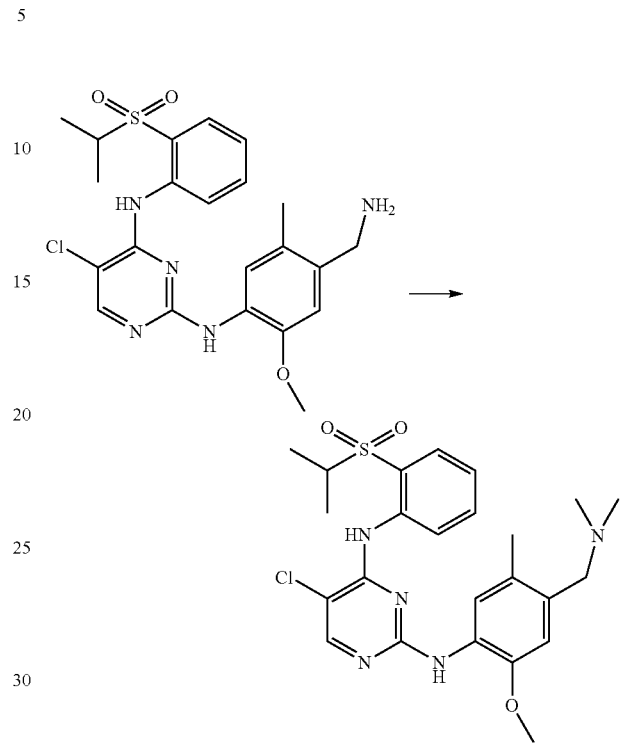

N2-(4-(aminomethyl)-2-methoxy-5-methylphenyl)-5-chloro-N4-(2-(isopropylsulfonyl)phenyl)pyrimidine-2,4-diamine (50.0 mg, 0.105 mmol) was dissolved in methanol (21.0 mL), to which one drop of acetic acid and formalin (35%) (19.8 mg, 0.051 mmol) were added at 0° C., followed by stirring at room temperature for 30 minutes. Sodiumcyanoborohydride (9.90 mg, 0.157 mmol) was added thereto, followed by stirring at room temperature for 30 minutes. Sodium hydrogen carbonate aqueous solution was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound 5-chloro-N2-(4-((dimethylamino)methyl)-2-methoxy-5-methylphenyl)-N4-(2-(isopropylsulfonyl)phenyl)pyrimidine-2,4-diamine as a white solid (30.0 mg, 0.059 mmol, yield: 57%).

¹H-NMR (300 MHz, CDCl₃) δ 9.49 (s, br, 1H), 8.57 (d, J=8.3 Hz, 1H), 8.16 (s, 1H), 8.02 (s, 1H), 7.92 (d, J=7.9 Hz, 1H), 7.63 (t, J=8.3 Hz, 1H), 7.53 (s, br, 1H), 7.26 (t, J=8.5 Hz, 1H), 6.87 (s, 1H), 3.88 (s, 3H), 3.36 (s, 2H), 3.25 (sept, J=6.9 Hz, 1H), 2.26 (s, 6H), 2.19 (s, 3H), 1.31 (d, J=6.9 Hz, 6H); LC/MS 503.9 [M+H⁺].

Example 71: Preparation of N-(4-((5-chloro-4-((2-(isopropylsulfonyl)phenyl)amino)pyrimidine-2-yl)amino)-5-methoxy-2-methylbenzyl)formamide

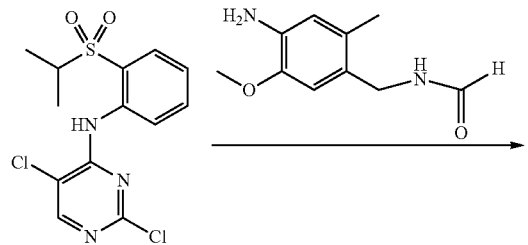

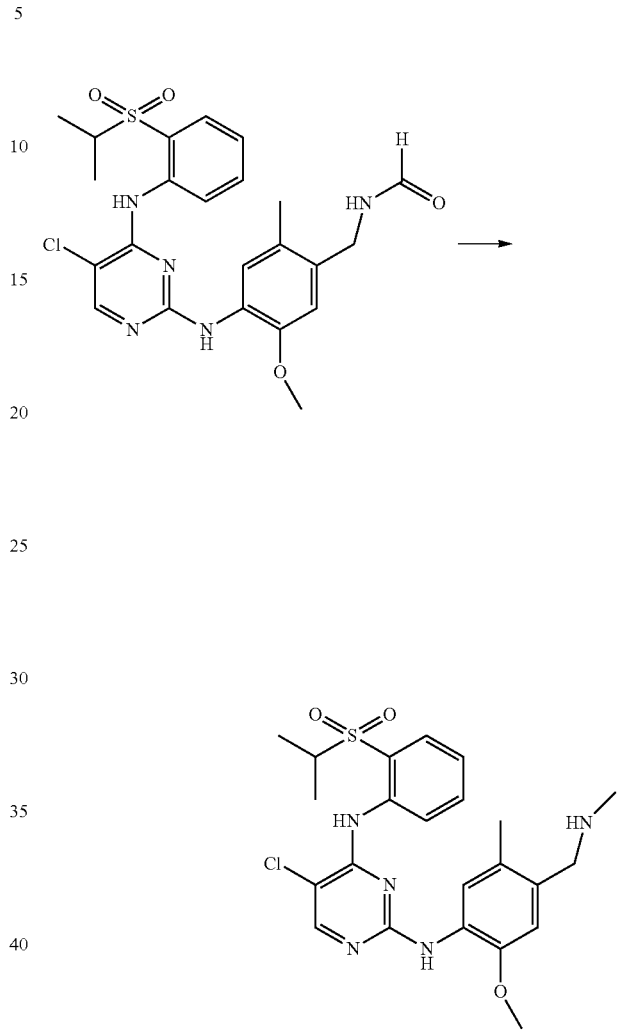

2,5-dichloro-N-(2-(isopropylsulfonyl)phenyl)pyrimidine-4-amine (214 mg, 0.617 mmol) and the compound (100 mg, 0.514 mmol) prepared in preparative example 26 were dissolved in 0.08 M HCl.ethoxyethanol (1 mL), followed by stirring at 80° C. for 12 hours. The reaction mixture was cooled to room temperature, neutralized with sodium hydrogen carbonate aqueous solution, and extracted twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound N-(4-((5-chloro-4-((2-(isopropylsulfonyl)phenyl)amino)pyrimidine-2-yl)amino)-5-methoxy-2-methylbenzyl)formamide as a white solid (110 mg, 0.218 mmol, yield: 42%).

$^1$H-NMR (300 MHz, CDCl$_3$) δ 9.52 (s, br, 1H), 8.54 (d, J=8.3 Hz, 1H), 8.25 (s, 1H), 8.16 (s, 1H), 8.09 (s, 1H), 7.93 (d, J=7.9 Hz, 1H), 7.63 (t, J=8.3 Hz, 1H), 7.53 (s, br, 1H), 7.26 (t, J=7.8 Hz, 1H), 6.78 (s, 1H), 5.59 (s, br, 1H), 4.44 (d, J=5.4 Hz, 2H), 3.88 (s, 3H), 3.25 (sept, J=6.9 Hz, 1H), 2.18 (s, 3H), 1.31 (d, J=6.9 Hz, 6H); LC/MS 503.6 [M+H$^+$].

Example 72: Preparation of 5-chloro-N4-(2-(isopropylsulfonyl)phenyl)-N2-(2-methoxy-5-methyl-4-((methylamino)methyl)phenyl)pyrimidine-2,4-diamine N-(4-((5-chloro-4-((2-(isopropylsulfonyl)phenyl)amino)pyrimidine-2-yl)amino)-5-methoxy-2-methylbenzyl)formamide (50.0 mg, 0.099 mmol) was dissolved in tetrahydrofuran (15.0 mL), to which lithium aluminum hydride (37.6 mg, 0.992 mmol) was added, followed by stirring at 60° C. for 12 hours. Water and sodium hydroxide aqueous solution were added thereto to terminate the reaction, and the reaction mixture was filtered. The filtrate was extracted twice with ethylacetate. The solvent was eliminated by distillation under reduced pressure. Then, purification was performed by silica gel column chromatography (eluent: methanol/dichloromethane, 1/9) to give the target compound 5-chloro-N4-(2-(isopropylsulfonyl)phenyl)-N2-(2-methoxy-5-methyl-4-((methylamino)methyl)phenyl)pyrimidine-2,4-diamine as a white solid (8.00 mg, 0.016 mmol, yield: 17%).

$^1$H-NMR (300 MHz, CDCl$_3$) δ 9.50 (s, br, 1H), 8.56 (d, J=8.3 Hz, 1H), 8.16 (s, 1H), 8.04 (s, 1H), 7.92 (d, J=7.9 Hz, 1H), 7.64 (t, J=8.4 Hz, 1H), 7.52 (s, br, 1H), 7.26 (t, J=8.3 Hz, 1H), 6.91 (s, 1H), 3.88 (s, 3H), 3.72 (s, 2H), 3.25 (sept, J=6.9 Hz, 1H), 2.51 (s, 3H), 2.19 (s, 3H), 2.02 (s, br, 1H), 1.31 (d, J=6.9 Hz, 6H); LC/MS 489.90 [M+H$^+$].

Example 73: Preparation of 5-chloro-N4-(2-(isopropylsulfonyl)phenyl)-N2-(2-methoxy-5-(2-(piperazine-1-yl)ethyl)phenyl)pyrimidine-2,4-diamine

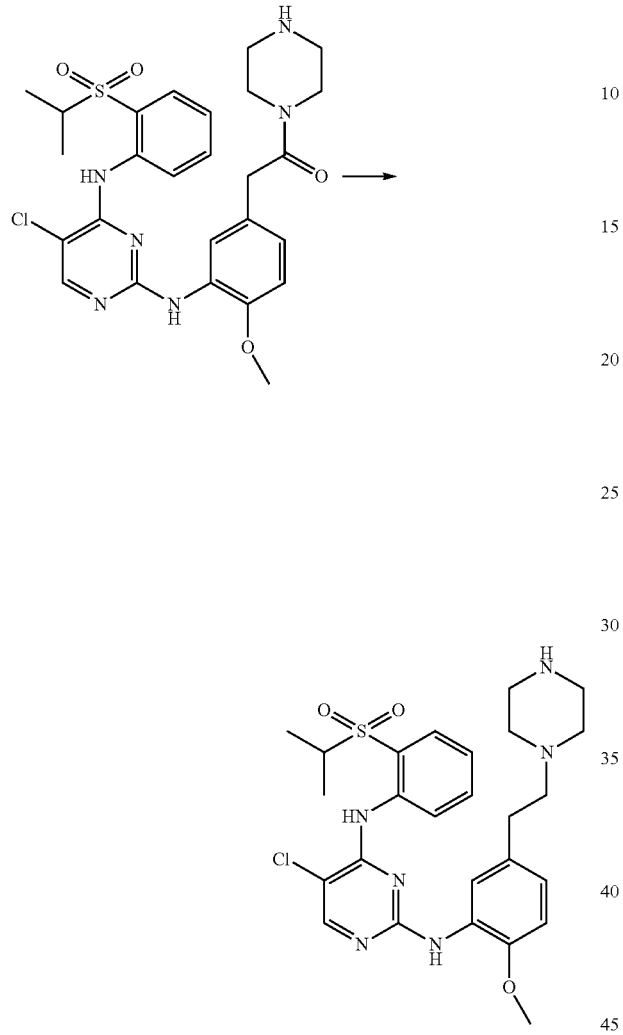

The compound (500 mg, 0.089 mmol) prepared in example 48 was dissolved in tetrahydrofuran (5.0 mL), to which lithium aluminum hydride (10 mg, 0.27 mmol) was added, followed by stirring at 60° C. for 1 hour. Water and sodium hydroxide aqueous solution were added thereto to terminate the reaction, and the reaction mixture was filtered. The filtrate was extracted twice with ethylacetate. The solvent was eliminated by distillation under reduced pressure. Then, purification was performed by silica gel column chromatography (eluent: methanol/dichloromethane, 1/9) to give the target compound 5-chloro-N4-(2-(isopropylsulfonyl)phenyl)-N2-(2-methoxy-5-(2-(piperazine-1-yl)ethyl)phenyl)pyrimidine-2,4-diamine as a yellow solid (11 mg, 0.020 mmol, yield: 23%).

$^1$H-NMR (300 MHz, CDCl$_3$) δ 9.56 (s, 1H), 8.58 (d, J=8.1 Hz, 1H), 8.18 (s, 1H), 8.14 (s, 1H), 7.92 (dd, J=7.9, 1.4 Hz, 1H), 7.63-7.69 (m, 1H), 7.55 (s, 1H), 7.22-7.28 (m, 1H), 6.81 (s, 1H), 3.88 (s, 3H), 3.26 (sept, J=6.8 Hz, 1H), 2.95-3.01 (m, 4H), 2.66-2.72 (m, 2H), 2.44-2.48 (m, 6H), 1.32 (d, J=6.8 Hz, 6H); LC/MS 545.2 [M+H+].

Example 74: Preparation of N2-(5-(2-aminoethyl)-2-ethoxy-4-(prop-1-ene-2-yl)phenyl)-5-chloro-N4-(2-(isopropylsulfonyl)phenyl)pyrimidine-2,4-diamine

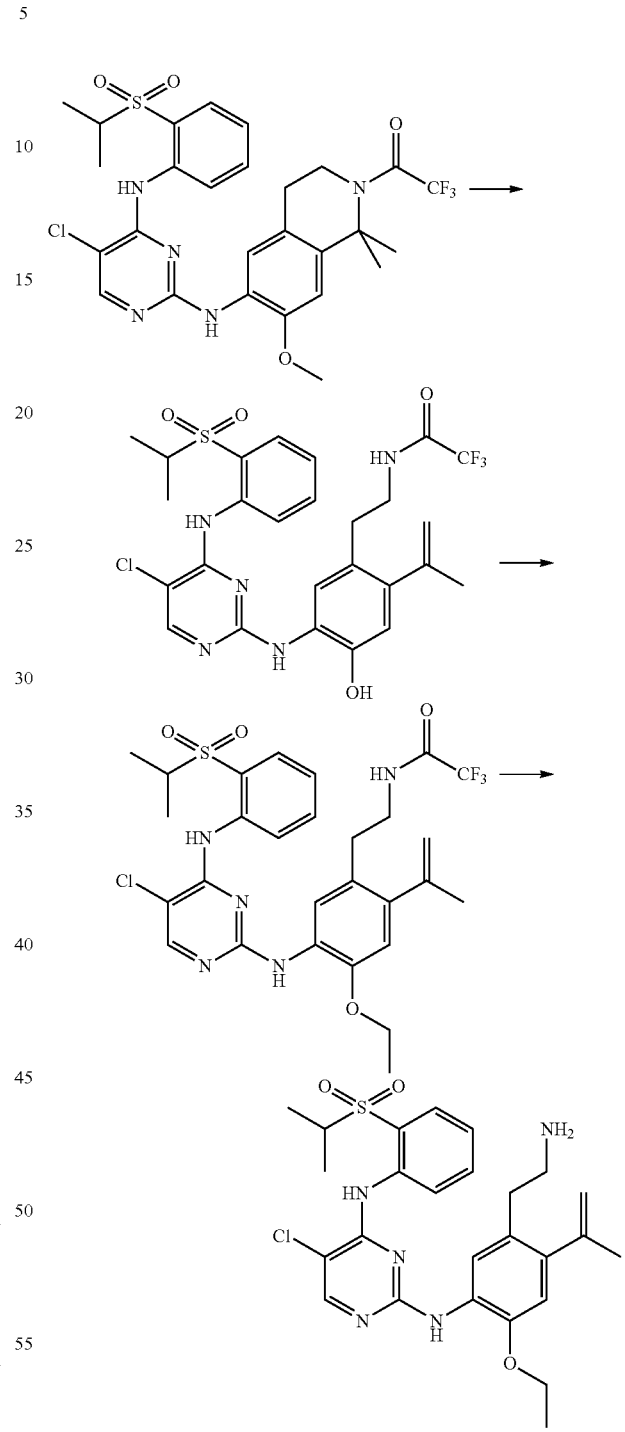

Step 1: Preparation of N-(5-((5-chloro-4-((2-(isopropylsulfonyl)phenyl)amino)pyrimidine-2-yl)amino)-4-hydroxy-2-(prop-1-ene-2-yl)phenethyl)-2,2,2-trifluoroacetamide 1-(6-(5-chloro-4-(2-(isopropylsulfonyl)phenylamino)pyrimidine-2-ylamino)-7-methoxy-1,1-dimethyl-3,4-dihydroisoquinoline-2(1H)-yl)-2,2,2-trifluoroethanone (500 mg, 0.770 mmol) was dissolved in dichloromethane (20 mL), to which 1 M borontribromide.dichloromethane (3.85 mL, 3.85 mmol) was added at −78° C., followed by stirring at room temperature for 1 hour. Water was added thereto to terminate the reaction, and the reaction mixture was filtered. The filtrate was extracted twice with dichloromethane. The solvent was eliminated by distillation under reduced pressure. Then, purification was performed by silica gel column chromatography (eluent: methanol/dichloromethane, 1/9) to give the target compound N-(5-((5-chloro-4-((2-(isopropylsulfonyl)phenyl)amino)pyrimidine-2-yl)amino)-4-hydroxy-2-(prop-1-ene-2-yl)phenethyl)-2,2,2-trifluoroacetamide as a yellow solid (200 mg, 0.334 mmol, yield: 43%).

no NMR data; LC/MS 598.1 [M+H+].

Step 2: Preparation of N-(5-((5-chloro-4-((2-(isopropylsulfonyl)phenyl)amino)pyrimidine-2-yl)amino)-4-ethoxy-2-(prop-1-ene-2-yl)phenethyl)-2,2,2-trifluoroacetamide The compound (50.00 mg, 0.083 mmol) prepared in step 1 was dissolved in dimethylformamide (1.0 mL), to which potassium carbonate (23.1 mg, 0.167 mmol) and ethyliodide (14.34 mg, 0.092 mmol) were added, followed by stirring at 80° C. for 30 minutes in a microwave reactor. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound N-(5-((5-chloro-4-((2-(isopropylsulfonyl)phenyl)amino)pyrimidine-2-yl)amino)-4-ethoxy-2-(prop-1-ene-2-yl)phenethyl)-2,2,2-trifluoroacetamide as a white solid (25.0 mg, 0.036 mmol, yield: 48%).

$^1$H-NMR (300 MHz, CDCl$_3$) δ 9.56 (s, br, 1H), 8.53 (d, J=8.3 Hz, 1H), 8.17 (s, 1H), 8.16 (s, 1H), 7.94 (d, J=7.9 Hz, 1H), 7.62 (t, J=7.0 Hz, 1H), 7.58 (s, br, 1H), 7.26 (t, J=7.3 Hz, 1H), 6.65 (s, 1H), 6.19 (s, br, 1H), 5.22 (s, 1H), 4.85 (s, 1H), 4.12 (q, J=6.9 Hz, 2H), 3.35-3.26 (m, 3H), 2.76 (t, J=6.9 Hz, 2H), 2.04 (s, 3H), 1.47 (t, J=6.9 Hz, 3H), 1.32 (d, J=6.9 Hz, 6H); LC/MS 626.20 [M+H+].

Step 3: Preparation of N2-(5-(2-aminoethyl)-2-ethoxy-4-(prop-1-ene-2-yl)phenyl)-5-chloro-N4-(2-(isopropylsulfonyl)phenyl)pyrimidine-2,4-diamine The compound (25.0 mg, 0.039 mmol) prepared in step 2 was dissolved in tetrahydrofuran (1.0 mL), methanol (0.50 mL), and water (0.50 mL), to which lithium hydroxide hydrate (10.05 mg, 0.239 mmol) was added, followed by stirring at 40° C. for 12 hours. The reaction mixture was distillated under reduced pressure. The reactant was diluted with water, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(5-(2-aminoethyl)-2-ethoxy-4-(prop-1-ene-2-yl)phenyl)-5-chloro-N4-(2-(isopropylsulfonyl)phenyl)pyrimidine-2,4-diamine as a white solid (8.0 mg, 0.015 mmol, yield: 38%).

$^1$H-NMR (300 MHz, CDCl$_3$) δ 9.56 (s, br, 0.3H), 9.50 (s, br, 0.5H), 8.60 (d, J=8.3 Hz, 0.3H), 8.53 (d, J=8.3 Hz, 0.7H), 8.17 (s, 1H), 8.10 (s, 0.3H), 8.08 (s, 0.6H), 7.95-7.88 (m, 1H), 7.65 (t, J=7.3 Hz, 1H), 7.56 (s br, 0.6H), 7.53 (s, br, 0.3H), 7.30-7.20 (m, 1H), 6.64 (s, 1H), 5.18 (s, 1H), 4.84 (s, 1H), 4.10 (q, J=6.9 Hz, 2H), 3.31-3.22 (m, 1.5H), 2.89-2.83 (m, 0.6H), 2.67-2.64 (m, 2.7H), 2.03 (s, 3H), 1.45 (t, J=6.9 Hz, 3H), 1.32 (d, J=6.9 Hz, 6H); LC/MS 529.90 [M+H+].

Example 75: Preparation of N2-(5-(2-aminoethyl)-2-methoxy-4-(prop-1-ene-2-yl)phenyl)-5-chloro-N4-(2-(isopropylsulfonyl)phenyl)pyrimidine-2,4-diamine

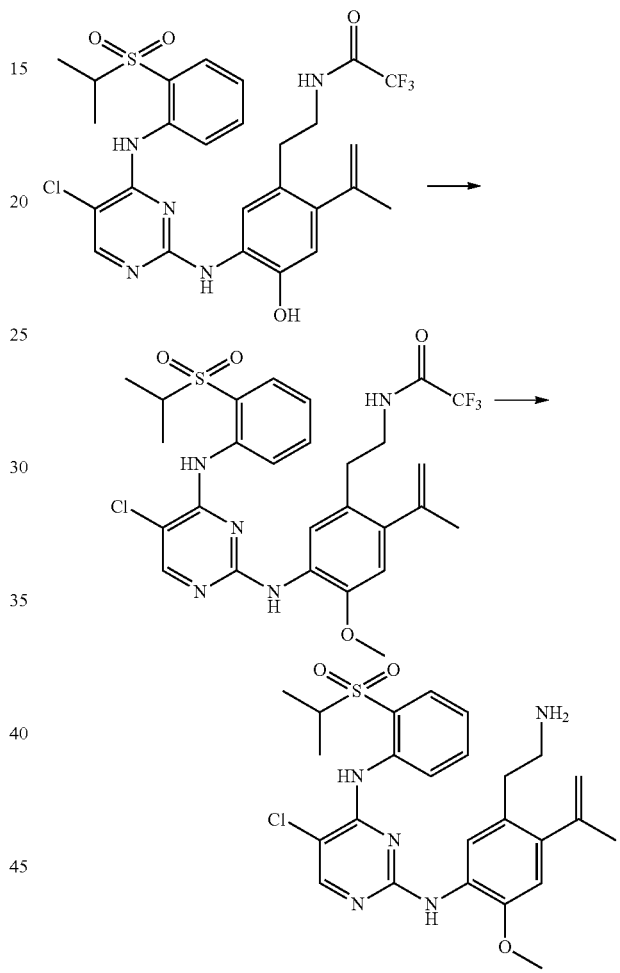

Step 1: Preparation of N-(5-((5-chloro-4-((2-(isopropylsulfonyl)phenyl)amino)pyrimidine-2-yl)amino)-4-methoxy-2-(prop-1-ene-2-yl)phenethyl)-2,2,2-trifluoroacetamide N-(5-(5-chloro-4-(2-(isopropylsulfonyl)phenylamino)pyrimidine-2-ylamino)-4-hydroxy-2-(prop-1-ene-2-yl)phenethyl)-2,2,2-trifluoroacetamide (50.00 mg, 0.083 mmol) was dissolved in dimethylformamide (1.0 mL), to which potassium carbonate (23.1 mg, 0.167 mmol) and methyliodide (13.05 mg, 0.092 mmol) were added, followed by stirring at 80° C. for 30 minutes in a microwave reactor. Water was added thereto to terminate the reaction, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/9) to give the target compound N-(5-((5-chloro-4-((2-(isopropylsulfonyl)phenyl)amino)pyrimidine-2-yl)amino)-4-methoxy-2-(prop-1-ene-2-yl)phenethyl)-2,2-trifluoroacetamide as a white solid (25.0 mg, 0.040 mmol, yield: 49%).

¹H-NMR (300 MHz, CDCl₃) δ 9.57 (s, br, 0.6H), 9.55 (s, br, 0.4H), 8.56-8.52 (m, 1H), 8.18-8.17 (m, 1.6H), 8.04 (s, 0.4H), 7.95-7.92 (m, 1H), 7.64 (t, J=7.2 Hz, 1H), 7.56 (s br, 0.3H), 7.53 (s, br, 0.6H), 7.32-7.23 (m, 1H), 6.75 (s, 0.4H), 6.66 (s, 0.7H), 6.22 (s, br, 1H), 5.23 (s, 1H), 4.87 (s, 1H), 3.91 (s, 1H), 3.89 (s, 2H), 3.65-3.56 (m, 1H), 3.42-3.35 (m, 1.4H), 3.26 (sept, J=6.9 Hz, 1H), 2.81-2.79 (m, 1.4H), 2.72-2.69 (m, 0.7H), 2.05 (s, 1H), 1.83 (s, 2H), 1.32 (d, J=6.9 Hz, 6H); LC/MS 611.50 [M+H+].

Step 2: Preparation of N2-(5-(2-aminoethyl)-2-methoxy-4-(prop-1-ene-2-yl)phenyl)-5-chloro-N4-(2-(isopropylsulfonyl)phenyl)pyrimidine-2,4-diamine The compound (25.0 mg, 0.040 mmol) prepared in step 1 was dissolved in tetrahydrofuran (1.0 mL), methanol (0.50 mL), and water (0.50 mL), to which lithium hydroxide hydrate (10.0 mg, 0.245 mmol) was added, followed by stirring at 40° C. for 12 hours. The reaction mixture was distillated under reduced pressure. The reactant was diluted with water, followed by extraction twice with ethylacetate. The extracted organic layer was dried over sodium sulfate and then filtered. The solvent was eliminated by distillation under reduced pressure. Then, purification was performed by silica gel column chromatography (eluent: methanol/dichloromethane, 1/10) to give the target compound N2-(5-(2-aminoethyl)-2-methoxy-4-(prop-1-ene-2-yl)phenyl)-5-chloro-N4-(2-(isopropylsulfonyl)phenyl)pyrimidine-2,4-diamine as a white solid (8.0 mg, 0.015 mmol, yield: 38%).

¹H-NMR (300 MHz, CDCl₃) δ 9.53 (s, br, 1H), 8.56 (d, J=8.4 Hz, 1H), 8.19 (s, 1H), 8.12 (s, 1H), 7.95 (d, J=8.1 Hz, 1H), 7.68 (t, J=8.1 Hz, 1H), 7.54 (s, br, 1H), 7.32-7.27 (t, J=7.8 Hz, 1H), 6.67 (s, 1H), 5.21 (s, 1H), 4.87 (s, 1H), 3.90 (s, 3H), 3.28 (sept, J=6.9 Hz, 1H), 2.73-2.67 (m, 4H), 2.07 (s, 3H), 1.34 (d, J=6.9 Hz, 6H); LC/MS 515.80 [M+H+].

TABLE 1

| Example | Compound Structure |
|---|---|
| 1 | 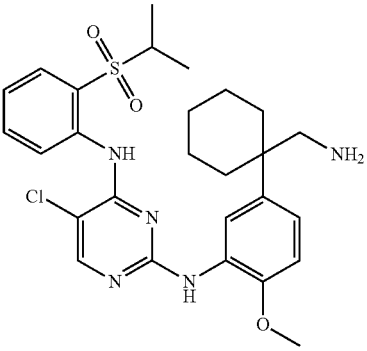 [SMILES: COc1ccc(C2(CN)CCCCC2)cc1Nc1ncc(Cl)c(Nc2ccccc2S(=O)(=O)C(C)C)n1] |
| 2 | 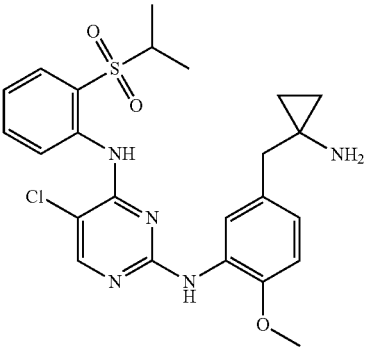 [SMILES: COc1ccc(CC2(N)CC2)cc1Nc1ncc(Cl)c(Nc2ccccc2S(=O)(=O)C(C)C)n1] |
| 3 | 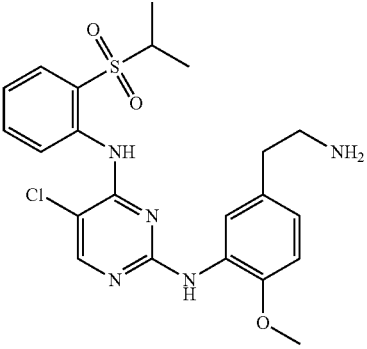 [SMILES: COc1ccc(CCN)cc1Nc1ncc(Cl)c(Nc2ccccc2S(=O)(=O)C(C)C)n1] |
| 4 | 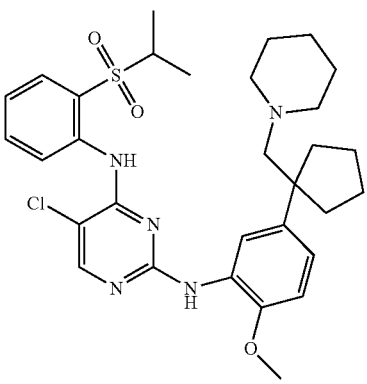 [SMILES: COc1ccc(C2(CN3CCCCC3)CCCC2)cc1Nc1ncc(Cl)c(Nc2ccccc2S(=O)(=O)C(C)C)n1] |
| 5 | 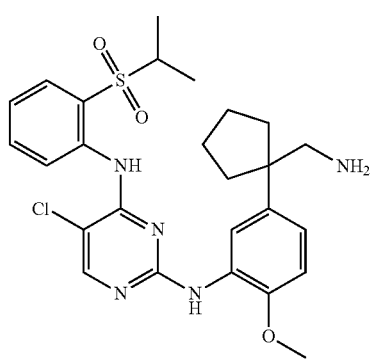 |

TABLE 1-continued

| Example | Compound Structure |
|---------|-------------------|
| 6 | (structure) |
| 7 | (structure) |
| 8 | (structure) |
| 9 | (structure) |
| 10 | (structure) |
| 11 | (structure) |
| 12 | (structure) |
| 13 | (structure) |

TABLE 1-continued

| Example | Compound Structure |
|---|---|
| 14 | (structure) |
| 15 | (structure) |
| 16 | (structure) |
| 17 | (structure) |
| 18 | (structure) |
| 19 | (structure) |
| 20 | (structure) |
| 21 | (structure) |

TABLE 1-continued
| Example | Compound Structure |
|---|---|
| 22 | 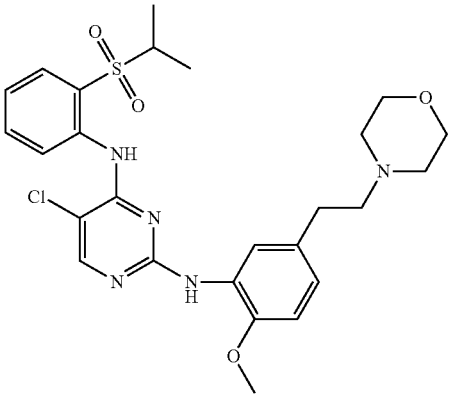 [SMILES: COc1ccc(CCN2CCOCC2)cc1Nc1ncc(Cl)c(Nc2ccccc2S(=O)(=O)C(C)C)n1] |
| 23 | 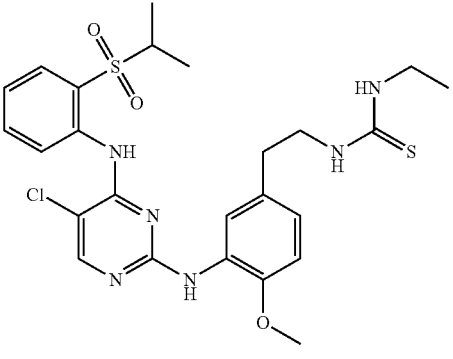 [SMILES: CCNC(=S)NCCc1ccc(OC)c(Nc2ncc(Cl)c(Nc3ccccc3S(=O)(=O)C(C)C)n2)c1] |
| 24 | 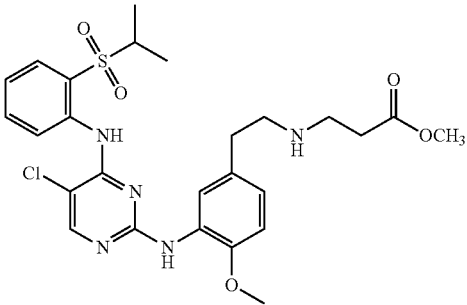 [SMILES: COC(=O)CCNCCc1ccc(OC)c(Nc2ncc(Cl)c(Nc3ccccc3S(=O)(=O)C(C)C)n2)c1] |
| 25 | 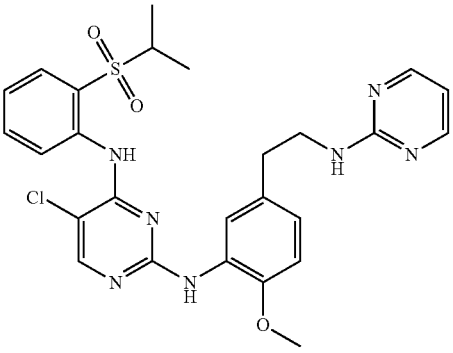 [SMILES: COc1ccc(CCNc2ncccn2)cc1Nc1ncc(Cl)c(Nc2ccccc2S(=O)(=O)C(C)C)n1] |
| 26 | 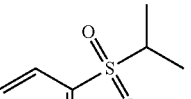 |
| 27 | 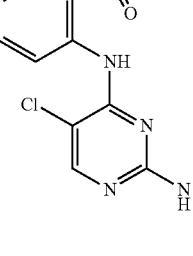 |
| 28 | 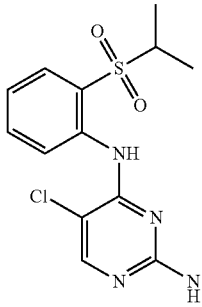 |
| 29 | 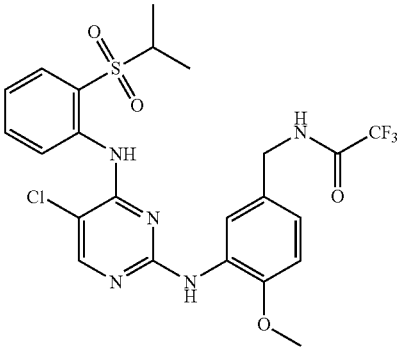 [SMILES: COc1ccc(CNC(=O)C(F)(F)F)cc1Nc1ncc(Cl)c(Nc2ccccc2S(=O)(=O)C(C)C)n1] |

TABLE 1-continued

| Example | Compound Structure |
|---|---|
| 30 | 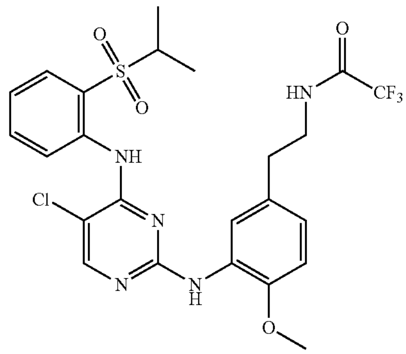 [SMILES: COc1ccc(CCNC(=O)C(F)(F)F)cc1Nc1ncc(Cl)c(Nc2ccccc2S(=O)(=O)C(C)C)n1] |
| 31 | 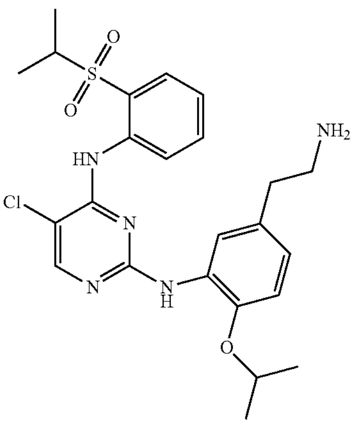 [SMILES: CC(C)Oc1ccc(CCN)cc1Nc1ncc(Cl)c(Nc2ccccc2S(=O)(=O)C(C)C)n1] |
| 32 | 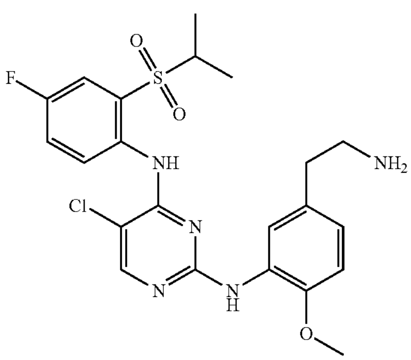 [SMILES: COc1ccc(CCN)cc1Nc1ncc(Cl)c(Nc2ccc(F)cc2S(=O)(=O)C(C)C)n1] |
| 33 | 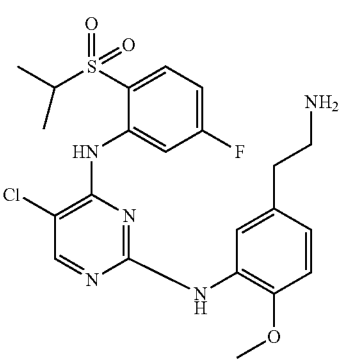 [SMILES: COc1ccc(CCN)cc1Nc1ncc(Cl)c(Nc2cc(F)ccc2S(=O)(=O)C(C)C)n1] |
| 34 | |
| 35 | |
| 36 | |
| 37 | |

TABLE 1-continued
| Example | Compound Structure |
|---|---|
| 38 | 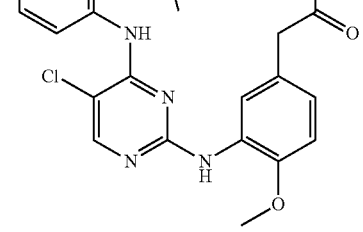 |
| 39 | 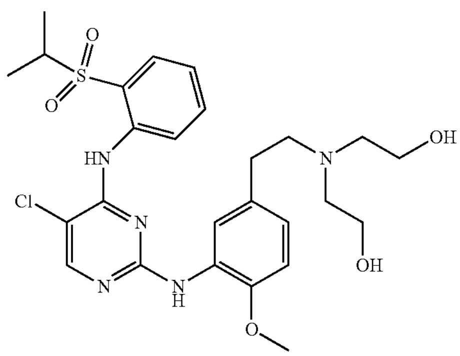 [SMILES: COc1ccc(CCN(CCO)CCO)cc1Nc1ncc(Cl)c(Nc2ccccc2S(=O)(=O)C(C)C)n1] |
| 40 | 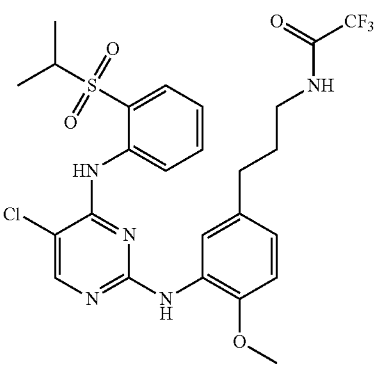 [SMILES: COc1ccc(CCCNC(=O)C(F)(F)F)cc1Nc1ncc(Cl)c(Nc2ccccc2S(=O)(=O)C(C)C)n1] |
| 41 | 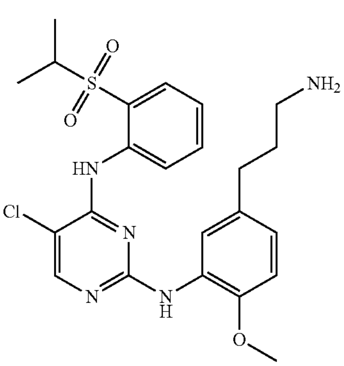 [SMILES: COc1ccc(CCCN)cc1Nc1ncc(Cl)c(Nc2ccccc2S(=O)(=O)C(C)C)n1] |
| 42 | 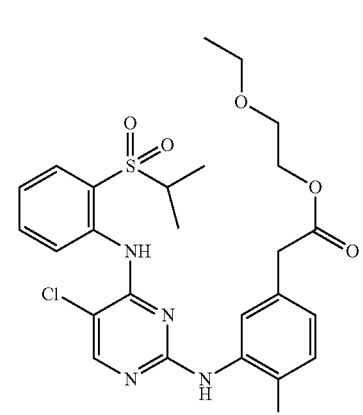 |
| 43 | |
| 44 | |
| 45 | |

TABLE 1-continued

| Example | Compound Structure |
|---------|-------------------|
| 46 | 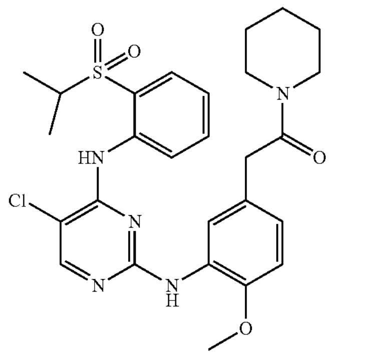 [SMILES: COc1ccc(CC(=O)N2CCCCC2)cc1Nc1ncc(Cl)c(Nc2ccccc2S(=O)(=O)C(C)C)n1] |
| 47 | 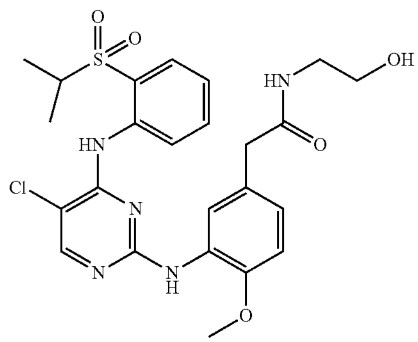 [SMILES: COc1ccc(CC(=O)NCCO)cc1Nc1ncc(Cl)c(Nc2ccccc2S(=O)(=O)C(C)C)n1] |
| 48 | 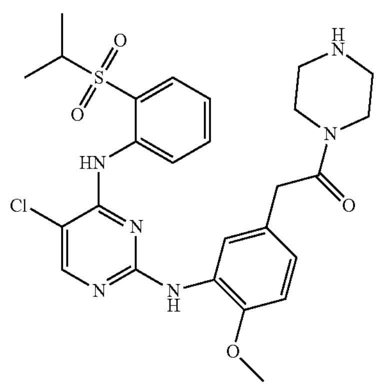 [SMILES: COc1ccc(CC(=O)N2CCNCC2)cc1Nc1ncc(Cl)c(Nc2ccccc2S(=O)(=O)C(C)C)n1] |
| 49 | 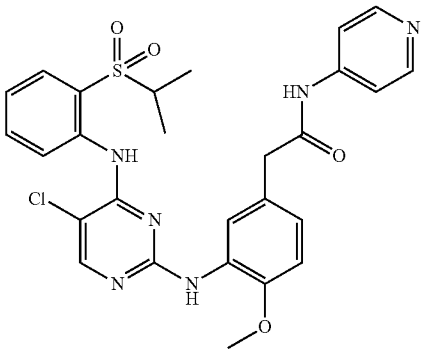 [SMILES: COc1ccc(CC(=O)Nc2ccncc2)cc1Nc1ncc(Cl)c(Nc2ccccc2S(=O)(=O)C(C)C)n1] |
| 50 | |
| 51 | |
| 52 | |
| 53 | |

TABLE 1-continued

| Example | Compound Structure |
|---|---|
| 54 | (structure) |
| 55 | (structure) |
| 56 | (structure) |
| 57 | (structure) |
| 58 | (structure) |
| 59 | (structure) |
| 60 | (structure) |
| 61 | (structure) |

TABLE 1-continued

| Example | Compound Structure |
|---|---|
| 62 | 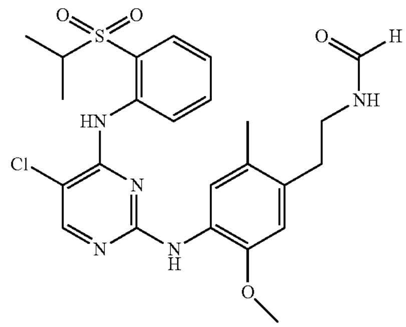 [SMILES: COc1cc(CCNC=O)c(C)cc1Nc1ncc(Cl)c(Nc2ccccc2S(=O)(=O)C(C)C)n1] |
| 63 | 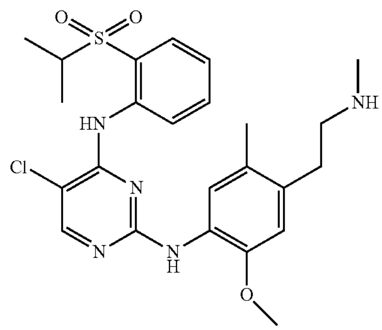 [SMILES: CNCCc1cc(OC)c(Nc2ncc(Cl)c(Nc3ccccc3S(=O)(=O)C(C)C)n2)cc1C] |
| 64 | 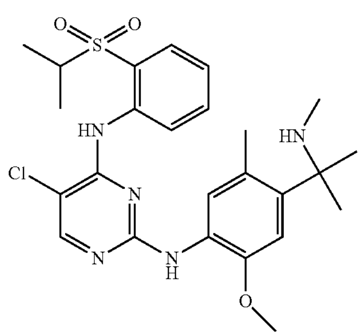 [SMILES: CNC(C)(C)c1cc(OC)c(Nc2ncc(Cl)c(Nc3ccccc3S(=O)(=O)C(C)C)n2)cc1C] |
| 65 | 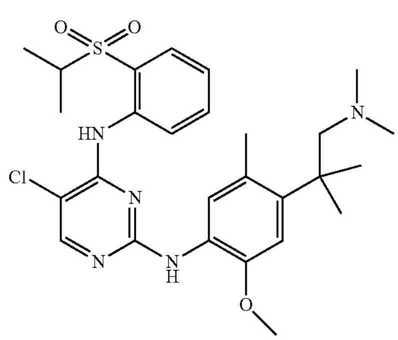 [SMILES: COc1cc(C(C)(C)CN(C)C)c(C)cc1Nc1ncc(Cl)c(Nc2ccccc2S(=O)(=O)C(C)C)n1] |
| 66 | |
| 67 | |
| 68 | |
| 69 | |

TABLE 1-continued

| Example | Compound Structure |
|---------|-------------------|
| 70 | 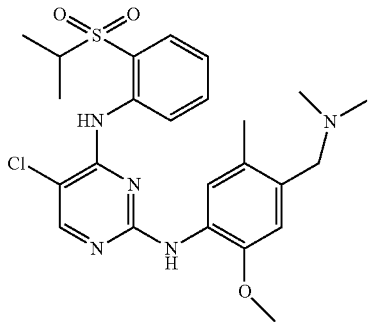 [SMILES: COc1cc(CN(C)C)c(C)cc1Nc1ncc(Cl)c(Nc2ccccc2S(=O)(=O)C(C)C)n1] |
| 71 | 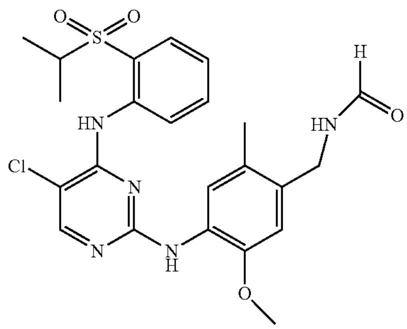 [SMILES: COc1cc(CNC=O)c(C)cc1Nc1ncc(Cl)c(Nc2ccccc2S(=O)(=O)C(C)C)n1] |
| 72 | 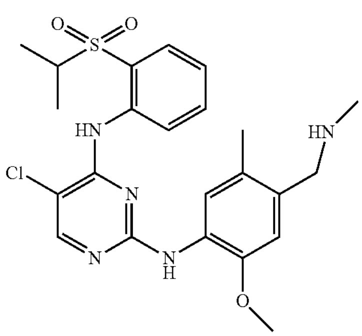 [SMILES: CNCc1cc(OC)c(Nc2ncc(Cl)c(Nc3ccccc3S(=O)(=O)C(C)C)n2)cc1C] |
| 73 | 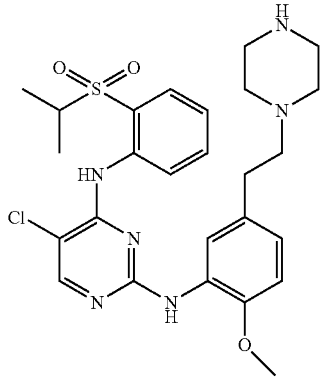 [SMILES: COc1ccc(CCN2CCNCC2)cc1Nc1ncc(Cl)c(Nc2ccccc2S(=O)(=O)C(C)C)n1] |
| 74 | 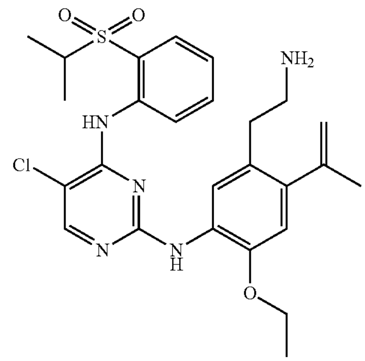 [SMILES: C=C(C)c1cc(OCC)c(Nc2ncc(Cl)c(Nc3ccccc3S(=O)(=O)C(C)C)n2)cc1CCN] |
| 75 | 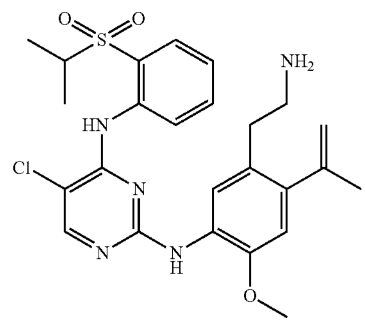 [SMILES: C=C(C)c1cc(OC)c(Nc2ncc(Cl)c(Nc3ccccc3S(=O)(=O)C(C)C)n2)cc1CCN] |

Experimental Example 1: Inhibition of ALK WT Anaplastic Lymphoma Kinase Activity The following experiment was performed in order to measure the activity of the N2-(2-methoxyphenyl)pyrimidine derivative represented by formula 1 of the present invention to inhibit anaplastic lymphoma kinase (ALK) activity at enzyme level.

To measure the activity to inhibit ALK, each of the compounds prepared in examples listed in table 2 (2 μl) was loaded in a 384 well plate. Then, each of the compounds was mixed with anaplastic lymphoma kinase (ALK) enzyme (1 μl) and biotin conjugated peptide substrate (2 μl), followed by culture for 15 minutes. ATP solution (5 μl) was added thereto, followed by kinase reaction at room temperature for 30 minutes. Streptavidin conjugated XL 665 (5 μl) dissolved in ethylenediaminetetraacetic acid solution and europium ($Eu^{3+}$) conjugated anti-phosphotyrosine antibody (5 μl) were added to the reaction solution to terminate the reaction. Upon completion of the reaction, one hour culture was performed, followed by analysis using homogeneous time-resolved fluorescence (HTRF, Cisbio). $OD_{615/665}$ was measured with Wallac Envision 2103. $IC_{50}$ of each compound was determined by using prism software (Version 5.01, Graphpad). The results are shown in table 2.

TABLE 2

| Example | ALK WT ($IC_{50}$ μM) |
|---------|----------------------|
| 1 | 2.8 |
| 2 | 0.43 |
| 3 | 0.012 |
| 4 | 0.00044 |
| 5 | 0.15 |

TABLE 2-continued

| Example | ALK WT (IC$_{50}$ μM) |
|---|---|
| 6 | 0.16 |
| 7 | 0.01 |
| 8 | 0.01 |
| 9 | 0.0037 |
| 10 | 0.004 |
| 11 | 0.004 |
| 12 | 0.02 |
| 13 | 0.00084 |
| 14 | 0.0019 |
| 15 | 0.0026 |
| 16 | 0.01 |
| 17 | 0.04 |
| 18 | 0.3 |
| 19 | 0.03 |
| 20 | 0.01 |
| 21 | 0.001 |
| 22 | 0.01 |
| 23 | 0.01 |
| 24 | 0.00088 |
| 25 | 0.04 |
| 26 | 0.0035 |
| 27 | 0.0038 |
| 28 | 0.097 |
| 29 | 0.002 |
| 30 | 0.05 |
| 31 | 0.01 |
| 32 | 0.03 |
| 33 | 0.42 |
| 34 | 0.17 |
| 35 | 0.03 |
| 36 | 0.21 |
| 37 | 0.74 |
| 38 | 2.1 |
| 39 | 0.04 |
| 40 | 0.2 |
| 41 | 0.0031 |
| 42 | 0.01 |
| 43 | 0.19 |
| 44 | 0.0095 |
| 45 | 0.026 |
| 46 | 0.19 |
| 47 | 0.012 |
| 48 | 0.0042 |
| 49 | 0.034 |
| 50 | 0.27 |
| 51 | 0.0034 |
| 52 | 0.0048 |
| 53 | 0.021 |
| 54 | 0.2 |
| 55 | 0.0027 |
| 56 | 0.0049 |
| 57 | 0.0015 |
| 58 | 0.0014 |
| 59 | 0.0078 |
| 60 | 0.0015 |
| 61 | 0.0021 |
| 62 | 0.004 |
| 63 | 0.0015 |
| 64 | 0.0012 |
| 65 | 0.0022 |
| 66 | 0.0028 |
| 67 | — |
| 68 | 0.001932 |
| 69 | 0.002001 |
| 70 | 0.003371 |
| 71 | 0.00472 |
| 72 | 0.001735 |
| 73 | 0.001 |
| 74 | — |
| 75 | — |

In Table 2 above, – indicates that the experiment was not performed.

As shown in table 2, the compounds of the present invention displayed excellent anaplastic lymphoma kinase (ALK WT) inhibition activity. Particularly, the compounds of examples 4, 7-11, 13-16, 20-24, 26-27, 29, 31, 41-42, 44, 48, 51-52, 55-56, and 68-73 exhibited excellent anaplastic lymphoma kinase (ALK WT) inhibition activity at the concentration of 0.01 μM or less.

Therefore, the N2-(2-methoxyphenyl)pyrimidine derivative represented by formula 1 of the present invention was confirmed to significantly inhibit the ALK activity, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 2: Inhibition of ALK L1196M Anaplastic Lymphoma Kinase Activity To measure the activity of the N2-(2-methoxyphenyl) pyrimidine derivative represented by formula 1 of the present invention to inhibit anaplastic lymphoma kinase (ALK) activity at enzyme level, the following experiment was performed by the same manner as described in experimental example 1 except that ALK L1196M protein was used instead of ALK WT protein. The results are shown in table 3.

TABLE 3

| Example | ALK L1196M (IC$_{50}$ μM) |
|---|---|
| 1 | 3.88 |
| 2 | 1.19 |
| 3 | 0.021 |
| 4 | 0.00085 |
| 5 | 0.1 |
| 6 | 10 |
| 7 | 0.05 |
| 8 | 0.1 |
| 9 | 0.01 |
| 10 | 0.05 |
| 11 | 0.04 |
| 12 | 0.32 |
| 13 | 0.01 |
| 14 | 0.01 |
| 15 | 0.02 |
| 16 | 0.06 |
| 17 | 0.78 |
| 18 | 2.2 |
| 19 | 0.24 |
| 20 | 0.06 |
| 21 | 0.01 |
| 22 | 0.03 |
| 23 | 0.18 |
| 24 | 0.01 |
| 25 | 0.23 |
| 26 | 0.02 |
| 27 | 0.02 |
| 28 | 0.66 |
| 29 | 0.014 |
| 30 | 1 |
| 31 | 0.06 |
| 32 | 0.11 |
| 33 | — |
| 34 | — |
| 35 | — |
| 36 | — |
| 37 | — |
| 38 | — |
| 39 | — |
| 40 | — |
| 41 | — |
| 42 | — |
| 43 | — |
| 44 | 0.045 |
| 45 | — |
| 46 | — |

TABLE 3-continued

| Example | ALK L1196M (IC$_{50}$ µM) |
|---|---|
| 47 | — |
| 48 | — |
| 49 | — |
| 50 | — |
| 51 | — |
| 52 | — |
| 53 | 0.036 |
| 54 | 0.57 |
| 55 | 0.0017 |
| 56 | 0.0034 |
| 57 | 0.0016 |
| 58 | 0.0013 |
| 59 | 0.0061 |
| 60 | 0.0017 |
| 61 | 0.0025 |
| 62 | 0.0044 |
| 63 | 0.0019 |
| 64 | 0.0014 |
| 65 | 0.0036 |
| 66 | 0.0015 |
| 67 | — |
| 68 | 0.0021 |
| 69 | 0.002 |
| 70 | 0.0021 |
| 71 | 0.0028 |
| 72 | 0.0022 |
| 73 | — |
| 74 | — |
| 75 | — |

In Table 3 above, – indicates that the experiment was not performed.

As shown in table 3, the compounds of the present invention displayed excellent anaplastic lymphoma kinase (ALK L1196M) inhibition activity. Particularly, the compounds of examples 4, 9, 13-14, 21, 24, 55-66, and 68-72 exhibited excellent anaplastic lymphoma kinase (ALK L1196M) inhibition activity at the concentration of 0.01 µM or less.

Therefore, the N2-(2-methoxyphenyl)pyrimidine derivative represented by formula 1 of the present invention was confirmed to significantly inhibit the ALK activity, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 3: Inhibition of ALK IR Anaplastic Lymphoma Kinase Activity To measure the activity of the N2-(2-methoxyphenyl)pyrimidine derivative represented by formula 1 of the present invention to inhibit anaplastic lymphoma kinase (ALK) activity at enzyme level, the following experiment was performed by the same manner as described in experimental example 1 except that IR (Insulin Receptor) protein was used instead of ALK WT protein. The results are shown in table 4.

TABLE 4

| Example | IR (IC$_{50}$ µM) |
|---|---|
| 1 | >10 |
| 2 | 1.82 |
| 3 | 0.043 |
| 4 | 0.0023 |
| 5 | 4.7 |
| 6 | 1.1 |
| 7 | 0.05 |
| 8 | 0.1 |
| 9 | 0.02 |
| 10 | 0.03 |
| 11 | 0.02 |
| 12 | 0.18 |
| 13 | 0.01 |
| 14 | 0.01 |
| 15 | 0.02 |
| 16 | 0.05 |
| 17 | 0.63 |
| 18 | 1.7 |
| 19 | 0.11 |
| 20 | 0.02 |
| 21 | 0.01 |
| 22 | 0.03 |
| 23 | 0.12 |
| 24 | 0.01 |
| 25 | 0.08 |
| 26 | 0.01 |
| 27 | 0.01 |
| 28 | 0.38 |
| 29 | 0.02 |
| 30 | 0.14 |
| 31 | 0.09 |
| 32 | 0.07 |
| 33 | — |
| 34 | — |
| 35 | — |
| 36 | — |
| 37 | — |
| 38 | — |
| 39 | — |
| 40 | — |
| 41 | 0.0021 |
| 42 | — |
| 43 | — |
| 44 | 0.057 |
| 45 | — |
| 46 | — |
| 47 | — |
| 48 | — |
| 49 | — |
| 50 | — |
| 51 | — |
| 52 | — |
| 53 | 0.12 |
| 54 | 0.55 |
| 55 | 0.0018 |
| 56 | 0.0032 |
| 57 | 0.0026 |
| 58 | 0.0023 |
| 59 | 0.018 |
| 60 | 0.0039 |
| 61 | 0.0061 |
| 62 | 0.017 |
| 63 | 0.0035 |
| 64 | 0.0019 |
| 65 | 0.0026 |
| 66 | 0.006 |
| 67 | — |
| 68 | 0.0057 |
| 69 | 0.0035 |
| 70 | 0.0048 |
| 71 | 0.006 |
| 72 | 0.0038 |
| 73 | — |
| 74 | — |
| 75 | — |

In Table 4 above, – indicates that the experiment was not performed.

As shown in table 4, the compounds of the present invention displayed excellent anaplastic lymphoma kinase (IR) inhibition activity. Particularly, the compounds of examples 4, 13-14, 21, 24, 26-27, 41, 55-58, 60-61, 63-66, and 68-72 exhibited excellent anaplastic lymphoma kinase (IR) inhibition activity at the concentration of 0.01 μM or less.

Therefore, the N2-(2-methoxyphenyl)pyrimidine derivative represented by formula 1 of the present invention was confirmed to significantly inhibit the ALK activity, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 4: Evaluation of Cytotoxicity of ALK Inhibitor in the Non-Small Cell Lung Cancer Cell Line H3122

The following experiment was performed to evaluate the cytotoxicity of the N2-(2-methoxyphenyl)pyrimidine derivative represented by formula 1 of the present invention in the non-small cell lung cancer cell line H3122.

Particularly, 4,000 H3122 cells containing ALK enzyme were distributed in each well of a 96 well plate together with 100 μl of DMEM (Dulbecco's Modified Eagle's Medium). One day later, the compound of the present invention was added to each well at different concentrations of 10 M, 2 M, 0.4 M, 0.08 M, 0.0016 M, and 0.00032 M. DMSO (dimethylsulfoxide) was added to the well that was not loaded with the compound by the same amount as the compound. Three days after the addition of the compound, DMEM was eliminated. 10% TCA (trichloroacetic acid) was added to fix the cells. The wells were washed with running water three times and the live cells were stained with SRB solution (1 sulphorodamine B). Then, OD was measured to calculate the population of the live cells. $IC_{50}$ of the experimental compound used in the experiment above was calculated by using prism software (Version 5.01, Graphpad). When the activity of H3122 containing ALK enzyme was reduced under 50%, it was considered that the compound demonstrated the inhibition effect. $GI_{50}$ values of the compound are shown in Table 5 below. $GI_{50}$ of the experimental compound used in the experiment above was calculated by using prism software (Version 5.01, Graphpad). The results are shown in Table 5.

TABLE 5

| Example | cytotoxicity H3122 ($GI_{50}$ μM) |
|---|---|
| 1 | 3.06 |
| 2 | 2.63 |
| 3 | 0.77 |
| 4 | 0.08 |
| 5 | 10 |
| 6 | 10 |
| 7 | 0.79 |
| 8 | 1.9 |
| 9 | 0.22 |
| 10 | 1.2 |
| 11 | 1.4 |
| 12 | 4.7 |
| 13 | 0.99 |
| 14 | 0.05 |
| 15 | 1.1 |
| 16 | 0.41 |
| 17 | 0.88 |
| 18 | 3.6 |
| 19 | 1.1 |
| 20 | 0.31 |
| 21 | 0.06 |
| 22 | 0.27 |
| 23 | 1.4 |
| 24 | 0.09 |
| 25 | 1.3 |
| 26 | 0.14 |
| 27 | 0.42 |
| 28 | 0.82 |
| 29 | 0.1 |
| 30 | 0.48 |
| 31 | 0.7 |
| 32 | 0.71 |
| 33 | 10 |
| 34 | 2.2 |
| 35 | 1.6 |
| 36 | 10 |
| 37 | 10 |
| 38 | 10 |
| 39 | 0.93 |
| 40 | 0.33 |
| 41 | 0.19 |
| 42 | 0.15 |
| 43 | >10 |
| 44 | 1 |
| 45 | 10 |
| 46 | 10 |
| 47 | 0.69 |
| 48 | 0.58 |
| 49 | 10 |
| 50 | 10 |
| 51 | 1.1 |
| 52 | 0.096 |
| 53 | 0.074 |
| 54 | 0.25 |
| 55 | 0.06 |
| 56 | 0.053 |
| 57 | 0.012 |
| 58 | 0.013 |
| 59 | 0.063 |
| 60 | 0.041 |
| 61 | 0.052 |
| 62 | 0.068 |
| 63 | 0.02 |
| 64 | 0.029 |
| 65 | 0.026 |
| 66 | 0.035 |
| 67 | 0.23 |
| 68 | 0.11 |
| 69 | 1.7 |
| 70 | 0.037 |
| 71 | 0.028 |
| 72 | 0.025 |
| 73 | 0.16 |
| 74 | 0.77 |
| 75 | 0.23 |

As shown in Table 5, the compounds of the examples of the present invention showed cytotoxic effect on H3122 cells, the non-small-cell lung cancer cells containing ALK enzyme. In particular, the compounds of examples 4, 14, 21, 24, 52-53, 55-66, and 70-72 demonstrated excellent cytotoxic effect on H3122 cells containing ALK enzyme at the concentration of 0.1 μM or less.

Therefore, the N2-(2-methoxyphenyl)pyrimidine derivative represented by formula 1 of the present invention was confirmed to have cytotoxic effect on H3122 cells, the non-small-cell lung cancer cells, containing ALK enzyme, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 5: Evaluation of Cytotoxicity of ALK Inhibitor in the Non-Small Cell Lung Cancer Cell Line H2228

To evaluate the cytotoxicity of the N2-(2-methoxyphenyl) pyrimidine derivative represented by formula 1 of the present invention in the non-small cell lung cancer cell line H2228, the following experiment was performed by the same manner as described in experimental example 4 except that the non-small cell lung cancer cell line H2228 was used instead of the non-small cell lung cancer cell line H3122. The results are shown in Table 6.

TABLE 6

| Example | Cytotoxicity H2228 ($GI_{50}$ µM) |
| --- | --- |
| 1 | 2.1 |
| 2 | 3.77 |
| 3 | 1.21 |
| 4 | 0.11 |
| 5 | 7.8 |
| 6 | 10 |
| 7 | 0.8 |
| 8 | 0.88 |
| 9 | 0.23 |
| 10 | 1.8 |
| 11 | 1.4 |
| 12 | 1.1 |
| 13 | 0.87 |
| 14 | 0.09 |
| 15 | 0.78 |
| 16 | 0.52 |
| 17 | 2.3 |
| 18 | 4.9 |
| 19 | 10 |
| 20 | 0.42 |
| 21 | 0.08 |
| 22 | 0.46 |
| 23 | 2.5 |
| 24 | 0.66 |
| 25 | 1.5 |
| 26 | 0.42 |
| 27 | 0.51 |
| 28 | 0.98 |
| 29 | 0.14 |
| 30 | 0.76 |
| 31 | 0.51 |
| 32 | 0.64 |
| 33 | 10 |
| 34 | 2.3 |
| 35 | 1.6 |
| 36 | 10 |
| 37 | 10 |
| 38 | 10 |
| 39 | 0.87 |
| 40 | — |
| 41 | — |
| 42 | — |
| 43 | — |
| 44 | — |
| 45 | — |
| 46 | — |
| 47 | — |
| 48 | — |
| 49 | — |
| 50 | — |
| 51 | — |
| 52 | — |
| 53 | — |
| 54 | — |
| 55 | — |
| 56 | — |
| 57 | — |
| 58 | — |
| 59 | — |
| 60 | — |
| 61 | — |
| 62 | — |
| 63 | — |
| 64 | — |
| 65 | — |
| 66 | — |
| 67 | — |
| 68 | — |
| 69 | — |
| 70 | — |
| 71 | — |
| 72 | — |
| 73 | — |
| 74 | — |
| 75 | — |

In Table 6 above, – indicates that the experiment was not performed.

As shown in Table 6, the compounds of the examples of the present invention showed cytotoxic effect on H2228 cells, the non-small-cell lung cancer cells containing ALK enzyme. In particular, the compounds of examples 4, 7-9, 13-16, 20-22, 24, 26-32, and 39 demonstrated excellent cytotoxic effect on H2228 cells containing ALK enzyme at the concentration of 1.0 µM or less.

Therefore, the N2-(2-methoxyphenyl)pyrimidine derivative represented by formula 1 of the present invention was confirmed to have cytotoxic effect on H2228 cells, the non-small-cell lung cancer cells containing ALK enzyme, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 6: Evaluation of Cytotoxicity of ALK Inhibitor in Ba/F3 EML4-ALK L1196M Cells To evaluate the cytotoxicity of the N2-(2-methoxyphenyl) pyrimidine derivative represented by formula 1 of the present invention in Ba/F3 EML4-ALK L1196M cells, the following experiment was performed.

Particularly, the experiment was performed by the same manner as described in experimental example 4 except that Ba/F3 EML4-ALK L1196M, the cell line prepared by introducing the EML4 (Echiinoderm Microtubule-Associated Protein-like 4)-ALK mutant form L1196M in the rodent IL-3-dependent pro-B lymphoma cell line Ba/F3 was used instead of the non-small cell lung cancer cell line H3122. The results are shown in Table 7.

TABLE 7

| Example | BaF3 EML4 ALK L1196M µM |
| --- | --- |
| 1 | 1.46 |
| 2 | 2.8 |

TABLE 7-continued

| Example | BaF3 EML4 ALK L1196M μM |
|---|---|
| 3 | 0.18 |
| 4 | 0.09 |
| 5 | 2 |
| 6 | 2.1 |
| 7 | 0.78 |
| 8 | 0.97 |
| 9 | 0.32 |
| 10 | 0.73 |
| 11 | 0.78 |
| 12 | 0.97 |
| 13 | 0.73 |
| 14 | 0.08 |
| 15 | 0.68 |
| 16 | 0.8 |
| 17 | 0.88 |
| 18 | 1.9 |
| 19 | 1.1 |
| 20 | 0.41 |
| 21 | 0.09 |
| 22 | 0.28 |
| 23 | 1.9 |
| 24 | 0.24 |
| 25 | 1.7 |
| 26 | 0.23 |
| 27 | 0.64 |
| 28 | 0.8 |
| 29 | 0.12 |
| 30 | 0.32 |
| 31 | 1.2 |
| 32 | 1.8 |
| 33 | 10 |
| 34 | 10 |
| 35 | 5 |
| 36 | 10 |
| 37 | 10 |
| 38 | 10 |
| 39 | 1.8 |
| 40 | 1.5 |
| 41 | 0.49 |
| 42 | 0.56 |
| 43 | >10 |
| 44 | >10 |
| 45 | 10 |
| 46 | 10 |
| 47 | 1.8 |
| 48 | 1.3 |
| 49 | 10 |
| 50 | 10 |
| 51 | 1.6 |
| 52 | 0.49 |
| 53 | 0.19 |
| 54 | 0.44 |
| 55 | 0.3 |
| 56 | 0.096 |
| 57 | 0.055 |
| 58 | 0.035 |
| 59 | 0.099 |
| 60 | 0.068 |
| 61 | 0.081 |
| 62 | 0.26 |
| 63 | 0.058 |
| 64 | 0.066 |
| 65 | 0.066 |
| 66 | 0.091 |
| 67 | 0.39 |
| 68 | 0.039 |
| 69 | >10 |
| 70 | 0.066 |
| 71 | 0.062 |
| 72 | 0.054 |
| 73 | 0.32 |
| 74 | 1.60 |
| 75 | 0.39 |

As shown in Table 7, the compounds of the examples of the present invention showed cytotoxic effect on EML4-ALK L1196M. In particular, the compounds of examples 56-61, 63-66, 68, and 70-72 demonstrated excellent cytotoxic effect on Ba/F3 EML4-ALK L1196M at the concentration of 0.01 μM or less.

Therefore, the N2-(2-methoxyphenyl)pyrimidine derivative represented by formula 1 of the present invention was confirmed to have cytotoxic effect on Ba/F3 EML4-ALK L1196M, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 7: Evaluation of Cytotoxicity of ALK Inhibitor in Ba/F3 EML4-ALK WT Cells To evaluate the cytotoxicity of the N2-(2-methoxyphenyl)pyrimidine derivative represented by formula 1 of the present invention in Ba/F3 EML4-ALK WT cells, the following experiment was performed.

Particularly, the experiment was performed by the same manner as described in experimental example 4 except that Ba/F3 EML4-ALK WT, the cell line prepared by introducing the EML4 (Echiinoderm Microtubule-Associated Protein-like 4)-ALK in the rodent IL-3-dependent pro-B lymphoma cell line Ba/F3 was used instead of the non-small cell lung cancer cell line H3122. The results are shown in Table 8.

TABLE 8

| Example | Ba/F3 EML-ALK WT (IC$_{50}$ μM) |
|---|---|
| 1 | 0.56 |
| 2 | 0.7 |
| 3 | 0.17 |
| 4 | 0.04 |
| 5 | 2 |
| 6 | 1.6 |
| 7 | 0.71 |
| 8 | 0.53 |
| 9 | 0.24 |
| 10 | 0.36 |
| 11 | 0.37 |
| 12 | 1.5 |
| 13 | 0.06 |
| 14 | 0.02 |
| 15 | 0.13 |
| 16 | 0.34 |
| 17 | 0.33 |
| 18 | 1 |
| 19 | 0.52 |
| 20 | 0.14 |
| 21 | 0.03 |
| 22 | 0.16 |
| 23 | 1.8 |
| 24 | 0.31 |
| 25 | 1.3 |
| 26 | 0.09 |
| 27 | 0.39 |
| 28 | — |
| 29 | — |
| 30 | 0.3 |
| 31 | — |
| 32 | — |
| 33 | — |
| 34 | — |
| 35 | — |
| 36 | — |
| 37 | — |
| 38 | — |

TABLE 8-continued

| Example | Ba/F3 EML-ALK WT (IC$_{50}$ μM) |
|---|---|
| 39 | — |
| 40 | 0.38 |
| 41 | 0.17 |
| 42 | 0.13 |
| 43 | >10 |
| 44 | 2.1 |
| 45 | 3 |
| 46 | 10 |
| 47 | 0.52 |
| 48 | 1.5 |
| 49 | 2.5 |
| 50 | 10 |
| 51 | 0.33 |
| 52 | 0.13 |
| 53 | 0.061 |
| 54 | 0.25 |
| 55 | 0.068 |
| 56 | 0.036 |
| 57 | 0.012 |
| 58 | 0.01 |
| 59 | 0.038 |
| 60 | 0.019 |
| 61 | 0.024 |
| 62 | 0.06 |
| 63 | 0.013 |
| 64 | 0.015 |
| 65 | 0.014 |
| 66 | 0.02 |
| 67 | 0.11 |
| 68 | 0.12 |
| 69 | >10 |
| 70 | 0.021 |
| 71 | 0.015 |
| 72 | 0.015 |
| 73 | 0.097 |
| 74 | 0.36 |
| 75 | 0.11 |

In Table 8 above, – indicates that the experiment was not performed.

As shown in Table 8, the compounds of the examples of the present invention showed cytotoxic effect on Ba/F3 EML4-ALK WT. In particular, the compounds of examples 4, 13-14, 21, 26, 53, 55-66, and 70-73 demonstrated excellent cytotoxic effect on Ba/F3 EML4-ALK WT at the concentration of 0.1 μM or less.

Therefore, the N2-(2-methoxyphenyl)pyrimidine derivative represented by formula 1 of the present invention was confirmed to have cytotoxic effect on Ba/F3 EML4-ALK WT, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 8: In Vivo Xenograft Evaluation for H3122 Induced Lung Cancer <8-1> Experiment Preparation The nude mice (BALB/c nu/nu, female) used in this experiment were purchased from Charles River Japan, Inc. and raised and tested under SPF (Specific Pathogen Free) control. The human non-small cell lung cancer cell line H3122 maintained by Korea Research Institute of Chemical Technology was used in this experiment.

<8-2> Experiment Method

The female nude mice adapted to the laboratory were implanted with cancer. Particularly, H3122 cells grown to the appropriate size for passage were cut into 3×3×3 mm$^3$, which was transplanted (s.c.) under the right side of the nude mouse. When the size of the implanted cancer reached about 200 mm$^3$, administration of the compound of example 58 was started; this was the first day (day 1). For the control, 20% PEG 400+3% Tween 80 in DDW was orally administered. For the experimental group (7 mice/group), the compound was dissolved in the same solvent of the control, which was orally administered 14 times in total (q.d.×14). The size of the cancer was measured every 2-3 days after the administration using a caliper and the diameters (long diameter (a), short diameter (b)) of the cancer were measured. The size of the cancer (volume, V) was calculated according to mathematical formula 1.

$$\text{Volume (mm}^3\text{)} = a \times b^2 / 2 \qquad \text{Mathematical Formula 1}$$

(In the mathematical formula 1,
a represents the horizontal length of the cancer; and
b represents the vertical short length of the cancer).

The results are shown in FIG. 1.

FIG. 1 is a graph showing the results of observing the size of cancer in the control group, the LDK378-treated group, and the group treated with the compound of example 58 over the time.

As shown in FIG. 1, the cancer size was significantly increased in the control group not treated with LDK378 or the compound of the invention. In the meantime, when the compound of example 58 of the present invention was treated, the effect of inhibiting cancer size was excellent, similar to LDK378.

Manufacturing Example 1: Preparation of Powders

| Compound of formula 1 | 2 g |
|---|---|
| Lactose | 1 g |

Powders were prepared by mixing all the above components, which were filled in airtight packs according to the conventional method for preparing powders.

Manufacturing Example 2: Preparation of Tablets

| Compound of formula 1 | 100 g |
|---|---|
| Corn starch | 100 g |
| Lactose | 100 g |
| Magnesium stearate | 2 mg |

Tablets were prepared by mixing all the above components by the conventional method for preparing tablets.

Manufacturing Example 3: Preparation of Capsules

| Compound of formula 1 | 100 g |
|---|---|
| Corn starch | 100 g |
| Lactose | 100 g |
| Magnesium stearate | 2 mg |

Capsules were prepared by mixing all the above components, which were filled in gelatin capsules according to the conventional method for preparing capsules.

Manufacturing Example 4: Preparation of Injectable Solution

| Compound of formula 1 | 500 g |
|---|---|
| Mannitol | 180 g |
| Na$_2$HPO$_4$•2H$_2$O | 26 g |
| Distilled water | 2974 mg |

Injectable solutions were prepared by mixing all the above components according to the conventional method for preparing injectable solutions.

Manufacturing Example 5: Preparation of Health Functional Food

| Compound of formula 1 | 500 g |
|---|---|
| Vitamin complex | proper amount |
| Vitamin A acetate | 70 mg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinic acid amide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

Manufacturing Example 6: Preparation of Health Beverages

| Compound of formula 1 | 500 g |
|---|---|
| Citric acid | 1000 mg |
| Oligosaccharide | 100 mg |
| Maesil (Prunus mume) Extract | 2 mg |
| Taurine | 1 mg |
| Purified water | 900 ml |

The above constituents were mixed according to the conventional method for preparing health beverages. The mixture was heated at 85° C. for 1 hour with stirring and then filtered. The filtrate was loaded in 2 liter sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

INDUSTRIAL APPLICABILITY

The N2-(2-methoxyphenyl)pyrimidine derivative, the optical isomer thereof, or the pharmaceutically acceptable salt thereof of the present invention is very effective in suppressing anaplastic lymphoma kinase (ALK) activity and as a result it can improve the effectiveness of treatment on cancer cells having anaplastic lymphoma kinase (ALK) fusion proteins such as EML4-ALK and NPM-ALK, so that it can be effectively used as a pharmaceutical composition for preventing or treating cancer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A compound, represented by formula 1, or a pharmaceutically acceptable salt of the same:

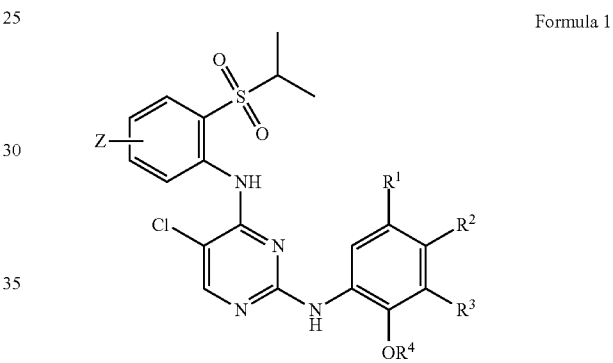

Formula 1 wherein

R$^1$ is hydrogen, C$_{1-5}$ straight or branched alkyl, —(CR$^5$R$^6$)$_\alpha$—(CR$^7$R$^8$)$_\beta$—(CR$^9$R$^{10}$)$_\gamma$—NR$^{11}$R$^{12}$, or —(CH$_2$)$_p$—C(=O)—R$^{13}$, R$^5$, R$^6$, R$^7$, R$^8$, R$^9$, and R$^{10}$ are independently hydrogen or C$_{1-10}$ straight or branched alkyl, R$^5$ and R$^6$ can form unsubstituted C$_{3-8}$ cycloalkyl along with the carbon atoms conjugated to the same, R$^7$ and R$^8$ can form unsubstituted C$_{3-10}$ cycloalkyl or oxo group (=O) along with the carbon atoms conjugated to the same, R$^{11}$ and R$^{12}$ are independently hydrogen, C$_{1-10}$ straight or branched alkyl wherein unsubstituted or one or more hydroxyl groups are substituted, C$_{1-10}$ straight or branched alkyl sulfonyl, unsubstituted C$_{6-10}$ aryl C$_{1-5}$ straight or branched alkyl, —(CH$_2$)$_n$—C(=X)R$^{14}$, unsubstituted C$_{6-10}$ heteroaryl containing one or more hetero atoms selected from the group consisting of N, O, and S, or unsubstituted C$_{6-10}$ aryl, wherein X is O or S, R$^{14}$ is hydrogen, —OH, C$_{1-10}$ straight or branched alkoxy, C$_{1-10}$ straight or branched alkyl wherein unsubstituted or one or more halogens are substituted, unsubstituted C$_{6-10}$ aryl C$_{1-5}$ straight or branched alkyl, or —NR$^{15}$R$^{16}$, R$^{15}$ and R$^{16}$ are independently hydrogen, C$_{1-5}$ straight or branched alkyl, unsubstituted C$_{5-10}$ cycloalkyl, unsubstituted C$_{6-10}$ aryl, or unsubstituted C$_{6-10}$ aryl C$_{1-5}$ alkyl, and n is an integer of 0-5, R¹¹ and R¹² can form unsubstituted $C_{5-10}$ heterocycloalkyl containing one or more hetero atoms selected from the group consisting of N, O, and S along with the nitrogen atoms conjugated to the same, α, β, and γ are independently integers of 0-2, R¹³ is —OH or —(OCH$_2$CH$_2$)$_q$—H, wherein q is an integer of 1-2, p is an integer of 1-2;

R² is hydrogen, halogen, unsubstituted or substituted $C_{5-10}$ heteroaryl containing one or more hetero atoms selected from the group consisting of N, O, and S, $C_{1-10}$ straight or branched alkyl wherein unsubstituted or one or more nitrile groups (—CN) are substituted, $C_{1-10}$ straight or branched alkyl wherein unsubstituted or one or more amine groups (—NH$_2$) are substituted, unsubstituted $C_{6-10}$, —(CR¹⁷R¹⁸)$_k$—(CR¹⁹R²⁰)$_j$—NR²¹R²², —C(=CH$_2$)—R²³, or —CH$_2$—N⁺(CH$_3$)$_3$ I⁻, the substituted $C_{5-10}$ heteroaryl can be substituted with $C_{1-5}$ straight or branched alkyl, R¹⁷, R¹⁸, R¹⁹, and R²⁰ are independently hydrogen or $C_{1-5}$ straight or branched alkyl, and k and j are independently integers of 0-2, R²¹ and R²² are independently hydrogen, formyl group (—C(=O)H), or $C_{1-5}$ straight or branched alkyl, R²³ is $C_{1-5}$ straight or branched alkyl;

R³ is hydrogen;

R⁴ is hydrogen or $C_{1-5}$ straight or branched alkoxy; and

Z is hydrogen, F, Cl, or Br, wherein the compound is selected from the group consisting of:

(1) N2-(5-(1-(aminomethyl)cyclopentyl)-2-methoxyphenyl)-5-chloro-N4-(2-(isopropylsulfonyl)phenyl)pyrimidine-2,4-diamine;
(2) N2-(5-(1-(aminomethyl)cyclohexyl)-2-methoxyphenyl)-5-chloro-N4-(2-(isopropylsulfonyl)phenyl)pyrimidine-2,4-diamine;
(3) N2-(5-((1-aminocyclopropyl)methyl)-2-methoxyphenyl)-5-chloro-N4-(2-(isopropylsulfonyl)phenyl)pyrimidine-2,4-diamine;
(4) N2-(5-(2-aminoethyl)-2-methoxyphenyl)-5-chloro-N4-(2-(isopropylsulfonyl)phenyl) pyrimidine-2,4-diamine;
(5) 5-chloro-N4-(2-(isopropylsulfonyl)phenyl-N2-(2-methoxy-5-(1-(piperidine-1-ylmethyl)cyclopentyl)phenyl)pyrimidine-2,4-diamine;
(6) 5-chloro-N4-(2-(isopropylsulfonyl)phenyl)-N2-(2-methoxy-5-(1-(morpholinomethyl)cyclopentyl)phenyl)pyrimidine-2,4-diamine;
(7) N-(3-(5-chloro-4-(2-(isopropylsulfonyl)phenylamino)pyrimidine-2-ylamino)-4-methoxyphenethyl)acetamide;
(8) N-(3-(5-chloro-4-(2-(isopropylsulfonyl)phenylamino)pyrimidine-2-ylamino)-4-methoxyphenethyl)methanesulfonamide;
(9) 5-chloro-N2-(5-(2-(dimethylamino)ethyl)-2-methoxyphenyl)-N4-(2-(isopropylsulfonyl)phenyl)pyrimidine-2,4-diamine;
(10) 5-chloro-N4-(2-(isopropylsulfonyl)phenyl)-N2-(2-methoxy-5-(2-(methylamino)ethyl)phenyl)pyrimidine-2,4-diamine;
(11) N2-(5-(2-(benzylamino)ethyl)-2-methoxyphenyl)-5-chloro-N4-(2-(isopropylsulfonyl)phenyl)pyrimidine-2,4-diamine;
(12) N-(3-(5-chloro-4-(2-(isopropylsulfonyl)phenylamino)pyrimidine-2-ylamino)-4-methoxyphenethyl)-2-phenylacetamide;
(13) 5-chloro-N2-(5-(2-(ethylamino)ethyl)-2-methoxyphenyl)-N4-(2-(isopropylsulfonyl)phenyl)pyrimidine-2,4-diamine;
(14) 5-chloro-N2-(5-(2-(diethylamino)ethyl)-2-methoxyphenyl)-N4-(2-(isopropylsulfonyl)phenyl)pyrimidine-2,4-diamine;
(15) 5-chloro-N2-(5-(2-(isopropylamino)ethyl)-2-methoxyphenyl)-N4-(2-(isopropylsulfonyl)phenyl)pyrimidine-2,4-diamine;
(16) 1-(3-(5-chloro-4-(2-(isopropylsulfonyl)phenylamino)pyrimidine-2-ylamino)-4-methoxyphenethyl)-3-ethylurea;
(17) 1-(3-(5-chloro-4-(2-(isopropylsulfonyl)phenylamino)pyrimidine-2-ylamino)-4-methoxyphenethyl)-3-cyclohexylurea;
(18) 1-(3-(5-chloro-4-(2-(isopropylsulfonyl)phenylamino)pyrimidine-2-ylamino)-4-methoxyphenethyl)-3-phenylurea;
(19) 1-(3-(5-chloro-4-(2-(isopropylsulfonyl)phenylamino)pyrimidine-2-ylamino)-4-methoxyphenethyl)-3-methylthiourea;
(20) 1-benzyl-3-(3-(5-chloro-4-(2-(isopropylsulfonyl)phenylamino)pyrimidine-2-ylamino)-4-methoxyphenethyl)thiourea;
(21) 5-chloro-N4-(2-(isopropylsulfonyl)phenyl)-N2-(2-methoxy-5-(2-(piperidine-1-yl)ethyl)phenyl)pyrimidine-2,4-diamine;
(22) 5-chloro-N4-(2-(isopropylsulfonyl)phenyl)-N2-(2-methoxy-5-(2-morpholinoethyl)phenyl)pyrimidine-2,4-diamine;
(23) 1-(3-(5-chloro-4-(2-(isopropylsulfonyl)phenylamino)pyrimidine-2-ylamino)-4-methoxyphenethyl)-3-ethylthiourea;
(24) methyl 3-(3-(5-chloro-4-(2-(isopropylsulfonyl)phenylamino)pyrimidine-2-ylamino)-4-methoxyphenethylamino)propanoate;
(25) 5-chloro-N4-(2-(isopropylsulfonyl)phenyl)-N2-(2-methoxy-5-(2-(pyrimidine-2-ylamino)ethyl)phenyl)pyrimidine-2,4-diamine;
(26) methyl 2-(3-(5-chloro-4-(2-(isopropylsulfonyl)phenylamino)pyrimidine-2-ylamino)-4-methoxyphenethylamino)acetate;
(27) 2-(3-(5-chloro-4-(2-(isopropylsulfonyl)phenylamino)pyrimidine-2-ylamino)-4-methoxyphenethylamino)acetic acid;
(28) N-(3-((5-chloro-4-((2-(isopropylsulfonyl)phenyl)amino)pyrimidine-2-yl)amino)-4-methoxybenzyl)-2,2,2-trifluoroacetamide;
(29) N2-(5-(aminomethyl)-2-methoxyphenyl)-5-chloro-N4-(2-(isopropylsulfonyl)phenyl)pyrimidine-2,4-diamine;
(30) N-(3-(5-chloro-4-(2-(isopropylsulfonyl)phenylamino)pyrimidine-2-ylamino)-4-methoxyphenethyl)-2,2,2-trifluoroacetamide;
(31) N2-(5-(2-aminoethyl)-2-isopropoxyphenyl)-5-chloro-N4-(2-(isopropylsulfonyl)phenyl)pyrimidine-2,4-diamine;
(32) N2-(5-(2-aminoethyl)-2-methoxyphenyl)-5-chloro-N4-(4-fluoro-2-(isopropylsulfonyl)phenyl)pyrimidine-2,4-diamine;
(33) N2-(5-(2-aminoethyl)-2-methoxyphenyl)-5-chloro-N4-(5-fluoro-2-(isopropylsulfonyl)phenyl)pyrimidine-2,4-diaminehydrochloride;
(34) N2-(5-(2-aminoethyl)-2-methoxyphenyl)-5-chloro-N4-(2-fluoro-6-(isopropylsulfonyl)phenyl)pyrimidine-2,4-diaminehydrochloride;

(35) N2-(5-(1-amino-2-methylpropane-2-yl)-2-methoxyphenyl)-5-chloro-N4-(2-(isopropylsulfonyl)phenyl)pyrimidine-2,4-diamine;
(36) N2-(5-(1-amino-2-methylpropane-2-yl)-2-methoxyphenyl)-5-chloro-N4-(4-fluoro-2-(isopropylsulfonyl)phenyl)pyrimidine-2,4-diamine;
(37) N2-(5-(1-amino-2-methylpropane-2-yl)-2-methoxyphenyl)-5-chloro-N4-(5-fluoro-2-(isopropylsulfonyl)phenyl)pyrimidine-2,4-diamine;
(38) N2-(5-(1-amino-2-methylpropane-2-yl)-2-methoxyphenyl)-5-chloro-N4-(2-fluoro-6-(isopropylsulfonyl)phenyl)pyrimidine-2,4-diamine;
(39) 2,2'-(3-(5-chloro-4-(2-(isopropylsulfonyl)phenylamino)pyrimidine-2-ylamino)-4-methoxyphenethylazeindiyl)diethanol;
(40) N-(3-(3-((5-chloro-4-((2-(isopropylsulfonyl)phenyl)amino)pyrimidine-2-yl)amino)-4-methoxyphenyl)propyl)-2,2,2-trifluoroacetamide;
(41) N2-(5-(3-aminopropyl)-2-methoxyphenyl)-5-chloro-N4-(2-(isopropylsulfonyl)phenyl)pyrimidine-2,4-diamine;
(42) 2-(3-((5-chloro-4-((2-(isopropylsulfonyl)phenyl)amino)pyrimidine-2-yl)amino)-4-methoxyphenyl)acetamide;
(43) 2-ethoxyethyl 2-(3-((5-chloro-4-((2-(isopropylsulfonyl)phenyl)amino)pyrimidine-2-yl)amino)-4-methoxyphenyl)acetate;
(44) 2-(3-((5-chloro-4-((2-(isopropylsulfonyl)phenyl)amino)pyrimidine-2-yl)amino)-4-methoxyphenyl)acetic acid;
(45) 2-(3-((5-chloro-4-((2-(isopropylsulfonyl)phenyl)amino)pyrimidine-2-yl)amino)-4-methoxyphenyl)-1-morpholinoethane-1-one;
(46) 2-(3-((5-chloro-4-((2-(isopropylsulfonyl)phenyl)amino)pyrimidine-2-yl)amino)-4-methoxyphenyl)-1-(piperidine-1-yl)ethane-1-one;
(47) 2-(3-((5-chloro-4-((2-(isopropylsulfonyl)phenyl)amino)pyrimidine-2-yl)amino)-4-methoxyphenyl)-N-(hydroxymethyl)acetamide;
(48) 2-(3-((5-chloro-4-((2-(isopropylsulfonyl)phenyl)amino)pyrimidine-2-yl)amino)-4-methoxyphenyl)-1-(piperazine-1-yl)ethane-1-one;
(49) 2-(3-((5-chloro-4-((2-(isopropylsulfonyl)phenyl)amino)pyrimidine-2-yl)amino)-4-methoxyphenyl)-N-(pyridine-4-yl)acetamide;
(50) 2-(3-((5-chloro-4-((2-(isopropylsulfonyl)phenyl)amino)pyrimidine-2-yl)amino)-4-methoxyphenyl)-N-phenylacetamide;
(51) N2-(5-(2-aminoethyl)-4-bromo-2-methoxyphenyl)-5-chloro-N4-(2-(isopropylsulfonyl)phenyl)pyrimidine-2,4-diamine;
(52) N2-(5-(2-aminoethyl)-2-methoxy-4-(1-methyl-1H-pyrazole-4-yl)phenyl)-5-chloro-N4-(2-(isopropylsulfonyl)phenyl)pyrimidine-2,4-diamine;
(53) 2-(4-((5-chloro-4-((2-(isopropylsulfonyl)phenyl)amino)pyrimidine-2-yl)amino)-5-methoxy-2-methylphenyl)acetonitrile;
(54) 2-(4-((5-chloro-4-((2-(isopropylsulfonyl)phenyl)amino)pyrimidine-2-yl)amino)-5-methoxy-2-methylphenyl)-2-methylpropanenitrile;
(55) N2-(4-(2-aminoethyl)-2-methoxy-5-methylphenyl)-5-chloro-N4-(2-(isopropylsulfonyl)phenyl)pyrimidine-2,4-diamine;
(56) N2-(4-(1-amino-2-methylpropane-2-yl)-2-methoxy-5-methylphenyl)-5-chloro-N4-(2-(isopropylsulfonyl)phenyl)pyrimidine-2,4-diamine;
(57) N2-(4-(2-aminopropane-2-yl)-2-methoxy-5-methylphenyl)-5-chloro-N4-(2-(isopropylsulfonyl)phenyl)pyrimidine-2,4-diamine;
(58) 5-chloro-N2-(4-(2-(dimethylamino)ethyl)-2-methoxy-5-methylphenyl)-N4-(2-(isopropylsulfonyl)phenyl)pyrimidine-2,4-diamine;
(59) N-(2-(4-((5-chloro-4-((2-(isopropylsulfonyl)phenyl)amino)pyrimidine-2-yl)amino)-5-methoxy-2-methylphenyl)-2-methylpropyl)formamide;
(60) 5-chloro-N4-(2-(isopropylsulfonyl)phenyl)-N2-(2-methoxy-5-methyl-4-(2-methyl-1-(methylamino)propane-2-yl)phenyl)pyrimidine-2,4-diamine;
(61) N-(2-(4-((5-chloro-4-((2-(isopropylsulfonyl)phenyl)amino)pyrimidine-2-yl)amino)-5-methoxy-2-methylphenyl)propane-2-yl) formamide;
(62) N-(4-((5-chloro-4-((2-(isopropylsulfonyl)phenyl)amino)pyrimidine-2-yl)amino)-5-methoxy-2-methylphenethyl)formamide;
(63) 5-chloro-N4-(2-(isopropylsulfonyl)phenyl)-N2-(2-methoxy-5-methyl-4-(2-(methylamino)ethyl)phenyl)pyrimidine-2,4-diamine;
(64) 5-chloro-N4-(2-(isopropylsulfonyl)phenyl)-N2-(2-methoxy-5-methyl-4-(2-(methylamino)propane-2-yl)phenyl)pyrimidine-2,4-diamine;
(65) 5-chloro-N2-(4-(1-(dimethylamino)-2-methylpropane-2-yl)-2-methoxy-5-methylphenyl)-N4-(2-(isopropylsulfonyl)phenyl)pyrimidine-2,4-diamine;
(66) 5-chloro-N2-(4-(2-(dimethylamino)propane-2-yl)-2-methoxy-5-methylphenyl)-N4-(2-(isopropylsulfonyl)phenyl)pyrimidine-2,4-diamine;
(67) N2-(2-(2-aminoethyl)-5-methoxybiphenyl-4-yl)-5-chloro-N4-(2-isopropylsulfonyl)phenyl)pyrimidine-2,4-diamine;
(68) N2-(4-(aminomethyl)-2-methoxy-5-methylphenyl)-5-chloro-N4-(2-(isopropylsulfonyl)phenyl)pyrimidine-2,4-diamine;
(69) 1-(4-((5-chloro-4-((2-(isopropylsulfonyl)phenyl)amino)pyrimidine-2-yl)amino)-5-methoxy-2-methylphenyl)-N,N,N-trimethylmethanealuminum iodide;
(70) 5-chloro-N2-(4-((dimethylamino)methyl)-2-methoxy-5-methylphenyl)-N4-(2-(isopropylsulfonyl)phenyl)pyrimidine-2,4-diamine;
(71) N-(4-((5-chloro-4-((2-(isopropylsulfonyl)phenyl)amino)pyrimidine-2-yl)amino)-5-methoxy-2-methylbenzyl)formamide;
(72) 5-chloro-N4-(2-(isopropylsulfonyl)phenyl)-N2-(2-methoxy-5-methyl-4-((methylamino)methyl)phenyl)pyrimidine-2,4-diamine;
(73) 5-chloro-N4-(2-(isopropylsulfonyl)phenyl)-N2-(2-methoxy-5-(2-(piperazine-1-yl)ethyl)phenyl)pyrimidine-2,4-diamine;
(74) N2-(5-(2-aminoethyl)-2-ethoxy-4-(prop-1-ene-2-yl)phenyl)-5-chloro-N4-(2-(isopropylsulfonyl)phenyl)pyrimidine-2,4-diamine; and
(75) N2-(5-(2-aminoethyl)-2-methoxy-4-(prop-1-ene-2-yl)phenyl)-5-chloro-N4-(2-(isopropylsulfonyl)phenyl)pyrimidine-2,4-diamine.

2. A method for preparing the compound according to claim 1, the method comprising reacting the compound represented by formula 2 with the compound represented by formula 3 (step 1) as shown in reaction formula 1 below:

Reaction Formula 1

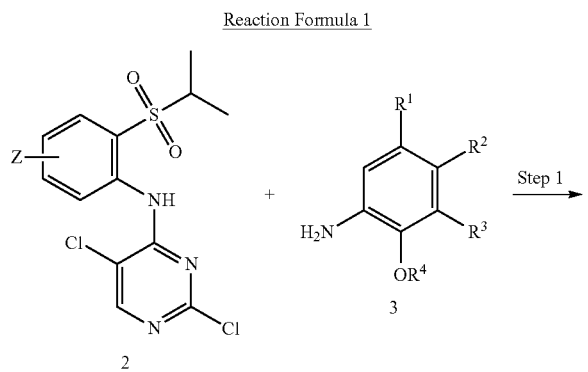

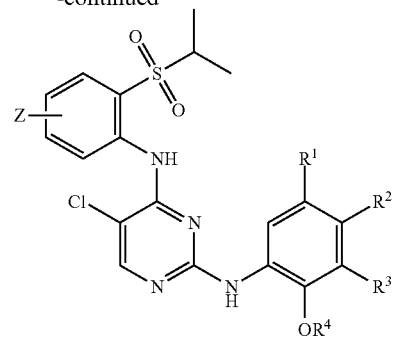

wherein
$R^1$, $R^2$, $R^3$, $R^4$, and Z are as defined in formula 1 according to claim 1.

3. A pharmaceutical composition comprising:
one or more excipients; and
the compound according to claim 1, or the pharmaceutically acceptable salt of the same as an active ingredient for the prevention or treatment of cancer.

4. A method of treating a non-small cell lung cancer comprising administering a pharmaceutically effective amount of the compound of claim 1, or the pharmaceutically acceptable salt thereof to a subject in need thereof.

* * * * *